(12) United States Patent
Glicklich et al.

(10) Patent No.: US 11,007,175 B2
(45) Date of Patent: May 18, 2021

(54) METHODS OF TREATING CONDITIONS RELATED TO THE S1P₁ RECEPTOR

(71) Applicant: Arena Pharmaceuticals, Inc., San Diego, CA (US)

(72) Inventors: Alan Glicklich, La Jolla, CA (US); Maria Matilde Sanchez Kam, Alexandria, VA (US); William R. Shanahan, Del Mar, CA (US)

(73) Assignee: Arena Pharmaceuticals, Inc., San Diego, CA (US)

( * ) Notice: Subject to any disclaimer, the term of this patent is extended or adjusted under 35 U.S.C. 154(b) by 0 days.

(21) Appl. No.: 15/541,496

(22) PCT Filed: Jan. 6, 2016

(86) PCT No.: PCT/US2016/012289
§ 371 (c)(1),
(2) Date: Jul. 6, 2017

(87) PCT Pub. No.: WO2016/112075
PCT Pub. Date: Jul. 14, 2016

(65) Prior Publication Data
US 2018/0263958 A1 Sep. 20, 2018

Related U.S. Application Data

(60) Provisional application No. 62/100,362, filed on Jan. 6, 2015, provisional application No. 62/159,550, filed on May 11, 2015.

(51) Int. Cl.
*A61K 31/403* (2006.01)
*A61P 29/00* (2006.01)
(Continued)

(52) U.S. Cl.
CPC .......... *A61K 31/403* (2013.01); *A61K 9/4825* (2013.01); *A61P 3/10* (2018.01);
(Continued)

(58) Field of Classification Search
None
See application file for complete search history.

(56) References Cited

U.S. PATENT DOCUMENTS 3,206,470 A 9/1965 William et al.
3,503,963 A 3/1970 Schweizer et al.
(Continued)

FOREIGN PATENT DOCUMENTS

AT 327605 6/2006
AU 492126 11/1975
(Continued)

OTHER PUBLICATIONS

Buzard, Discovery of APD334: Design of a Clinical Stage Functional Antagonist of the Sphingosine-1-phosphate-1 Receptor, ACS Med. Chem. Lett., 2014, 5, pp. 1313-1317. (Year: 2014).*

(Continued)

*Primary Examiner* — Savitha M Rao
*Assistant Examiner* — Andrew P Lee
(74) *Attorney, Agent, or Firm* — Fish & Richardson P.C.

(57) ABSTRACT

Provided are methods of treatment of a sphingosine 1-phosphate subtype 1 (S1P₁) receptor-associated disorder comprising prescribing and/or administering to an individual in need thereof a standard dose of (R)-2-(7-(4-cyclopentyl-3-(trifluoro-methyl)benzyloxy)-1,2,3,4-tetrahydrocyclopenta[b]indol-3-yl)acetic acid (Compound 1), or a pharmaceutically acceptable salt, hydrate, or solvate thereof, in an amount equivalent to about 1.5 to about 2.5 mg of Compound 1, for example, a disease or disorder mediated by lymphocytes, an autoimmune disease or disorder, an inflam- (Continued)

Observed Lymphocyte Counts (10³/μl) in the Safety Population (Placebo)

matory disease or disorder, ankylosing spondylitis, biliary cirrhosis, cancer, psoriasis, psoriatic arthritis, rheumatoid arthritis, Crohn's disease, transplant rejection, multiple sclerosis, systemic lupus erythematosus, inflammatory bowel disease, ulcerative colitis, type I diabetes, hypertensive nephropathy, glomerulosclerosis, myocardial ischemia-reperfusion injury, and acne.

21 Claims, 18 Drawing Sheets

(51) Int. Cl.
*A61P 37/02* (2006.01)
*A61K 9/48* (2006.01)
*A61P 17/10* (2006.01)
*A61P 17/06* (2006.01)
*A61P 19/02* (2006.01)
*A61P 3/10* (2006.01)
*A61P 35/00* (2006.01)
*A61K 9/20* (2006.01)

(52) U.S. Cl.
CPC .............. *A61P 17/06* (2018.01); *A61P 17/10* (2018.01); *A61P 19/02* (2018.01); *A61P 29/00* (2018.01); *A61P 35/00* (2018.01); *A61P 37/02* (2018.01); *A61K 9/20* (2013.01)

(56) References Cited

U.S. PATENT DOCUMENTS

| | | |
|---|---|---|
| 3,592,932 A | 7/1971 | Duerr et al. |
| 3,598,801 A | 8/1971 | Beffa et al. |
| 3,608,087 A | 9/1971 | Patchett et al. |
| 3,686,238 A | 8/1972 | Zaffaroni et al. |
| 3,690,834 A | 9/1972 | Goldstein et al. |
| 3,849,420 A | 11/1974 | Tong |
| 3,852,434 A | 12/1974 | Kahan et al. |
| 3,862,117 A | 1/1975 | Leverenz |
| 3,887,329 A | 6/1975 | Hegar et al. |
| 3,948,914 A | 4/1976 | Fischer |
| 3,966,744 A | 6/1976 | Goldstein et al. |
| 3,966,764 A | 6/1976 | Goldstein et al. |
| 3,975,384 A | 8/1976 | Narr et al. |
| 3,984,411 A | 10/1976 | Claverie et al. |
| 4,057,559 A | 11/1977 | Asselin et al. |
| 4,101,541 A | 7/1978 | Petitpierre et al. |
| 4,139,705 A | 2/1979 | Dunbar et al. |
| 4,189,427 A | 2/1980 | Komorowski |
| 4,189,579 A | 2/1980 | Dunbar et al. |
| 4,242,507 A | 12/1980 | Itoh et al. |
| 4,267,174 A | 5/1981 | Berger et al. |
| 4,273,870 A | 6/1981 | Endo et al. |
| 4,275,148 A | 6/1981 | Endo et al. |
| 4,343,804 A | 8/1982 | Munison et al. |
| 4,397,848 A | 8/1983 | Bosies et al. |
| 4,493,726 A | 1/1985 | Burdeska et al. |
| 4,517,183 A | 5/1985 | Bosies et al. |
| 4,612,376 A | 9/1986 | Takaya et al. |
| 4,643,995 A | 2/1987 | Engel et al. |
| 4,766,213 A | 8/1988 | Juraszyk et al. |
| 4,782,076 A | 11/1988 | Mobilio et al. |
| 4,797,484 A | 1/1989 | Moriya et al. |
| 4,810,699 A | 3/1989 | Sabatucci et al. |
| 4,880,932 A | 11/1989 | Moriya et al. |
| 5,221,678 A | 6/1993 | Atkinson et al. |
| 5,571,815 A | 11/1996 | Schaper et al. |
| 5,624,941 A | 4/1997 | Barth et al. |
| 5,691,364 A | 11/1997 | Buckman et al. |
| 5,776,967 A | 7/1998 | Kreft et al. |
| 5,830,911 A | 11/1998 | Failli et al. |
| 5,849,759 A | 12/1998 | Amaiz et al. |
| 5,948,786 A | 9/1999 | Fujiwara et al. |
| 5,952,504 A | 9/1999 | Yoo et al. |
| 5,962,479 A | 10/1999 | Chen |
| 6,008,234 A | 12/1999 | Kochanny et al. |
| 6,060,478 A | 5/2000 | Gilligan |
| 6,107,301 A | 8/2000 | Aldrich et al. |
| 6,187,777 B1 | 2/2001 | Norman et al. |
| 6,191,149 B1 | 2/2001 | Chokai et al. |
| 6,218,431 B1 | 4/2001 | Schoen et al. |
| 6,239,126 B1 | 5/2001 | Kelly et al. |
| 6,267,985 B1 | 7/2001 | Chen et al. |
| 6,294,671 B1 | 9/2001 | Frietze |
| 6,350,750 B1 | 2/2002 | Den Hartog et al. |
| 6,410,583 B1 | 6/2002 | Labelle et al. |
| 6,414,002 B1 | 7/2002 | Cheng et al. |
| 6,506,762 B1 | 1/2003 | Horvath et al. |
| 6,525,064 B1 | 2/2003 | Dellaria et al. |
| 6,545,016 B1 | 4/2003 | Dellaria et al. |
| 6,545,017 B1 | 4/2003 | Dellaria et al. |
| 6,552,192 B1 | 4/2003 | Hanus et al. |
| 6,569,879 B2 | 5/2003 | Liu et al. |
| 6,583,154 B1 | 6/2003 | Norman et al. |
| 6,620,821 B2 | 9/2003 | Robl et al. |
| 6,660,744 B1 | 12/2003 | Hirst et al. |
| 6,713,508 B2 | 3/2004 | Sahoo et al. |
| 6,787,542 B2 | 9/2004 | Wang et al. |
| 6,844,351 B1 | 1/2005 | Chen et al. |
| 6,849,636 B2 | 2/2005 | Waddell et al. |
| 6,956,047 B1 | 10/2005 | Chen et al. |
| 6,960,692 B2 | 11/2005 | Kohno et al. |
| 7,056,942 B2 | 6/2006 | Hildesheim et al. |
| 7,057,046 B2 | 6/2006 | Sher et al. |
| 7,083,933 B1 | 8/2006 | Griffin |
| 7,098,235 B2 | 8/2006 | Sher et al. |
| 7,132,426 B2 | 11/2006 | Jones et al. |
| 7,250,441 B2 | 7/2007 | Gopalsamy et al. |
| 7,276,249 B2 | 10/2007 | Ryde et al. |
| 7,417,039 B2 | 8/2008 | Davis |
| 7,425,630 B2 | 9/2008 | Gharbaoui et al. |
| 7,470,699 B2 | 12/2008 | Jones et al. |
| 7,625,906 B2 | 12/2009 | Jones et al. |
| 7,763,278 B2 | 7/2010 | Cooper et al. |
| 7,812,159 B2 | 10/2010 | Gharbaoui et al. |
| 7,838,525 B2 | 11/2010 | Jones et al. |
| 8,293,751 B2 | 10/2012 | Jones et al. |
| 8,362,248 B2 | 1/2013 | Jones et al. |
| 8,410,119 B2 | 4/2013 | Jones et al. |
| 8,415,484 B2 | 4/2013 | Jones et al. |
| 8,580,841 B2 | 11/2013 | Jones et al. |
| 8,853,419 B2 | 10/2014 | Montalban et al. |
| 9,126,932 B2 | 9/2015 | Jones et al. |
| 9,175,320 B2 | 11/2015 | Montalban et al. |
| 9,447,041 B2 | 9/2016 | Montalban et al. |
| 9,522,133 B2 | 12/2016 | Jones et al. |
| 2002/0058026 A1 | 5/2002 | Hammerly |
| 2002/0137755 A1 | 9/2002 | Bilodeau et al. |
| 2002/0156081 A1 | 10/2002 | Hirst et al. |
| 2003/0083269 A1 | 5/2003 | Brouillette et al. |
| 2003/0211421 A1 | 11/2003 | Hanabata et al. |
| 2003/0224058 A1 | 12/2003 | Ryde et al. |
| 2004/0110241 A1 | 6/2004 | Segal |
| 2004/0224941 A1 | 11/2004 | Seko et al. |
| 2004/0254222 A1 | 12/2004 | Kohno et al. |
| 2005/0004114 A1 | 1/2005 | Whitehouse et al. |
| 2005/0009786 A1 | 1/2005 | Pan et al. |
| 2005/0014724 A1 | 1/2005 | Marsilje et al. |
| 2005/0014725 A1 | 1/2005 | Mi et al. |
| 2005/0014728 A1 | 1/2005 | Pan et al. |
| 2005/0033055 A1 | 2/2005 | Bugianesi et al. |
| 2005/0043327 A1 | 2/2005 | Coe et al. |
| 2005/0070562 A1 | 3/2005 | Jones et al. |
| 2005/0182067 A1 | 8/2005 | Balan et al. |
| 2005/0197353 A1 | 9/2005 | Ritzeler et al. |
| 2005/0209251 A1 | 9/2005 | Linker et al. |
| 2005/0239899 A1 | 10/2005 | Fecke et al. |
| 2006/0004010 A1 | 1/2006 | Habashita et al. |
| 2006/0063821 A1 | 3/2006 | Gopalsamy et al. |
| 2006/0079542 A1 | 4/2006 | Nestor |
| 2006/0122222 A1 | 6/2006 | Whitehouse et al. |
| 2006/0154866 A1 | 7/2006 | Chu et al. |

(56) References Cited

U.S. PATENT DOCUMENTS

| | | |
|---|---|---|
| 2006/0155128 A1 | 7/2006 | Jones et al. |
| 2006/0160771 A1 | 7/2006 | Kohno et al. |
| 2006/0211656 A1 | 9/2006 | Albert et al. |
| 2006/0217379 A1 | 9/2006 | Jones et al. |
| 2006/0223866 A1 | 10/2006 | Evindar et al. |
| 2007/0010494 A1 | 1/2007 | Ehrhardt et al. |
| 2007/0043014 A1 | 2/2007 | Doherty et al. |
| 2007/0060573 A1 | 3/2007 | Wortmann et al. |
| 2007/0066590 A1 | 3/2007 | Jones et al. |
| 2007/0072844 A1 | 3/2007 | Jones et al. |
| 2007/0078150 A1 | 4/2007 | Jones et al. |
| 2007/0082874 A1 | 4/2007 | Jones et al. |
| 2007/0149595 A1 | 6/2007 | Tanaka et al. |
| 2007/0149597 A1 | 6/2007 | Nishi et al. |
| 2007/0167413 A1 | 7/2007 | Srinivas et al. |
| 2007/0167425 A1 | 7/2007 | Nakade et al. |
| 2007/0167473 A1 | 7/2007 | Jones et al. |
| 2007/0173487 A1 | 7/2007 | Saha et al. |
| 2007/0173507 A1 | 7/2007 | Hirata |
| 2007/0191313 A1 | 8/2007 | Beard et al. |
| 2007/0191371 A1 | 8/2007 | Bennett et al. |
| 2007/0191468 A1 | 8/2007 | Nishi et al. |
| 2007/0225351 A1 | 9/2007 | Lippa et al. |
| 2007/0244155 A1 | 10/2007 | Sharma et al. |
| 2007/0254886 A1 | 11/2007 | Habashita et al. |
| 2007/0259928 A1 | 11/2007 | Yoshida et al. |
| 2008/0051418 A1 | 2/2008 | Maekawa et al. |
| 2008/0153882 A1 | 6/2008 | Nishi et al. |
| 2008/0200535 A1 | 8/2008 | Ohmori et al. |
| 2008/0207584 A1 | 8/2008 | Habashita et al. |
| 2008/0319077 A1 | 12/2008 | Suzuki et al. |
| 2009/0012093 A1 | 1/2009 | Fukatsu et al. |
| 2009/0036434 A1 | 2/2009 | Jones et al. |
| 2009/0076070 A1 | 3/2009 | Harada et al. |
| 2009/0131438 A1 | 5/2009 | Ono et al. |
| 2009/0137685 A1 | 5/2009 | Kojima et al. |
| 2009/0203676 A1 | 8/2009 | Barba et al. |
| 2009/0270409 A1 | 10/2009 | Alper et al. |
| 2009/0286816 A1 | 11/2009 | Jones et al. |
| 2009/0325907 A1 | 12/2009 | Kohno et al. |
| 2010/0004272 A1 | 1/2010 | Jones et al. |
| 2010/0029650 A1 | 2/2010 | Fang et al. |
| 2010/0160359 A1 | 6/2010 | Jones et al. |
| 2010/0267778 A1 | 10/2010 | Kusuda et al. |
| 2010/0273806 A1 | 10/2010 | Jones et al. |
| 2010/0292233 A1 | 11/2010 | Jones et al. |
| 2011/0082134 A1 | 4/2011 | Jones et al. |
| 2011/0112060 A1 | 5/2011 | Jones et al. |
| 2011/0160243 A1 | 6/2011 | Jones et al. |
| 2011/0230457 A1 | 9/2011 | Berghausen et al. |
| 2012/0064060 A1 | 3/2012 | Habashita et al. |
| 2012/0329848 A1 | 12/2012 | Jones et al. |
| 2013/0023494 A1 | 1/2013 | Jones et al. |
| 2013/0023527 A1 | 1/2013 | Jones et al. |
| 2013/0184307 A1 | 7/2013 | Jones et al. |
| 2014/0038889 A1 | 2/2014 | Jones |
| 2014/0051629 A1 | 2/2014 | Jones et al. |
| 2015/0336966 A1 | 8/2015 | Jones et al. |
| 2015/0284399 A1 | 10/2015 | Jones et al. |
| 2015/0335618 A1 | 11/2015 | Jones et al. |
| 2017/0159088 A1 | 6/2017 | Montalban et al. |
| 2017/0217885 A1 | 8/2017 | Jones et al. |

FOREIGN PATENT DOCUMENTS

| | | |
|---|---|---|
| BE | 829845 | 12/1975 |
| BE | 868796 | 1/1979 |
| CA | 2499497 | 4/2004 |
| CH | 560197 | 3/1975 |
| CN | 1212117 | 7/2005 |
| DE | 2048375 | 4/1971 |
| DE | 2223644 | 11/1972 |
| DE | 2356644 | 5/1974 |
| DE | 2341925 | 3/1975 |
| DE | 2460238 | 7/1975 |
| DE | 2503136 | 7/1975 |
| DE | 2831850 | 2/1980 |
| DE | 3334455 | 9/1984 |
| DE | 3406329 | 8/1985 |
| DE | 3601196 | 7/1987 |
| DE | 19602095 | 7/1997 |
| DE | 19737723 | 2/1999 |
| DE | 19962936 | 6/2001 |
| EP | 0014976 | 9/1980 |
| EP | 0053678 | 10/1981 |
| EP | 0050671 | 5/1982 |
| EP | 0055693 | 7/1982 |
| EP | 0123402 | 10/1984 |
| EP | 0149088 | 12/1984 |
| EP | 0154190 | 9/1985 |
| EP | 0191603 | 8/1986 |
| EP | 0193249 | 9/1986 |
| EP | 0283261 | 9/1988 |
| EP | 0324426 | 7/1989 |
| EP | 0468785 | 1/1992 |
| EP | 0518675 | 12/1992 |
| EP | 0526004 | 2/1993 |
| EP | 0556889 | 8/1993 |
| EP | 0565488 | 10/1993 |
| EP | 0604800 | 7/1994 |
| EP | 0667343 | 8/1995 |
| EP | 0801059 | 10/1997 |
| EP | 0857483 | 8/1998 |
| EP | 0940 387 | 9/1999 |
| EP | 1074549 | 2/2001 |
| EP | 1097709 | 5/2001 |
| EP | 1287133 | 3/2003 |
| EP | 1040831 | 5/2003 |
| EP | 1338651 | 8/2003 |
| EP | 1340749 | 9/2003 |
| EP | 1475094 | 11/2004 |
| EP | 1650186 | 4/2006 |
| EP | 1826197 | 8/2007 |
| EP | 1902730 | 3/2008 |
| EP | 2003132 | 12/2008 |
| EP | 1772145 | 3/2011 |
| EP | 2017263 | 11/2011 |
| FR | 1551400 | 12/1968 |
| GB | 935595 | 8/1963 |
| GB | 1250624 | 10/1971 |
| GB | 1311956 | 3/1973 |
| GB | 1393993 | 5/1975 |
| GB | 1436893 | 5/1976 |
| GB | 1493380 | 11/1977 |
| GB | 1495665 | 12/1977 |
| JP | 55-17382 | 2/1980 |
| JP | 61-057587 | 3/1986 |
| JP | 05-33359 | 12/1993 |
| JP | 07-53546 | 2/1995 |
| JP | 11-193277 | 7/1999 |
| JP | 2000-038350 | 2/2000 |
| JP | 2001-089452 | 4/2001 |
| JP | 200467575 | 3/2004 |
| JP | 2004-269468 | 9/2004 |
| JP | 2004-269469 | 9/2004 |
| JP | 2007262009 | 10/2007 |
| NL | 66144961 | 4/1967 |
| NL | 6814810 | 4/1969 |
| RU | 2067978 | 10/1996 |
| RU | 2119917 | 10/1998 |
| RU | 2153495 | 7/2000 |
| RU | 2158258 | 10/2000 |
| RU | 2198879 | 2/2003 |
| RU | 2200734 | 3/2003 |
| SU | 938 559 | 11/1993 |
| WO | WO 81/03174 | 11/1981 |
| WO | WO 1991/06537 | 5/1991 |
| WO | WO 92/01697 | 2/1992 |
| WO | WO 92/12976 | 8/1992 |
| WO | WO 94/07858 | 4/1994 |
| WO | WO 94/13677 | 6/1994 |
| WO | WO 95/33750 | 12/1995 |
| WO | WO 96/28427 | 9/1996 |
| WO | WO 96/32383 | 10/1996 |

(56) References Cited

FOREIGN PATENT DOCUMENTS

| | | |
|---|---|---|
| WO | WO 96/33980 | 10/1996 |
| WO | WO 96/33994 | 10/1996 |
| WO | WO 96/35689 | 11/1996 |
| WO | WO 96/36613 | 11/1996 |
| WO | WO 97/08152 | 3/1997 |
| WO | WO 1997/014674 | 4/1997 |
| WO | WO 97/26252 | 7/1997 |
| WO | WO 97/28137 | 8/1997 |
| WO | WO 97/29109 | 8/1997 |
| WO | WO 97/40832 | 11/1997 |
| WO | WO 97/48696 | 12/1997 |
| WO | WO 97/49706 | 12/1997 |
| WO | WO 98/04528 | 2/1998 |
| WO | WO 98/08846 | 3/1998 |
| WO | WO 98/08847 | 3/1998 |
| WO | WO 98/11094 | 3/1998 |
| WO | WO 98/13354 | 4/1998 |
| WO | WO 98/19998 | 5/1998 |
| WO | WO 98/27081 | 6/1998 |
| WO | WO 98/35967 | 8/1998 |
| WO | WO 98/47874 | 10/1998 |
| WO | WO 98/47903 | 10/1998 |
| WO | WO 99/09026 | 2/1999 |
| WO | WO 99/51599 | 10/1999 |
| WO | WO 2000/11003 | 3/2000 |
| WO | WO 2000/27825 | 5/2000 |
| WO | WO 2000/31068 | 6/2000 |
| WO | WO 2000/031258 | 6/2000 |
| WO | WO 2000/34241 | 6/2000 |
| WO | WO 2000/35875 | 6/2000 |
| WO | WO 2000/35886 | 6/2000 |
| WO | WO 2000/55153 | 9/2000 |
| WO | WO 2000/064888 | 11/2000 |
| WO | WO 2001/60807 | 2/2001 |
| WO | WO 2001/22938 | 4/2001 |
| WO | WO 2001/23387 | 4/2001 |
| WO | WO 2001/23388 | 4/2001 |
| WO | WO 2001/25210 | 4/2001 |
| WO | WO 2001/27107 | 4/2001 |
| WO | WO 2001/037831 | 5/2001 |
| WO | WO 2001/046204 | 6/2001 |
| WO | WO 2001/47887 | 7/2001 |
| WO | WO 2001/49677 | 7/2001 |
| WO | WO 2001/53263 | 7/2001 |
| WO | WO 2001/58900 | 8/2001 |
| WO | WO 2001/60870 | 8/2001 |
| WO | WO 2001/62233 | 8/2001 |
| WO | WO 2001/76573 | 10/2001 |
| WO | WO 2001/85699 | 11/2001 |
| WO | WO 2001/87829 | 11/2001 |
| WO | WO 2001/87892 | 11/2001 |
| WO | WO 2001/90082 | 11/2001 |
| WO | WO 2002/02539 | 1/2002 |
| WO | WO 2002/02549 | 1/2002 |
| WO | WO 2002/06237 | 1/2002 |
| WO | WO 2002/06274 | 1/2002 |
| WO | WO 2002/08188 | 1/2002 |
| WO | WO 2002/45652 | 2/2002 |
| WO | WO 2002/19975 | 3/2002 |
| WO | WO 2002/24169 | 3/2002 |
| WO | WO 2002/032408 | 4/2002 |
| WO | WO 2002/32893 | 4/2002 |
| WO | WO 2002/039987 | 5/2002 |
| WO | WO 2002/40451 | 5/2002 |
| WO | WO 2002/40456 | 5/2002 |
| WO | WO 2002/40458 | 5/2002 |
| WO | WO 2002/40480 | 5/2002 |
| WO | WO 2002/44362 | 6/2002 |
| WO | WO 2002/045652 | 6/2002 |
| WO | WO 2002/050071 | 6/2002 |
| WO | WO 2002/59083 | 8/2002 |
| WO | WO 2002/060388 | 8/2002 |
| WO | WO 2002/064094 | 8/2002 |
| WO | WO 2002/064616 | 8/2002 |
| WO | WO 2002/070485 | 9/2002 |
| WO | WO 2002/072101 | 9/2002 |
| WO | WO 2002/081454 | 10/2002 |
| WO | WO 2002/85892 | 10/2002 |
| WO | WO 2002/092068 | 11/2002 |
| WO | WO 2002/98864 | 12/2002 |
| WO | WO 2002/98878 | 12/2002 |
| WO | WO 2002/102313 | 12/2002 |
| WO | WO 2003/000666 | 1/2003 |
| WO | WO 2003/002544 | 1/2003 |
| WO | WO 2003/04498 | 1/2003 |
| WO | WO 2003/018556 | 3/2003 |
| WO | WO 2003/026661 | 4/2003 |
| WO | WO 2003/029205 | 4/2003 |
| WO | WO 2003/032989 | 4/2003 |
| WO | WO 2003/050117 | 6/2003 |
| WO | WO 2003/051822 | 6/2003 |
| WO | WO 2003/057689 | 7/2003 |
| WO | WO 2003/059378 | 7/2003 |
| WO | WO 2003/061663 | 7/2003 |
| WO | WO 2003/062252 | 7/2003 |
| WO | WO 2003/073986 | 9/2003 |
| WO | WO 2003/074008 | 9/2003 |
| WO | WO 2003/076418 | 9/2003 |
| WO | WO 2003/077656 | 9/2003 |
| WO | WO 2003/080070 | 10/2003 |
| WO | WO 2003/087064 | 10/2003 |
| WO | WO 2003/088962 | 10/2003 |
| WO | WO 2003/093269 | 11/2003 |
| WO | WO 2003/94845 | 11/2003 |
| WO | WO 2003/061567 | 12/2003 |
| WO | WO 2003/103632 | 12/2003 |
| WO | WO 2003/103633 | 12/2003 |
| WO | WO 2003/103640 | 12/2003 |
| WO | WO 2003/104208 | 12/2003 |
| WO | WO 2003/105763 | 12/2003 |
| WO | WO 2003/105771 | 12/2003 |
| WO | WO 2003/106450 | 12/2003 |
| WO | WO 2004/000762 | 12/2003 |
| WO | WO 2004/000819 | 12/2003 |
| WO | WO 2004/000843 | 12/2003 |
| WO | WO 2004/002495 | 1/2004 |
| WO | WO 2004/004777 | 1/2004 |
| WO | WO 2004/004778 | 1/2004 |
| WO | WO 2004/009596 | 1/2004 |
| WO | WO 2004/009597 | 1/2004 |
| WO | WO 2004/009602 | 1/2004 |
| WO | WO 2004/010936 | 2/2004 |
| WO | WO 2004/010992 | 2/2004 |
| WO | WO 2004/013633 | 2/2004 |
| WO | WO 2004/014871 | 2/2004 |
| WO | WO 2004/017896 | 3/2004 |
| WO | WO 2004/019869 | 3/2004 |
| WO | WO 2004/020408 | 3/2004 |
| WO | WO 2004/020409 | 3/2004 |
| WO | WO 2004/024943 | 3/2004 |
| WO | WO 2004/029204 | 4/2004 |
| WO | WO 2004/031189 | 4/2004 |
| WO | WO 2004/033431 | 4/2004 |
| WO | WO 2004/033710 | 4/2004 |
| WO | WO 2004/035588 | 4/2004 |
| WO | WO 2004/037823 | 5/2004 |
| WO | WO 2004/041164 | 5/2004 |
| WO | WO 2004/056748 | 7/2004 |
| WO | WO 2004/056825 | 7/2004 |
| WO | WO 2004/056829 | 7/2004 |
| WO | WO 2004/058174 | 7/2004 |
| WO | WO 2004/058727 | 7/2004 |
| WO | WO 2004/062665 | 7/2004 |
| WO | WO 2004/065380 | 8/2004 |
| WO | WO 2004/066963 | 8/2004 |
| WO | WO 2004/058149 | 9/2004 |
| WO | WO 2004/074218 | 9/2004 |
| WO | WO 2004/074297 | 9/2004 |
| WO | WO 2004/076413 | 9/2004 |
| WO | WO 2004/010949 | 10/2004 |
| WO | WO 2004/071442 | 10/2004 |
| WO | WO 2004/085401 | 10/2004 |
| WO | WO 2004/096752 | 11/2004 |
| WO | WO 2004/096757 | 11/2004 |

(56) References Cited

FOREIGN PATENT DOCUMENTS

| | | |
|---|---|---|
| WO | WO 2004/098583 | 11/2004 |
| WO | WO 2004/099144 | 11/2004 |
| WO | WO 2004/103279 | 12/2004 |
| WO | WO 2004/103306 | 12/2004 |
| WO | WO 2004/103309 | 12/2004 |
| WO | WO 2004/103997 | 12/2004 |
| WO | WO 2004/104205 | 12/2004 |
| WO | WO 2004/110368 | 12/2004 |
| WO | WO 2004/110979 | 12/2004 |
| WO | WO 2004/111000 | 12/2004 |
| WO | WO 2004/113330 | 12/2004 |
| WO | WO 2005/000833 | 1/2005 |
| WO | WO 2005/007647 | 1/2005 |
| WO | WO 2005/007658 | 1/2005 |
| WO | WO 2005/016894 | 2/2005 |
| WO | WO 2005/020920 | 3/2005 |
| WO | WO 2005/021503 | 3/2005 |
| WO | WO 2005/023762 | 3/2005 |
| WO | WO 2005/025554 | 3/2005 |
| WO | WO 2005/026148 | 3/2005 |
| WO | WO 2005/020882 | 4/2005 |
| WO | WO 2005/030127 | 4/2005 |
| WO | WO 2005/030129 | 4/2005 |
| WO | WO 2005/030751 | 4/2005 |
| WO | WO 2005/032465 | 4/2005 |
| WO | WO 2005/033099 | 4/2005 |
| WO | WO 2005/035525 | 4/2005 |
| WO | WO 2005/037215 | 4/2005 |
| WO | WO 2005/040095 | 5/2005 |
| WO | WO 2005/041899 | 5/2005 |
| WO | WO 2005/042488 | 5/2005 |
| WO | WO 2005/044780 | 5/2005 |
| WO | WO 2005/046603 | 5/2005 |
| WO | WO 2005/047297 | 5/2005 |
| WO | WO 2005/049033 | 6/2005 |
| WO | WO 2005/058315 | 6/2005 |
| WO | WO 2005/058848 | 6/2005 |
| WO | WO 2005/058849 | 6/2005 |
| WO | WO 2005/061489 | 7/2005 |
| WO | WO 2005/063750 | 7/2005 |
| WO | WO 2005/070886 | 8/2005 |
| WO | WO 2005/072530 | 8/2005 |
| WO | WO 2005/075426 | 8/2005 |
| WO | WO 2005/079788 | 9/2005 |
| WO | WO 2005/080330 | 9/2005 |
| WO | WO 2005/082089 | 9/2005 |
| WO | WO 2005/082841 | 9/2005 |
| WO | WO 2005/085179 | 9/2005 |
| WO | WO 2005/090348 | 9/2005 |
| WO | WO 2005/097745 | 10/2005 |
| WO | WO 2005/100365 | 10/2005 |
| WO | WO 2005/058295 | 11/2005 |
| WO | WO 2005/117909 | 12/2005 |
| WO | WO 2005/121121 | 12/2005 |
| WO | WO 2005/123677 | 12/2005 |
| WO | WO 2006/001463 | 1/2006 |
| WO | WO 2006/009092 | 1/2006 |
| WO | WO 2006/010379 | 2/2006 |
| WO | WO 2006/011554 | 2/2006 |
| WO | WO 2006/013948 | 2/2006 |
| WO | WO 2006/020951 | 2/2006 |
| WO | WO 2006/010544 | 3/2006 |
| WO | WO 2006/034337 | 3/2006 |
| WO | WO 2006/034446 | 3/2006 |
| WO | WO 2006/039325 | 4/2006 |
| WO | WO 2006/040966 | 4/2006 |
| WO | WO 2006/043149 | 4/2006 |
| WO | WO 2006/043490 | 4/2006 |
| WO | WO 2006/047195 | 5/2006 |
| WO | WO 2006/047516 | 5/2006 |
| WO | WO 2006/050946 | 5/2006 |
| WO | WO 2006/052566 | 5/2006 |
| WO | WO 2006/064757 | 6/2006 |
| WO | WO 2006/067531 | 6/2006 |
| WO | WO 2006/067532 | 6/2006 |
| WO | WO 2006/070208 | 7/2006 |
| WO | WO 2006/076231 | 7/2006 |
| WO | WO 2006/076243 | 7/2006 |
| WO | WO 2006/076455 | 7/2006 |
| WO | WO 2006/078992 | 7/2006 |
| WO | WO 2006/079406 | 8/2006 |
| WO | WO 2006/083491 | 8/2006 |
| WO | WO 2006/088944 | 8/2006 |
| WO | WO 2006/100631 | 9/2006 |
| WO | WO 2006/100633 | 9/2006 |
| WO | WO 2006/100635 | 9/2006 |
| WO | WO 2006/063033 | 11/2006 |
| WO | WO 2006/131336 | 12/2006 |
| WO | WO 2006/137019 | 12/2006 |
| WO | WO 2006/137509 | 12/2006 |
| WO | WO 2007/003964 | 1/2007 |
| WO | WO 2007/005673 | 1/2007 |
| WO | WO 2007/024922 | 3/2007 |
| WO | WO 2007/035355 | 3/2007 |
| WO | WO 2007/037196 | 4/2007 |
| WO | WO 2007/039470 | 4/2007 |
| WO | WO 2007/060626 | 5/2007 |
| WO | WO 2007/080542 | 7/2007 |
| WO | WO 2007/083089 | 7/2007 |
| WO | WO 2007/085451 | 8/2007 |
| WO | WO 2007/086001 | 8/2007 |
| WO | WO 2007/089335 | 8/2007 |
| WO | WO 2007/091396 | 8/2007 |
| WO | WO 2007/091501 | 8/2007 |
| WO | WO 2007/092638 | 8/2007 |
| WO | WO 2007/098474 | 8/2007 |
| WO | WO 2007/100617 | 9/2007 |
| WO | WO 2007/109330 | 9/2007 |
| WO | WO 2007/109334 | 9/2007 |
| WO | WO 2007/095561 | 10/2007 |
| WO | WO 2007/115820 | 10/2007 |
| WO | WO 2007/116866 | 10/2007 |
| WO | WO 2007/120689 | 10/2007 |
| WO | WO 2007/120702 | 10/2007 |
| WO | WO 2007/061458 | 11/2007 |
| WO | WO 2007/092190 | 11/2007 |
| WO | WO 2007/129473 | 11/2007 |
| WO | WO 2007/129745 | 11/2007 |
| WO | WO 2007/132307 | 11/2007 |
| WO | WO 2008/005569 | 1/2008 |
| WO | WO 2008/005576 | 1/2008 |
| WO | WO 2008/008895 | 1/2008 |
| WO | WO 2008/016674 | 2/2008 |
| WO | WO 2008/018427 | 2/2008 |
| WO | WO 2008/019090 | 2/2008 |
| WO | WO 2008/023783 | 2/2008 |
| WO | WO 2008/024196 | 2/2008 |
| WO | WO 2008/016692 | 3/2008 |
| WO | WO 2008/025798 | 3/2008 |
| WO | WO 2008/028937 | 3/2008 |
| WO | WO 2008/029371 | 3/2008 |
| WO | WO 2008/030843 | 3/2008 |
| WO | WO 2008/035239 | 3/2008 |
| WO | WO 2008/029306 | 5/2008 |
| WO | WO 2008/070692 | 6/2008 |
| WO | WO 2008/074820 | 6/2008 |
| WO | WO 2008/074821 | 6/2008 |
| WO | WO 2008/076243 | 6/2008 |
| WO | WO 2008/076356 | 6/2008 |
| WO | WO 2008/079382 | 7/2008 |
| WO | WO 2008/089015 | 7/2008 |
| WO | WO 2008/091967 | 7/2008 |
| WO | WO 2008/114157 | 9/2008 |
| WO | WO 2008/128832 | 10/2008 |
| WO | WO 2008/128951 | 10/2008 |
| WO | WO 2008/097819 | 11/2008 |
| WO | WO 2008/137435 | 11/2008 |
| WO | WO 2008/152149 | 12/2008 |
| WO | WO 2009/019167 | 2/2009 |
| WO | WO 2009/019506 | 2/2009 |
| WO | WO 2009/011850 | 3/2009 |
| WO | WO 2009/038974 | 3/2009 |
| WO | WO 2009/064250 | 5/2009 |
| WO | WO 2009/078983 | 6/2009 |

(56) References Cited

FOREIGN PATENT DOCUMENTS

| | | |
|---|---|---|
| WO | WO 2009/094157 | 7/2009 |
| WO | WO 2009/103552 | 8/2009 |
| WO | WO 2009/115954 | 9/2009 |
| WO | WO 2009/125434 | 10/2009 |
| WO | WO 2009/126245 | 10/2009 |
| WO | WO 2009/126535 | 10/2009 |
| WO | WO 2009/151529 | 12/2009 |
| WO | WO 2009/151621 | 12/2009 |
| WO | WO 2009/151626 | 12/2009 |
| WO | WO 2010/011316 | 1/2010 |
| WO | WO 2010/027431 | 3/2010 |
| WO | WO 2010/072703 | 7/2010 |
| WO | WO 2010/074271 | 7/2010 |
| WO | WO 2010/075239 | 7/2010 |
| WO | WO 2010/075271 | 7/2010 |
| WO | WO 2010/075273 | 7/2010 |
| WO | WO 2010/084944 | 7/2010 |
| WO | WO 2010/093704 | 8/2010 |
| WO | WO 2011/005290 | 1/2011 |
| WO | WO 2011/005295 | 1/2011 |
| WO | WO 2011/005929 | 1/2011 |
| WO | WO 2011/008663 | 1/2011 |
| WO | WO 2011/030139 | 3/2011 |
| WO | WO 2011/059784 | 5/2011 |
| WO | WO 2011/094008 | 8/2011 |
| WO | WO 2011/109471 | 9/2011 |
| WO | WO 2011/127051 | 10/2011 |
| WO | WO 2012/015758 | 2/2012 |
| WO | WO 2012/040279 | 3/2012 |
| WO | WO 2012/135570 | 10/2012 |
| WO | WO 2012/145361 | 10/2012 |
| WO | WO 2012/145603 | 10/2012 |
| WO | WO 2012/145604 | 10/2012 |
| WO | WO 2012/170702 | 12/2012 |
| WO | WO 2013/055910 | 4/2013 |

OTHER PUBLICATIONS

Actelion, Clinical Trials.gov, "Multicenter, Randomized, Double-blind, Placebo-controlled, Phase IIa Study to Evaluate the Efficacy, Safety, and Tolerability of ACT-128800, an S1P1 Receptor Agonist, Administered for 6 Weeks to Subjects With Moderate to Severe Chronic Plaque Psoriasis" http://clinicaltrials.gov/ct2/show/NCT00852670, 2009.
Arbiser, "Why targeted therapy hasn't worked in advanced cancer," J Clinical Invest., Oct. 2007, 117(10):2762-2765.
Avoiding Fatal Responses to Flu Infection, ScienceDaily, http://www.sciencedaily.com/releases/2011/09/110915134410.htm, Sep. 15, 2011, 2 pages.
Balaton et al., "FTY720 sustains and restores neuronal function in the DA rat model of MOG-induced experimental autoimmunue encephalomyelitis," Brain Res. Bull., 2007, 74:307-316.
Bar-Haim et al., "Interrelationship between Dendritic Cell Trafficking and Francisella tularensis Dissemination following Airway Infection," PLoS Pathog., 2008, 4(11):e1000211, 15 pages.
Baumruker et al., "FTY720, an immunomodulatory sphingolipid mimetic: translation of a novel mechanism into clinical benefit in multiple sclerosis," Expert Opin. Investig. Drugs, 2007, 16(3):283-289.
Biopharmatiques, "Merging Pharma and Biotech", http://www.biopharmaceutiques.com/fr/tables/clinical_studies_709.html, 2009.
Bioreversible Carriers in Drug Design, ed. Edward B. Roche, American Pharmaceutical Association and Pergamon Press 1987 *too voluminous.
Boismenu et al., "Insights from mouse models of colitis," K. Leukoc Biol, 67:267-278, 2000.
Bolic et al., "Sphingosine-1-Phosphate Prevents Tumor Necrosis Factor-alpha-Mediated Monocyte Adhesion to Aortic Endothelium in Mice," Arterioscler. Thromb. Vasc. Biol., 2005, 25:976-981.
Brinkman, "Sphingosine 1-phosphate receptors in health and disease: Mechanistic insights from gene deletion studies and reverse pharmacology," Pharmacol. Ther., 2007, 115:84-105.
Brinkmann et al., "FTY720 Alters Lymphocyte Homing and Protects Allografts Without Inducing General Immunosuppression," Transplantation Proc., 2001, 33:530-531.
Brinkmann et al., "FTY720: Altered Lymphocyte Traffic Results in Allograft Protection," Transplantation, Sep. 2001, 72(5):764-769.
Brinkmann et al., "The Immune Modulator FTY720 Targets Sphingosine 1-Phosphate Receptors," J Biol. Chem., 2002, 277(24):21453-21457.
Brinkmann, "FTY720 (fingolimod) in Multiple Sclerosis: therapeutic effects in the immune and the central nervous system", British Journal of Pharmacology, 158: 1173-1182, 2009.
Budde et al., "First Human Trial of FTY720, a Novel Immunomodulator, in Stable Renal Transplant Patients," J Am Soc. Nephrol., 2002, 13:1073-1083.
Buzard , Daniel J. et al, "Recent Progress in the Development of Selective S1P1 Receptor Agonists for the Treatment of Inflammatory and Autoimmune Disorders", Expert Opinion, 1141-1159, 2008.
Buzard et al., "Discovery and Characterization of Potent and Selective 4-Oxo-4-(5-(5-phenyl-1,2,4-oxadiazol-3-yl)indolin-1-yl)butanoic acids as S1P1 Agonists", Biorganic Med. Chem Lett, 2011, 6013-6018.
Buzard, Daniel J. et al., "Discovery and Characterization of Potent and Selective 4-Oxo-4-(5-(phenyl-1,2,4-oxadiazol-3-yl)indolin-1-yl)butanoic acids as S1P1 Receptor Agonists", Arena Pharmaceuticals, Inc., MEDI099, ACS, Mar. 2011.
Buzard, et al., "Discovery of APD334: Design of a Clinical Stage Functional Antagonist of the Sphingosine-1-phosphate-1 Receptor", ACS Med. Chem. Lett. 2014, 5, 1313-1317.
Chawla et al., Challenges in Polymorphism of Pharmaceuticals, CRIPS, Jan.-Mar. 2004, vol. 5, No. 1, 4 pages.
Chiba et al., "Role of Sphingosine 1-Phosphate Receptor Type 1 in Lumphocyte Egress from Secondary Lymphoid Tissues and Thymus," Cell Mole Immunol., Feb. 2006, 3(1):11-19.
Chiba, "FTY720, a new class of immunomodulator, inhibits lymphocyte egress from secondary lymphoid tissues and thymus by agonistic activity at sphingosine 1-phosphate receptors," Pharmacol. Ther., 2005, 108:308-319.
Chun et al., "International Union of Pharmacology. XXXIV. Lysophospholipid Receptor Nomenclature," Pharmacol. Rev., 2002, 54(2):256-269.
Coelho et al., "The Immunomodulator FTY720 has a direct cytoprotective effect in oligodendrocyte Progenitors," J Pharmacol. Exp. Ther., 2007, 323:626-635.
Coste et al., "Antinociceptive activity of the S1P-receptor agonist FTY720," J Cell Moll Med., 2008, 12(3):995-1004.
Daniel et al., "FTY720 Ameliorates Th1-Mediated Colitis in Mice by Directly Affecting the Functional Activity of DC4+CD25+ Regulatory T Cell1," J Immunol., 2007, 178:2458-2468.
Deguchi et al., "The S1P receptor modulator FTY720 prevents the development of experimental colitis in mice," Oncol. Rep., 2006, 16:699-703.
Dev et al., "Brain sphingosine-1-phosphate receptors: Implication for FTY720 in the treatment of multiple sclerosis," Pharmacol Ther., 2008, 117:77-93.
Fingolimod, Wikipedia, the free encyclopedia, retrieved on Jul. 22, 2014, http://en.wikipedia.org/wiki/Fingolimod, 6 pages.
Fischer et al., "Targeting receptor tyrosine kinase signalling in small cell lung cancer (SCLC): What have we learned so far?" Cancer Treatment Revs., 2007, 33:391-406.
Fu et al., "Long-term islet graft survival in streptozotocin- and autoimmune-induced diabetes models by immunosuppressive and potential insulinotropic agent FTY720," Transplantation, May 2002, 73(9):1425-1430.
Fujii et al., "FTY720 suppresses CD4+CD44highCD62L-effector memory T cell-mediated colitis," Am J Physol Gastrointest Liver Physiol., 2006, 291:G267-G274.
Fujino et al., "Amerliomtion of Experimental Autoimmune Encephalomyelitis in Lewis Rats by FTY720 Treatment," J Pharmacol. Exp. Ther., 2003, 305(1):70-77.
Fujishiro et al., "Change from Cyclosporine to Combination Therapy of Mycophenolic Acid with the New Sphinogosine-l-phosphate

(56) References Cited

OTHER PUBLICATIONS

Receptor Agonist, KRP-203, Prevents Host Nephrotoxicity and Transplant Vasculopathy in Rats," J Heart Lung Transplant, 2006, 25:825-833.
Gabriel et al., "High throughput screening technologies for direct cyclic AMP measurement", ASSAY and Drug Development Technologies, 2003, 1(2):291-303.
Golub et al., "Molecular Classification of Cancer: Class Discovery and Class Prediction by Gene Expression Monitoring," Science, 1999, 286:531-537.
Griesser, "The Importance of Solvates" in *Polymorphism in the Pharmaceutical Industry*, 211-233 (Rolf Hilfiker, ed., 2006).
Groeneveld, "Vascular pharmacology of acute lung injury and acute respiratory distress syndrome," Vascular Pharmacol., 2003, 39:247-256.
Hale et al., "Potent S1P receptor agonists replicate the pharmacologic actions of the novel immune modulator FTY720," Bioorganic Med Chem. Lett., 2004, 14:3351-335.
Han, Sangdon et al., "Discovery of 2-(7-(5-phenyl-1,2,4-oxadiazol-3-yl)-1,2,3,4-tetrahydrocyclopenta[b]indol-3-yl)acetic acids: Potent and Selective Sphingosine-1-phosphate (S1P1) Receptor Agonists", Arena Pharmaceuticals, Inc., MEDI098, ACS Poster, Mar. 2011.
Herzinger et al., "Sphingosine-1-Phosphate Signaling and the Skin," Am J Clin Dermatol., 2007, 8(6):329-336.
Hwang et al., "FTY720, a New Immunosuppressant, Promotes Long-Term Graft Survival and Inhibits the Progression of Graft Coronary Artery Disease in a Murine Model of Cardiac Transplantation," Circulation, 1999, 100:1322-1329.
Idzko et al., "Local application of FTY720 to the lung abrogates experimental asthma by altering dendritic cell function," J Clinc Invest., Nov. 2006, 116(11):2935-2944.
Ishii et al., "Sphingosine-1-phosphate mobilizes osteoclast precursors and regulates bone homeostasis," Nature, Mar. 2009, 458(7237):524-528.
Jones, "The Discovery of APD334, A Selective S1P1 Functional Antagonist", EFMC-ISMC (2014), Sep. 8, 2014 (Powerpoint).
Jones, Robert M., "Discovery of Potent and Selective Sphingosine-1-Phosphate 1 (S1P1) Receptor Agonists", CHI 6th Annual Drug Discovery Chemistry, San Diego, CA, Apr. 12, 2011.
Jones, Robert M., "Discovery of Potent and Selective Sphingosine-1-Phosphate 1(S1P1) Receptor Agonists", CHI 6th Annual Discovery on Target, Boston, MA, Nov. 3, 2011.
Jung et al., "Functional Consequences of S1P Receptor Modulation in Rat Oligodendroglial Lineage Cells," Glia, 2007, 55:1656-1667.
Kaneider et al., "The immune modulator FTY720 targets sphingosine-kinase-dependent migration of human monocytes in response to amyloid beta-protein and its precursor," FASEB J, 2004, 18:309-311.
Kappos et al., "Oral Fingolimod (FTY720) for Relapsing Multiple Sclerosis," N Engl J Med., 2006, 355:1124-1140.
Kataoka et al., "FTY720, Sphingosine 1-Phosphate Receptor Modulator, Ameliorates Experimental Autoimmune Encephalomyelitis by Inhibition of T Cell Infiltration," Cell Mol. Immunol., Dec. 2005, 2(6):439-448.
Kaudel et al., "FTY720 for Treatment of Ischemia-Reperfusion Injury Following Complete Renal Ischemia; Impact on Long-Term Survival and T-Lymphocyte Tissue Infiltration," Transplantation Proc., 2007, 39:499-502.
Kawasaki, Andrew et al., "Discovery and Characterization of 2-(7-(5-phenyl-1,2,4-oxadiazol-3-yl)-2,3-dihydro-1H-pyrrolo[1,2-a]indol-1-yl)acetic acid Derivatives as Potent & Selective Human S1P1 Receptor Agonists", Arena Pharmaceuticals, Inc., MEDI254, ACS, Mar. 2011.
Keul et al., "The Sphinogosine-l-Phosphate Analogue FTY720 Reduces Atherosclerosis in Apolipoprotein E-Deficient Mice," Arterioscler Thromb Vasc Biol., 2007, 27:607-613.
Kim et al., "Sphingosine-1-phosphate inhibits human keratinocyte proliferation via Akt/protein kinase B inactivation," Cell Signal, 2004, 16:89-95.

Kimura et al., "Essential Roles of Sphingosine 1-Phosphate/S1P1 Receptor Axis in the Migration of Neural Stem Cells Toward a Site of Spinal Cord Injury," Stem Cells, 2007, 25:115-124.
Kitabayashi et al., "FTY720 Prevents Development of Experimental Autoimmune Myocarditis Through Reduction of Circulating Lymphocytes," J Cardiovasc. Pharmacol. 2000, 35:410-416.
Kohno et al., "A Novel Immunomodulator, FTY720, Prevents Development of Experimental Autoimmune Myasthenia Gravis in C57BL/6 Mice," Biol Pharma Bull., 2005, 28(4):736-739.
Kohno et al., "A Novel Immunomodulator, FTY720, Prevents Spontaneous Dermatitis in NC/Nga Mice," BIol. Pharm. Bull., 2004, 27(9):1392-1396.
Koreck et al., "The Role of Innate Immunity in the Pathogensis of Acne," Dermatol., 2003, 206:96-105.
Kurose et al., "Effects of FTY720, a novel immunosuppressant, on experimental autoimmune uveoretinitis in rats," Exp. Eye Res., 2000, 70:7-15.
Lala et al., "Role of nitric oxide in tumor progression: Lessons from experimental tumors," Cancer Metastasis Rev., 1998, 17:91-106.
LaMontagne et al., "Antagonism of Sphingosine-1-Phosphate Receptors by FTY720 Inhibits Angiogenesis and Tumor Vascularization," Cancer Res., 2006, 66:221-231.
Lee et al., "FTY720: A Promising Agent for Treatment of Metastatic Hepatocellular Carcinoma," Clin. Cancer Res., 2005, 11:8458-8466.
Lima et al., "FTY720 Treatment Prolongs Skin Graft Survival in a Completely Incompatible Strain Combination," Transplant Proc., 2004, 36:1015-1017.
Liu et al., "Long-Term Effect of FTY720 on Lymphocyte Count and Islet Allograft Survival in Mice," Microsurgery, 2007, 27:300-304.
Lleo et al., "Etiopathogenesis of primary viliary cirrhosis," *World J Gastroenterol*, Jun. 2008, 14(21):3328-3337.
Madhusudan et al., "Tyrosine kinase inhibitors in cancer therapy," Clinical Biochem., 2004, 37:618-635.
Maki et al., "Prevention and Cure of Autoimmune Diabetes in Nonobese Diabetic Mice by Continuous Administration of FTY720," Transplantation, 2005, 79:1051-1055.
Maki et al., "Prevention of autoimmune diabetes by FTY720 in Nonobese diabetic mice," Transplantation, Dec. 2002, 74(12):1684-1686.
Martini et al., "Current perspectives on FTY720," Expert Opin. Investig. Drugs, 2007, 16:505-518.
Martini et al., "S1P modulator FTY720 limits matrix expansion in acute anti-thyl mesangioproliferative glomerulonephritis," Am J Physiol Renal Physiol., 2007, 292:F1761-F1770.
Matloubian et al., "Lymphocyte egress from thymus and peripheral lymphoid organs in dependent on S1P receptor 1," Nature, Jan. 2004, 427:355-360.
Matsuura et al., "Effect of FTY720, a novel immunosuppressant, on adjuvant- and collagen-induced arthritis in rats," Int. J Immunopharmacol. 2000, 22:323-331.
Matsuura et al., "Effect of FTY720, a novel immunosuppressant, on adjuvant-induced arthritis in rats," Inflamm Res. 2000, 49:404-410.
Miron et al., "FTY720 Modulates Human Oligodendrocyte Progenitor Process Extension and Survival," Ann Neurol, 2008, 63:61-71.
Miyamoto et al., "Therapeutic Effects of FTY720, a New Immunosuppressive Agent, in a Murine Model of Acute Viral Myocarditis," J Am Coll Cardiol., 2001, 37(6):1713-1718.
Mizushima et al., "Therapeutic Effects of a New Lymphocyte Homing Reagent FTY720 in Interleukin-10 Gene-deficient Mice with Colitis," Inflamm Bowel Dis., May 2004, 10(3):182-192.
Nakashima et al., "Impaired Initiation of Contact Hypersensitivity by FTY720," J Invest Dermatol., 2008, 128:2833-2841.
Neurath et al., "Antibodies to Interleukin 12 Abrogate Established Experimental Colitis in Mice," J. Exp. Med, 182:1281-1290, 1995.
Newman et al., "Solid-state analysis of active pharmaceutical ingredient in drug products," DDT, Oct. 2003, 8(19):898-905.
Nofer et al., "FTY720, a Synthetic Sphingosine 1 Phosphate Analogue, Inhibits Development of Atherosclerosis in Low-Density Lipoprotein Receptor Deficient Mice," Circulation, 2007, 115:501-508.

(56) References Cited

OTHER PUBLICATIONS

Ogawa et al., "A novel sphingosine-1-phosphate receptor agonist KRP-203 attenuates rate autoimmune myocarditis," Biochem. Biophys. Res. Commun., 2007, 361:621-628.

Okayasu et al, "A Novel Method in the Induction of Reliable Experimental Acute and Chronic Ulcerative Colitis in Mice," Gastroenterology, 98:694-702, 1990.

Okazaki et al., "Effects of FTY720 in MRL-Ipr/Ipr mice: therapeutic potential in systemic lupus erythematosus," J Rheumatol., 2002, 29:707-716.

Oo et al., "Immunosuppressive and Anti-angiogenic Sphingosine 1-Phosphate Receptor-1 Agonists Induce Ubiquitinylation and Proteasomal Degradation of the Receptor," J Biol Chem., 2007, 282(12):9082-9089.

Pan et al., "A Monoselective Sphingosine-1-Phosphate Receptor-1 Agonist Prevents Allograft Rejection in a Stringent Rat Heart Transplantation Model," Chem. Biol., 2006, 13:1227-1234.

Pheilschifter et al., "Treatment with immunomodulator FTY720 does not promote spontaneous bacterial infections after experimental stroke mice," Experimental Translational Stroke Med., 2011, 3, 6 pages.

Premenko-Lanier et al., "Transient FTY720 treatment promotes immune-mediated clearance of a chronic viral infection," Nature, Aug. 2008, 454:894-899.

Rausch et al., "Predictability of FTY720 Efficacy in Experimental Autoimmune Encephalomyelitis by In Vivo Macrophage Tracking: Clinical Implications for Ultrasmall Superparamagnetic Iron Oxide-Enhanced Magnetic Resonance Imaging," 2004, J Magn. Reson. Imaging, 2004, 20:16-24.

Raveney et al., "Fingolimod (FTY720) as an Acute Rescue Therapy for Intraocular Inflammatory Disease," Arch Ophthalmol, 2008, 126(10):1390-1395.

Remington, The Science and Practice of Pharmacy, 20$^{th}$ Edition, 2000, Lippincott Williams & Wilkins, (Editors: Gennaro et al) * (too voluminous).

Rheumatoid Arthritis Health Center—Most Common Types of Arthritis, WebMD, http://www.webmd.com/rheumatoid-arthritis/guide/most-common-arthritis-types, 2012, 2 pages.

RN 380350-42-5, STN/CAPLUS (Year: 2002).

Ronald Hoffman, M.D., "Crohns disease and ulcerative colitis," Sep. 1995, http://www.drhoffman.com/page.cfm/171, 5 pages.

Rosen et al., "Egress: a receptor-regulated step in lymphocyte trafficking," Immunol. Rev. 2003, 195:160-177.

Sakagawa et al., "Rejection following donor or recipient preoperative treatment with FTY720 in rat small bowel transplantation," Transpl. Immunol., 2004, 13:161-168.

Sanchez et al., "Phosphorylation and Action of the Immunomodulator FTY720 Inhibits Vascular Endothelial Cell Growth Factor-induced Vascular Permeability," J Biol Chem., 2003, 278(47):47281-47290.

Sanna et al., "Enhancement of cappillary leakage and restoration of lymphocyte egress by a chiral S1P1 antagonist in vivo," Nature Chem Biol., Aug. 2006, 2(8):434-441.

Sanna et al., "Sphingosine 1-Phosphate (S1P) Receptor Subtypes S1P1 and S1P3, Respectively, Regulate Lymphocyte Recirculation and Heart Rate," J. Biol Chem., 2004, 279(14):13839-13848.

Sauer et al., "Involvement of Smad Signlaing in Sphingosine 1-Phosphate-mediated Biological Responses of Keratinocytes," J Biol. Chem., 2004, 279:38471-38479.

Sawicka et al., "Inhibition of Th1- and Th2-Mediated Airway Inflammation by the Sphingosine 1-Phosphate Receptor Agonist FTY720," J Immunol., 2003, 171:6206-6214.

Schafiee et al., "An efficent enzyme-catalyzed kinetic resolution: large-scale preparation of an enantiomerically pure indole-ethyl ester derivative, a key component for the synthesis of a prostaglandin D2 receptor antagonist, an anti-allergic rhinitis drug candidate," Tetrahedron: Asymmetry, Sep. 2005, 16:3094-3098.

Schmid et al., "The Immunosuppressant FTY720 inhibits tumor Angiogenesis via the Sphingosine 1-Phosphate Receptor 1," J Cell Biochem., 2007, 101:259-270.

Schwab and Cyster, "Finding a way out: lymphocyte egress from lymphoid organs," Nature Immunol., Dec. 2007, 8(12):1295-1301.

Schafiee et al., "An efficent enzyme-catalyzed kinetic resolution: large-scale preparation of an enantiomerically pure indole-ethyl ester derivative, a key component for the synthesis of a prostaglandin D2 receptor antagonist, an anti-allergic rhinitis drug candidate," Tetrahedron: Asymmetry, Sep. 2005. 16:3094-3098.

Shimizu et al., "KRP-203, a Novel Synthetic Immunosuppressant, Prolongs Graft Survival and Attenuates Chronic Rejection in Rat Skin and Heart Allografts," Circulation, 2005, 111:222-229.

Stahly, "Diversity in Single- and Multiple-Component Crystals. The Search for and Prevalence of Polymorphs and Cocrystals," Crystal Growth & Design (2007), 7(6), 1007-1026.

Storey, et al., "Automation of Solid Form Screening Procedures in the Pharmaceutical Industry—How to Avoid the Bottlenecks", Crystallography Reviews, 10(1):45-46 (2004).

Sturino et al: "Discovery of a potent and selective prostaglandin D2 receptor antagonist, [(3R)-4-(4-chloro-benzyl)-7-Fluoro-5-(methylsulfonyl)-1,2,3,4-tetrahydrocyclopenta[b]indol-3-yl]-acetic acid (MK-0524)", Journal of Medicinal Chemistry, Feb. 22, 2007, pp. 794-806

Suzuki et al., "Efficacy of Mycophenolic Acid Combined with KRP-203, a Novel Immunomodulator, in a Rat Heart Transplantation Model," J Heart Lung Transplant, 2006, 25:302-309.

Suzuki et al., "Immunosuppressive effect of a new drug, FTY720, on lymphocyte responses in vitro and cardiac allograft survival in rats," Transplant Immunol., 1996, 4:252-255.

Taylor et al., "Insights into the mechanism of FTY720 and compatibility with regulatory T cells for the inhibition of graft-versus-host disease (GVHD)," Blood, 2007, 110:3480-3488.

Truong et al., "Human Islet Function is not Impaired by the Sphingosine-1-Phosphate Receptor Modulator FTY720," Am J Transplantation, 2007, 7:2031-2038.

Truppo et al., "Optimization and Scale-Up of a Lipase-Catalyzed Enzymatic Resolution of an Indole Ester Intermediate for a Prostaglandin D2 (DP) Receptor Antagonist Targeting Allergic Rhinitis," Organic Process Research and Development, Feb. 2006, 10(3):592-598.

Vachal et al., "Highly selective and potent agonists of sphinogosin-1-phosphate 1 (S1P1) receptor," Bioorganic Med Chem Lett., Jul. 2006, 16(14):3684-3687.

Valdimarsson et al., "Psoriasis—as an autoimmune disease caused by molecular mimicry," Trends in Immunology, Oct. 2009, 30(10):494-501.

Villullas et al, "Characterisation of a Sphingosine 1-Phosphate-Activated Ca2+ Signalling Pathway in Human Neuroblastoma Cells," J. Neurosci. Res, 73:215-226, 2003.

Vippagunta, et al., "Crystalline Solids," Adv. Drug Delivery Rev., 48:3-26 (2001).

Webb et al., "Sphingosine 1-phosphate receptors agonists attenuate relapsing—remitting experimental autoimmune encephalitis in SJL mice," J Neuroimmunol., 2004, 153:108-121.

Webster, "The Pathophysiology of Acne," Cutis, 2005, 76(suppl. 2):4-7.

Whetzel et al., "Sphingosine-1 Phosphate Prevents Monocyte/Endothelial Interactions in Type 1 Diabetic NOD Mice Through Activation of the S1P1 Receptor," Circ. Res., 2006, 99:731-739.

Yan et al., "Discovery of 3-arylpropionic acids as potent agonists of sphingosine-1-phosphate receptor-1 (S1P1) with high selectivity against all other known S1P receptor subtypes," Bioorg. Med. Chem. Lett., 2006, 16:3679-3683.

Yanagawa et al., "FTY720, a Novel Immunosuppressant, Induces Sequestration of Circulating Mature Lymphocytes by Acceleration of Lymphocyte Homing in Rats. II. FTY720 Prolongs Skin Allograft Survival by Decreasing T Cell Infiltration into Grafts but not cytokine production in vivo," J Immunol., 1998, 160:5493-5499.

Yang et al., "The immune modulator FYT720 prevents autoimmune diabetes in nonobese diabetic mice," Clin. Immunol., 2003, 107:30-35.

Zhang et al., "FTY720 attenuates accumulation of EMAP-II+ and MHC-II+ monocytes in early lesions of rat traumatic brain injury," J Cell Mol Med., 2007, 11(2):307-314.

(56) References Cited

OTHER PUBLICATIONS

Zhang et al., "FTY720: A Most Promising Immunosuppressant Modulating Immune Cell Functions," Mini Rev. Med Chem., 2007, 7:845-850.
"Dyslipidemia Prevalent in Type 2 Diabetes," American Diabetes Association, Jul. 2010, http://docnews.diabetesjournals.org/content/3/3/19.1.full, retrieved on Sep. 24, 2014, 2 pages.
"Metabolic Syndrome," Cleveland Clinic, http://my.clevelandclinic.org/disorders/metabolic_syndrome/hic_metabolic_syndrome.aspx, Dec. 2009, retrieved on Sep. 24, 2014, 2 pages.
"Syndrome X," The Diabetes mall, Feb. 2002, http://www.diabetesnet.com/diabetes_types/syndrome_x.php, retrieved on Sep. 24, 2014, 1 page.
Abbott et al, "Blockade of the neuropeptide Y Y2 receptor with the specific antagonist BIIE0246 attenuates the effect of endogenous and exogenous peptide YY $_{(3-36)}$ on food intake," Brain Res, 2005, 1043:139-144.
Abdalla et al., "Synthesis and reaction of 3-cyano 2-(1H)-pyridones," Pakistan Journal of Scientific and Industrial Research, Jun. 1977, 30(3):139-149.
Abe et al., "First Synthesis and Determination of the Absolute Configuration of Sulphostin, a Novel Inhibitor of Dipeptidyl Peptidase IV," J. Nat. Prod., 2004, 67:999-1004.
Abramovitch et al., "Solution and flash vacuum pyrolysis of some 2.6-disubstituted β-phenethyslulfonyl azides and of β-styrenesulfonyl azide," J. Org Chem, 1985, 50-2066-2073.
Abstract #107, p. 56, Toward Understanding Islet Biology, Jan. 21, 2003-Jan. 26, 2003, Keystone, Colorado.
Abstract #112, p. 42, Diabetes Mellitus: Molecular Mechanisms, Genetics and New Therapies, Jan. 27, 2005-Feb. 2, 2005, Keystone, Colorado.
Abstract #117 & Poster, Diabetes: Molecular Genetics, Signaling Pathways and Integrated Physiology, Jan. 14, 2007-Jan. 19, 2007, Keystone, Colorado.
Abstract #228, p. 54, Diabetes Mellitus: Molecular Mechanisms, Genetics and New Therapies, Jan. 27, 2005-Feb. 2, 2005, Keystone, Colorado.
Abstract #230 & Poster, Diabetes: Molecular Genetics, Signaling Pathways and Integrated Physiology, Jan. 14, 2007-Jan. 19, 2007, Keystone, Colorado.
Accession No. 2003:2246299 Chemicals, IH-Pyrazolo [3,4-d] pyrimidin-4-amine, N-cyclohexyl-N-methyl-1-(3-methyphenyl)—(2003).
Accession No. 2003:2246300 Chemicals, 1H-Pyrazolo [3,4-d] pyrimidin-4-amine, N-cyclohexyl-1-(2,4-dimethlphenyl)-N-methyl—(2003).
Accession No. 2003:2415108 CHEMCATS, Interbioscreen Compound Library, Chemical Name: 1H-Pyrazolo[3,4-d]pyrimidine-4-amine, N-cyclohexyl-N-methyl-1-(3-methylphenyl)-, XP-002311326, 2003, CAS Registry No. 393844-90-1.
Accession No. 2003:2415906 CHEMCATS, Interbioscreen Compound Library, Chemical Name: 1H-Pyrazolo[3,4-d]pyrimidine-4-amine, N-cyclohexyl-1-1-(4-methylphenyl)-, XP-002311325, 2003, CAS Registry No. 393844-89-8.
Accession No. 2003:2416398 CHEMCATS, Interbioscreen Compound Library, Chemical Name: 1H-Pyrazolo [3,4-d]pyrimidine-4-amine, N-cyclohexyl-1-1-(2,4-dimethylphenyl)-N-methyl-, XP-002311324, 2003, CAS Registry No. 393844-91-2.
Accession No. 2003:2417080 CHEMCATS, Interbioscreen Compound Library, Chemical Name: 1H-Pyrazolo[3,4-d]pyrimidine-4-amine, N-cyclohexyl-N-methyl-1-phenyl)-, XP-002311323, 2003, CAS Registry No. 393844-87-6.
Adrian et al., "Human Distribution and Release of a Putative New Gut Hormone, Peptide YY," Gastroenterol., 1985, 89(5):1070-1077.
Ahren et al., "Inhibition of Dipeptidyl Peptidase-4 Augments Insulin Secretion in Response to Exogenously Administered Glucagon-Like Peptide-1, Glucose-Dependent Insulinotropic Polypeptide, Pituitary Adenylate Cyclase-Activating Polypeptide, and Gastrin-Releasing Peptide in Mice," Endocrinology, 2005, 146(4):2055-2059.
Ahren et al., "Inhibition of Dipeptidyl Peptidase-4 Reduces Glycemia, Sustains Insulin Levels, and Reduces Glucagon Levels in Type 2 Diabetes," J. Clin. Endocrinol. Metab., 2004, 89:2078-2084.
Ahren et al., "Inhibition of Dipeptidyl Peptidease IV Improves Metabolic Control Over a 4-week Study Period in Type 2 Diabetes," Diabetes Care, 2002, 25:869-875.
Aidsinfo.nih.gov, "Dyslipidemia", updated Nov. 1, 2012, retrieved Jan. 22, 2014, http://aidsinfo.nih.gov/guidelines/html/2/pediatric-arv-guidelines/91/dyslipidemia, 4 pages.
American Diabetes Association, "Hyperglycemia (High blood sugar)," accessed Jul. 1, 2011, http://www.diabetes.org/living-with-diabetes/treatment-and-care/blood-glucose-control/hyperglycemia html , 1 page.
American Heart Association, Metabolic Syndrome, http://www.americanheart.org/pre-senter.jhtml?identifier=4756, posted on or before Nov. 2001, retrieved on Sep. 24, 2014, 3 pages.
Appukkuttan et al, "Translation-Metal-Free Sonogashira-Type Coupling Reactions in Water," European Journal of Organic Chemistry, 2003, 24-4713-4716.
Arehart et al, "Acceleration of Cardiovascular Disease by a Dysfunctional Prostacyclin Receptor Mutation—Potential Implications for Cyclooxygenase-2 Inhibition," Circ Res, 2008, 102:986-993.
Arvanitis et al., "CRF Ligands via Suzuki and negishi couplings of 3-pyridyl boronic acids or halides with 2-benzyloxy-4-chloro-3-nitropyridione," Bioorganic & Medicinal Chemistry Letters, 2003, 13(2)-289-291.
Arvanitis et al., "Imidazo[4,5-b]ppyridines as corticotropin releasing factor receptor ligands," Bioorganic & Medicinal Chemistry Letters, 2003, 12(1):125-128.
Arvanitis et al., "Non-peptide corticotropin-releasing hormone antagonists; syntheses and structure-activity relationships of 2-anilinopyrimidines and triaznes," J Med Chem., 1999, 42(5):805-18.
Arvela et al., "Rapid cyanation of aryl iodides in water using microwave promotion," Org. Bio. Chem., 2003, 1:1119-1121.
Arvela et al., "Rapid, Easy Cyanation of Aryl Bromides and Chlorides Using Nickel Salts in Conjunction with Microwave Promotion," J. Org. Chem., 2003, 68:9122-9125.
Atik et al., "Burden of Osteoporosis," Clin Orthop Relat Res, 2006, 443:19-24.
Atwal et al., "Synthesis and Biological Activity of 5-aryl-4-(5-methyl-1H-imidazol-4-yl)piperidin-1-yl)pyrimidine Analogs as Potent, Highly Selective, and Orally Bioavailable NHE-1 Inhibitors," Bioorganic & Medicinal Chemistry Letters, 2006, 16(18):4796-4799.
Augustyns, et al., "Inhibitors of proline-specific dipeptidyl peptidases: DPP IV inhibitors as a novel approach for the treatment of type 2 diabetes," Expert Opin. Ther. Patents, 2005, 15:1387-1407.
Bailey et al., "Interactions Between Grapefruit Juice and Cardiovascular Drugs," American Journal of Cardiovascular Drug, 2004, 4(5):281-297.
Baindur et al., "Solution-Phase Synthesis of a Library of 3,5,7-Trisubstituted 3H-[1,2,3]triazolo[4,5-Id]pyrimidines," J. Comb. Chem., 2003, 5:653-659.
Bakkestuen et al., "Regioselective N-9 arylation of purines employing arylboronic acids in presence of Cu(II)," Tetrahedron Letters, 2003, 44:3359-3362.
Balasubramaniam et al, "Neuropeptide Y (NPY) Y2 receptor-selective agonist inhibits food intake and promotes fat metabolism in mice: Combined anorectic effects of $Y_2$ and $Y_4$ receptor-selective agonists," Peptides, 2007, 28:235-240.
Balasubramaniam et al, "Structure-Activity Studies Including a Ψ(CH—NH) Scan of Peptide YY (PYY) Active Site, PYY(22-36), for Interaction with Rat Intestinal PYY Receptors: Development of Analogues with Potent in Vivo Activity in the Intestine," J. Med. Chem., 2000, 43:3420-3427.
Baraldi et al., "An efficient one-pot synthesis of 6-alkoxy-8,9-dialkylpurines via reaction of 5-amino-4-chloro-6-alkylaminopyrimidines with N,N-dimethylalkaneamides and alkoxide ions," Tetrahedron, 2002, 58:7607-7611.
Barta et al, "Synthesis and activity of selective MMP inhibitors with an aryl backbone," Bioorg & Med Chem Ltrs, 2000, 10(24): 2815-2817.

(56) References Cited

OTHER PUBLICATIONS

Baskin et al., "A mild, convenient synthesis of sulfinic acid salts and sulfonamides from alkyl and aryl halides," *Tetrahedron Letters*, 2002, 43:8479-8483.

Baskin et al., "An Efficient Copper Catalyst for the Formation of Sulfones from Sulfinic Acid Salts and Aryl Iodides," *Org. Lett.*, 2002, 4(25):4423-4425.

Batterham et al, "Gut hormone $PYY_{3-36}$ physiologically inhibits food intake," *Nature*, 2002, 418:650-654.

Bayes et al., "Apolipoprotein E alleles, Dyslipemia, and Kidney Transplantation", *Transplantation Proceeding*, 2002, 34(1):373.

Becalski et al., "Synthesis of carbolines by the Graebe-Ullmann method," *Acta Pol Pharm.*, 1977, 41:601-606.

Bedford et al., "Nonquaternary Cholinesterase Reactivators. 3.3(5)-Substituted 1,2,4-Oxadiazol-5(3)-Aldoximes and 1,2,4-Oxadiazole-5(3)-Thiocarbohydroximates as Reactivators of Organophsphonate-Inhibited Eel and Hunan Acetylcholinesterase In Vitro," *J Med Chem*, 1986, 29(11):2174-2183.

Behre, "Adiponectin, obesity and atherosclerosis," *Scand J Clin Lab Invest*, 2007, 67:449-458.

Beller et al., "Based-catalyzed amination of olefins; an example of an environmentally friendly synthesis of amines," *Chemosphere*, 2001, 43(1):21-26.

Berge et al., "Pharmaceutical Salts," *Journal of Pharmaceutical Sciences*, Jan. 1977, 66(1):1-19.

Betti, et al., "Novel 3-Aralkyl-7 (amino-substituted)-1,2,3-triazole[4,5-d]primidines with High Affinity toward A1 Adenosine Receptors," *J. Med. Chem*, 1998, 41:668-673.

Bhatt and Thakkar, "Preparation and study of a nickel(II) ion selective electrode," *Indian J Chem*, May 1994, 33A:436-437.

Biagi et al, "Synthesis of 4,6-Disubstituted- and 4,5,6-trisubstituted 2-phenyl-pyrimidines and their affinity towards $A_1$ adenosine receptors," *Farnaco*, 1997, 52(1):61-65.

Bilchik et al, "Peptide YY is a Physiological Regulator of Water and Electrolyte Absorption in the Canine Small Bowel in Vivo," *Gastroenterol.*, 1993, 105:1441-1448.

Boey et al, "Peptide YY ablation in mice leads to the development of hyperinsulinaemia and obesity," *Diabetologia*, 2006, 49:1360-1370.

Boey et al, "PYY transgenic mice are protected against diet-induced and genetic obesity," *Neuropeptides*, 2008, 42:19-30.

Bol'but, et al., "A new synthetic approach to fused pyrimidin-4-ones", Institute of Organic Chemistry, National Academy of Sciences of Ukraine, 2003, accessed Mar. 30, 2008, http://conf.iflab.kiev.ua/eng/reports/show/?id=348, 2 pages (Abstract).

Boldt et al, "Simple Synthesis of 2,4-diaminopyridines," Angewandie Chemie International Edition, 1970, 5 pages.

Bollag et al., "Glucose-dependent insulinotropic peptide is an integrative hormone with osteotropic effects," *Mol Cell Endocrinol*, 2001, 177:35-41.

Bollag et al., "Osteoblast-Derived Cells Express Functional Glucose-Dependent Insulinotropic Peptide Receptors," *Endocrinology*, 2000, 141:1228-1235.

Bomika et al, "Some Nucleophilic Substitution Reactions of 2-Chloro-3-Cyanopyridines," *Khimiya Geterotsiklicheskikh Soedinenii*, Aug. 1976, 8:1085-1088 (Translated pp. 896-899).

Boschelli et al, "1,3,4-Oxadiazole, 134-thiadiazole, and 1,3,4-triazole analogs of the fenamates: in vitro inhibition of cyclooxygenase and 5-Lipoxygenase activities," *J Med Chem*, 1953, 36:1802-1810.

Boswell et al, "Synthesis of Some N-carboxylic acid derivatives of phenoxypyrrolidines, 4-phenoxypiperidines, and 3-phenoxynortropanes with muscle relaxant and anticonvulsant activities," *J Med Chem*, 1974, 17(9):100-1008.

Bradley, "TNF-mediated inflammatory disease," *J Pathol*, 2008, 214:149-160.

Brancati et al., "Body Weight Patterns from 20 to 49 Years of Age and Subsequent Risk for Diabetes Mellitus," *Arch. Intern. Med.*, 1999, 159:957-963.

Breuer, "Hypertriglyceridemia: A Review of Clinical Relevance and Treatment Options: Focus on Cerivastatin," *Current Medical Research and Opinion*, 2001, 17(1):60-73.

Brewer, "Benefit-Risk Assessment of Rosuvastatin 10 to 40 Milligrams," *American Journal of Cardiology*, 2003, 92(4B):23K-29K.

Brinkmann et al., "Fingolimod (FYU720): discovery and development of an oral drug to treat multiple sclerosis," Nature Reveiws, Nov. 2010, 9:883-897.

Bromidge et al., "Design of [R-(Z)-]-(+)-α-(methoxylmino)-lazabicyclo[2.2.2]octane-3-acetonitri le (SB 202026), a functionally selective azabicyclic muscarinic M1 against incorporating the N-methoxy imidoyl nitrile group as a novel ester bioisostere," *J Med Chem*, 1997, 40(26):4265-4280.

Buehler et al, "Physiologically active compounds. VI. Cyclic amino thiolesters of substituted chloracetic, benzilic and glycolic acids," *J Med Chem*, 1965, 8:643-647.

Bulger et al., "An investigation into the alkylation of 1,2,4-triazole," *Tetrahedron Letters*, 2000, 41:1297-1301.

Caldwell et al., "Fluoropyrrolidine amides as dipeptidyl peptidase IV inhibitors," *Bioorg. Med.Chem. Lett.*, 2004, 14:1265-1268.

Capuzzi et al., "Beneficial Effects of Rosuvastatin Alone and in Combination with a Extended-Release Niacin in Patients with a Combined Hyperlipidemia and Low High-Density Lipoprotein Cholesterol Levels," *American Journal of Cardiology*, 2003, 91(11):1304-1310.

Capuzzi et al., "Rosuvastatin Alone or With Extended-Release Niacin: A New Therapeutic Option for Patients with Combined Hyperlipidemia," *Preventive Cardiology*, Fall 2004, 7(4):176-181.

Carswell et al., "Rosuvastatin," *Drugs*, 2002, 62(14):2075-2085.

Chan et al., "Isoquinoline-6-Carboxamides as Potent and Selective Anti-Human Cytomegalovirus (HCMV)Inhibitors," *Bioorganic & Medicinal Chemistry Letters*, 1999, 9:2583-2586.

Chapman et al., "Non-High-Density Lipoprotein Cholesterol as a Risk Factor: Addressing Risk Associated with Apolipoprotein B-Containing Lipoproteins," *European Heart Journal Supplements*, 2004, 6(Suppl. A):A43-A48.

Chapoulaud et al., "Synthesis of 4,8-Diarylcinnolines and Quinazolines with Potential Applications in Nonlinear Optics. Diazines. Part 28," *Tetrahedron* (2000) 56:5499-5507.

Chaudhri et al, "Gastrointestinal Satiety Signals," *Annu Rev Physiol*, 2008, 70:239-255.

Chen et al., "Design and Synthesis of a Series of Non-Peptide High-Affinity Human Corticotropin-Releasing Factor$_1$ Receptor Antagonists," *J Med. Chem.*, 1996, 39:4358-4360.

Chen et al., "Free Radical Method for the Synthesis of Spiro-Piperidinyl Heterocycles," *Tetrahedron Letters*, 1996, 37(3):5233-5234.

Chen et al., "Inhibitory Effect of Candesartan and Rosuvastatin on CD40 and MMPs Expression in Apo-E Knockout Mice: Novel Insights into the Role of RAS and Dyslipidemia in Atherogenesis," *Journal of Cardiovascular Pharmacology*, 2004, 44(4):446-452.

Chen et al., "Optimization of 3-phyenylprazolo[1,5-alpha]pyrimidines as potent corticotrophin-releasing factor-I antagonists with adequate lipophilicity and water solubility," *Bioorganic & Medicinal Chemistry Letters*, 2004, 14:3669-3673.

Chen et al., "Synthesis and Oral Efficacy of a 4-(Bulylethylamino)pyrrolo[2,3-d]pyrimidine: A Centrally Active Corticotropin-Releasing Factor: Receptor Antagonist," *J. Med. Chem.*, 1997, 40:1749-1754.

Cheng and Robins, "Potential purin antagonists. VI. Synthesis of 1-alkyl and 1-aryl-4-substituted pyrazolo[3,4-d]pyrimidines," J. Org Chem, 1956, 21:1240-1256.

Cheng, "Rosuvastatin in the Management of Hyperlipidemia," Clinical Therapeutics, 2004, 26(9):1368-1387.

Cheng-Lai, "Cerivastatin," Heart Disease, 2000, (2):93-99.

Cheng-Lai, Rosuvastatin: A New HMG-CoA Reductase Inhibitor for the Treatment of Hypercholesterolemia; Heart Disease, 5(1), 72-78 (2003).

Chorvat et al,, "Synthesis, Corticotropin-Releasing Factor Receptor Binding Affinity, and Pharmacokinetic Properties of Triazolo-, Imidazo-, and Pyrrolopyrimidines and -pyridines," J. Med. Chem., 1999, 42:833-848.

(56) References Cited

OTHER PUBLICATIONS

Chu et al., "A Role for Intestinal Endocrine Cell-Expressed GPR119 in Glycemic Control by Enhancing GLP-1 and Glucose-Dependent Insulinotropic Peptide Release," Endrocrinology, 2008, 149(5):2038-2047.

Chu et al., "A role for β-cell-expressed G protein-coupled receptor 119 in glycemic control by enhancing glucose-dependent insulin release," Endocrinology, 2007, 148:2601-2609.

Chu, "Section 1: Drug Development," Cancer: Principles and Ptractice of Oncology, 2005, Lippincott Williams & Wilkins, 27 pages.

Citkowitz, "Hypertriglyceridemia," eMedicine Endorinology, Jul. 2008, http://emedicine.medscape.com/article/126568-print, retrieved on Sep. 24, 2014, 18 pages.

Clark et al., "Synthesis and Analgesic Activity of 1,3-Dihydro-3-(Substituted phenyl)imidazo(4,5-b]pyridine-2-ones and 3-(Substituted phenyl)-1,2,3-triazolo(4,5bpyridines," J. Med. Chem., 1978, 21(9):965-978.

Clark, "Treating Dyslipidemia with Statins: The Risk-Benefit Profile," American Heart Journal, 2003, 145(3):387-396.

Cocco et al., "Transformation of 6-Methylthiopyrimidines. Preparation of New Pyrimidine Derivatives and Fused Azolopyrimidines," Journal of Heterocyclic Chemistry, 2000, 37(4):707-710.

Cocuzza et al, "Use of the Suzuki Reaction for the Synthesis of Aryl-Substituted Heterocycles as Corticotropin-Releasing Hormone (CRH) Antagonists," Bioorganic & Medicinal Chemistry Letters, 1999, 9:1063-1066.

Cohen et al., "The Preparation and Properties of 6-Halomethylpurines," Div. of Nucleoprotein Chemistry, Sloan-Kettering Institute for Cancer Research, and Sloan Kettering Div. Grad. School of Med. Sci., Cornell Univ. Med. College, 1962, 27:3545-3549.

Colandrea et al., "Synthesis and regioselective alkylation of 1,6-and 1,7-naphythridines," Tetrahedron Letters, 2000, 41:8053-8057.

Collier et al, "Radiosynthesis and in-vivo evaluation of the pseudopeptide 8-opioid antagonist [125I]-ITIPP(Ψ)," J. Labeled Comp. Radiopharm., 1999, 42(Suppl.1):S264-S266.

Cossey et al, "Pyridines and pyridinium salts from cyanoacetamides," Australian Journal of Chemistry, 1976, 29(5):1039-1050.

Cover Sheet and 23 Compounds, ChemCats file, 11 pp., (2006).

Cover Sheet and 1185 Compounds, CAS Registry and ChemCats files, 391 pp., (various dates—Jan. 12, 2005-Nov. 10, 2006).

Cover Sheet and 18 Compounds, CAS Registry, 9 pp., (various dates—Aug. 1, 2004-Jan. 13, 2005).

Cover Sheet and 2534 Compounds, CAS Registry and ChemCats files, 817 pp., (various dates—Feb. 7, 2006-Nov. 6, 2006).

Cover Sheet and 54 Compounds, CAS Registry and ChemCats files, 23 pp., (various dates—Jan. 15, 1998-Jun. 16, 2004).

Cox, "Peptide YY: A neuroendocrine neighbor of note," Peptides, 2007, 28:345-351.

Crouse, et al., "Measuring Effects on Intima Media Thickness: An Evaluation of Rosuvastatin in Subclinical Atherosclerosis—The Rationale and Methodology of the METEOR Study," Cardiovascular Drugs and Therapy, 2004, 18(3):231-238.

Cruze et al, "The Y2 receptor mediates increases in collateral-dependent blood flow in a model of peripheral arterial insufficiency," Peptides, 2007, 28:269-280.

Cryan et al, "Behavioral characterization of the novel GABAB receptor-postive modulator GS539783 (N,N'-dicyclopentyl-2-methylsulfanyl-5nitropyrmidine-4,6 diamine): Anxiolytic-like activity without side effects associated with baclofen or benzodiazepines," Journal of Pharmacology and Experimental Therapeutics, 2004, 310(3):952-963.

Dai et al., "The first general method for palladium-catalyzed Negishi cross-coupling of anyl and vinyl chlorides: use of commercially available Pd(P(t-Bu)3)2 as a catalyst," J Am Chem Soc, 2001, 123(12):2179-2724.

Davidson, "Rosuvastatin: A Highly Efficacious Statin for the Treatment of Dyslipidemia," Expert Opinion on Investigational Drugs, 2002, 11(3):455.

De Denus et al., "Dyslipidemias and HMG-CoA Reductase Inhibitor Prescription in Heart Transplant Recipients," Annals of Pharmacotherapy, 2004, 28 (7/8):1136-1141.

Deacon et al, "Degradation of Endogenous and Exogenous Gastric Inhibitory Polypeptide in Healthy and in Type 2 Diabetic Subjects as Revealed Using a New Assay for the Intact Peptide," J Clin Endocrinol Metab, 2000, 85:3575-3581.

Deacon, "Therapeutic Strategies Based on Glucagon-Like Peptide 1," Diabetes, Sep. 2004, 53:2181-2189.

Deacon, "What do we know about the secretion and degradation of incretin hormones?" Regul Pept, 2005, 128:117-124.

Deighan, et al., "Comparative Effects of Cerivastatin and Fenofibrate on the Atherogenic Lipoprotein Phenotype in Proteinuric Renal Disease," Journal of the American Society of Nephrology, 2001, 12(2):341-348.

Delmas and Meunier, "The Management of Paget's Disease of Bone," The New England Journal of Medicine, Feb. 1997, 336: 558-566.

Demuth et al., "Type 2 diabetes—Therapy with dipeptidyl peptidase IV inhibitors," Biochim. Biophys. Acta, 2005, 1751: 33-44.

Desimoni et al, "Polynuclear Isoxazole Types-I-Isoxazolo[4,5-d]Pyrimidines," Tetrahedron, 1967, 23:675-680.

Devita et al, "Identification and initial structure-activity relationships of a novel non-peptide quinolone GnRH receptor antagonist," Bioorg & Med Chem Ltrs, 1999, 9(17):2615-2620.

Di Braccio et al., "Synthesis and preliminary pharmacological examination of 2,4-disubstituted N,N-dialkyl-1,8-napthyridine-3-carboxamides," Farmaco (1989) 44(9):865-881.

Ding et al., "A Combinatorial Scaffold Approach toward Kinase-Directed Heterocycle Libraries" J. Am. Chem. Soc. (2002) 124:1594-1596.

Dorwald, Side Reactions in Organic Synthesis, 2005, Wiley (Table of Contents Only).

Drucker, "The biology of incretin hormones," Cell Metab, 2006, 3:153-165.

Drucker et al., "The incretin system: glucagon-linke peptide-1 receptor agonists and dipeptidyl peptidase-4 inhibitors in type 2 diabetes," Lancet, 2006, 368:1696-1705.

Dubau-Assibat et al., "Lawesson's Reagent: An Efficient 1,3-Dipole Trapping Agent", J. Org. Chem., 1995, 60(12):3904-3906.

Dugue et al., "Detection and Incidence of Muscular Adverse Drug Reactions: A prospective Analysis from Laboratory Signals," European Journal of Clinical Pharmacology, 2004, 60(4):285-292.

During et al., "Glucagon-like peptide-1 receptor is involved in learning and neuroprotection," Nat. Med., 2003, 9:1173-1179.

Dzierba et al., "Synthesis, Structure-Activity Relationships, and in Vivo Properties of 3,4-Dihydo-1H-pyrido [2,3b]pyrazin-2-ones as Corticotropin-Releasing Factor-1 Receptor Antagonists," Journal of Medicinal Chemistry, 2004, 47(23):5783-5790.

Eberlein et al, "A New Molecular Form of PYY: Structural Characterization of Human PYY (3-36) and PYY(1-36)," Peptides, 1989, 10:797-803.

Edmondson et al., "Potent and selective proline derived dipeptidyl peptidase IV inhibitors," Bioorg. Med. Chem. Lett., 2004, 14:5151-5155.

Eicher et al., "Reaction of Triafulvenes with Isonitriles. A simple synthesis of diphenyl-substituted functionalized cyclobutene derivatives and related products," Synthesis (1987)(7):619-626.

Ekblad et al, "Distribution of pancreatic polypeptide and peptide YY," Peptides, 2002, 23:251-261.

Ekstrand et al, "Deletion of neuropeptide Y (NPY) 2 receptor in mice results in blockage of NPY-induced angiogenesis and delayed wound healing," PNAS USA, 2003, 100:6033-6038.

El Bahh et al, "The anti-epileptic actions of neuropeptide Y in the hippocampus are mediated by Y2 and not Y5 receptors," Eur. J. Neurosci., 2005, 22:1417-1430.

emedicinehealth.com, "High Blood Sugar", http://www.emedicinehealth.com/high_blood_sugar_hyperglycemia/page9_em.htm, accessed Jul. 1, 2011, 3 pgs.

Escher et al, "Cyclopentylamine Substituted Triazolo[4,5-D]Pyrimidine: Implications for Binding to the Adenosine Receptor," Tetrahedron Letters (1991) 32(29):3583-3584.

(56) References Cited

OTHER PUBLICATIONS

Estel et al., "Synthesis of Ortho-Substituted Aminopyridines. Metalation of Pivaloylamino Derivatives," J. Heterocyclic Chem., 1989, 26:105-112.
Fellstrom, et al, "Why Do We Need a Statin Trial in Hemodialysis Patients?" Kidney International Supplement, 2003 63(84):S204-S206.
Flock et al., "GPR119 Regulates Murine Glucose Homeostasis Through Incretin Receptor-Dependent and Independent Mechanisms," Endocrinology, Feb. 2011, 152(2):374-383.
Fyfe et al. "GPR119 agonists as potential new oral agents for the treatment of type 2 diabetes and obesity," Expert Opinion on Drug Discovery, 2008, 3(4):403-413.
Fyfe et al., "GPR119 Agonists Are Potential Novel Oral Agents for the Treatment of Diabesity," Diabetes, 2007, 56(1):A142 (Abstract).
Gangloff et al., "Synthesis of 3,5-disubstituted-1,2,4-oxadiazoles using tetrabutylammonium fluoride as a mild and efficient catalyst," Tetrahedron Letters, 2001, 42:1441-1443.
Garcia, et al., "Effects of Cerivastatin in Dyslipemia and Other Cardiovascular Risk Factors after Renal Transplantation," Transplantation Proceedings, 2002, 34(1),:401-402.
Gewald and Hellmann, "Synthese and Raektionen von 4-aminosothizolen," Leibigs Ann. Chim, 1979, 10:1534-1546.
Gilligan et al., "Corticotropin-releasing factor antagonists: Recent advances and exciting prospects for the treatment of human diseases," Current Opinion in Drug Discovery & Development, 2004, 7(4):487-497.
Gilligan, et al., "Corticotropin Releasing Factor (CRF) Receptor Modulators: Progress and Opportunities for New Therapeutic Agents," J. Med. Chem, 2000, 43(9):1641-1660.
Giner-Sorolla et al., "The Synthesis and Properties of 6-Mercaptomethylpurine and Derivatives," Cornell University Medical College, 1965, 8:667-672.
Girouard and Iadecola, "Neurovascular coupling in the normal brain and in hypertension, stroke and Alzheimer disease," J. Appl. Physiol., 2006, 100:328-335.
Goldner et al., "Die Darstellung 2,9-; 2,6,9- and 6,9-substituierter Purine," Journal fuer Praktische Chemie (Leipzig), 1961, 12:242-252.
Gomez et al, "Intestinal peptide YY: ontogeny of gene expression in rat bowel and trophic actions on rat and mouse bowel," Am. J. Physiol., 1995, 268:G71-G81.
Gomtsyan et al., "Design, synthesis, and structure-activity relationship of 6-alkynylpyrimidines as potent adenosine kinase inhibitors," J Med Chem. (2002) 45(17):3639-3648.
Gonon et al, "Adiponectin protects against myocardial ischaemia-reperfusion injury via AMP-activated protein kinase, Akt, and nitric oxide," Cardiovasc Res., 2008, 78:116-122.
Gottlieb et al., "NMR Chemical Shifts of Common Laboratory Solvents as Trace Impurities" J. Org. Chem., 1997, 62,7512-7515.
Grandt et al, "Two molecular forms of Peptide YY (PYY) are abundant in human blood: characterization of a radioimmunoassay recognizing PYY 1-36 and PYY 3-36," Regul. Pept., 1994, 51:151-159.
Greene, T. W. and Wuts, P. G. M., Protective Groups in Organic Synthesis, 3rd Edition, 1999 [Wiley]**too voluminous to provide.
Greig et al., "New Therapeutic Strategies and Drug Candidates for Neurodegenerative Diseases," Ann N Y Acad Sci, 2004, 1035:290-315.
Grise et al, "Peptide YY Inhibits Growth of Human Breast Cancer in Vitro and in Vivo," J. Surg. Res., 1999, 82:151-155.
Groger "Moderne methoden der Suzuki-kreuzkupplung: die langerwarteten universellen synthesevarianten mit arylchloriden," J Prakt Chem , 2000, 342(4):334-339 (English Abstract).
Guerre-Millo, "Adiponectin: An Update," Diabetes & Metabolism, 2008, 34:12-18.
Guilherme et al., "Adipocyte dysfunctions linking obesity to insulin resistance and type 2 diabetes," Molecular Cell Biology, May 2008, 9:367-377.

Guillory, "Generation of Polymorphs, Hydrates, Solvates, and Amorphous Solids," Polymorphism in Pharmaceutical Solids, ed. Harry G. Britain, Marcel Dekker, Inc., New York, 1999, 95:202-209.
Gundersen "Synthesis of purinecarbonitriles by Pd(0)-catalysed coupling of halopurines with zinc cyanide," Acia Chemica Scandinavia (1996) 50:58-63.
Hafenbradl et al., "In vitro Characterization of Small-Molecule Kinase Inhibitors," Protein Kinase as Drug Targets, 2011 (B. Kiebl et al. eds) 185 pages.
Hamada et al., "An Improved Synthesis of Arylsulfonyl Chlorides From Aryl Halides," Synthesis, 1986, 852-854.
Hansmann et al, "Pulmonary Arterial Hypertension is Linked to Insulin Resistance and Reversed by Peroxisome Proliferator-Activated Receptor-γ Activation," Circulation, 2007, 115:1275-1284.
Hara et al, "Measurement of the High-Molecular Weight Form a Adiponectin in Plasma is Useful for the Prediction of Insulin Resistance and Metabolic Syndrome," Diabetes Care, 2006, 29:1357-1362.
Hay et al, "Inflammatory Bowel Disease: Costs-of-Illness," J Clin Gastroenterol, 1992, 14:309-317.
He et al., "4-(1,3-Dimethozyprop-2-ylamino)-2,7-dimethyl-8-(2,4-dichlorophenyl)-pyrazolo [1,5-al-1,3,5-triazine: A Potent, Orally Bioavailable CRF1 Receptor Antagonist," J. Med. Chem., 2000, 43:449-456.
Hecht et al., "On the 'activation' of cytokins," J Biological Chemistry, 1975, 250(18):7343-7351.
Hersperger et al., "Palladium-Catalyzed Cross-Coupling Reactions for the Synthesis of 6,8-Disubstituted 1,7-Naphthyridines: A Novel Class of Potent and Selective Phosphodiesterase Type 4D Inhibitors," J. Med. Chem., 2000, 43:675-682.
Higuchi and Stella, "Pro-drugs as Novel Delivery Systems," vol. 14 of the A.C.S. Symposium Series, 1975, 129 pages *too voluminous to provide.
Hill and Peters, "Environmental Contributions to the Obesity Epidemic," Science, 1998, 280:1371-1374.
Hocek et al., "An Efficient Synthesis of 2-Substituted 6-Methylpurine Bases and Nucleosides by Fe- or Pd-Catalyzed Cross-Coupling Reactions of 2,6-Dichloropurines," J. Org. Chem., 2003, 68:5773-5776.
Holdgate et al., "Molecular Mechanism for Inhibition of 3-hydroxy-3-methylglutaryl CoA (HMG-CoA) Reductase by Rosuvastatin," Biochemical Society Transactions, 2003, 31(3):528-531.
Huang et al., "Synthesis and Antiplatelet Activity of Phenyl Quinolones," Bioorganic & Medicinal Chemistry, 1998, 6:1657-1662.
International Preliminary Report on Patentability in International Application No. PCT/US2011/031243, dated Oct. 9, 2012, 8 pages.
Irwin et al., "Therapeutic potential of the original incretin hormone glucose-dependent insulinotropic polypeptide: diabetes, obesity, osteoporosis and Alzheimer's disease," Expert Opinion Investi. Drugs, 2010, 19(9):1039-1048.
Ismail et al., "Number and Type of Vertebral Deformities: Epidemiological Characteristics and Relation to Back Pain and Height Loss," Osteoporosis International, 1999, 9:206-213.
Jia et al., "Design, Synthesis and Biological Activity of Novel Non-Amidine Factor Xa Inhibitors. Part 1: P1 Structure-Activity Relationships of the Substituted 1-(2-Naphtyl)-1H-pyrazole-5-carboxylamides," Bioorganic & Medicinal Chemistry Letters, 2002,12:1651-1655.
Jogie et al., "Unusual protein-binding specificity and capacity of aza-arenophilic gels," Journal of Molecular Recognition, 1998, 11:261-262.
Jones and Leonard, "The Emergence of GPR119 Agonists as Anti-Diabetic Agents," Ann. Rep. Med. Chem., 2009, 44:149-170.
Jones et al., "GPR119 agonists for the treatment of type 2 diabetes," Expert Opin. Ther. Patents, 2009, 19(10): 1339-1359.
Joshi et al., "Endogenous PYY and GLP-1 mediate L-glutamine responses in intestinal mucosa," British Journal of Pharmacology, 2013, 170:1092-1101.
Judge and Bever, "Potassium channel blockers in multiple sclerosis: Neuronal $K_V$ channels and effects of symptomatic treatment," Pharmacology & Therapeutics, 2006, 111:224-259.

(56) References Cited

OTHER PUBLICATIONS

Kametani et al. "Benzyene Reaction. IX. Benzyene Reaction of o-halobenzenes with acetonitrile or phenylacetonitrile in organic solvents," J. Org. Chem., 1972, 36(2):327-330.
Kanstrup et al., "Quality of Lipid-Lowering Therapy in Patients with Ischaemic Heart disease: A Register-Based Study in 3477 Patients," Journal of Internal Medicine, 2004, 255(3):367-372.
Kawakita et al., CAPLUS Abstract 115:136096, 1991, 3 pages.
Kawase et al., "a-trifluoromethylated acyloins induce apoptosis in human oral tumor cell lines," Bioorg & Med Chem Ltrs, 1999, 9(21):3113-3118.
Keane et al., "The CHORUS (Cerivastatin in Heart Outcomes in Renal Disease: Understanding Survival) Protocol: A Double-Blind, Placebo-Controlled Trial in Patients with ESRD," American Journal of Kidney Diseases, 2001, 37(1, Suppl. 2):S48-S53.
Keighley and Stockbrugger, "Inflammatory bowel disease," Ailment Pharmacol Ther, 2003, 18:66-70.
Keire et al., "Primary structures of PYY, [Pro34]PYY, and PYY-(3-36) confer different conformations and receptor selectivity," Am. J. Physiol. Gastrointest. Liver Physiol., 2000, 279:G126-G131.
Kelley et al., "Benzodiazepine receptor binding activity of 8-substituted-9-(3-substituted-benzyl)-6 diamethylamino)-9H-purines," Med Chem, 1990, 33(1):196-202.
Kelly et at., "A Synthesis of Aaptamine," Tetrahedron,1985, 41(15):3033-3066.
Kempson et al., "Fused pyrimidine based inhibitors of phosphodiesterase 7 (PDE7): synthesis and initial" structure-activity relationships, Bioorganic & Medicinal Chemstry Letters, 2005, 15:1829-1833.
Khattab et al., "Quinolines with heteroatom substituents in position 2 and 4. Nucleophilic substitution of 2,4-dichloro-3-phenylquinolines," ACH—Models in Chemistry, 1994, 131(3-4):521-527.
Kim and Egan, "The Role of Incretins in Glucose Homeostasis and Diabetes Treatment," Pharmacological Reviews, 2008, 60(4):470-512.
Klotzer et al., "Chlorierende formylierungsreaktionen an pyrimidinen," Monatshefte fuer Chemie, 1965, 96(5):1567-1572 (English Abstract).
Kolosov et al., "The interaction between 4-[phenyl-5-acetyl-6-methyl-3,4-dihydropyrimidine-2-one and 4-brombenzaldehyde", Institute of Organic Chemistry, Kharkiv, retrieved on Mar. 30, 2008, http://conf.iflab.kiev.ua/eng/reports/show/?id=926, 2 pages (Abstract Only).
Kotian et al., "Synthesis, ligand binding, and quantitative structure-activity relationship study of 3β-(4'-substituted phenyl)-2β-heterocyclic tropanes: evidence for an electrostatic interaction at the 2β-position," J Med Chem, 1996, 39(14):2753-2763.
Koumbourlis, "Scoliosis and the respiratory system," Paediatric Respiratory Reviews, 2006. 7:152-160.
Krauze et al., "Derivatives of 3-cyano-6-phenyl-4-(3'-pyridyl)-pyridine-2(1H)-thione and their neurotropic activity," European Journal of Medicinal Chemistry, 1999, 34(4):301-310.
Krauze et al., "Synthesis of 3-oxoisothiazolo[5,4-b]pyridines," Khimiya Geterotsiklicheskikh Soedinenii, 1982, (4):508-512.
Kreisberg et al, "Hyperlipidemia (High Blood Fat)," The Journal of Clinical Endocrinology & Metabolism, 2005, 90:0, 2 pgs.
Kubota et al, "Disruption of Adiponectin Causes Insulin Resistance and Neointimal Formation," J. Biol. Chem., 2002, 2002, 277:25863-25866.
Kumagai et al., "Synthesis, SAR and biological activities of CRH1 Receptor: Novel 3- or 4-carbamoyl-1,2,5,6- tetrahydropyridinopyr-rolopyrimidine derivative," 4th ACS National Meeting, Aug. 18-22, 2002, Boston, MA. Poster #259.
Lai et al, "Association between Obesity and Hyperlipidemia Among Children," Yale Journal of Biology and Medicine 74 (2001), pp. 205-210.
Lai et al., "A one-pot method for the efficient conversion of aryl-and acyl-substituted methyl alcohols into chlorides," Synthetic Communications, 2003, 33(10):1727-1732.
Lan, "GPR119 is Required for Physiological Regulation of Gucagon-like Peptide-1 Secretion but not for Metabolic Homeostasis," J. Endocrinol., 2009, 201:219-230.
Lanier et al., "Small molecule corticotrophin-releasing factor antagonists," Expert Opinion, 2002, 12(11):1619-1630.
Le Bas et al., "Radioiodinated analogs of EP 00652218 for the exploration of the tachykinin NK1 receptor by spect," J. Labeled Compd. Radiopharm., 2001, 44:S280-S282.
Le Stunff and Bougneres, "Early Changes in Postprandial Insulin Secretion, Not in Insulin Sensitivity, Characterize Juvenile Obesity," Diabetes, 1994, 43:696-702.
Leadbeater et al., "First Examples of Transition-Metal Free Sonogashira-Type Couplings," Organic Letters, 2003, 5(21):3919-3922.
Leadbeater et al., "Transition-metal Free Sonogashira-type Couplings," Organic Letters, 2003 5(21):-3922.
Lechleitner, "Dyslipidaemia and Renal Disease—Pathophysiology and Lipid Lowering Therapy in Patients with Impaired Renal Function," Journal of Clinical and Basic Cardiology, 2000, 3(1):3-6.
Lee et al, "Neuropeptide Y induces ischemia angiogenesis and restores function of ischemic skeletal muscles," J. Clin. Invest., 2003, 111:1853-1862.
Lee et al., "Impaired angiogenesis in neuropeptide Y (NPY)-Y2 receptor knockout mice," Peptides, 2003, 24:99-106.
Lee et al., "Synthesis and biological evaluation of clitocine analogues as adenosine kinase inhibitors," Bioorg & Med Chem Ltrs, 2001, 11(18):2419-2422.
Leese et al., "Potential antipurines. Part II. Synthesis of 6- and 9-substituted purines and 8-azapurines," Journal of the Chemical Society, 1958, 4107-4110.
LeWitt, "Levodopa for the Treatment of Parkinson's Disease," The New England Journal of Medicine, Dec. 2008, 359(23):2468-2476.
Lin, et al., "Synthesis and Antitumor Activity of Halogen-Substituted 4-(3,3-Dimethyl-1-triazeno)umolones," J. Med. Chem., 1978, 21(3):268-272.
Lindvall and Kokaia, "Stem cells for the treatment of neurological disorders," Nature, 2006, 44:1094-1096.
Litvak et al., "Polynucleotides and Their Components in the Processes of Aromatic Nucleophilic Substitution: II.1 Nucleophilic Modification of 3',5'-Bis-O-(a,β,α',β'-tetrafluoropyrid-y-yl)thymidine," Russian Journal of Bioorganic Chemistry, 2004, 30(4):337-343.
Litvinov et at., "Naphthyridines. Structure, physicochemical properties and general methods of synthesis," Russian Chemical Reviews, 2000, 69(3):201-220.
Liu et al, "Human Pancreatic Cancer Growth is inhibited by Peptide YY and BIM-43004-1," J. Surg. Res., 1995, 58:707-712.
Liu et al, "Pancreatic Peptide YY mRNA Levels Increase during Adaptation after Small Intestinal Resection," J. Surg. Res., 1995, 58:6-11.
Liu et al, "Peptide YY: A Potential Proabsorptive Hormone for the Treatment of Malabsorptive Disorders," Am Surg., 1996, 62:232-236.
Liu et al, "Y2 receptors decrease human pancreatic cancer growth and intracellular cyclic adenosine monophosphate levels," Surgery, 1995, 118:229-236.
Loupy et al., "Easy and efficient SNAr Reactions on halopyridines in solvent free conditions," Heterocycles, 1991, 32(10):1947-1952.
Lumb et al, "Novel Selective Neuropeptide Y2 Receptor PEGylated Peptide Agonists Reduce Food Intake and Body Weight in Mice," J. Med. Chem., 2007, 50:2264-2268.
Lundberg et al., "Localization of peptide YY (PYY) in gastrointestinal endocrine cells and effects on intestinal blood flow and motility," PNAS USA, 1982, 79:4471-4475.
Luo et al., "Microwave-assisted synthesis of aminopyrimidines," Tetrahedron Letters, 2002, 43:5739-5742.
Ma, et at. "Mild Method for Ullmann Coupling Reaction of Amines and Aryl Halides," Organic Letters, 2003, 5(14):2453-2455.
Macchia et al., "New N-n-propyl-substituted 3-aryl- and 3-cyclohexylpiperidines as partial agonists at the D4 dopamine receptor," J Med Chem, 2003, 46(1):161-168.
Mackman et al., "2-(2-Hydroxy-3-alkoxyphenyl)-IH-benzimidazole-5-carboxamidine derivatives as potent and selective urokinase-type plasminogen activator inhibitors," Bioorganic & Medicinal Chemistry Letters, 2002, 12(15):2019-2022.
Maeda et al., "Diet-induced insulin resistance in mice lacking adiponectin/ACRP30," Nat. Med., 2002, 8:731-737.

(56) References Cited

OTHER PUBLICATIONS

Majeed et al, "Stannylation Reactions and Cross-Couplings in Pyrimidines," Tetrahedron, 1989, 45(4):993-1006.

Markwalder, et al., "Synthesis and biological evaluation of 1-aryl-4,5-dihydro-1H-pyrazolo [3,4-d]pyrimidin-4-one inhibitors of cyclin-dependent kinases", J. Med. Chem., (2004), 47:5894-5911.

Marso et al., "Low Adiponectin Levels are Associated with Atherogenic Dyslipidemia and Lipid-Rich Plaque in Nondiabetic Coronary Arteries," Diabetes Care, 2008, 31:989-994.

Martin et al., "A Double-Blind, Randomized, Incomplete Crossover Trial to Assess the Dose Proportionality of Rosuvastatin in Healthy Volunteers," Clinical Therapeutics, 2003, 25(8):2215-2224.

Martin et al., "Absolute Oral Bioavailability of Rosuvastatin in Healthy White Adult Male Volunteers," Clinical Therapeutics, 2003, 25(10):2553-2563.

Martin et al., "An Open-Label, Randomized, Three-Way Crossover Trial of the Effects of Coadministration of Rosuvastatin and Fenofibrate on the Pharmacokinetic Properties of Rosuvastatin and Fenofibric Acid in Healthy Male Volunteers," Clinical Therapeutics, 2003, 25(2): 459-471.

Martin et al., "Metabolism, Excretion, and Pharmacokinetics of Rosuvastatin in Healthy Adult Male Volunteers," Clinical Therapeutics, 2003, 25(11):2822-2835.

Matsuda et al., "Role of Adiponectin in Preventing Vascular Stenosis: The Missing Link of Adipo-Vascular Axis," J Biol Chem, 2002, 277:37487-37491.

Matsui et al., "Highly Potent Inhibitors of TNF-A Production. Part II: Metabolic Stabilization of a Newly Found Chemical Lead and Conformational Analysis of an Active Diastereoisomer," Bioorganic & Medicinal Chemistry, 2002, 10(12):3787-3805.

Matsuno et al., "Potent and Selective Inhibitors of Platelet-Derived Growth Factor Receptor Phosphorylation. 3. Replacement of Quinazoline Moiety and Improvement of Metabolic Polymorphism of 4-[4-N-Substituted (thio) caramoyl]-1-piperazinyl]-6,7-diamethoxyquinazoline Derivatives," J Med Chem, 2003, 46(23):4910-4925.

Mayo Clinic, "Metabolic syndrome", accessed 18 Jul. 18, 2013, http://www.mayoclinic.com/health/metabolic%20syndrome/DSOO522, 2 pages.

MayoClinic.com "Obesity: Prevention", retrieved on Jan. 22, 2014, http://www.mayoclinic.com/health/obesity/ds00314/dsection-prevention, 4 pages.

MayoClinic.com, "Type 2 diabetes," downloaded from http://www.mayoclinic.com/health/type-2-Diabetes/DS00585/METHOD=print on Jan. 28, 2011, 14 pages.

McFadden et al., "Peptide YY inhibits the growth of Barrett's esophageal adenocarcinoma in vitro," Am. J. Surg., 2004, 188:516-519.

McIntosh et al., "Dipeptidyl peptidase IV inhibitors: How do they work as new antidiabetic agents," Regulatory Peptides, 2005, 128:159-165.

Mentlein, "Therapeutic assessment of glucagon-like peptide-1 agonists compared with dipeptidyl peptidase IV inhibitors as potential antidiabetic drugs," Expert Opin Investig Drugs, 2005, 14(1):57-64.

Mesguiche et al., "4-Alkoxy-2,6-diaminopyrimidine Derivatives: Inhibitors of Cyclin Dependent Kinases 1 and 2," Bioorganic & Medicinal Chemistry Letters, 2003, 13(2):217-222.

Metzger et al., "Einstufensynthese von 2,4-Bis(sec-alkylamino-6-halogen-3-pyridincathonitrilen**," Liebigs Annalen der Chemie (1980) (6):946-953.

Mitchell and Borasio, "Amyotrophic lateral sclerosis," The Lancet, Jun. 2007, 369: 2031-2041.

Mitsunobu, "The Use of Diethyl Azodicarboxylate and Triphenylphosphine in Synthesis and Transformation of Natural Products", Synthesis, 1981, 1-28.

Mittelbach and Junek., "Syntheses with Nitriles. 60. (1). Preparation of 4-Amino-5-cyano-6-phenylpyrimidines from 2-Amino-1,1-dicyano-2-phenylethene," J. Heterocyclic Chem, 1980, 17(7):1385-1387.

Miyashita et al., "Preparation of Heteroarenecarbonitriles by Reaction of Haloheteroarenes with Potassium Cyanide Catalyzed by Sodium p-Toluenesulfinate," Heterocycles, 1994, 39(1):345-350.

Mohan et al., "Solid-Phase Synthesis of N-Substituted Amidinophenoxy Pyridines as Factor XA Inhibitors," Bioorganic & Medicinal Chemistry Letters, 1998, 8(14):1877-1882.

Mombereau et al., "Genetic and Pharmacological Evidence of a Role for GABA$_B$ Receptors in the Modulation of Anxiety- and Antidepressant-Like Behavior," Neuropsychopharmacology, 2004, 29(6):1050-1062.

Mongin and Queguiner, "Advances in the directed metallation of azines and diazines (pyridines, pyrimidines, pyrazines, pyridazines, quinolines, benzodiazines and carbolines). Part 1: Metallation of pyridines, quinolines and carbolines," Tetrahedron, 2001, 57(19):4059-4090.

Montgomery et al., "Isonucleosides. I. Preparation of Methyl 2-Deoxy-2-(purin-9-yl)arabinofuranosides and Methyl 3-Deoxy-3-(purin-9-yl)xylofuranosides," Journal of Organic Chemistry,1975, 40(13):1923-1927.

Morimoto et al., "Potent and selective ET-A Antagonists. 1. Syntheses and Structure-Activity Relationships of N-(6-(2-(Aryloxy)ethoxy)-4-pyrimidinyl)sulfonamide Derivatives," J Med Chem, 2001, 44 (21):3355-3368.

Morissetie et al., High-throughput crystallization: polymorphs, salts, co-crystals and solvates of pharmaceutical solids, Advance Drug Delivery Reviews, 2004, 56: 275-300.

Moschitskii et al., "Reaction of 2, 3, 5, 6-Tetrachloro-4-Pyridyl-Vinyl Sulfone with Nuleophilic Agents," Khimiya Geterotsiklicheskikh Soedinenii,1972, 1634-1637, (Translated pp. 1482-1485).

Mosti et al., "4-Substituted 1-Phenyl-1H-Indazoles With Analgesic, Antiinflammatoiy, Antipyretic and Local Anesthetic Activities," IL Farmaco, 1990, 45(4):415-429.

Mosti et al., "Synthesis and Preliminary biological Evaluation of Novel N-Substited 1-Amino-3-[1-methyl(phenyl)-1H-indazol-4-yloxy]-propan-2-ols Interesting as Potential Antiarrhythmic, Local Anaesthetic and Anagesic Agents," Arzneim-Forsch Drug Res, 2000, 50(11):963-972.

Muci and Buchwald, "Practical Palladium Catalysts for C—N and C—O Bond Formation," Topics in Current Chemistry, 2002, 219:131-209.

Muck et al., "Lack of Pharmacokinetic Drug-Drug Interaction between Orlistat and Cerivastatin," Clinical Drug Investigation, 2000, 19(1):71-73.

Muller et al., "7-Deaza-2-phenyladenines: Structure-Activity Relationships of Potent A$_1$ Selective Adenosine Receptor Antagonists," J Med Chem, 1990, 33:2822-2828.

Nakamura et al., "Effect of Cerivastatin on Endothelial Dysfunction and Aortic CD36 Expression in Diabetic Hyperlipidemic Rats," Hypertens Res, 2004, 27(8):589-598.

Nakazato et al., "Design, Synthesis and Structure-Affinity Relationships of 4-Methylidenepiperidine and 4-Aryl-1,2,3,6-tetrahydropyridine Derivatives as Corticotropin-Releasing Factor1 Receptor Antagonists," Bioorganic & Medicinal Chemistry, 2000, 8(5):1183-1193.

Nakazato et al., "Synthesis, SAR and biological activities of CRH1 receptor: Novel 3- or 4-carbamoyl-1,2,5,6-tetrahydropyridinoquinoline derivative," 24th ACS National Meeting, Aug. 18-22, 2002, Boston, MA. Poster #258.

National Diabetes Information Clearinghouse, "Insulin resistance and Pre-Diabetes," http://diabetes.niddk.nih.gov/dm/pubs/insulinresistance/, accessed Jul. 1, 2011, 6 pgs.

National Library of Medicine, "Glucose Metabolism Disorders", accessed Jan. 11, 2011, http://www.nlm.nih.gov/cgilmesh/2011 /M B cg i?mode=&term=Glucos8+Metabolism+Disorders&field= entry, 3 pages.

Nauck et al., "Gastric Inhibitory Polypeptide and Glucagon-Like Peptide-1 in the Pathogenesis of Type 2 Diabetes," Diabetes, 2004, 53(3):S190-196.

Nauck et al., "Incretins and Their Analogues as New Antidiabetic Drugs," Drug News Perspect, 2003, 16(7):413-422.

ndep.nih.gov, "Diabetes Prevention" (May 26, 2009) http://ndep.nih.gov/diabetes/prev/prevention.htm, accessed Jul. 1, 2011, 7 pages.

(56) References Cited

OTHER PUBLICATIONS

Nesi et al., "New Difunctionalized 4-Nitroisoxazoles from α-Nitroacetophenone Oxime," Heterocycles, 1985, 23(6):1465-1469.
Nezasa et al., "Uptake of rosuvastatin by isolated rat hepatocytes: comparison with pravastatin," Xenobiotica, 2003, 33(4):379-388.
Nicewonger et al., "Microwave-assisted acylation of 7-amino-5-aryl-6-cyanopyrido [2,3-d] pyrimidines," Molecular Diversity, 2003, 7(2-4):247-252.
Niementowski, J. Praktika Chem., [2] "Synthesen von Chinazolinverbindugen" (1895), 51, 564-572.
Nightingale et al., "Gastrointestinal hormones in short bowel syndrome. Peptide YY may be the 'colonic brake' to gastric emptying," Gut, 1996, 39:267-272.
Nishimura et al., "Adiponectin Prevents Cerebral Ischemic Injury Through Endothelial Nitric Oxide Synthase-Dependent Mechanisms," Circulation, 2008, 117:216-223.
Norman et al., "Structure-Activity Relationships of a Series of Pyrrolo[3,2-d] pyrimidine Derivatives and Related Compounds as Neuropeptide Y5 Receptor Antagonists," J Med Chem, 2000, 43(22):4288-4312.
Novinson et al., "Novel Heterocyclic Nitrofurfural Hydrazones. In vivo Antitrypanosomal Activity," J Med Chem, 1976, 19(4):512-516.
O'Brien et al., "Vascular cognitive impairment," The Lancet Neurology, Feb. 2003, 2:89-98.
Okada et al., "Peripherally Not Centrally Administered Peptide YY(PYY) Decreases High Fat Diet Intake," Endocrine Society, 1993, 520 B:180.
Oku et al., "Adiponectin deficiency suppresses ABCA1 expression and ApoA-I synthesis in the liver," FEBS Letters, 2007, 581:5029-5033.
Olesen, "The use of bioisosteric groups in lead optimization," Current Opinion in Drug Discovery & Development, 2001, 4(4):471-478.
Olsson et al., "Rosuvastatin: A Highly Effective New HMG-CoA Reductase Inhibitor," Cardiovascular Drug Reviews, 2002, 20(4):303-328.
Olsson, "Statins: how far have we come? A review of rosuvastatin," International Journal of Clinical Practice, 2003, Supplement 137:15-25.
Organic Chemistry of Sulfur; Oae S., Ed.; Plenum Press: New York (1977) * *too voluminous to provide.
Ortiz et al., "A Novel Long-Acting Selective Neuropeptide Y2 Receptor Polyethylene Glycol-Conjugated Peptide Agonist Reduces Food Intake and Body Weight and Improves Glucose Metabolism in Rodents," JPET, 2007, 323:692-700.
Ouchi and Walsh, "Adiponectin as an anti-inflammatory factor," Clinica Chimica Acta, 2007, 380:24-30.
Ouchi et al., "Novel Modulator for Endothelial Adhesion Molecules: Adipocyte-Derived Plasma Protein Adiponectin," Circulation, 1999, 100:2473-2476.
Overton et al., "GPR119 a Novel G Protein-coupled Receptor Target for the Treatment of Type 2 Diabetes and Obesity," Brit. J. Pharmacol., 2008, 153:576-581.
Overton et al., "Deorphanization of a G protein-coupled receptor for oleoylethanolamide and its use in the discovery of small-molecule hypophagic agents," Cell Metabolism, 2006, 3:167-175.
Oxford Online Dictionary, Definition of Prescription, 2017, 4pp.
Ozeki el al., "Studies on Antiallergy Agent. 1. Synthesis of 1,4-Dihydro-4-oxo-3-quinolinecarboxylic Acids" Yakugaku Zasshi, 1987, 107(2):123-134.
Parker and Balasubramaniam, "Neuropeptide Y Y2 receptor in health and disease," British Journal of Pharmacology, 2008, 153:420-431.
Parlow et al., "Design, Synthesis, and Crystal Structure of Selective 2-Pyridone Tissue Factor VIIa Inhibitors," J Med Chem, 2003, 46(22):4696-4701.
Paulsen et al., "Darstellung von Bausteinen zur Synthese calbocyclischer furanose-analoga," Chemische Berichte (1981)114(1):346-358.

Pearson, "Inflammatory bowel disease," Nursing Times, 2004, 100(9):86-90.
Peat et al., "Novel pyrazolopyrimidine derivatives as GSK-3 inhibitors", Bioorganic & Medicinal Chemistry Letters, 2004, 14:2121-2125.
Pederson, "The Impact of Obesity on the Pathogenesis of Non-Insulin-Dependent Diabetes Mellitus: A Review of Current Hypotheses," Diabetes/Metabolism Reviews., 1989, 5(6):495-509.
Pei et al., "Discovery and Structure-Activity Relationships of Piperidinone- and Piperidine-Constrained Phenethylamines as Novel, Potent, and Selective Dipeptidyl Peptidase IV Inhibitors," J Med Chem, 2007, 50:1983-1987.
Pelat et al., "Rosuvastatin Decreases Caveolin-1 and Improves Nitric Oxide-Dependent Heart Rate and Blood Pressure Variability in Apolipoprotein E−/− Mice in Vivo," Circulation, 2003, 107(19):2480-2486.
Perry et al., "Prospective study of risk factors for development of non-insulin dependent diabetes in middle aged British men," BMJ, 1995, 310:560-564.
Peters et al., "Aminomethylpyrimidines as novel DPP-IV inhibitors: A 105-fold activity increase by optimization of aromatic substituents," Bioorganic & Medicinal Chemistry Letters, 2004, 14:1491-1493.
Peterson et al., "Expanding the Scope of Crystal Form Evaluation in Pharmaceutical Science," J Pharm Pharmaceut Sci, 2006, 9(3):317-326.
Phillips et al., "Discovery of N-[2-[5-[Amino(imino)methyl]-2-hydroxyphenoxyl]-3,5-difluoro-6-[3-(4,5-dihydro-1-methyl-1H-imidazol-2-yl)phenoxy]pyridin-4-yl)-N-methylglycine(ZK-807834): A Potent, Selective, and Orally Active Inhibitor of the Blood Coagulation Enzyme Factor Xal-," J Med Chem, 1998, 41(19):3557-3562.
Pittner et al., "Effects of PYY[3-36] in rodent models of diabetes and obesity," International Journal of Obesity,2004, 28:963-971.
Pomorski, "Synthesis of Acids, Derivatives of 4-Hydroxy-1,5-Naphthyridine," Roczniki Chemii Ann Soc Chim Polonorum, 1974, 48:321-325.
Poienza and Lerner, "A Rapid Quantitative Bioassay for Evaluating the Effects of Ligands Upon Receptors That Modulate cAMP Levels in a Melanophore Cell Line," Pigment Cell Research, 1992, 5(6):372-378.
Poupaert, "Drug Design: Basic Principles and Applications," Encyclopedia of Pharmaceutical Technology, 2007, 1362-1369 (James Swalbrick 3rd ed.).
Prasad et al., "Convenient Methods for the Reduction of Amides, Nitriles, Carboxylic Esters, Acids and Hydroboration of Alkenes Using NaBH4/I2 System," Tetrahedron, 1992, 48(22):4623-4628.
Press et al., "Synthesis and SAR of 6-Substituted Purine Derivatives as Novel Selective Positive Inotropes," J Med Chem, 1992, 35(24):4509-4515.
Quesada et al., "2-Amino-5-nitro-4,6-dipiperidionpyrimidinium hydrogensulfate monohydrate: hydrogen-bonded sheets containing highly distorted cations," Acta Cryst, 2003, 59:102-104 (Abstract; 1 page).
Quintela et al., "6-Dimethylamino 1H-Pyrazolo[3,4-d]pyrimidine Derivatives as New Inhibitors of Inflammatory Mediators in Intact Cells," Bioorganic &Medicinal Chemistry (2003) 11:863-868.
Quintela et al., "Pyrazolopyrimidines: synthesis, effect on histamine release from rat peritoneal mast cells and cytotoxic activity," Eur J Med Chem (2001) 36:321-332.
Raffel et al., "Diabetes Mellitus," Principles and Practice of Medical Genetics, 1996, 1:1401-1440.
Raisz, "Pathogenesis of osteoporosis: concepts, conflicts, and prospects," J Clin Invest, 2005, 115(12):3318-3325.
Ram et al., "Chemotherapeutic agents: Part XXII—Synthesis of p-deficient pyrimidines as leishmanicides," Indian Journal of Chemistry, 1991, 30B(10):962-965.
Rao et al., "Impaired Glucose Tolerance and Impaired Fasting Glucose," 1962, American Family Physician, 69(8):1961-1968.
Rayasam et al., "Fatty acid receptors as new therapeutic targets for diabetes," Expert Opin Thera Targets, 2007, 11(5):661-671.
Reed and Scribner, "In-vivo and in-vitro models of type 2 diabetes in pharmaceutical drug discovery," Diabetes Obes Metab, 1999 1(2):75-86.

(56) References Cited

OTHER PUBLICATIONS

Rehwald and Gewald, "Syntheses of Thieno[2,3-d]Pyrimidines and Aminopyrimidines from 2-Alkoxy-5-Cyano-4-Thioxopyrimidine Intermediates," Heterocycles, 1998, 48(6):1157-1167.
*Remington's Pharmaceutical Sciences*, 1985, *Mack Publishing Company*, 17:1418-1419.
Renshaw and Batterham, "Peptide YY: A Potential Therapy for Obesity," Current Drug Targets, 2005, 6:171-179.
Rewcastle et al., "Tyrosine Kinase Inhibitors. 10. Isomeric 4-[(3-Bromophenyl)amino]pyrido[d]-pyrimidines Are Potent ATP Binding Site Inhibitors of the Tyrosine Kinase Function of the Epidermal Growth Factor Receptor," J Med Chem, 1996, 39:1823-1835.
Rimoin et al., "Emery and Rimoin's Principles and Practice of Medical Genetics", 1996, 3:1401-1402.
Roberts and Suschitzky, "Peroxy-acid Oxidation of NN-Disubstituted Aminotetrafluoro-, Amino-3-chlorotrifluoro-, and Amino-3,5-dichlorodifluoro-pyridines," Journal of the Chemical Society, 1969 11:1485-1491.
Roberts et at., "Polychloroaromatic compounds. Part I. Oxidation of pentachloropyridine and its NN-disubstituted amino-derivatives with peroxyacids," Journal of the Chemical Society (Section) C: Organic (1968) (12):1537-1541.
Roberts, "Two More Drugs for Dyslipidemia", American Journal of Cardiology, 2004 93:809-811.
Robev, "4-Cyclopropylamino- and 4-Cyclobutylaminoderivatives of some Arylsubstituted 5-Cyanopyrimidines," Doktady Bolgarskoi Akademii Nauk, 1981 34(12):1677-1680.
Robins and Lin, "Potential Purine Antagonists. IV. Synthesis of Some 9-Methyl-6-substituted purinesl," Dep of Chem, 1957, 79:490-494.
Roche, Bioreversible Carriers in Drug Design, ed., American Pharmaceutical Association and Pergamon Press (1987) *too voluminous to provide.
Rodriguez-Spong et al., "General Principles of Pharmaceutical Solid Polymorphism: A Supramolecular Perspective", Adv Drug Delivery Rev, 2004, 56:241-274.
Rondinone, "Diabetes: the latest developments in inhibitors, insulin sensitisers, new drug targets and novel approaches" Expert Opin, 2005, 9(2):415-418.
Rosenson, "Rosuvastatin. A new inhibitor of HMG-CoA reductase for the treatment of dyslipidemia", Expert Review of Cardiovascular Therapy, 2003, 1(4):495-505.
Rotwein et al., "Polymorphism in the 5' flanking region of the human insulin gene: a genetic marker for non-insulin-dependent diabetes," N Engl J Med, 1983, 308(2):65-71.
Ruggeri, "Platelets in atherothrombosis," Nat Med, 2002, 8(11):1227-1234.
Sage, Document regarding search, Feb. 2003, 1 page.
Schafer et al., "Zur synthese von 4-aminochinolinen durch intramolekulare Friedel-Cfafts-Reaktion," Montash fur Chemie (1978) 109:527-535 (English Abstract).
Schuster, "Rosuvastatin—A Highly Effective New 3-hydroxy-3-methylglutaryl Coenzyme A Reductase Inhibitor: Review of clinical Trial Data at 10-40 mg doses in Dyslipidemic Patients" Cardiology, 99(3):126-139 (2003).
Schwartz and Holst, "An Enteroendocrine Full Package Solution," Cell Metabolism, 2010, 11:445-447.
Scott et al., "Rosuvastatin: A Review of Its Use in the Management of Dyslipidemia," American Journal of Cardiovascular Drugs, 4(2), 117-138 (2004).
Semple et al., "Discovery of a second generation of the orphan G-protein coupled receptor GPR119 with an improved profile," Biooganic & Medicinal Chemistry Letters, 2012, 22:1750-1755.
Shah et al., "Current Approaches in the treatment of Alzheimer's disease," Biomedicine &Phamacotherapy, 2008, 62:199-207.
Shah, "GPR119 Agonists for the Potential Treatment of Type 2 Diabetes and Related Metabolic Disorders," Vitamins & Hormones, 2010, 84:415-448.

Shah, "GPR119 agonists: A promising new approach for the treatment of type 2 diabetes and related metabolic disorders," Current Opin Drug Discov Develop., 2009, 12:519-532.
Shepherd et al., "Safety of Rosuvastatin," American Journal of Cardiology, 94(7):882-888 (2004).
Shibata et al., "Adiponectin protects against myocardial ischemia-reperfusion injury through AMPK-and COX-2-dependent mechanisms," Nat Med, 2005, 11:1096-1103.
Shibata et al., "Adiponectin Stimulates Angiogenesis in Response to Tissue Ischemia through Stimulation of AMP-activated Protein Kinase Signaling," J. Biol. Chem., 2004, 279:28670-28674.
Shibata et al., "Adiponection protects against the development of systolic dysfunction following myocardial infarction," J. Mol. Cell Cardiol., 2007, 42:1065-1074.
Shore et al., "Adiponectin attenuates allergen-induced airway inflammation and hyperresponsiveness in mice," J. Allergy Clin. Immunol, 2006, 118:389-395.
Showell et al., "Tetrahydropyridyloxadiazoles: semirigid muscarinic ligands," J Med Chem (1991) 34(3):1086-1094.
Sigma-Aldrich, catalog entry for 2-amino-6-chloro-4-pyrimidinol hydrate (catalog No. 07460); 1 page; retrieval date Mar. 16, 2010.
Sigma-Aldrich, catalog entry for 2-amino-6-hydroxy-2-mercaptopyrimidine monohydrate (catalog No. A57406); 1 page; retrieval date Mar. 16, 2010.
Sigma-Aldrich, catalog entry for 4,5-diamino-6-hydroxy-2-mercaptopyrimidine hemisulfate salt hydrate (392464); 1 page; retrieval date Mar. 16, 2010.
Sigma-Aldrich, catalog entry for 4,6-diamino-2-mercaptopyrimidine hydrate (catalog No. 125830); 1 page; retrieval date Mar. 16, 2010.
Silhar et al., "Facile and Efficient Synthesis of 6-(Hydroxymethyl)purines," Org. Lett. (2004) 6(19):3225-3228.
Silvestri et at, "Novel indolyl aryl sulfones active against HIV-1 carrying NNRTI resistance mutations: synthesis and SAR studies," J Med Chem (2003) 46(12):2482-2493.
Smith et al., "Effects of positive allosteric modulators of the GABAB receptor on cocaine self-administration in rats," Psychopharmacology (2004)173(1-2):105-111.
Soga et al., "Lysophosphatidylcholine enhances glucose-dependent insulin secretion via an orphan G-protein-coupled receptor," Biochem Biophys Res Commun (2005) 326:744-751.
Spruce, Lyle W., Document regarding search, 2004, 1 page.
Starosotnikov et al., "Synthesis of 3-substituted 1-aryl-4,6-dinitro-1H-indazoles based on picrylacetaldehyde and their behavior in nucleophilic substitution reactions," Russian Chemical Bulletin 2003, 52(8), 1782-1709.
Steensma et al., "A novel method for the synthesis of aryl sulfones," Tetrahedron Ltrs (2001) 42:2281-2283.
Stein, "Management of Dyslipidemia in the High-Risk Patient," American Heart Journal, 144(6):543-550 (2002).
Sternfeld et al., "Synthesis and serotonergic activity of 3-[2-(pyrrolidin-1-yl)ethyl]indoles: potent agonists for the h5-HT1D receptor with high selectivity over the h5-HT1B receptor," J. Med Chem, 1999, 28(6):761-769.
Strupczewski et al., "Synthesis and neuroleptic activity of 3-(1-substituted-4-piperidinyl)-1,2-benzisoxazoles," J Med Chem (1985) 28(6):761-769.
Suami et al., "Nucleoside analogs. I. Synthesis of 1,3-dihydroxy-2-(6-substituted-9-purinyl)cyclohexane," Journal of Heterocyclic Chemistry (1969) 6(5):663-665.
Sugimoto et al., "Lithiation of 1H-Pyrazolo[3,4-d]pyrimidine Derivative Using Lithium Alkanetellurolate," Tetrahedron Letters (1999) 40:2139-2140.
Sugimoto et al., "Preparation of Nitrogen-Containing π-Deficient Heteroaromatic Grignard Reagents: Oxidative Magnesiation of Nitrogen-Containing n-Deficient Halgenoheteroaromatics Using Active Magnesium," J. Org. Chem. (2003) 68:2054-2057.
Summer et al., "Alveolar macrophage activation and an emphysema-like phenotype in adiponectin-deficient mice," Am J. Physiol. Lung Cell Mol. Physiol, 2008, 294:L1035-L1042.
Takei et al., "A New Synthetic Method for Some Pyrazolo[4,3-]pyrimidines1)," Bulletin of the Chemical Society of Japan, Aug. 23, 2005, 52(1):208-211.

(56) References Cited

OTHER PUBLICATIONS

Tao et al., "Adiponectin Cardioprotection After Myocardial Ischemia/Reperfusion Involves the Reduction of Oxidative/Nitrative Stress," Circulation, 2007, 115:1408-1416.
Tatemoto and Mutt, "Isolation of two novel candidate hormones using a chemical method for finding naturally occurring polypeptides," Nature, 1980, 285:417-418.
Terashima et al "Inhibition of human 06-alkylguanine-DNA alkyltransferase and potentiation of the cytotoxicity of chloroethylni. trosourea by 4(6)-(benzyloxy)-2,6(4)-diamino-5-(nitro or nitroso)pyrimidine derivatives and analogues," J Med Chem (1998) 41(4):503-508.
The Pocket Oxford American Dictionary of Current English, "Advise" and "Prescribe" Oxford University Press, New York: 2002, pp. 11 and 623.
Thompson et al., "N6,9-Disubstituted Adenines: Potent, Selective Antagonists at the A1 Adenosine Receptor," J. Med. Chem. (1991) 34:2877-2882.
Thompson et al., "Synthesis and evaluation of 6-(dibromomethyl)-5-nitropyrimidines as potential antitumor agents," J Med Chem (1997) 40(5):766-770.
Tilg and Moschen, "Adipocytokines: mediators linking adipose tissue, inflammation and immunity," Nat. Rev. Immunol., 2006, 2006, 6:772-783.
Trejo et al., "Design and Synthesis of 4-Azaindoles as Inhibitors of p38 MAP Kinase," J. Med. Chem., (2003) 46:4702-4713.
Tseng and Liu, "Peptide YY and cancer: current findings and potential clinical applications," Peptides, 2002, 23:389-395.
Tsukiyama et al., "Gastric Inhibitory Polypeptide as an Endogenous Factor Promoting New Bone Formation after Food Ingestion," Mol Endocrinol., 2006, 20:1644-1651.
Tuomilehto et al., "A Review of the Efficacy of Rosuvastatin in Patients with Type 2 Diabetes," International Journal of Clinical Practice, Supplement, 143, 30-40 (2004).
Turck et al., "Advances in the directed metallation of azines and diazines (pyridines, pyrimidines, pyrazines, pyridazines, quinolones, benzodiazines and carbolines). Part 2: Metallation of pyrimidines, pyrazines, pyridazines and benzodiazines," Tetrahedron (2001) 57(21):4489-4505.
Ueno et al., "The role of PYY in feeding regulation," Regul Pept., 2008, 145:12-16.
Ulrich, "Crystallization," Kirk-Othmer Encyclopedia of the Chemical Technology, 2002, Chapter 4, 8:95-147.
University of Maryland Medical Center, "Familial hypercholesterolemia", http://www.umm.edu/ency/article/000392prv.htm, accessed Jul. 1, 2011, 4 pgs.
Ural et al., "Treatment with Cervistatin in Primary Mixed Hyperlipidemia Induces Changes in Platelet Aggregation and Coagulation System Components," International Journal of Hematology, 76(3):279-283 (2002).
Urgaonkar et al., "Pd/P(i-BuNCH2CH2)3N: an efficient catalyst for Suzuki cross-coupling of aryl bromides and chlorides with arylboronic adds," Tetrahedron Letters (2002) 43(49):8921-8924.
Urwyler et al., "N,N'-Dicydopentyl-2-methylsulfanyl-5-nitropyrimidine-4,6-diamine (GS39783) and structurally related compounds: Novel allosteric enhancers of y-aminobutyric acidB receptor function," Journal of Pharmacology and Experimental Therapeutics (2003) 307(1):322-330.
Vascular Web, "Hyperlipidemia," downloaded from https://www.vascularweb.org/vascularhealth/Pages/Hyperlipidemia.aspx on Jan. 28, 2011, 4 pgs.
Vaughan et al., "The Reformatsky Reaction. I. Zinc and Ethyl α-Bromoisobutyrate," J. Org. Chem, Jun. 1965, 30:1790-1795.
Vice,et al., "Concise Formation of 4-Benzyl Piperidines and Related Derivatives Using a Suzuki Protocol," J. Org. Chem. (2001) 66:2487-2492, Supporting Information, pp. S1-S32.
Vice,et al., "Concise Formation of 4-Benzyl Piperidines and Related Derivatives Using a Suzuki Protocol," J. Org. Chem. (2001) 66:2487-2492.

Villhauer et al., "1-[[(3-Hydroxy-1-adamantypl)amino]acetyl]-2-cyano-(S)-pyrrolidine: A Potent, Selective, and Orally Bioavailable Dipeptidyl Peptidase IV Inhibitor with Antihyperglycemic Properties," J. Med. Chem., 2003, 46:2774-2789.
Villhauer et al., "1-[2-[(5-Cyanopyridin-2-yl)amino]-ethylamino]acetyl-2-(S)-pyrrolidine-carbonitrile: A Potent, Selective, and Orally Bioavailable Dipeptidyl Peptidase IV Inhibitor with Antihyperglycemic Properties," J. Med. Chem., 2002, 45:2362-2365.
Vinogradov et al., "Synthesis and reactions of 1-aryl-3-formyl-4,6-dinitro-1H-indazoles," Mendeleev Communications, 2002, (5), 198-200.
Vippagunta et al., "Crystalline Solids," Advanced Drug Delivery Reviews, 28 (2001) 3-26.
Vona-Davis and McFadden, "PYY and the pancreas: Inhibition of tumor growth and inflammation," Peptides, 2007, 28:334-338.
Wang et al., "Amino-Substituted Heterocycles as Isosteres of Trans-Cinnamides: Design and Synthesis of Heterocyclic Biaryl Sulfides as Potent Antagonists of LFA-1/ICAM-1 Binding," Bioorganic & Medicinal Chemistry Letters, 15(1), 195-201 (2005).
Wang et al., "Improving the oral efficacy of CNS drug candidates: discovery of highly orally efficacious piperidinyl piperidine M2 muscarinic receptor antagonists," J Med Chem (2002). 45(25):5415-5418.
Weber et al., "Microbic Superinfection in Relapse of Inflammatory Bowel Disease," J Clin Gastroenterol., 1992, 14(4):302-308.
Webmd.com, "Type I Diabetes Prevention," http://diabetes.webmd.com/tc/type-1-diabetes-prevention, accessed May 26, 2009, 3 pgs.
Wells et al., Regioselective nucleophilic substitutions of fluorobenzene derivatives, Tetrahedron Letters, (1996) 37(36):6439-6442.
Werbel et al., "Synthesis and antimalarial effects of 5,6-dichioro-2-[(4-[[ [4-(diethylamino)1-methylbutyl]amino [[-6-methyl-2-pyrimidinyl)amino] benzimidazole and related benzimidazoles and I,H-Imidazo[4,5-b] pyridines," J. Het. Chem (1973) vol. 10, 363-382.
West, Solid State Chemistry and its application, New York, 1988, pp. 358 & 365.
Wilson et al., "Microwave-assisted synthesis of 2-aminoquinolines," Tetrahedron Letters (2002) 43(4):581-583.
Winkelmann et al., "Haplotypes of the Cholesteryl Ester Transfer Protein Gene Predict Lipid-Modifying Response to Statin Therapy," Germany Pharmacogenomics Journal, 3(5): 284-296 (2003).
Woldbye et al., "Differential suppression of seizures via Y2 and Y5 neuropeptide Y receptors," Neurobiology of Disease, 2005, 20:760-772.
Wolfe et al., "Scope and limitations of the Pd/BINAP-catalyzed amination of aryl bromides," J Org Chem, 2000, 65(4):1144-1157.
Wolfe et al., "Simple, efficient catalyst system for the palladium-catalyzed amination of aryl chlorides, bromides, and triflates," J Org Chem, 2000, 65(4):1158-1174.
Wolter et al., "Copper-Catalyzed Coupling of Aryl Iodides with Aliphatic Alcohols," Organic Letters, 2002, 4(6):973-976.
Wolter et al., "Copper-Catalyzed Coupling of Aryl Iodides with Aliphatic Alcohols," Organic Letters, 2002, 4(6):973-976, Supporting Information, pp. S1-S16.
World Health Organization Technical Report Series 921, "Prevention and Management of Osteopoosis," 2003, 206 pages.
Wortley et al., "Peptide YY Regulates Bone Turnover in Rodents," Gastroenterol., 2007, 133:1534-1543.
Wu et al., "One-Pot Two-Step Microwave-Assisted Reaction in Constructing 4,5-Disubstituted Pyrazolopyrimidines," Org. Lett., (2003) 5(20):3587-3590.
Wuts, Protective Groups in Organic Synthesis, 3rd edition. John Wiley & Sons, New York (1999) *too voluminous to provide.
Xia et al., "Discovery of a nortropanol derivative as a potent and orally active GPR119 agonist for type 2 diabetes," Bioorganic Med. Chem. Lett., 2011, 21:3290-3296.
Xie et al., "Glucose-dependent insulinotropic polypeptide receptor knockout mice have altered bone turnover," Bone, 2005 37:759-769.
Yamamoto et al., "Correlation of the adipocyte-derived protein adiponectin with insulin resistance index and serum high-density lipoprotein-cholesterol, independent of body mass index, in the Japanese population," Clinical Science, 2002, 103:137-142.

(56) References Cited

OTHER PUBLICATIONS

Yarovenko et al., "New method for the preparation of 5-amino-1,2,4-oxadiazoles," Bull Acad Sci, USSR Div Chem Sci, (1991) 40:1924.

Yokota et al., "Adiponectin, a new member of the family of soluble defense collagens, negatively regulates the growth of myelomonocytic progenitors and the functions of macrophages," Blood, 2000, 96:1723-1732.

Yoon et al., "Reaction of Diisobutylaluminum Hydride with Selected Organic Compounds Containing Representative Functional Groups," J. Org. Chem., (1985) 50:2443-2450.

Yoshida et al., "AS1907417, a novel GPR119 agonist, as an insulinotropic and β-cell preservative agent for the treatment of type 2 diabetes," Biochemical and Biophysical Research Communicaitons, 2010, 400:745-751.

Yuan et al., "3-Aryl pyrazolo[4,3-d]pyrimidine derivatives nonpeptide CRF-1 antagonists," Bioorganic Medicinal Chemistry Lett. (2002) 2133-2136.

Zamponi et al., "Unique structure-activity relationship for 4-isoxazolyl-1,4-dihydropyridines," J Med Chem (2003) 46:87-96.

Zamponi et al., "Unique structure-activity relationship for 4-isoxazolyl-1,4-dihydropyridines," J Med Chem (2003), Supporting Information., pp. 1-31.

Zander et al., "Effect of 6-week course of glucagon-like peptide 1 on glycaemic control, insulin sensitivity, and β-cell function in type 2 diabetes: a parallel-group study," Lancet, 2002, 359:824-830.

Zhang, et al., "Preparation of 1-(Tri-n-Butylstannyl) Furanoid Glycals and Their Use in Palladium-Mediated Coupling Reactions," Tetrahedron Letters (1993) 34(10):1571-1574.

Zhong et al., "Effects of glucose-dependent insulinotropic peptide on osteoclast function," Am J Physiol Endocrinol Metab, 2007, 292:E543-E548.

Zhu et al., Synthesis and mode of action of (125)1- and (3)H-labeled thieno[2,3-c]pyridine antagonists of cell adhesion molecule expression, J Org Chem. (2002) 67(3):943-948.

Zon and Pe Person, "In vivo Drug Discovery in the Zebrafish," Nature Reviews, Jan. 2005, 4:35-44.

Reinsich et al., "Adalimumab for induction of clinical remission in moderately to severely active ulcerative colitis: results of a randomised controlled trial," Gut, 2011, 60:780-787.

* cited by examiner

TIME POINT

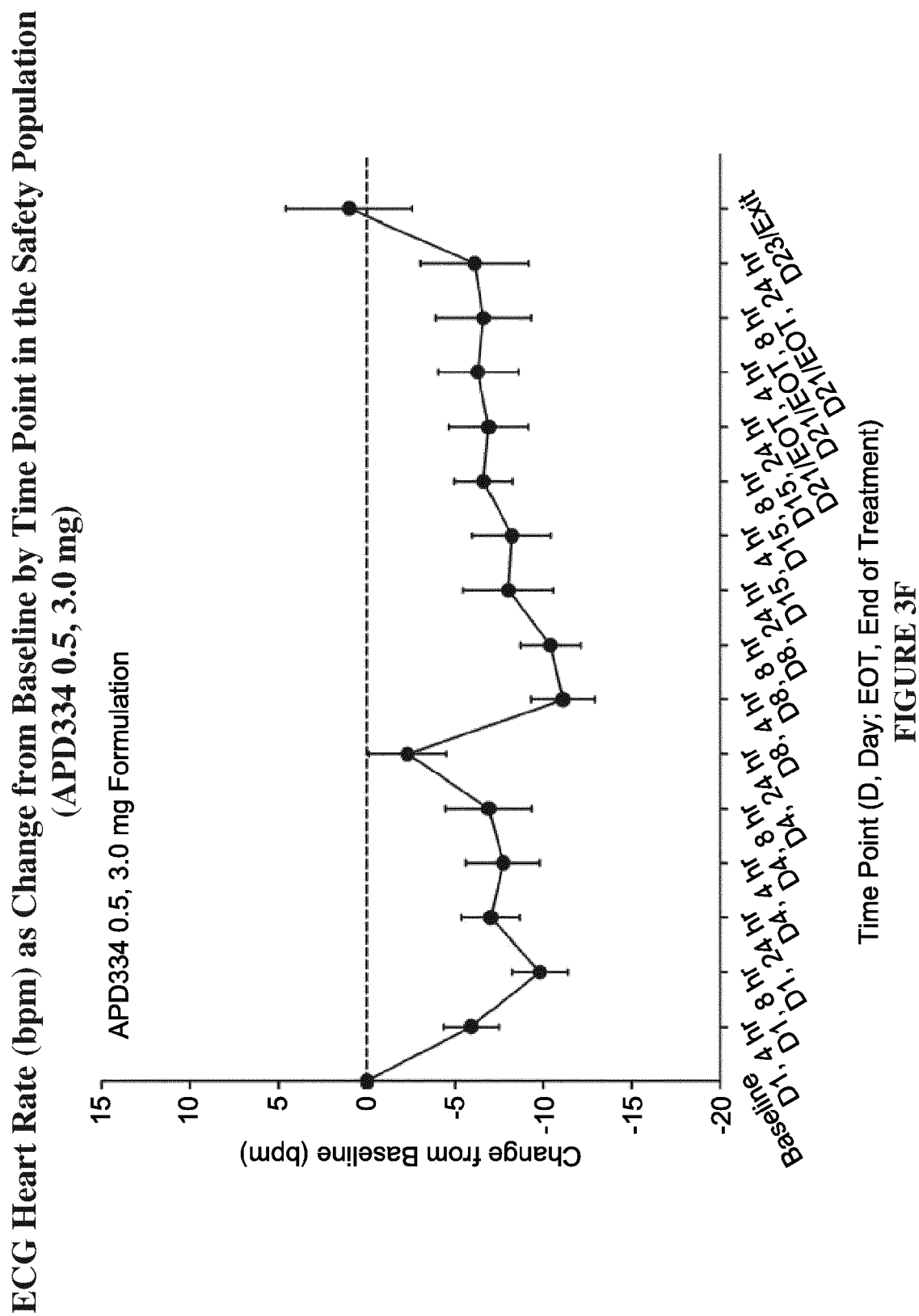

METHODS OF TREATING CONDITIONS RELATED TO THE S1P₁ RECEPTOR

CROSS-REFERENCE TO RELATED APPLICATIONS

This application is a National Stage of International Application No. PCT/US2016/012289, filed Jan. 6, 2016, which claims the benefit of U.S. Provisional Application No. 62/100,362, filed Jan. 6, 2015 and U.S. Provisional Application No. 62/159,550, filed May 11, 2015.

FIELD OF THE INVENTION

Provided are methods useful in the treatment of: sphingosine 1-phosphate subtype 1 ($S1P_1$ or SIP1) receptor-associated disorders.

The sphingosine-1-phosphate (SIP) receptors 1-5 constitute a family of G protein-coupled receptors with a seven-transmembrane domain. These receptors, referred to as $S1P_1$ to $S1P_5$ (formerly termed endothelial differentiation gene (EDG) receptor-1, -5, -3, -6, and -8, respectively; Chun et al., *Pharmacological Reviews*, 54:265-269, 2002), are activated via binding by sphingosine-1-phosphate, which is produced by the sphingosine kinase-catalyzed phosphorylation of sphingosine. $S1P_1$, $S1P_4$, and $S1P_5$ receptors activate Gi but not Gq, whereas $S1P_2$ and $S1P_3$ receptors activate both Gi and Gq. The $S1P_3$ receptor, but not the $S1P_1$ receptor, responds to an agonist with an increase in intracellular calcium.

In view of the growing demand for $S1P_1$ agonists useful in the treatment of $S1P_1$ receptor-associated disorders, the compound (R)-2-(7-(4-cyclopentyl-3-(trifluoromethyl)benzyloxy)-1,2,3,4-tetrahydrocyclopenta[b]indol-3-yl)acetic acid (Compound 1, APD334), or a pharmaceutically acceptable salt, solvate, or hydrate thereof,

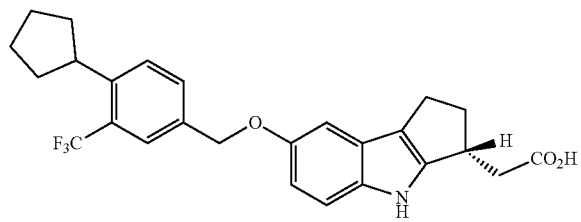 [SMILES: O=C(O)C[C@H]1CCc2c1[nH]c1ccc(OCc3ccc(C4CCCC4)c(C(F)(F)F)c3)cc21]

has emerged as an important new compound, see PCT patent application, Serial No. PCT/US2009/004265 hereby incorporated by reference in its entirety. Compound 1, or a pharmaceutically acceptable salt, solvate, or hydrate thereof, is an investigational drug candidate intended for the treatment of sphingosine 1-phosphate subtype 1 ($S1P_1$) receptor-associated disorders.

There exists a need for effectively treating individuals who are in need of treatment with Compound 1, or a pharmaceutically acceptable salt, solvate, or hydrate thereof. The present disclosure satisfies this need and provides related advantages as well.

Citation of any reference throughout this application is not to be construed as an admission that such reference is prior art to the present application.

SUMMARY

Provided is a method of treatment of a sphingosine 1-phosphate subtype 1 ($S1P_1$) receptor-associated disorder comprising prescribing and/or administering to an individual in need thereof a standard dose of (R)-2-(7-(4-cyclopentyl-3-(trifluoromethyl)benzyloxy)-1,2,3,4-tetrahydrocyclopenta[b]indol-3-yl)acetic acid (Compound 1), or a pharmaceutically acceptable salt, hydrate, or solvate thereof, in an amount equivalent to about 1.5 to about 2.5 mg of Compound 1.

Also provided is a method of treatment of a sphingosine 1-phosphate subtype 1 (S1P1) receptor-associated disorder comprising: prescribing and/or administering to an individual in need thereof a standard dose of (R)-2-(7-(4-cyclopentyl-3-(trifluoromethyl)benzyloxy)-1,2,3,4-tetrahydrocyclopenta[b]indol-3-yl)acetic acid (Compound 1), or a pharmaceutically acceptable salt, hydrate, or solvate thereof, in an amount equivalent to about 2.0 mg of Compound 1.

Also provided is a use of (R)-2-(7-(4-cyclopentyl-3-(trifluoromethyl)benzyloxy)-1,2,3,4-tetrahydrocyclopenta[b]indol-3-yl)acetic acid (Compound 1), or a pharmaceutically acceptable salt, hydrate, or solvate thereof, in the manufacture of a medicament for the treatment of a sphingosine 1-phosphate subtype 1 ($S1P_1$) receptor-associated disorder, the treatment comprising prescribing and/or administering to an individual in need thereof a standard dose of Compound 1, or a pharmaceutically acceptable salt, hydrate, or solvate thereof, in an amount equivalent to about 1.5 to about 2.5 mg of Compound 1.

Also provided is a use of (R)-2-(7-(4-cyclopentyl-3-(trifluoromethyl)benzyloxy)-1,2,3,4-tetrahydrocyclopenta[b]indol-3-yl)acetic acid (Compound 1), or a pharmaceutically acceptable salt, hydrate, or solvate thereof, in the manufacture of a medicament for the treatment of a sphingosine 1-phosphate subtype 1 (S1P1) receptor-associated disorder, the treatment comprising prescribing and/or administering to an individual in need thereof a standard dose of Compound 1, or a pharmaceutically acceptable salt, hydrate, or solvate thereof, in an amount equivalent to about 2.0 mg of Compound 1.

Also provided is a compound that is (R)-2-(7-(4-cyclopentyl-3-(trifluoromethyl)benzyloxy)-1,2,3,4-tetrahydrocyclopenta[b]indol-3-yl)acetic acid (Compound 1), or a pharmaceutically acceptable salt, hydrate, or solvate thereof, for use in a method of treatment of a sphingosine 1-phosphate subtype 1 ($S1P_1$) receptor-associated disorder, the treatment comprising prescribing and/or administering to an individual in need thereof a standard dose of Compound 1, or a pharmaceutically acceptable salt, hydrate, or solvate thereof, in an amount equivalent to about 1.5 to about 2.5 mg of Compound 1. Also provided is a compound that is (R)-2-(7-(4-cyclopentyl-3-(trifluoromethyl)benzyloxy)-1,2,3,4-tetrahydrocyclopenta[b]indol-3-yl)acetic acid (Compound 1), or a pharmaceutically acceptable salt, hydrate, or solvate thereof, for use in a method of treatment of a sphingosine 1-phosphate subtype 1 ($S1P_1$) receptor-associated disorder, the treatment comprising prescribing and/or administering to an individual in need thereof a standard dose of Compound 1, or a pharmaceutically acceptable salt, hydrate, or solvate thereof, in an amount equivalent to about 2.0 mg of Compound 1.

Also provided is a titration package for enabling compliance with a regimen of changing dosage of medication over a period of time for the treatment of a sphingosine 1-phosphate subtype 1 ($S1P_1$) receptor-associated disorder, wherein the medication is (R)-2-(7-(4-cyclopentyl-3-(trifluoromethyl)benzyloxy)-1,2,3,4-tetrahydrocyclopenta[b]indol-3-yl)acetic acid (Compound 1), or a pharmaceutically acceptable salt, hydrate, or solvate thereof, the package comprising:

a first number of daily units of a pharmaceutical composition comprising one or more doses of Compound 1, or a pharmaceutically acceptable salt, hydrate, or solvate thereof, wherein each dose is in an amount equivalent to about 1 mg or less of Compound 1, and a second number of daily units of a pharmaceutical composition comprising a standard dose of Compound 1, or a pharmaceutically acceptable salt, hydrate, or solvate thereof, is in an amount equivalent to about 1.5 to about 2.5 mg of Compound 1.

Also provided is a kit comprising a titration package as described herein, and instructions indicating that the medication is to be administered to an individual in need of treatment of a sphingosine 1-phosphate subtype 1 ($S1P_1$) receptor-associated disorder.

Also provided is a method of treating a sphingosine 1-phosphate subtype 1 ($S1P_1$) receptor-associated disorder comprising providing a kit as described herein to an individual in need thereof.

Also provided is a method of treatment of inflammatory bowel disease comprising: prescribing and/or administering to an individual in need thereof a standard dose of (R)-2-(7-(4-cyclopentyl-3-(trifluoromethyl)benzyloxy)-1,2,3,4-tetrahydrocyclopenta[b]indol-3-yl)acetic acid (Compound 1), or a pharmaceutically acceptable salt, hydrate, or solvate thereof, in an amount equivalent to about 0.5 to about 2.5 mg of Compound 1.

Also provided is a use of (R)-2-(7-(4-cyclopentyl-3-(trifluoromethyl)benzyloxy)-1,2,3,4-tetrahydrocyclopenta[b]indol-3-yl)acetic acid (Compound 1), or a pharmaceutically acceptable salt, hydrate, or solvate thereof, in the manufacture of a medicament for the treatment of inflammatory bowel disease, the treatment comprising prescribing and/or administering to an individual in need thereof a standard dose of Compound 1, or a pharmaceutically acceptable salt, hydrate, or solvate thereof, in an amount equivalent to about 0.5 to about 2.5 mg of Compound 1.

Also provided is a compound that is (R)-2-(7-(4-cyclopentyl-3-(trifluoromethyl)benzyloxy)-1,2,3,4-tetrahydrocyclopenta[b]indol-3-yl)acetic acid (Compound 1), or a pharmaceutically acceptable salt, hydrate, or solvate thereof, for use in a method of treatment of inflammatory bowel disease, the treatment comprising prescribing and/or administering to an individual in need thereof a standard dose of Compound 1, or a pharmaceutically acceptable salt, hydrate, or solvate thereof, in an amount equivalent to about 0.5 to about 2.5 mg of Compound 1.

Also provided is a method of treatment of a sphingosine 1-phosphate subtype 1 ($S1P_1$) receptor-associated disorder comprising:

prescribing and/or administering to an individual in need thereof a standard dose of (R)-2-(7-(4-cyclopentyl-3-(trifluoromethyl)benzyloxy)-1,2,3,4-tetrahydrocyclopenta[b]indol-3-yl)acetic acid (Compound 1), or a pharmaceutically acceptable salt, hydrate, or solvate thereof, in an amount equivalent to about 0.5 to about 2.5 mg of Compound 1, wherein the individual had demonstrated an inadequate response to, loss of response to, or intolerance of at least one agent selected from oral 5-aminosalicylates, corticosteroids, immunosuppressives, TNFα antagonists, and integrin antagonists.

Also provided is a use of (R)-2-(7-(4-cyclopentyl-3-(trifluoromethyl)benzyloxy)-1,2,3,4-tetrahydrocyclopenta[b]indol-3-yl)acetic acid (Compound 1), or a pharmaceutically acceptable salt, hydrate, or solvate thereof, in the manufacture of a medicament for the treatment of a sphingosine 1-phosphate subtype 1 ($S1P_1$) receptor-associated disorder, the treatment comprising prescribing and/or administering to an individual in need thereof a standard dose of Compound 1, or a pharmaceutically acceptable salt, hydrate, or solvate thereof, in an amount equivalent to about 0.5 to about 2.5 mg of Compound 1, wherein the individual had demonstrated an inadequate response to, loss of response to, or intolerance of at least one of agent selected from oral 5-aminosalicylates, corticosteroids, immunosuppressives, TNFα antagonists, and integrin antagonists.

Also provided is a compound that is (R)-2-(7-(4-cyclopentyl-3-(trifluoromethyl)benzyloxy)-1,2,3,4-tetrahydrocyclopenta[b]indol-3-yl)acetic acid (Compound 1), or a pharmaceutically acceptable salt, hydrate, or solvate thereof, for use in a method of treatment of a sphingosine 1-phosphate subtype 1 ($S1P_1$) receptor-associated disorder, the treatment comprising prescribing and/or administering to an individual in need thereof a standard dose of Compound 1, or a pharmaceutically acceptable salt, hydrate, or solvate thereof, in an amount equivalent to about 0.5 to about 2.5 mg of Compound 1, wherein the individual had demonstrated an inadequate response to, loss of response to, or intolerance of at least one of agent selected from oral 5-aminosalicylates, corticosteroids, immunosuppressives, TNFα antagonists, and integrin antagonists.

Also provided is a method of treatment of a sphingosine 1-phosphate subtype 1 ($S1P_1$) receptor-associated disorder comprising:

prescribing and/or administering to a fasted individual in need thereof a standard dose of (R)-2-(7-(4-cyclopentyl-3-(trifluoromethyl)benzyloxy)-1,2,3,4-tetrahydrocyclopenta[b]indol-3-yl)acetic acid (Compound 1), or a pharmaceutically acceptable salt, hydrate, or solvate thereof, in an amount equivalent to about 0.5 to about 2.5 mg of Compound 1.

Also provided is a use of (R)-2-(7-(4-cyclopentyl-3-(trifluoromethyl)benzyloxy)-1,2,3,4-tetrahydrocyclopenta[b]indol-3-yl)acetic acid (Compound 1), or a pharmaceutically acceptable salt, hydrate, or solvate thereof, in the manufacture of a medicament for the treatment of a sphingosine 1-phosphate subtype 1 ($S1P_1$) receptor-associated disorder, the treatment comprising prescribing and/or administering to a fasted individual in need thereof a standard dose of Compound 1, or a pharmaceutically acceptable salt, hydrate, or solvate thereof, in an amount equivalent to about 0.5 to about 2.5 mg of Compound 1.

Also provided is a compound that is (R)-2-(7-(4-cyclopentyl-3-(trifluoromethyl)benzyloxy)-1,2,3,4-tetrahydrocyclopenta[b]indol-3-yl)acetic acid (Compound 1), or a pharmaceutically acceptable salt, hydrate, or solvate thereof, for use in a method of treatment of a sphingosine 1-phosphate subtype 1 ($S1P_1$) receptor-associated disorder, the treatment comprising prescribing and/or administering to a fasted individual in need thereof a standard dose of Compound 1, or a pharmaceutically acceptable salt, hydrate, or solvate thereof, in an amount equivalent to about 0.5 to about 2.5 mg of Compound 1.

These and other aspects of the invention disclosed herein will be set forth in greater detail as the patent disclosure proceeds.

DETAILED DESCRIPTION

Figure 1A:
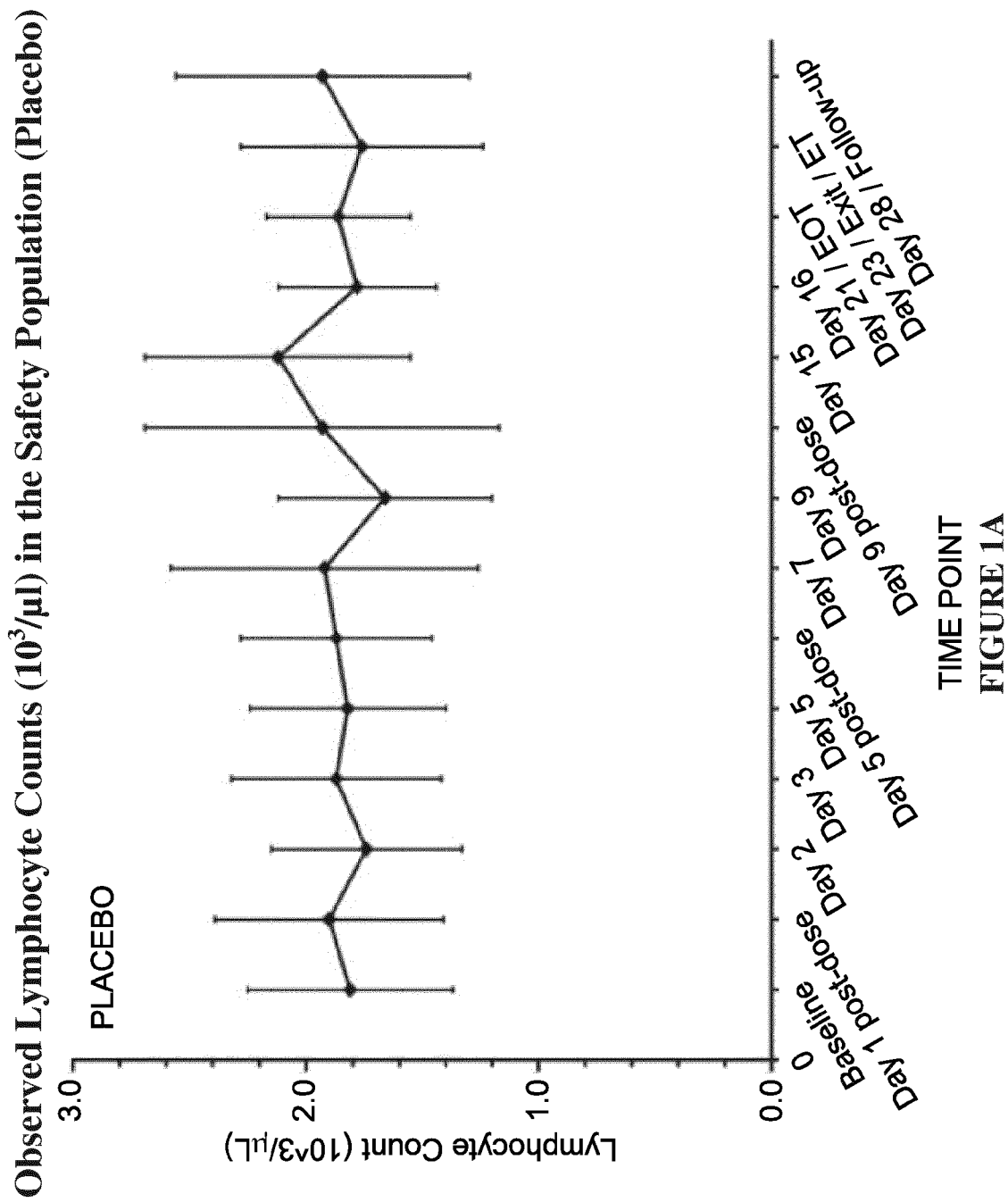
FIG. 1 shows observed lymphocyte counts ($10^3/\mu L$) in the safety population.

As used in the present specification, the following words and phrases are generally intended to have the meanings as set forth below, except to the extent that the context in which they are used indicates otherwise.

Compound 1:

As used herein, "Compound 1" means (R)-2-(7-(4-cyclopentyl-3-(trifluoromethyl)benzyloxy)-1,2,3,4-tetrahydrocyclopenta[b]indol-3-yl)acetic acid including crystalline forms thereof. As a non-limiting example, Compound 1 may be present as an anhydrous, non-solvated crystalline form as described in WO 2010/011316 (incorporated by reference herein in its entirety). As another non-limiting example, an L-arginine salt of Compound 1 may be present as an anhydrous, non-solvated crystalline form as described in WO 2010/011316 and WO 2011/094008 (each of which is incorporated by reference herein in its entirety). As another non-limiting example, a calcium salt of Compound 1 may be present as a crystalline form as described in WO 2010/011316 (incorporated by reference herein in its entirety).

Administering:

As used herein, "administering" means to provide a compound or other therapy, remedy, or treatment. For example, a health care practitioner can directly provide a compound to an individual in the form of a sample, or can indirectly provide a compound to an individual by providing an oral or written prescription for the compound. Also, for example, an individual can obtain a compound by themselves without the involvement of a health care practitioner. Administration of the compound may or may not involve the individual actually internalizing the compound. In the case where an individual internalizes the compound the body is transformed by the compound in some way.

Prescribing:

As used herein, "prescribing" means to order, authorize, or recommend the use of a drug or other therapy, remedy, or treatment. In some embodiments, a health care practitioner can orally advise, recommend, or authorize the use of a compound, dosage regimen or other treatment to an individual. In this case the health care practitioner may or may not provide a prescription for the compound, dosage regimen, or treatment. Further, the health care practitioner may or may not provide the recommended compound or treatment. For example, the health care practitioner can advise the individual where to obtain the compound without providing the compound. In some embodiments, a health care practitioner can provide a prescription for the compound, dosage regimen, or treatment to the individual. For example, a health care practitioner can give a written or oral prescription to an individual. A prescription can be written on paper or on electronic media such as a computer file, for example, on a hand held computer device. For example, a health care practitioner can transform a piece of paper or electronic media with a prescription for a compound, dosage regimen, or treatment. In addition, a prescription can be called in (oral), faxed in (written), or submitted electronically via the internet to a pharmacy or a dispensary. In some embodiments, a sample of the compound or treatment can be given to the individual. As used herein, giving a sample of a compound constitutes an implicit prescription for the compound. Different health care systems around the world use different methods for prescribing and/or administering compounds or treatments and these methods are encompassed by the disclosure.

A prescription can include, for example, an individual's name and/or identifying information such as date of birth. In addition, for example, a prescription can include: the medication name, medication strength, dose, frequency of administration, route of administration, number or amount to be dispensed, number of refills, physician name, physician signature, and the like. Further, for example, a prescription can include a DEA number and/or state number.

A healthcare practitioner can include, for example, a physician, nurse, nurse practitioner, or other related health care professional who can prescribe or administer compounds (drugs) for the treatment of a sphingosine 1-phosphate subtype 1 ($S1l)_1$) receptor-associated disorder. In addition, a healthcare practitioner can include anyone who can recommend, prescribe, administer, or prevent an individual from receiving a compound or drug including, for example, an insurance provider.

Prevent, Preventing, or Prevention:

As used herein, the term "prevent," "preventing", or "prevention" such as prevention of a sphingosine 1-phosphate subtype 1 ($S1l)_1$) receptor-associated disorder or the occurrence or onset of one or more symptoms associated with the particular disorder and does not necessarily mean the complete prevention of the disorder. For example, the term "prevent," "preventing" and "prevention" means the administration of therapy on a prophylactic or preventative basis to an individual who may ultimately manifest at least one symptom of a disease or condition but who has not yet done so. Such individuals can be identified on the basis of risk factors that are known to correlate with the subsequent occurrence of the disease. Alternatively, prevention therapy can be administered without prior identification of a risk factor, as a prophylactic measure. Delaying the onset of at least one symptom can also be considered prevention or prophylaxis.

Treat, Treating, or Treatment:

As used herein the term "treat," "treating", or "treatment" means the administration of therapy to an individual who already manifests at least one symptom of a disease or condition or who has previously manifested at least one symptom of a disease or condition. For example, "treating" can include alleviating, abating or ameliorating a disease or condition symptoms, preventing additional symptoms, ameliorating the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition. For example, the term "treating" in reference to a disorder means a reduction in severity of one or more symptoms associated with that particular disorder. Therefore, treating a disorder does not necessarily mean a reduction in severity of all symptoms associated with a disorder and does not necessarily mean a complete reduction in the severity of one or more symptoms associated with a disorder.

Tolerate:

As used herein, an individual is said to "tolerate" a dose of a compound if administration of that dose to that individual does not result in an unacceptable adverse event or an unacceptable combination of adverse events. One of skill in the art will appreciate that tolerance is a subjective measure and that what may be tolerable to one individual may not be tolerable to a different individual. For example, one individual may not be able to tolerate headache, whereas a second individual may find headache tolerable but is not able to tolerate vomiting, whereas for a third individual, either headache alone or vomiting alone is tolerable, but the individual is not able to tolerate the combination of headache and vomiting, even if the severity of each is less than when experienced alone.

Adverse Event:

As used herein, an "adverse event" is an untoward medical occurrence that is associated with treatment with Compound 1 or a pharmaceutically acceptable salt, solvate, or hydrate thereof. In one embodiment, an adverse event is selected from: leukopenia, constipation, diarrhea, nausea, abdominal pain, neutropenia, vomiting, back pain, and menstrual disorder. In one embodiment, an adverse event is heart block, for example, a first degree atrioventricular heart block. In one embodiment, an adverse event is an abnormal pulmonary function test finding, such as an FEV1 below 80%, FVC. In one embodiment, an adverse event is an abnormal liver function test, such as an elevated ALT & AST<2×ULN. In one embodiment, an adverse event is an acute heart rate reduction.

In Need of Treatment and in Need Thereof:

As used herein, "in need of treatment" and "in need thereof" when referring to treatment are used interchangeably to mean a judgment made by a caregiver (e.g. physician, nurse, nurse practitioner, etc. in the case of humans; veterinarian in the case of animals, including non-human mammals) that an individual or animal requires or will benefit from treatment. This judgment is made based on a variety of factors that are in the realm of a caregiver's expertise, but that includes the knowledge that the individual or animal is ill, or will become ill, as the result of a disease, condition or disorder that is treatable by the compounds of the invention. Accordingly, the compounds of the invention can be used in a protective or preventive manner; or compounds of the invention can be used to alleviate, inhibit or ameliorate the disease, condition or disorder.

Individual:

As used herein, "individual" means any animal, including mammals, preferably mice, rats, other rodents, rabbits, dogs, cats, swine, cattle, sheep, horses, or primates and most preferably humans.

Desensitization of the Heart:

As used herein, "desensitization of the heart" means the absence of an acute heart rate reduction after drug administration.

Acute Heart Rate Reduction:

As used herein, "acute heart rate reduction" means a heart rate decrease from normal sinus rhythm of, for example, 10 or more beats per minute (bpm), such as less than about 5 bpm, e.g., less than about 4 bpm or less than about 3 bpm or less than 2 bpm, that is maximal within a few hours, for example 1-3 hours, after drug administration, and thereafter the heart rate returns towards the pre-dose value.

Normal Sinus Rhythm:

As used herein, "normal sinus rhythm" means the sinus rhythm of the individual when not undergoing treatment. The evaluation of normal sinus rhythm is within the ability of a physician. A normal sinus rhythm will generally give rise to a heart rate in the range from 60-100 bpm.

Dose:

As used herein, "dose" means a quantity of Compound 1, or a pharmaceutically acceptable salt, solvate, or hydrate thereof, given to the individual for treating or preventing the disease or disorder at one specific time.

Standard Dose:

As used herein, "standard dose" means the dose of Compound 1, or a pharmaceutically acceptable salt, solvate, or hydrate thereof, that is given to the individual for treating or preventing the disease or disorder. In some embodiments, administration of the standard dose achieves a target reduction in peripheral blood lymphocyte counts, e.g., a reduction in baseline of at least 35%, such as at least 40%, such as at least 45%, such as at least 50%, such as at least 55%, such as at least 60%, such as at least 65%, such as at least 70%. In some embodiments, administration of the standard dose achieves a reduction in baseline of about 35% to about 70%, such as about 40% to about 65%, such as about 50% to about 65%. In some embodiments, administration of the standard dose achieves target peripheral blood lymphocyte counts, e.g., less than 1000 lymphocytes per microliter, such as 400-800 lymphocytes per microliter. The target dose may vary depending on the nature and severity of the disease to be treated.

One or More Doses:

As used herein, "one or more doses" as used in the phrase "one or more doses, each of which is less than the standard dose" means one or a plurality of doses of Compound 1, or a pharmaceutically acceptable salt, solvate, or hydrate thereof, that is given to the individual during the first period of time and each is less than the standard dose. In some embodiments, the first period comprises a plurality of subperiods wherein a different dose of Compound 1, or a pharmaceutically acceptable salt, solvate, or hydrate thereof, is given to the individual in each of the subperiods. In some embodiments, administration of one or more doses during the first period will have an effect on peripheral blood lymphocyte counts. In some embodiments, administration of one or more doses during the first period will not have effect on peripheral blood lymphocyte counts.

Fasted Individual:

As used herein, "fasted individual" means an individual who has not eaten any food, i.e., has fasted for at least 6-8 hours, such as about 8 hours, before the administration of Compound 1, or a pharmaceutically acceptable salt, hydrate, or solvate thereof, and who does not eat any food and continues to fast for at least 1 hour after the administration of Compound 1, or a pharmaceutically acceptable salt, hydrate, or solvate thereof. In certain embodiments, the individual may also refrain from ingesting certain non-food substances during the fasting period. For example, in certain embodiments the individual does not ingest any supplements and/or drugs during the fasting period. In certain embodiments, the individual does not ingest any high calorie liquids during the fasting period. In certain embodiments, the individual does not ingest any liquids other than water during the fasting period. In certain embodiments, the individual may ingest small amounts of low calorie beverages, such as tea, coffee, or diluted juices.

Mayo Clinic Score (MCS):

As used herein, "Mayo Clinic Score" or "MCS" means an instrument designed to measure disease activity of ulcerative colitis and consists of 4 subscores: stool frequency, rectal bleeding, findings of flexible proctosigmoidoscopy, and physician global assessment with each component ranging from 0 to 3 (0=normal, 1=mild, 2=moderate, 3=severe). Total score therefore ranges from 0 to 12, with a higher score indicating more severe disease. The 6-point Mayo score is based on stool frequency and rectal bleeding PROs collected daily using electronic patient diaries and excludes the findings on endoscopy and the physician's global assessment. The physician's global assessment acknowledges the three other criteria findings of the MCS, the individual's daily record of abdominal discomfort and general sense of well-being, and other observations, such as physical findings and the individual's performance.

Mildly to Moderately Active Ulcerative Colitis:

As used herein, "mildly to moderately active ulcerative colitis" means ulcerative colitis characterized by a 4-component MCS of 4 to 10.

Moderately to Severely Active Ulcerative Colitis:

As used herein, "moderately to severely active ulcerative colitis" means ulcerative colitis characterized by a 3-component MCS of 4 to 9 including an endoscopic subscore of ≥2 and a rectal bleeding score of ≥1. The 3-component MCS uses 3 of the 4 components of the complete MCS (endoscopic findings, rectal bleeding, and stool frequency).

Clinical Remission:

As used herein, "clinical remission" with respect to ulcerative colitis means a 3-component Mayo Clinic score as follows: an endoscopy score (using flexible proctosigmoidoscopy) of 0 or 1, a rectal bleeding score of 0, and a stool frequency score of 0 or 1 with a decrease of ≥1 point from baseline subscore.

Clinical Response:

As used herein, "clinical response" with respect to ulcerative colitis means a reduction in the 3-component Mayo Clinic score of ≥2 points and a decrease of ≥30% from baseline with an accompanying decrease in rectal bleeding subscore of ≥1 or absolute rectal bleeding score of 0 or 1.

Endoscopic Improvement:

As used herein, "endoscopic improvement" with respect to ulcerative colitis means ulcerative colitis characterized by a Mayo endoscopic subscore (using findings of flexible proctosigmoidoscopy) of ≤1 point.

Endoscopic Remission:

As used herein, "endoscopic remission" with respect to ulcerative colitis means ulcerative colitis characterized by findings from flexible proctosigmoidoscopy subscore of the Mayo Clinic score=0.

Improvement in Rectal Bleeding:

As used herein, "improvement in rectal bleeding" with respect to ulcerative colitis means a change from baseline <0.

Histologic Healing:

As used herein, "histologic healing" with respect to ulcerative colitis means a score of <3.1 on the Geboes Index.

Improvement in Stool Frequency:

As used herein, "improvement in stool frequency" with respect to ulcerative colitis means a change from baseline <0.

5-Aminosalicylates:

As used herein, "5-aminosalicylates", means a class of drugs that include, for example, CANASA® (mesalamine), COLAZAL® (balsalazide disodium), ASACOL® (mesalamine), DELZICOL® (mesalamine), and DIPENTUM® (olsalazine).

Immunosuppressives:

As used herein, "immunosuppressives", means a class of drugs that include, for example, AZASAN® (Azathioprine), IMURAN® (Azathioprine), GENGRAF® (Cyclosporine), NEORAL® (Cyclosporine), and SANDIMMUNE® (Cyclosporine).

Glucocorticosteroids:

As used herein, "glucocorticosteroids", means a class of drugs that include, for example, UCERIS® (budesonide); DELTASONE® (prednisone), MEDROL® (methylprednisolone), and hydrocortisone.

TNFα Antagonists:

As used herein, "TNFα antagonists" or "tumor necrosis factor-α antagonists", means a class of drugs that include, for example, SIMPONI® (golimumab), REMICADE® (infliximab), and HUMIRA® (adalimumab).

Integrin Receptor Antagonists:

As used herein, "integrin receptor antagonists", means a class of drugs that include, for example, ENTYVIO® (vedolizumab).

Pharmaceutical Composition:

As used here, "pharmaceutical composition" means a composition comprising at least one active ingredient, such as Compound 1; including but not limited to, salts, solvates, and hydrates of Compound 1, whereby the composition is amenable to investigation for a specified, efficacious outcome in a mammal (for example, without limitation, a human) Those of ordinary skill in the art will understand and appreciate the techniques appropriate for determining whether an active ingredient has a desired efficacious outcome based upon the needs of the artisan.

Agonist:

As used herein, "agonist" means a moiety that interacts with and activates a G-protein-coupled receptor, such as the $S1P_1$ receptor, such as can thereby initiate a physiological or pharmacological response characteristic of that receptor. For example, an agonist activates an intracellular response upon binding to the receptor, or enhances GTP binding to a membrane. In certain embodiments, an agonist of the invention is an $S1P_1$ receptor agonist that is capable of facilitating sustained $S1P_1$ receptor internalization (see e.g., Matloubian et al., Nature, 427, 355, 2004).

Antagonist:

As used herein, "antagonist" means a moiety that competitively binds to the receptor at the same site as an agonist (for example, the endogenous ligand), but which does not activate the intracellular response initiated by the active form of the receptor and can thereby inhibit the intracellular responses by an agonist or partial agonist. An antagonist does not diminish the baseline intracellular response in the absence of an agonist or partial agonist.

Inverse Agonist:

As used herein, "inverse agonist" means a moiety that binds to the endogenous form of the receptor or to the constitutively activated form of the receptor and which inhibits the baseline intracellular response initiated by the active form of the receptor below the normal base level of activity which is observed in the absence of an agonist or partial agonist, or decreases GTP binding to a membrane. In some embodiments, the baseline intracellular response is inhibited in the presence of the inverse agonist by at least 30%. In some embodiments, the baseline intracellular response is inhibited in the presence of the inverse agonist by at least 50%. In some embodiments, the baseline intracellular response is inhibited in the presence of the inverse agonist by at least 75%, as compared with the baseline response in the absence of the inverse agonist.

Hydrate:

As used herein, "hydrate" means a compound of the invention or a salt thereof, that further includes a stoichiometric or non-stoichiometric amount of water bound by non-covalent intermolecular forces.

Safety Population:

As used herein, "safety population" means all randomized subjects who received study medication. See, e.g., Tables 3 and 4 below.

Solvate:

As used herein, "solvate" means a compound of the invention or a salt, thereof, that further includes a stoichiometric or non-stoichiometric amount of a solvent bound by non-covalent intermolecular forces. Preferred solvents are volatile, non-toxic, and/or acceptable for administration to humans in trace amounts.

The compounds according to the invention may optionally exist as pharmaceutically acceptable salts including pharmaceutically acceptable acid addition salts prepared from pharmaceutically acceptable non-toxic acids including inorganic and organic acids. Representative acids include, but are not limited to, acetic, benzenesulfonic, benzoic, camphorsulfonic, citric, ethenesulfonic, dichloroacetic, formic, fumaric, gluconic, glutamic, hippuric, hydrobromic, hydrochloric, isethionic, lactic, maleic, malic, mandelic, methanesulfonic, mucic, nitric, oxalic, pamoic, pantothenic, phosphoric, succinic, sulfiric, tartaric, oxalic, p-toluenesulfonic and the like, such as those pharmaceutically acceptable salts listed by Berge et al., *Journal of Pharmaceutical Sciences*, 66:1-19 (1977), incorporated herein by reference in its entirety.

The acid addition salts may be obtained as the direct products of compound synthesis. In the alternative, the free base may be dissolved in a suitable solvent containing the appropriate acid and the salt isolated by evaporating the solvent or otherwise separating the salt and solvent. The compounds of this invention may form solvates with standard low molecular weight solvents using methods known to the skilled artisan.

It is understood that when the phrase "pharmaceutically acceptable salts, solvates and hydrates" or the phrase "pharmaceutically acceptable salt, solvate, or hydrate" is used when referring to Compound 1, it embraces pharmaceutically acceptable solvates and/or hydrates of Compound 1, pharmaceutically acceptable salts of Compound 1, as well as pharmaceutically acceptable solvates and/or hydrates of pharmaceutically acceptable salts of Compound 1. It is also understood that when the phrase "pharmaceutically acceptable solvates and hydrates" or the phrase "pharmaceutically acceptable solvate or hydrate" is used when referring to Compound 1 that are salts, it embraces pharmaceutically acceptable solvates and/or hydrates of such salts.

It will be apparent to those skilled in the art that the dosage forms described herein may comprise, as the active component, either Compound 1 or a pharmaceutically acceptable salt or as a solvate or hydrate thereof. Moreover, various hydrates and solvates of Compound 1 and their salts will find use as intermediates in the manufacture of pharmaceutical compositions. Typical procedures for making and identifying suitable hydrates and solvates, outside those mentioned herein, are well known to those in the art; see for example, pages 202-209 of K. J. Guillory, "Generation of Polymorphs, Hydrates, Solvates, and Amorphous Solids," in: Polymorphism in Pharmaceutical Solids, ed. Harry G. Britain, Vol. 95, Marcel Dekker, Inc., New York, 1999. Accordingly, one aspect of the present disclosure pertains to methods of prescribing and/or administering hydrates and solvates of Compound 1 and/or its pharmaceutical acceptable salts, that can be isolated and characterized by methods known in the art, such as, thermogravimetric analysis (TGA), TGA-mass spectroscopy, TGA-Infrared spectroscopy, powder X-ray diffraction (XRPD), Karl Fisher titration, high resolution X-ray diffraction, and the like. There are several commercial entities that provide quick and efficient services for identifying solvates and hydrates on a routine basis. Example companies offering these services include Wilmington PharmaTech (Wilmington, Del.), Avantium Technologies (Amsterdam) and Aptuit (Greenwich, Conn.).

The present disclosure includes all isotopes of atoms occurring in the present compounds, salts, solvates, and hydrates. Isotopes include those atoms having the same atomic number but different mass numbers. One aspect of the present invention includes every combination of one or more atoms in the present compounds, salts, solvates, and hydrates that is replaced with an atom having the same atomic number but a different mass number. One such example is the replacement of an atom that is the most naturally abundant isotope, such as $^1$H or $^{12}$C, found in one the present compounds, salts, solvates, and hydrates, with a different atom that is not the most naturally abundant isotope, such as $^2$H or $^3$H (replacing $^1$H), or $^{11}$C, $^{13}$C, or $^{14}$C (replacing $^{12}$C). When such a replacement has taken place it is commonly referred to as being isotopically-labeled. Isotopic-labeling of the present compounds, salts, solvates, and hydrates can be accomplished using any one of a variety of different synthetic methods know to those of ordinary skill in the art and they are readily credited with understanding the synthetic methods and available reagents needed to conduct such isotopic-labeling. By way of general example, and without limitation, isotopes of hydrogen include $^2$H (deuterium) and $^3$H (tritium). Isotopes of carbon include $^{11}$C, $^{13}$C, and $^{14}$C. Isotopes of nitrogen include $^{13}$N and $^{15}$N. Isotopes of oxygen include $^{15}$O, $^{12}$O, and $^{18}$O. An isotope of fluorine includes $^{18}$F. An isotope of sulfur includes $^{35}$S. An isotope of chlorine includes $^{36}$Cl. Isotopes of bromine include $^{75}$Br, $^{76}$Br, $^{77}$Br, and $^{82}$Br. Isotopes of iodine include $^{123}$I, $^{124}$I, $^{125}$I, and $^{131}$I. Another aspect of the present invention includes compositions, such as, those prepared during synthesis, preformulation, and the like, and pharmaceutical compositions, such as, those prepared with the intent of using in a mammal for the treatment of one or more of the disorders described herein, comprising one or more of the present compounds, salts, solvates, and hydrates, wherein the naturally occurring distribution of the isotopes in the composition is perturbed. Another aspect of the present invention includes compositions and pharmaceutical compositions comprising the compounds, salts, solvates, and hydrates, as described herein wherein the salt is enriched at one or more positions with an isotope other than the most naturally abundant isotope. Methods are readily available to measure such isotope perturbations or enrichments, such as, mass spectrometry, and for isotopes that are radio-isotopes additional methods are available, such as, radio-detectors used in connection with HPLC or GC.

Compounds of the present invention can be converted to "prodrugs." The term "prodrugs" means compounds that have been modified with specific chemical groups known in the art and that when administered into an individual undergo biotransformation to give the parent compound. Prodrugs can thus be viewed as compounds of the invention containing one or more specialized non-toxic protective groups used in a transient manner to alter or to eliminate a property of the compound. In one general aspect, the "prodrug" approach is utilized to facilitate oral absorption. A thorough discussion is provided in T. Higuchi and V. Stella, Prodrugs as Novel Delivery Systems Vol. 14 of the A.C.S. Symposium Series; and in *Bioreversible Carriers in Drug Design*, ed. Edward B. Roche, American Pharmaceutical Association and Pergamon Press, 1987, both of which are hereby incorporated by reference in their entirety.

When an integer is used in a method disclosed herein, the term "about" can be inserted before the integer.

Throughout this specification, unless the context requires otherwise, the word "comprise", or variations such as "comprises" or "comprising" will be understood to imply the inclusion of a stated step or element or integer or group of steps or elements or integers but not the exclusion of any other step or element or integer or group of elements or integers.

Throughout this specification, unless specifically stated otherwise or the context requires otherwise, reference to a single step, composition of matter, group of steps, or group of compositions of matter shall be taken to encompass one and a plurality (i.e. one or more) of those steps, compositions of matter, groups of steps, or groups of compositions of matter.

Each embodiment described herein is to be applied mutatis mutandis to each and every other embodiment unless specifically stated otherwise.

Those skilled in the art will appreciate that the invention(s) described herein is susceptible to variations and modifications other than those specifically described. It is to be understood that the invention(s) includes all such variations and modifications. The invention(s) also includes all of the steps, features, compositions and compounds referred to or indicated in this specification, individually or collectively, and any and all combinations or any two or more of said steps or features unless specifically stated otherwise.

The present invention(s) is not to be limited in scope by the specific embodiments described herein, which are intended for the purpose of exemplification only. Functionally-equivalent products, compositions, and methods are clearly within the scope of the invention(s), as described herein.

It is appreciated that certain features of the invention(s), which are, for clarity, described in the context of separate embodiments, can also be provided in combination in a single embodiment. Conversely, various features of the invention(s), which are, for brevity, described in the context of a single embodiment, can also be provided separately or in any suitable subcombination. For example, a method that recites prescribing and/or administering Compound 1 or a pharmaceutically acceptable salt, solvate, or hydrate thereof can be separated into two methods; one method reciting prescribing Compound 1 or a pharmaceutically acceptable salt, solvate, or hydrate thereof and the other method reciting administering Compound 1 or a pharmaceutically acceptable salt, solvate, or hydrate thereof. In addition, for example, a method that recites prescribing Compound 1 or a pharmaceutically acceptable salt, solvate, or hydrate thereof and a separate method of the invention reciting administering Compound 1 or a pharmaceutically acceptable salt, solvate, or hydrate thereof can be combined into a single method reciting prescribing and/or administering Compound 1 or a pharmaceutically acceptable salt, solvate, or hydrate thereof.

Provided is a method of treatment of a sphingosine 1-phosphate subtype 1 ($S1P_1$) receptor-associated disorder comprising prescribing and/or administering to an individual in need thereof a standard dose of (R)-2-(7-(4-cyclopentyl-3-(trifluoromethyl)benzyloxy)-1,2,3,4-tetrahydrocyclopenta[b]indol-3-yl)acetic acid (Compound 1), or a pharmaceutically acceptable salt, hydrate, or solvate thereof, in an amount equivalent to about 1.5 to about 2.5 mg of Compound 1.

Also provided is a method of treatment of a sphingosine 1-phosphate subtype 1 ($S1P_1$) receptor-associated disorder comprising:
prescribing and/or administering to an individual in need thereof a standard dose of (R)-2-(7-(4-cyclopentyl-3-(trifluoromethyl)benzyloxy)-1,2,3,4-tetrahydrocyclopenta[b]indol-3-yl)acetic acid (Compound 1), or a pharmaceutically acceptable salt, hydrate, or solvate thereof, in an amount equivalent to about 0.5 to about 2.5 mg of Compound 1,
wherein the individual had demonstrated an inadequate response to, loss of response to, or intolerance of at least one agent selected from oral 5-aminosalicylates, corticosteroids, immunosuppressives, TNFα antagonists, and integrin antagonists.

Also provided is a method of treatment of a sphingosine 1-phosphate subtype 1 ($S1P_1$) receptor-associated disorder comprising:
prescribing and/or administering to a fasted individual in need thereof a standard dose of (R)-2-(7-(4-cyclopentyl-3-(trifluoromethyl)benzyloxy)-1,2,3,4-tetrahydrocyclopenta[b]indol-3-yl)acetic acid (Compound 1), or a pharmaceutically acceptable salt, hydrate, or solvate thereof, in an amount equivalent to about 0.5 to about 2.5 mg of Compound 1.

Also provided is a method of treatment of inflammatory bowel disease comprising:
prescribing and/or administering to an individual in need thereof a standard dose of (R)-2-(7-(4-cyclopentyl-3-(trifluoromethyl)benzyloxy)-1,2,3,4-tetrahydrocyclopenta[b]indol-3-yl)acetic acid (Compound 1), or a pharmaceutically acceptable salt, hydrate, or solvate thereof, in an amount equivalent to about 0.5 to about 2.5 mg of Compound 1.

In some embodiments, the treatment further comprises prescribing and/or administering to the individual Compound 1, or a pharmaceutically acceptable salt, hydrate, or solvate thereof, one or more doses, each of which is less than the standard dose, for a first period of time prior to prescribing and/or administering to the individual Compound 1, or a pharmaceutically acceptable salt, hydrate, or solvate thereof, at the standard dose.

In some embodiments, the treatment reduces a lymphocyte count in the individual by at least 40%. In some embodiments, the treatment reduces a lymphocyte count in the individual by at least 45%, 50%, 55%, 60%, or 65%.

In some embodiments, the treatment further comprises monitoring for adverse events during the administration of Compound 1, or a pharmaceutically acceptable salt, hydrate, or solvate thereof, and optionally, interrupting, or terminating the administration of Compound 1, or a pharmaceutically acceptable salt, hydrate, or solvate thereof.

In some embodiments, the treatment further comprises monitoring heart rate during the administration, monitoring pulmonary function during the administration, or monitoring liver function during the administration.

In some embodiments, the treatment further comprises monitoring heart rate during the administration.

In some embodiments, the treatment further comprises monitoring pulmonary function during the administration.

In some embodiments, the treatment further comprises monitoring liver function during the administration.

In some embodiments of the method of treatment of inflammatory bowel disease, e.g., ulcerative colitis, such as moderately to severely active ulcerative colitis, the treatment results in inducing clinical remission. In some embodiments of the method of treatment of inflammatory bowel disease, e.g., ulcerative colitis, such as moderately to severely active ulcerative colitis, the treatment results in maintaining clinical remission. In some embodiments of the method of treatment of inflammatory bowel disease, e.g., ulcerative colitis, such as moderately to severely active ulcerative colitis, the treatment results in inducing and maintaining clinical remission.

In some embodiments of the method of treatment of inflammatory bowel disease, e.g., ulcerative colitis, such as moderately to severely active ulcerative colitis, the treatment results in inducing clinical response. In some embodiments of the method of treatment of inflammatory bowel disease, e.g., ulcerative colitis, such as moderately to severely active ulcerative colitis, the treatment results in maintaining clinical response. In some embodiments of the method of treatment of inflammatory bowel disease, e.g., ulcerative colitis, such as moderately to severely active ulcerative colitis, the treatment results in inducing and maintaining clinical response.

In some embodiments of the method of treatment of inflammatory bowel disease, e.g., ulcerative colitis, such as moderately to severely active ulcerative colitis, the treatment results in endoscopic improvement, e.g., improving endoscopic appearance of the mucosa.

In some embodiments of the method of treatment of inflammatory bowel disease, e.g., ulcerative colitis, such as moderately to severely active ulcerative colitis, the treatment results in corticosteroid-free remission.

In some embodiments of the method of treatment of inflammatory bowel disease, e.g., ulcerative colitis, such as moderately to severely active ulcerative colitis, the treatment results in endoscopic remission.

In some embodiments of the method of treatment of inflammatory bowel disease, e.g., ulcerative colitis, such as moderately to severely active ulcerative colitis, the treatment results in an improvement in rectal bleeding.

In some embodiments of the method of treatment of inflammatory bowel disease, e.g., ulcerative colitis, such as moderately to severely active ulcerative colitis, the treatment results in histologic healing.

In some embodiments of the method of treatment of inflammatory bowel disease, e.g., ulcerative colitis, such as moderately to severely active ulcerative colitis, the treatment results in an improvement in stool frequency.

In some embodiments of the method of treatment of inflammatory bowel disease, e.g., ulcerative colitis, such as moderately to severely active ulcerative colitis, the treatment further comprises monitoring the level of level of fecal calprotectin.

In some embodiments of the method of treatment of inflammatory bowel disease, e.g., ulcerative colitis, such as moderately to severely active ulcerative colitis, the treatment further comprises monitoring the level of level of c-reactive protein (CRP).

In some embodiments, the standard dose is in an amount equivalent to 1 mg of Compound 1.

In some embodiments, the standard dose is in an amount equivalent to 2 mg of Compound 1.

In some embodiments, the standard dose is administered to the individual throughout the treatment.

In some embodiments, the standard dose of Compound 1, or a pharmaceutically acceptable salt, hydrate, or solvate thereof is administered once daily to the individual.

In some embodiments, each of the one or more doses is an amount sufficient to induce desensitization of the heart and is administered at a frequency that sustains desensitization of the heart, until no further acute heart rate reduction occurs.

In some embodiments, one dose of Compound 1, or a pharmaceutically acceptable salt, hydrate, or solvate thereof, is less than the standard dose, are prescribed and/or administered for the first period of time, i.e., an equivalent dose of Compound 1, or a pharmaceutically acceptable salt, hydrate, or solvate thereof, is prescribed and/or administered each day of the first period of time.

In some embodiments, two or more doses of Compound 1, or a pharmaceutically acceptable salt, hydrate, or solvate thereof, each of which is less than the standard dose, are prescribed and/or administered for the first period of time.

In some embodiments, two doses of Compound 1, or a pharmaceutically acceptable salt, hydrate, or solvate thereof, each of which is less than the standard dose and wherein the second dose is more than the first dose, are prescribed and/or administered for the first period of time. In some embodiments, each of the two doses is prescribed and/or administered for one or more days. In some embodiments, two doses of Compound 1, or a pharmaceutically acceptable salt, hydrate, or solvate thereof, each of which is less than the standard dose and wherein the second dose is less than the first dose, are prescribed and/or administered for the first period of time.

In some embodiments, three or more doses of Compound 1, or a pharmaceutically acceptable salt, hydrate, or solvate thereof, each of which is less than the standard dose, are prescribed and/or administered for the first period of time.

In some embodiments, the three or more doses escalate in amount such that the first dose is less than the second dose, which in turn is less than the third dose, etc.

In some embodiments, the three or more doses do not escalate in amount. For example, in some embodiments, the three or more doses step down or de-escalate in amount such that the first dose is more than the second dose, which in turn is more than the third dose, etc. Alternatively, in some embodiments, the first dose is more than the second dose but the second dose is also more than the third dose.

In some embodiments, each of the one or more doses is about 2-fold to about 8-fold lower than the standard dose, about 3-fold to about 7-fold lower than the standard dose, about 4-fold lower than the standard dose, or about 6-fold lower than the standard dose. In some embodiments, each of the one or more doses is about 2-fold to about 8-fold lower than the standard dose. In some embodiments, one of the one or more doses is about 2-fold to about 8-fold lower than the standard dose. In some embodiments, at least one of the one or more doses is about 2-fold to about 8-fold lower than the standard dose. In some embodiments, more than one of the one or more doses is about 2-fold to about 8-fold lower than the standard dose.

In some embodiments, each of the one or more doses is about 3-fold to about 7-fold lower than the standard dose. In some embodiments, one of the one or more doses is about 3-fold to about 7-fold lower than the standard dose. In some embodiments, at least one of the one or more doses is about 3-fold to about 7-fold lower than the standard dose. In some embodiments, more than one of the one or more doses is about 3-fold to about 7-fold lower than the standard dose.

In some embodiments, each of the one or more doses is about 4-fold lower than the standard dose. In some embodiments, one of the one or more doses is about 4-fold lower than the standard dose. In some embodiments, at least one of the one or more doses is about 4-fold lower than the standard dose. In some embodiments, more than one of the one or more doses is about 4-fold lower than the standard dose.

In some embodiments, each of the one or more doses is about 6-fold lower than the standard dose. In some embodiments, one of the one or more doses is about 6-fold lower than the standard dose. In some embodiments, at least one of the one or more doses is about 6-fold lower than the standard dose. In some embodiments, more than one of the one or more doses is about 6-fold lower than the standard dose.

In some embodiments, at least one of the one or more doses is about 6-fold lower than the standard dose and at least one of the one or more doses is about 4-fold lower than the standard dose. In some embodiments, one of the one or more doses is about 6-fold lower than the standard dose and one of the one or more doses is about 4-fold lower than the standard dose.

In some embodiments, each of the one or more doses of Compound 1, or a pharmaceutically acceptable salt, hydrate, or solvate thereof, is equivalent to about 0.1 to about 1 mg of Compound 1, about 0.3 to about 0.8 mg of Compound 1, about 0.35 mg of Compound 1, or about 0.5 mg of Compound 1. In some embodiments, each of the one or more doses of Compound 1, or a pharmaceutically acceptable salt, hydrate, or solvate thereof, is equivalent to about 0.1 to about 1 mg of Compound 1. In some embodiments, at least one of the one or more doses of Compound 1, or a pharmaceutically acceptable salt, hydrate, or solvate thereof, is equivalent to about 0.1 to about 1 mg of Compound 1. In some embodiments, one of the one or more doses of Compound 1, or a pharmaceutically acceptable salt, hydrate, or solvate thereof, is equivalent to about 0.1 to about 1 mg of Compound 1. In some embodiments, more than one of the one or more doses of Compound 1, or a pharmaceutically acceptable salt, hydrate, or solvate thereof, is equivalent to about 0.1 to about 1 mg of Compound 1.

In some embodiments, each of the one or more doses of Compound 1, or a pharmaceutically acceptable salt, hydrate, or solvate thereof, is equivalent to about 0.2 to about 0.8 mg of Compound 1. In some embodiments, at least one of the one or more doses of Compound 1, or a pharmaceutically acceptable salt, hydrate, or solvate thereof, is equivalent to about 0.2 to about 0.8 mg of Compound 1. In some embodiments, one of the one or more doses of Compound 1, or a pharmaceutically acceptable salt, hydrate, or solvate thereof, is equivalent to about 0.2 to about 0.8 mg of Compound 1. In some embodiments, more than one of the one or more doses of Compound 1, or a pharmaceutically acceptable salt, hydrate, or solvate thereof, is equivalent to about 0.2 to about 0.8 mg of Compound 1.

In some embodiments, each of the one or more doses of Compound 1, or a pharmaceutically acceptable salt, hydrate, or solvate thereof, is equivalent to about 0.25 mg of Compound 1. In some embodiments, at least one of the one or more doses of Compound 1, or a pharmaceutically acceptable salt, hydrate, or solvate thereof, is equivalent to about 0.25 mg of Compound 1. In some embodiments, one of the one or more doses of Compound 1, or a pharmaceutically acceptable salt, hydrate, or solvate thereof, is equivalent to about 0.25 mg of Compound 1. In some embodiments, more than one of the one or more doses of Compound 1, or a pharmaceutically acceptable salt, hydrate, or solvate thereof, is equivalent to about 0.25 mg of Compound 1.

In some embodiments, each of the one or more doses of Compound 1, or a pharmaceutically acceptable salt, hydrate, or solvate thereof, is equivalent to about 0.3 to about 0.8 mg of Compound 1. In some embodiments, at least one of the one or more doses of Compound 1, or a pharmaceutically acceptable salt, hydrate, or solvate thereof, is equivalent to about 0.3 to about 0.8 mg of Compound 1. In some embodiments, one of the one or more doses of Compound 1, or a pharmaceutically acceptable salt, hydrate, or solvate thereof, is equivalent to about 0.3 to about 0.8 mg of Compound 1. In some embodiments, more than one of the one or more doses of Compound 1, or a pharmaceutically acceptable salt, hydrate, or solvate thereof, is equivalent to about 0.3 to about 0.8 mg of Compound 1.

In some embodiments, each of the one or more doses of Compound 1, or a pharmaceutically acceptable salt, hydrate, or solvate thereof, is equivalent to about 0.35 mg of Compound 1. In some embodiments, at least one of the one or more doses of Compound 1, or a pharmaceutically acceptable salt, hydrate, or solvate thereof, is equivalent to about 0.35 mg of Compound 1. In some embodiments, one of the one or more doses of Compound 1, or a pharmaceutically acceptable salt, hydrate, or solvate thereof, is equivalent to about 0.35 mg of Compound 1. In some embodiments, more than one of the one or more doses of Compound 1, or a pharmaceutically acceptable salt, hydrate, or solvate thereof, is equivalent to about 0.35 mg of Compound 1.

In some embodiments, each of the one or more doses of Compound 1, or a pharmaceutically acceptable salt, hydrate, or solvate thereof, is equivalent to about 0.5 mg of Compound 1. In some embodiments, at least one of the one or more doses of Compound 1, or a pharmaceutically acceptable salt, hydrate, or solvate thereof, is equivalent to about 0.5 mg of Compound 1. In some embodiments, one of the one or more doses of Compound 1, or a pharmaceutically acceptable salt, hydrate, or solvate thereof, is equivalent to about 0.5 mg of Compound 1. In some embodiments, more than one of the one or more doses of Compound 1, or a pharmaceutically acceptable salt, hydrate, or solvate thereof, is equivalent to about 0.5 mg of Compound 1.

In some embodiments, each of the one or more doses of Compound 1, or a pharmaceutically acceptable salt, hydrate, or solvate thereof, is in an amount equivalent to 0.5 mg of Compound 1; and the standard dose of Compound 1, or a pharmaceutically acceptable salt, hydrate, or solvate thereof, is in an amount equivalent to 1 mg of Compound 1. In some embodiments, at least one of the one or more doses of Compound 1, or a pharmaceutically acceptable salt, hydrate, or solvate thereof, is in an amount equivalent to 0.5 mg of Compound 1; and the standard dose of Compound 1, or a pharmaceutically acceptable salt, hydrate, or solvate thereof, is in an amount equivalent to 1 mg of Compound 1. In some embodiments, one of the one or more doses of Compound 1, or a pharmaceutically acceptable salt, hydrate, or solvate thereof, is in an amount equivalent to 0.5 mg of Compound 1; and the standard dose of Compound 1, or a pharmaceutically acceptable salt, hydrate, or solvate thereof, is in an amount equivalent to 1 mg of Compound 1. In some embodiments, more than one of the one or more doses of Compound 1, or a pharmaceutically acceptable salt, hydrate, or solvate thereof, is in an amount equivalent to 0.5 mg of Compound 1; and the standard dose of Compound 1, or a pharmaceutically acceptable salt, hydrate, or solvate thereof, is in an amount equivalent to 1 mg of Compound 1.

In some embodiments, each of the one or more doses of Compound 1, or a pharmaceutically acceptable salt, hydrate, or solvate thereof, is in an amount equivalent to 0.5 mg of Compound 1; and the standard dose of Compound 1, or a pharmaceutically acceptable salt, hydrate, or solvate thereof, is in an amount equivalent to 2 mg of Compound 1. In some embodiments, at least one of the one or more doses of Compound 1, or a pharmaceutically acceptable salt, hydrate, or solvate thereof, is in an amount equivalent to 0.5 mg of Compound 1; and the standard dose of Compound 1, or a pharmaceutically acceptable salt, hydrate, or solvate thereof, is in an amount equivalent to 2 mg of Compound 1. In some embodiments, one of the one or more doses of Compound 1, or a pharmaceutically acceptable salt, hydrate, or solvate thereof, is in an amount equivalent to 0.5 mg of Compound 1; and the standard dose of Compound 1, or a pharmaceutically acceptable salt, hydrate, or solvate thereof, is in an amount equivalent to 2 mg of Compound 1. In some embodiments, more than one of the one or more doses of Compound 1, or a pharmaceutically acceptable salt, hydrate, or solvate thereof, is in an amount equivalent to 0.5 mg of Compound 1; and the standard dose of Compound 1, or a pharmaceutically acceptable salt, hydrate, or solvate thereof, is in an amount equivalent to 2 mg of Compound 1.

In some embodiments, each of the one or more doses of Compound 1, or a pharmaceutically acceptable salt, hydrate, or solvate thereof, is in an amount equivalent to 0.35 mg of Compound 1; and the standard dose of Compound 1, or a pharmaceutically acceptable salt, hydrate, or solvate thereof, is in an amount equivalent to 1 mg of Compound 1. In some embodiments, at least one of the one or more doses of Compound 1, or a pharmaceutically acceptable salt, hydrate, or solvate thereof, is in an amount equivalent to 0.35 mg of Compound 1; and the standard dose of Compound 1, or a pharmaceutically acceptable salt, hydrate, or solvate thereof, is in an amount equivalent to 1 mg of Compound 1. In some embodiments, one of the one or more doses of Compound 1, or a pharmaceutically acceptable salt, hydrate, or solvate thereof, is in an amount equivalent to 0.35 mg of Compound 1; and the standard dose of Compound 1, or a pharmaceutically acceptable salt, hydrate, or solvate thereof, is in an amount equivalent to 1 mg of Compound 1. In some embodiments, more than one of the one or more doses of Compound 1, or a pharmaceutically acceptable salt, hydrate, or solvate thereof, is in an amount equivalent to 0.35 mg of Compound 1; and the standard dose of Compound 1, or a pharmaceutically acceptable salt, hydrate, or solvate thereof, is in an amount equivalent to 1 mg of Compound 1.

In some embodiments, each of the one or more doses of Compound 1, or a pharmaceutically acceptable salt, hydrate, or solvate thereof, is in an amount equivalent to 0.35 mg of Compound 1; and the standard dose of Compound 1, or a pharmaceutically acceptable salt, hydrate, or solvate thereof, is in an amount equivalent to 2 mg of Compound 1. In some embodiments, at least one of the one or more doses of Compound 1, or a pharmaceutically acceptable salt, hydrate, or solvate thereof, is in an amount equivalent to 0.35 mg of Compound 1; and the standard dose of Compound 1, or a pharmaceutically acceptable salt, hydrate, or solvate thereof, is in an amount equivalent to 2 mg of Compound 1. In some embodiments, one of the one or more doses of Compound 1, or a pharmaceutically acceptable salt, hydrate, or solvate thereof, is in an amount equivalent to 0.35 mg of Compound 1; and the standard dose of Compound 1, or a pharmaceutically acceptable salt, hydrate, or solvate thereof, is in an amount equivalent to 2 mg of Compound 1. In some embodiments, more than one of the one or more doses of Compound 1, or a pharmaceutically acceptable salt, hydrate, or solvate thereof, is in an amount equivalent to 0.35 mg of Compound 1; and the standard dose of Compound 1, or a pharmaceutically acceptable salt, hydrate, or solvate thereof, is in an amount equivalent to 2 mg of Compound 1.

In some embodiments, each of the one or more doses of Compound 1, or a pharmaceutically acceptable salt, hydrate, or solvate thereof, is in an amount equivalent to 0.25 mg of Compound 1; and the standard dose of Compound 1, or a pharmaceutically acceptable salt, hydrate, or solvate thereof, is in an amount equivalent to 1 mg of Compound 1. In some embodiments, at least one of the one or more doses of Compound 1, or a pharmaceutically acceptable salt, hydrate, or solvate thereof, is in an amount equivalent to 0.25 mg of Compound 1; and the standard dose of Compound 1, or a pharmaceutically acceptable salt, hydrate, or solvate thereof, is in an amount equivalent to 1 mg of Compound 1. In some embodiments, one of the one or more doses of Compound 1, or a pharmaceutically acceptable salt, hydrate, or solvate thereof, is in an amount equivalent to 0.25 mg of Compound 1; and the standard dose of Compound 1, or a pharmaceutically acceptable salt, hydrate, or solvate thereof, is in an amount equivalent to 1 mg of Compound 1. In some embodiments, more than one of the one or more doses of Compound 1, or a pharmaceutically acceptable salt, hydrate, or solvate thereof, is in an amount equivalent to 0.25 mg of Compound 1; and the standard dose of Compound 1, or a pharmaceutically acceptable salt, hydrate, or solvate thereof, is in an amount equivalent to 1 mg of Compound 1.

In some embodiments, each of the one or more doses of Compound 1, or a pharmaceutically acceptable salt, hydrate, or solvate thereof, is in an amount equivalent to 0.25 mg of Compound 1; and the standard dose of Compound 1, or a pharmaceutically acceptable salt, hydrate, or solvate thereof, is in an amount equivalent to 2 mg of Compound 1. In some embodiments, at least one of the one or more doses of Compound 1, or a pharmaceutically acceptable salt, hydrate, or solvate thereof, is in an amount equivalent to 0.25 mg of Compound 1; and the standard dose of Compound 1, or a pharmaceutically acceptable salt, hydrate, or solvate thereof, is in an amount equivalent to 2 mg of Compound 1. In some embodiments, one of the one or more doses of Compound 1, or a pharmaceutically acceptable salt, hydrate, or solvate thereof, is in an amount equivalent to 0.25 mg of Compound 1; and the standard dose of Compound 1, or a pharmaceutically acceptable salt, hydrate, or solvate thereof, is in an amount equivalent to 2 mg of Compound 1. In some embodiments, more than one of the one or more doses of Compound 1, or a pharmaceutically acceptable salt, hydrate, or solvate thereof, is in an amount equivalent to 0.25 mg of Compound 1; and the standard dose of Compound 1, or a pharmaceutically acceptable salt, hydrate, or solvate thereof, is in an amount equivalent to 2 mg of Compound 1.

In some embodiments, each of the one or more doses of Compound 1, or a pharmaceutically acceptable salt, hydrate, or solvate thereof is administered once daily to the individual.

In some embodiments, the first period of time is no more than about two weeks.

In some embodiments, the first period of time is no more than about 10 days, is no more than about one week, is about one week, or is 5 days.

In some embodiments, the first period of time is no more than about 10 days.

In some embodiments, the first period of time is no more than about one week.

In some embodiments, the first period of time is about one week.

In some embodiments, the first period of time is 5 days.

In some embodiments, the first period of time is for a minimum of at least 10 days.

In some embodiments, the first period of time is for a minimum of at least 7 days.

In some embodiments, the first period of time is for a minimum of at least 5 days.

In some embodiments, the first period of time is for a minimum of at least 3 days.

In some embodiments, the first period of time comprises a plurality of subperiods.

In some embodiments, the first period of time comprises two subperiods. In some embodiments, the first period of time comprises three subperiods. In some embodiments, each of the subperiods is the same length of time. In some embodiments, one of the subperiods is longer than the other subperiods. In some embodiments, each of the subperiods is of different lengths of time.

In some embodiments, the first subperiod of time is 1 day. In some embodiments, the first subperiod of time is 2 days. In some embodiments, the first subperiod of time is at least 3 days. In some embodiments, the first subperiod of time is 3 days. In some embodiments, the first subperiod of time is at least 4 days. In some embodiments, the first subperiod of time is 4 days. In some embodiments, the first subperiod of time is 5 days. In some embodiments, the first subperiod of time is 6 days. In some embodiments, the first subperiod of time is at least 7 days. In some embodiments, the first subperiod of time is 7 days. In some embodiments, the first subperiod of time is at least 10 days. In some embodiments, the first subperiod of time is 10 days.

In some embodiments, the second subperiod of time is 1 day. In some embodiments, the second subperiod of time is 2 days. In some embodiments, the second subperiod of time is at least 3 days. In some embodiments, the second subperiod of time is 3 days. In some embodiments, the second subperiod of time is at least 4 days. In some embodiments, the second subperiod of time is 4 days. In some embodiments, the second subperiod of time is 5 days. In some embodiments, the second subperiod of time is 6 days. In some embodiments, the second subperiod of time is at least 7 days. In some embodiments, the second subperiod of time is 7 days. In some embodiments, the second subperiod of time is at least 10 days. In some embodiments, the second subperiod of time is 10 days.

In some embodiments, the third subperiod of time is 1 day. In some embodiments, the third subperiod of time is 2 days. In some embodiments, the third subperiod of time is at least 3 days. In some embodiments, the third subperiod of time is 3 days. In some embodiments, the third subperiod of time is at least 4 days. In some embodiments, the third subperiod of time is 4 days. In some embodiments, the third subperiod of time is 5 days. In some embodiments, the third subperiod of time is 6 days. In some embodiments, the third subperiod of time is at least 7 days. In some embodiments, the third subperiod of time is 7 days. In some embodiments, the third subperiod of time is at least 10 days. In some embodiments, the third subperiod of time is 10 days.

In some embodiments, the first subperiod is 3 days and the second subperiod is 4 days. In some embodiments, the first subperiod is 4 days and the second subperiod is 3 days. In some embodiments, the first subperiod is 7 days and the second subperiod is 7 days.

In some embodiments, the first subperiod is 3 days and Compound 1, or a pharmaceutically acceptable salt, hydrate, or solvate thereof, is administered during the first subperiod in an amount equivalent to 0.25 mg of Compound 1. In some embodiments, the first subperiod is 3 days and Compound 1, or a pharmaceutically acceptable salt, hydrate, or solvate thereof, is administered during the first subperiod in an amount equivalent to 0.35 mg of Compound 1. In some embodiments, the first subperiod is 3 days and Compound 1, or a pharmaceutically acceptable salt, hydrate, or solvate thereof, is administered during the first subperiod in an amount equivalent to 0.5 mg of Compound 1. In some embodiments, the first subperiod is 3 days and Compound 1, or a pharmaceutically acceptable salt, hydrate, or solvate thereof, is administered during the first subperiod in an amount equivalent to 1 mg of Compound 1.

In some embodiments, the first subperiod is 4 days and Compound 1, or a pharmaceutically acceptable salt, hydrate, or solvate thereof, is administered during the first subperiod in an amount equivalent to 0.25 mg of Compound 1. In some embodiments, the first subperiod is 4 days and Compound 1, or a pharmaceutically acceptable salt, hydrate, or solvate thereof, is administered during the first subperiod in an amount equivalent to 0.35 mg of Compound 1. In some embodiments, the first subperiod is 4 days and Compound 1, or a pharmaceutically acceptable salt, hydrate, or solvate thereof, is administered during the first subperiod in an amount equivalent to 0.5 mg of Compound 1. In some embodiments, the first subperiod is 4 days and Compound 1, or a pharmaceutically acceptable salt, hydrate, or solvate thereof, is administered during the first subperiod in an amount equivalent to 1 mg of Compound 1.

In some embodiments, the first subperiod is 7 days and Compound 1, or a pharmaceutically acceptable salt, hydrate, or solvate thereof, is administered during the first subperiod in an amount equivalent to 0.25 mg of Compound 1. In some embodiments, the first subperiod is 7 days and Compound 1, or a pharmaceutically acceptable salt, hydrate, or solvate thereof, is administered during the first subperiod in an amount equivalent to 0.35 mg of Compound 1. In some embodiments, the first subperiod is 7 days and Compound 1, or a pharmaceutically acceptable salt, hydrate, or solvate thereof, is administered during the first subperiod in an amount equivalent to 0.5 mg of Compound 1. In some embodiments, the first subperiod is 7 days and Compound 1, or a pharmaceutically acceptable salt, hydrate, or solvate thereof, is administered during the first subperiod in an amount equivalent to 1 mg of Compound 1.

In some embodiments, the second subperiod is 3 days and Compound 1, or a pharmaceutically acceptable salt, hydrate, or solvate thereof, is administered during the second subperiod in an amount equivalent to 0.25 mg of Compound 1. In some embodiments, the second subperiod is 3 days and Compound 1, or a pharmaceutically acceptable salt, hydrate, or solvate thereof, is administered during the second subperiod in an amount equivalent to 0.35 mg of Compound 1. In some embodiments, the second subperiod is 3 days and Compound 1, or a pharmaceutically acceptable salt, hydrate, or solvate thereof, is administered during the second subperiod in an amount equivalent to 0.5 mg of Compound 1. In some embodiments, the second subperiod is 3 days and Compound 1, or a pharmaceutically acceptable salt, hydrate, or solvate thereof, is administered during the second subperiod in an amount equivalent to 1 mg of Compound 1.

In some embodiments, the second subperiod is 4 days and Compound 1, or a pharmaceutically acceptable salt, hydrate, or solvate thereof, is administered during the second subperiod in an amount equivalent to 0.25 mg of Compound 1. In some embodiments, the second subperiod is 4 days and Compound 1, or a pharmaceutically acceptable salt, hydrate, or solvate thereof, is administered during the second subperiod in an amount equivalent to 0.35 mg of Compound 1. In some embodiments, the second subperiod is 4 days and Compound 1, or a pharmaceutically acceptable salt, hydrate, or solvate thereof, is administered during the second subperiod in an amount equivalent to 0.5 mg of Compound 1. In some embodiments, the second subperiod is 4 days and Compound 1, or a pharmaceutically acceptable salt, hydrate, or solvate thereof, is administered during the second subperiod in an amount equivalent to 1 mg of Compound 1.

In some embodiments, the second subperiod is 7 days and Compound 1, or a pharmaceutically acceptable salt, hydrate, or solvate thereof, is administered during the second subperiod in an amount equivalent to 0.25 mg of Compound 1. In some embodiments, the second subperiod is 7 days and Compound 1, or a pharmaceutically acceptable salt, hydrate, or solvate thereof, is administered during the second subperiod in an amount equivalent to 0.35 mg of Compound 1. In some embodiments, the second subperiod is 7 days and Compound 1, or a pharmaceutically acceptable salt, hydrate, or solvate thereof, is administered during the second subperiod in an amount equivalent to 0.5 mg of Compound 1. In some embodiments, the second subperiod is 7 days and Compound 1, or a pharmaceutically acceptable salt, hydrate, or solvate thereof, is administered during the second subperiod in an amount equivalent to 1 mg of Compound 1.

In some embodiments, the third subperiod is 3 days and Compound 1, or a pharmaceutically acceptable salt, hydrate, or solvate thereof, is administered during the third subperiod in an amount equivalent to 0.25 mg of Compound 1. In some embodiments, the third subperiod is 3 days and Compound 1, or a pharmaceutically acceptable salt, hydrate, or solvate thereof, is administered during the third subperiod in an amount equivalent to 0.35 mg of Compound 1. In some embodiments, the third subperiod is 3 days and Compound 1, or a pharmaceutically acceptable salt, hydrate, or solvate thereof, is administered during the third subperiod in an amount equivalent to 0.5 mg of Compound 1. In some embodiments, the third subperiod is 3 days and Compound 1, or a pharmaceutically acceptable salt, hydrate, or solvate thereof, is administered during the third subperiod in an amount equivalent to 1 mg of Compound 1.

In some embodiments, the third subperiod is 4 days and Compound 1, or a pharmaceutically acceptable salt, hydrate, or solvate thereof, is administered during the third subperiod in an amount equivalent to 0.25 mg of Compound 1. In some embodiments, the third subperiod is 4 days and Compound 1, or a pharmaceutically acceptable salt, hydrate, or solvate thereof, is administered during the third subperiod in an amount equivalent to 0.35 mg of Compound 1. In some embodiments, the third subperiod is 4 days and Compound 1, or a pharmaceutically acceptable salt, hydrate, or solvate thereof, is administered during the third subperiod in an amount equivalent to 0.5 mg of Compound 1. In some embodiments, the third subperiod is 4 days and Compound 1, or a pharmaceutically acceptable salt, hydrate, or solvate thereof, is administered during the third subperiod in an amount equivalent to 1 mg of Compound 1.

In some embodiments, the third subperiod is 7 days and Compound 1, or a pharmaceutically acceptable salt, hydrate, or solvate thereof, is administered during the third subperiod in an amount equivalent to 0.25 mg of Compound 1. In some embodiments, third subperiod is 7 days and Compound 1, or a pharmaceutically acceptable salt, hydrate, or solvate thereof, is administered during the third subperiod in an amount equivalent to 0.35 mg of Compound 1. In some embodiments, the third subperiod is 7 days and Compound 1, or a pharmaceutically acceptable salt, hydrate, or solvate thereof, is administered during the third subperiod in an amount equivalent to 0.5 mg of Compound 1. In some embodiments, the third subperiod is 7 days and Compound 1, or a pharmaceutically acceptable salt, hydrate, or solvate thereof, is administered during the third subperiod in an amount equivalent to 1 mg of Compound 1.

In some embodiments, the first time period has two subperiods; the first subperiod is 3 days; Compound 1, or a pharmaceutically acceptable salt, hydrate, or solvate thereof, is administered during the first subperiod in an amount equivalent to 0.25 mg of Compound 1; the second subperiod is 4 days; and Compound 1, or a pharmaceutically acceptable salt, hydrate, or solvate thereof, is administered during the second subperiod in an amount equivalent to 1 mg of Compound 1.

In some embodiments, the first time period has two subperiods; the first subperiod is 3 days; Compound 1, or a pharmaceutically acceptable salt, hydrate, or solvate thereof, is administered during the first subperiod in an amount equivalent to 0.35 mg of Compound 1; the second subperiod is 4 days; and Compound 1, or a pharmaceutically acceptable salt, hydrate, or solvate thereof, is administered during the second subperiod in an amount equivalent to 1 mg of Compound 1.

In some embodiments, the first time period has two subperiods; the first subperiod is 3 days; Compound 1, or a pharmaceutically acceptable salt, hydrate, or solvate thereof, is administered during the first subperiod in an amount equivalent to 0.5 mg of Compound 1; the second subperiod is 4 days; and Compound 1, or a pharmaceutically acceptable salt, hydrate, or solvate thereof, is administered during the second subperiod in an amount equivalent to 1 mg of Compound 1.

In some embodiments, the first time period has two subperiods; the first subperiod is 4 days; Compound 1, or a pharmaceutically acceptable salt, hydrate, or solvate thereof, is administered during the first subperiod in an amount equivalent to 0.25 mg of Compound 1; the second subperiod is 3 days; and Compound 1, or a pharmaceutically acceptable salt, hydrate, or solvate thereof, is administered during the second subperiod in an amount equivalent to 1 mg of Compound 1.

In some embodiments, the first time period has two subperiods; the first subperiod is 4 days; Compound 1, or a pharmaceutically acceptable salt, hydrate, or solvate thereof, is administered during the first subperiod in an amount equivalent to 0.35 mg of Compound 1; the second subperiod is 3 days; and Compound 1, or a pharmaceutically acceptable salt, hydrate, or solvate thereof, is administered during the second subperiod in an amount equivalent to 1 mg of Compound 1.

In some embodiments, the first time period has two subperiods; the first subperiod is 4 days; Compound 1, or a pharmaceutically acceptable salt, hydrate, or solvate thereof, is administered during the first subperiod in an amount equivalent to 0.5 mg of Compound 1; the second subperiod is 3 days; and Compound 1, or a pharmaceutically acceptable salt, hydrate, or solvate thereof, is administered during the second subperiod in an amount equivalent to 1 mg of Compound 1.

In some embodiments, the first time period has two subperiods; the first subperiod is 7 days; Compound 1, or a pharmaceutically acceptable salt, hydrate, or solvate thereof, is administered during the first subperiod in an amount equivalent to 0.25 mg of Compound 1; the second subperiod is 7 days; and Compound 1, or a pharmaceutically acceptable salt, hydrate, or solvate thereof, is administered during the second subperiod in an amount equivalent to 1 mg of Compound 1.

In some embodiments, the first time period has two subperiods; the first subperiod is 7 days; Compound 1, or a pharmaceutically acceptable salt, hydrate, or solvate thereof, is administered during the first subperiod in an amount equivalent to 0.35 mg of Compound 1; the second subperiod is 7 days; and Compound 1, or a pharmaceutically acceptable salt, hydrate, or solvate thereof, is administered during the second subperiod in an amount equivalent to 1 mg of Compound 1.

In some embodiments, the first time period has two subperiods; the first subperiod is 7 days; Compound 1, or a pharmaceutically acceptable salt, hydrate, or solvate thereof, is administered during the first subperiod in an amount equivalent to 0.5 mg of Compound 1; the second subperiod is 7 days; and Compound 1, or a pharmaceutically acceptable salt, hydrate, or solvate thereof, is administered during the second subperiod in an amount equivalent to 1 mg of Compound 1.

In some embodiments, the first time period has three subperiods; the first subperiod is 3 days; Compound 1, or a pharmaceutically acceptable salt, hydrate, or solvate thereof, is administered during the first subperiod in an amount equivalent to 0.25 mg of Compound 1; the second subperiod is 4 days; Compound 1, or a pharmaceutically acceptable salt, hydrate, or solvate thereof, is administered during the second subperiod in an amount equivalent to 0.35 mg of Compound 1; the third subperiod is 7 days; and Compound 1, or a pharmaceutically acceptable salt, hydrate, or solvate thereof, is administered during the third subperiod in an amount equivalent to 0.5 mg of Compound 1.

In some embodiments, the first time period has three subperiods; the first subperiod is 3 days; Compound 1, or a pharmaceutically acceptable salt, hydrate, or solvate thereof, is administered during the first subperiod in an amount equivalent to 0.25 mg of Compound 1; the second subperiod is 4 days; Compound 1, or a pharmaceutically acceptable salt, hydrate, or solvate thereof, is administered during the second subperiod in an amount equivalent to 0.5 mg of Compound 1; the third subperiod is 7 days; and Compound 1, or a pharmaceutically acceptable salt, hydrate, or solvate thereof, is administered during the third subperiod in an amount equivalent to 1 mg of Compound 1.

In some embodiments, the first time period has three subperiods; the first subperiod is 3 days; Compound 1, or a pharmaceutically acceptable salt, hydrate, or solvate thereof, is administered during the first subperiod in an amount equivalent to 0.35 mg of Compound 1; the second subperiod is 4 days; Compound 1, or a pharmaceutically acceptable salt, hydrate, or solvate thereof, is administered during the second subperiod in an amount equivalent to 0.5 mg of Compound 1; the third subperiod is 7 days; and Compound 1, or a pharmaceutically acceptable salt, hydrate, or solvate thereof, is administered during the third subperiod in an amount equivalent to 1 mg of Compound 1.

In some embodiments, the first time period has three subperiods; the first subperiod is 4 days; Compound 1, or a pharmaceutically acceptable salt, hydrate, or solvate thereof, is administered during the first subperiod in an amount equivalent to 0.25 mg of Compound 1; the second subperiod is 3 days; Compound 1, or a pharmaceutically acceptable salt, hydrate, or solvate thereof, is administered during the second subperiod in an amount equivalent to 0.35 mg of Compound 1; the third subperiod is 7 days; and Compound 1, or a pharmaceutically acceptable salt, hydrate, or solvate thereof, is administered during the third subperiod in an amount equivalent to 0.5 mg of Compound 1.

In some embodiments, the first time period has three subperiods; the first subperiod is 4 days; Compound 1, or a pharmaceutically acceptable salt, hydrate, or solvate thereof, is administered during the first subperiod in an amount equivalent to 0.25 mg of Compound 1; the second subperiod is 3 days; Compound 1, or a pharmaceutically acceptable salt, hydrate, or solvate thereof, is administered during the second subperiod in an amount equivalent to 0.5 mg of Compound 1; the third subperiod is 7 days; and Compound 1, or a pharmaceutically acceptable salt, hydrate, or solvate thereof, is administered during the third subperiod in an amount equivalent to 1 mg of Compound 1.

In some embodiments, the first time period has three subperiods; the first subperiod is 4 days; Compound 1, or a pharmaceutically acceptable salt, hydrate, or solvate thereof, is administered during the first subperiod in an amount equivalent to 0.35 mg of Compound 1; the second subperiod is 3 days; Compound 1, or a pharmaceutically acceptable salt, hydrate, or solvate thereof, is administered during the second subperiod in an amount equivalent to 0.5 mg of Compound 1; the third subperiod is 7 days; and Compound 1, or a pharmaceutically acceptable salt, hydrate, or solvate thereof, is administered during the third subperiod in an amount equivalent to 1 mg of Compound 1.

In some embodiments, the first time period has three subperiods; the first subperiod is 7 days; Compound 1, or a pharmaceutically acceptable salt, hydrate, or solvate thereof, is administered during the first subperiod in an amount equivalent to 0.25 mg of Compound 1; the second subperiod is 7 days; Compound 1, or a pharmaceutically acceptable salt, hydrate, or solvate thereof, is administered during the second subperiod in an amount equivalent to 0.35 mg of Compound 1; the third subperiod is 7 days; and Compound 1, or a pharmaceutically acceptable salt, hydrate, or solvate thereof, is administered during the third subperiod in an amount equivalent to 0.5 mg of Compound 1.

In some embodiments, the first time period has three subperiods; the first subperiod is 7 days; Compound 1, or a pharmaceutically acceptable salt, hydrate, or solvate thereof, is administered during the first subperiod in an amount equivalent to 0.25 mg of Compound 1; the second subperiod is 7 days; Compound 1, or a pharmaceutically acceptable salt, hydrate, or solvate thereof, is administered during the second subperiod in an amount equivalent to 0.5 mg of Compound 1; the third subperiod is 7 days; and Compound 1, or a pharmaceutically acceptable salt, hydrate, or solvate thereof, is administered during the third subperiod in an amount equivalent to 1 mg of Compound 1.

In some embodiments, the first time period has three subperiods; the first subperiod is 7 days; Compound 1, or a pharmaceutically acceptable salt, hydrate, or solvate thereof, is administered during the first subperiod in an amount equivalent to 0.35 mg of Compound 1; the second subperiod is 7 days; Compound 1, or a pharmaceutically acceptable salt, hydrate, or solvate thereof, is administered during the second subperiod in an amount equivalent to 0.5 mg of Compound 1; the third subperiod is 7 days; and Compound 1, or a pharmaceutically acceptable salt, hydrate, or solvate thereof, is administered during the third subperiod in an amount equivalent to 1 mg of Compound 1.

In some embodiments, Compound 1, or a pharmaceutically acceptable salt, hydrate, or solvate thereof, is administered orally.

In some embodiments, Compound 1, or a pharmaceutically acceptable salt, hydrate, or solvate thereof, is formulated as a capsule or tablet suitable for oral administration.

In some embodiments, Compound 1, or a pharmaceutically acceptable salt, hydrate, or solvate thereof, is Compound 1, or a pharmaceutically acceptable salt thereof.

In some embodiments, Compound 1, or a pharmaceutically acceptable salt, hydrate, or solvate thereof, is selected from:
Compound 1;
a calcium salt of Compound 1; and
an L-arginine salt of Compound 1.

In some embodiments, Compound 1, or a pharmaceutically acceptable salt, hydrate, or solvate thereof, is an L-arginine salt of Compound 1.

In some embodiments, Compound 1, or a pharmaceutically acceptable salt, hydrate, or solvate thereof, is an anhydrous, non-solvated crystalline form of an L-arginine salt of Compound 1.

In some embodiments, Compound 1, or a pharmaceutically acceptable salt, hydrate, or solvate thereof, is an anhydrous, non-solvated crystalline form of Compound 1.

In some embodiments, the individual had demonstrated an inadequate response to, loss of response to, or intolerance of at least one agent selected from oral 5-aminosalicylates, corticosteroids, immunosuppressives, TNFα antagonists, and integrin antagonists.

In some embodiments, the individual had demonstrated, over the previous 3 month period, an inadequate response to, loss of response to, or intolerance of at least one agent selected from oral 5-amino salicylates, corticosteroids, immunosuppressives, TNFα antagonists, and integrin antagonists. In some embodiments, the individual had demonstrated, over the previous 6 month period, an inadequate response to, loss of response to, or intolerance of at least one agent selected from oral 5-aminosalicylates, corticosteroids, immunosuppressives, TNFα antagonists, and integrin antagonists. In some embodiments, the individual had demonstrated, over the previous 9 month period, an inadequate response to, loss of response to, or intolerance of at least one agent selected from oral 5-aminosalicylates, corticosteroids, immunosuppressives, TNFα antagonists, and integrin antagonists. In some embodiments, the individual had demonstrated, over the previous 1 year period, an inadequate response to, loss of response to, or intolerance of at least one agent selected from oral 5-aminosalicylates, corticosteroids, immunosuppressives, TNFα antagonists, and integrin antagonists. In some embodiments, the individual had demonstrated, over the previous 2 year period, an inadequate response to, loss of response to, or intolerance of at least one agent selected from oral 5-aminosalicylates, corticosteroids, immunosuppressives, TNFα antagonists, and integrin antagonists. In some embodiments, the individual had demonstrated, over the previous 3 year period, an inadequate response to, loss of response to, or intolerance of at least one agent selected from oral 5-aminosalicylates, corticosteroids, immunosuppressives, TNFα antagonists, and integrin antagonists. In some embodiments, the individual had demonstrated, over the previous 4 year period, an inadequate response to, loss of response to, or intolerance of at least one agent selected from oral 5-amino salicylates, corticosteroids, immunosuppressives, TNFα antagonists, and integrin antagonists. In some embodiments, the individual had demonstrated, over the previous 5 year period, an inadequate response to, loss of response to, or intolerance of at least one agent selected from oral 5-aminosalicylates, corticosteroids, immunosuppressives, TNFα antagonists, and integrin antagonists.

In some embodiments, the individual also is administered a therapeutic dose of an oral 5-ASA compound.

In some embodiments, the individual also is administered a therapeutic dose of an oral corticosteroid therapy. In some embodiments, the corticosteroid is prednisone, e.g., prednisone at a dose ≤20 mg/day, or an equivalent steroid. In some embodiments, the corticosteroid is budesonide, e.g., at a dose ≤9 mg/day, or an equivalent steroid.

In some embodiments, the individual also is administered a therapeutic dose of an immunosuppressive agent. In some embodiments, the individual also is administered a therapeutic dose of azathioprine. In some embodiments, the individual also is administered a therapeutic dose of 6-mercaptopurine.

In some embodiments, the individual also is administered a therapeutic dose of a probiotic. In some embodiments, the individual also is administered a therapeutic dose of Culturelle. In some embodiments, the individual also is administered a therapeutic dose of *Saccharomyces boulardii*.

In some embodiments, the individual also is administered a therapeutic dose of an antidiarrheal. In some embodiments, the individual also is administered a therapeutic dose of loperamide. In some embodiments, the individual also is administered a therapeutic dose of diphenoxylate with atropine.

S1P receptor agonists having agonist activity on the $S1P_1$ receptor have been shown to rapidly and reversibly induce lymphopenia (also referred to as peripheral lymphocyte lowering (PLL); Hale et al., *Bioorg. Med. Chem. Lett.*, 14:3351-3355, 2004). This is attended by clinically useful immunosuppression by virtue of sequestering T- and B-cells in secondary lymphoid tissue (lymph nodes and Peyer's patches) and thus apart from sites of inflammation and organ grafts (Rosen et al., *Immunol. Rev.*, 195:160-177, 2003; Schwab et al., *Nature Immunol.*, 8:1295-1301, 2007). This lymphocyte sequestration, for example in lymph nodes, is thought to be a consequence of concurrent agonist-driven functional antagonism of the $S1P_1$ receptor on T-cells (whereby the ability of S1P to mobilize T-cell egress from lymph nodes is reduced) and persistent agonism of the $S1P_1$ receptor on lymph node endothelium (such that barrier function opposing transmigration of lymphocytes is increased) (Matloubian et al., *Nature*, 427:355-360, 2004; Baumruker et al., *Expert Opin. Investig. Drugs*, 16:283-289, 2007). It has been reported that agonism of the $S1P_1$ receptor alone is sufficient to achieve lymphocyte sequestration (Sanna et al., *J. Biol. Chem.*, 279:13839-13848, 2004) and that this occurs without impairment of immune responses to systemic infection (Brinkmann et al., *Transplantation*, 72:764-769, 2001; Brinkmann et al., *Transplant. Proc.*, 33:530-531, 2001).

That agonism of endothelial $S1P_1$ receptors has a broader role in promoting vascular integrity is supported by work implicating the $S1P_1$ receptor in capillary integrity in mouse skin and lung (Sanna et al., *Nat. Chem. Biol.*, 2:434-441, 2006). Vascular integrity can be compromised by inflammatory processes, for example as may derive from sepsis, major trauma and surgery so as to lead to acute lung injury or respiratory distress syndrome (Johan Groeneveld, *Vascul. Pharmacol.*, 39:247-256, 2003).

An exemplary S1P receptor agonist having agonist activity on the $S1P_1$ receptor is FTY720 (fingolimod), an immunosuppressive agent that has undergone clinical trials (Martini et al., *Expert Opin. Investig. Drugs*, 16:505-518, 2007) and was recently approved by the FDA for the treatment of individuals with relapsing forms of multiple sclerosis (MS) to reduce the frequency of clinical exacerbations and to delay the accumulation of physical disability. FTY720 acts as a prodrug which is phosphorylated in vivo; the phosphorylated derivative is an agonist for $S1P_1$, $S1P_3$, $S11)_4$ and $S1P_5$ receptors (but not the $S1P_2$ receptor) (Chiba, *Pharmacology & Therapeutics*, 108:308-319, 2005). FTY720 has been shown to rapidly and reversibly induce lymphopenia; Hale et al., *Bioorg. Med. Chem. Lett.*, 14:3351-3355, 2004). This is attended by clinically useful immunosuppression by virtue of sequestering T- and B-cells in secondary lymphoid tissue (lymph nodes and Peyer's patches) and thus apart from sites of inflammation and organ grafts (Rosen et al., *Immunol. Rev.*, 195:160-177, 2003; Schwab et al., *Nature Immunol.*, 8:1295-1301, 2007).

In clinical trials, FTY720 elicited an adverse event (i.e., transient asymptomatic bradycardia) which may be due to its agonism of the $S1P_3$ receptor (Budde et al., *J. Am. Soc.*

Nephrol., 13:1073-1083, 2002; Sanna et al., *J. Biol. Chem.*, 279:13839-13848, 2004; Ogawa et al., BBRC, 361:621-628, 2007).

FTY720 has been reported to have therapeutic efficacy in at least: a rat model for autoimmune myocarditis and a mouse model for acute viral myocarditis (Kiyabayashi et al., *J. Cardiovasc. Pharmacol.*, 35:410-416, 2000; Miyamoto et al., *J. Am. Coll. Cardiol.*, 37:1713-1718, 2001); mouse models for inflammatory bowel disease including colitis (Mizushima et al., *Inflamm. Bowel Dis.*, 10:182-192, 2004; Deguchi et al., *Oncology Reports*, 16:699-703, 2006; Fujii et al., *Am. J. Physiol. Gastrointest. Liver Physiol.*, 291:G267-G274, 2006; Daniel et al., *J. Immunol.*, 178:2458-2468, 2007); a rat model for progressive mesangioproliferative glomerulonephritis (Martini et al., *Am. J. Physiol. Renal Physiol.*, 292:F1761-F1770, 2007); a mouse model for asthma, suggested to be primarily through the $S1P_1$ receptor on the basis of work using the $S1P_1$ receptor agonist SEW2871 (Idzko et al., *J. Clin. Invest.*, 116:2935-2944, 2006); a mouse model for airway inflammation and induction of bronchial hyperresponsiveness (Sawicka et al., *J. Immunol.*, 171; 6206-6214, 2003); a mouse model for atopic dermatitis (Kohno et al., *Biol. Pharm. Bull.*, 27:1392-1396, 2004); a mouse model for ischemia-reperfusion injury (Kaudel et al., *Transplant. Proc.*, 39:499-502, 2007); a mouse model for systemic lupus erythematosus (SLE) (Okazaki et al., *J. Rheumatol.*, 29:707-716, 2002; Herzinger et al., *Am. J. Clin. Dermatol.*, 8:329-336, 2007); rat models for rheumatoid arthritis (Matsuura et al., *Int. J. Immunopharmacol.*, 22:323-331, 2000; Matsuura et al., *Inflamm. Res.*, 49:404-410, 2000); a rat model for autoimmune uveitis (Kurose et al., *Exp. Eye Res.*, 70:7-15, 2000); mouse models for type I diabetes (Fu et al., *Transplantation*, 73:1425-1430, 2002; Maki et al., *Transplantation*, 74:1684-1686, 2002; Yang et al., *Clinical Immunology*, 107:30-35, 2003; Maki et al., *Transplantation*, 79:1051-1055, 2005); mouse models for atherosclerosis (Nofer et al., *Circulation*, 115:501-508, 2007; Keul et al., *Arterioscler. Thromb. Vasc. Biol.*, 27:607-613, 2007); a rat model for brain inflammatory reaction following traumatic brain injury (TBI) (Zhang et al., *J. Cell. Mol. Med.*, 11:307-314, 2007); and mouse models for graft coronary artery disease and graft-versus-host disease (GVHD) (Hwang et al., *Circulation*, 100:1322-1329, 1999; Taylor et al., *Blood*, 110:3480-3488, 2007). In vitro results suggest that FTY720 may have therapeutic efficacy for β-amyloid-related inflammatory diseases including Alzheimer's disease (Kaneider et al., *FASEB J.*, 18:309-311, 2004). KRP-203, an S1P receptor agonist having agonist activity on the $S1P_1$ receptor, has been reported to have therapeutic efficacy in a rat model for autoimmune myocarditis (Ogawa et al., BBRC, 361:621-628, 2007). Using the $S1P_1$ receptor agonist SEW2871, it has been shown that agonism of endothelial $S1P_1$ receptors prevents proinflammatory monocyte/endothelial interactions in type I diabetic vascular endothelium (Whetzel et al., *Circ. Res.*, 99:731-739, 2006) and protects the vasculature against TNFα-mediated monocyte/endothelial interactions (Bolick et al., *Arterioscler. Thromb. Vasc. Biol.*, 25:976-981, 2005).

Additionally, FTY720 has been reported to have therapeutic efficacy in experimental autoimmune encephalomyelitis (EAE) in rats and mice, a model for human multiple sclerosis (Brinkmann et al., *J. Biol. Chem.*, 277:21453-21457, 2002; Fujino et al., *J. Pharmacol. Exp. Ther.*, 305: 70-77, 2003; Webb et al., *J. Neuroimmunol.*, 153:108-121, 2004; Rausch et aL, *J. Magn. Reson. Imaging*, 20:16-24, 2004; Kataoka et al., *Cellular & Molecular Immunology*, 2:439-448, 2005; Brinkmann et al., *Pharmacology & Therapeutics*, 115:84-105, 2007; Baumruker et al., *Expert Opin. Investig. Drugs*, 16:283-289, 2007; Balatoni et al., *Brain Research Bulletin*, 74:307-316, 2007). Furthermore, FTY720 has been found to have therapeutic efficacy for multiple sclerosis in clinical trials. In Phase II clinical trials for relapsing-remitting multiple sclerosis, FTY720 was found to reduce the number of lesions detected by magnetic resonance imaging (MRI) and clinical disease activity in individuals with multiple sclerosis (Kappos et al., *N. Engl. J. Med.*, 355:1124-1140, 2006; Martini et al., *Expert Opin. Investig. Drugs*, 16:505-518, 2007; Zhang et al., *Mini-Reviews in Medicinal Chemistry*, 7:845-850, 2007; Brinkmann, *Pharmacology & Therapeutics*, 115:84-105, 2007). Phase III clinical studies with FTY720 in individuals with remitting-relapsing multiple sclerosis have been reported (Brinkmann, *Pharmacology & Therapeutics*, 115:84-105, 2007; Baumruker et al., *Expert. Opin. Investig. Drugs*, 16:283-289, 2007; Dev et al., *Pharmacology and Therapeutics*, 117:77-93, 2008).

FTY720 has also been reported to have anti-viral activity. Specific data has been presented in the lymphocytic choriomeningitis virus (LCMV) mouse model, wherein the mice were infected with either the Armstrong or the clone 13 strain of LCMV (Premenko-Lanier et al., *Nature*, 454, 894, 2008).

FTY720 has been reported to impair migration of dendritic cells infected with *Francisella tularensis* to the mediastinal lymph node, thereby reducing the bacterial colonization of it. *Francisella tularensis* is associated with tularemia, ulceroglandular infection, respiratory infection and a typhoidal disease (E. Bar-Haim et al., *PLoS Pathogens,* 4(11): e1000211, published 21 Nov. 2008; info:doi/10.1371/journal.ppat.1000211, 2008).

It has also been recently reported that a short-term high dose of FTY720 rapidly reduced ocular infiltrates in experimental autoimmune uveoretinitis. When given in the early stages of ocular inflammation, FTY720 rapidly prevented retinal damage. It was reported that FTY720 not only prevented infiltration of target organs, but also reduce existing infiltration (Raveney et al., *Arch. Ophthalmol.,* 126(10), 1390, 2008).

It has been reported that treatment with FTY720 relieved ovariectomy-induced osteoporosis in mice by reducing the number of mature osteoclasts attached to the bone surface. The data provided evidence that S1P controlled the migratory behavior of osteoclast precursors, dynamically regulating bone mineral homeostasis (Ishii et al., *Nature*, advance online publication, 8 Feb. 2009, doi:10.1038/nature07713).

Agonism of the $S1P_1$ receptor has been implicated in enhancement of survival of oligodendrocyte progenitor cells. Survival of oligodendrocyte progenitor cells is a required component of the remyelination process. Remyelination of multiple sclerosis lesions is considered to promote recovery from clinical relapses (Miron et al., *Ann. Neurol.,* 63:61-71, 2008; Coelho et al., *J. Pharmacol. Exp. Ther.,* 323:626-635, 2007; Dev et al., *Pharmacology and Therapeutics,* 117:77-93, 2008). It also has been shown that the $S1P_1$ receptor plays a role in platelet-derived growth factor (PDGF)-induced oligodendrocyte progenitor cell mitogenesis (Jung et al., *Glia,* 55:1656-1667, 2007).

Agonism of the $S1P_1$ receptor has also been reported to mediate migration of neural stem cells toward injured areas of the central nervous system (CNS), including in a rat model of spinal cord injury (Kimura et al., *Stem Cells,* 25:115-124, 2007).

Agonism of the $S1P_1$ receptor has been implicated in the inhibition of keratinocyte proliferation (Sauer et al., *J. Biol.*

Chem., 279:38471-38479, 2004), consistent with reports that S1P inhibits keratinocyte proliferation (Kim et al., *Cell Signal*, 16:89-95, 2004). The hyperproliferation of keratinocytes at the entrance to the hair follicle, which can then become blocked, and an associated inflammation are significant pathogenetic factors of acne (Koreck et al., *Dermatology*, 206:96-105, 2003; Webster, *Cutis*, 76(2 Suppl):4-7, 2005).

FTY720 has been reported to have therapeutic efficacy in inhibiting pathologic angiogenesis, such as that as may occur in tumor development. Inhibition of angiogenesis by FTY720 is thought to involve agonism of the $S1P_1$ receptor (Oo et al., *J. Biol. Chem.*, 282; 9082-9089, 2007; Schmid et al., *J. Cell Biochem.*, 101:259-270, 2007). FTY720 has been reported to have therapeutic efficacy for inhibiting primary and metastatic tumor growth in a mouse model of melanoma (LaMontagne et al., *Cancer Res.*, 66:221-231, 2006). FTY720 has been reported to have therapeutic efficacy in a mouse model for metastatic hepatocellular carcinoma (Lee et al., *Clin. Cancer Res.*, 11:84588466, 2005).

It has been reported that oral administration of FTY720 to mice potently blocked VEGF-induced vascular permeability, an important process associated with angiogenesis, inflammation, and pathological conditions such as sepsis, hypoxia, and solid tumor growth (T Sanchez et al., *J. Biol. Chem.*, 278(47), 47281-47290, 2003).

Cyclosporin A and FK506 (calcineurin inhibitors) are drugs used to prevent rejection of transplanted organs. Although they are effective in delaying or suppressing transplant rejection, classical immunosuppressants such as cyclosporin A and FK506 are known to cause several undesirable side effects including nephrotoxicity, neurotoxicity, β-cell toxicity and gastrointestinal discomfort. There is an unmet need in organ transplantation for an immunosuppressant without these side effects which is effective as a monotherapy or in combination with a classical immunosuppressant for inhibiting migration of, e.g., alloantigen-reactive T-cells to the grafted tissue, thereby prolonging graft survival.

FTY720 has been shown to have therapeutic efficacy in transplant rejection both as a monotherapy and in synergistic combination with a classical immunosuppressant, including cyclosporin A, FK506, and RAD (an mTOR inhibitor). It has been shown that, unlike the classical immunosuppressants cyclosporin A, FK506 and RAD, FTY720 has efficacy for prolonging graft survival without inducing general immunosuppression, and this difference in drug action is believed to be relevant to the synergism observed for the combination (Brinkmann et al., *Transplant Proc.*, 33:530-531, 2001; Brinkmann et al., *Transplantation*, 72:764-769, 2001).

Agonism of the $S1P_1$ receptor has been reported to have therapeutic efficacy for prolonging allograft survival in mouse and rat skin allograft models (Lima et al., *Transplant Proc.*, 36:1015-1017, 2004; Yan et al., *Bioorg. & Med. Chem. Lett.*, 16:3679-3683, 2006). FTY720 has been reported to have therapeutic efficacy for prolonging allograft survival in a rat cardiac allograft model (Suzuki et al., *Transpl. Immunol.*, 4:252-255, 1996). FTY720 has been reported to act synergistically with cyclosporin A to prolong rat skin allograft survival (Yanagawa et al., *J. Immunol.*, 160:5493-5499, 1998), to act synergistically with cyclosporin A and with FK506 to prolong rat cardiac allograft survival, and to act synergistically with cyclosporin A to prolong canine renal allograft survival and monkey renal allograft survival (Chiba et al., *Cell Mol. Biol.*, 3:11-19, 2006). KRP-203, an S1P receptor agonist has been reported to have therapeutic efficacy for prolonging allograft survival in a rat skin allograft model and both as monotherapy and in synergistic combination with cyclosporin A in a rat cardiac allograft model (Shimizu et al., *Circulation*, 111:222-229, 2005). KRP-203 also has been reported to have therapeutic efficacy in combination with mycophenolate mofetil (MMF; a prodrug for which the active metabolite is mycophenolic acid, an inhibitor of purine biosynthesis) for prolonging allograft survival both in a rat renal allograft model and in a rat cardiac allograft model (Suzuki et al., *J. Heart Lung Transplant*, 25:302-209, 2006; Fujishiro et al., *J. Heart Lung Transplant*, 25:825-833, 2006). It has been reported that an agonist of the $S1P_1$ receptor, AUY954, in combination with a subtherapeutic dose of RAD001 (Certican/Everolimus, an mTOR inhibitor) can prolong rat cardiac allograft survival (Pan et al., *Chemistry & Biology*, 13:1227-1234, 2006). In a rat small bowel allograft model, FTY720 has been reported to act synergistically with cyclosporin A to prolong small bowel allograft survival (Sakagawa et al., *Transpl. Immunol.*, 13:161-168, 2004). FTY720 has been reported to have therapeutic efficacy in a mouse islet graft model (Fu et al., *Transplantation*, 73:1425-1430, 2002; Liu et al., *Microsurgery*, 27:300-304; 2007) and in a study using human islet cells to evidence no detrimental effects on human islet function (Truong et al., *American Journal of Transplantation*, 7:2031-2038, 2007).

FTY720 has been reported to reduce the nociceptive behavior in the spared nerve injury model for neuropathic pain which does not depend on prostaglandin synthesis (O. Costu et al., *Journal of Cellular and Molecular Medicine* 12(3), 995-1004, 2008).

FTY720 has been reported to impair initiation of murine contact hypersensitivity (CHS). Adoptive transfer of immunized lymph node cells from mice treated with FTY720 during the sensitization phase was virtually incapable of inducing CHS response in recipients (D. Nakashima et al., *J. Investigative Dermatology* (128(12), 2833-2841, 2008).

It has been reported that prophylactic oral administration of FTY720 (1 mg/kg, three times a week), completely prevented the development of experimental autoimmune myasthenia gravis (EAMG) in C57BL/6 mice (T. Kohono et al., *Biological & Pharmaceutical Bulletin*, 28(4), 736-739, 2005).

In one embodiment, the present invention encompasses compounds which are agonists of the $S1P_1$ receptor having selectivity over the $S1P_3$ receptor. Using a combined chemical approach with S1P receptor null mice, Sanna et al. reported that sustained bradycardia was induced by nonselective S1P receptor immunosuppressive agonists in wild-type mice but was abolished in $S1P_3$-/- mice whereas an $S1P_1$-selective agonist did not produce bradycardia. Thus suggesting that the $S1P_3$ receptor, and not the $S1P_1$ receptor, was responsible for bradycardia (Sanna et al., *J. Biol. Chem.*, 279:13839-13848, 2004). Therefore, an $S1P_1$ receptor agonist selective over at least the $S1P_3$ receptor has advantages over current therapies by virtue of an enhanced therapeutic window, allowing better tolerability with higher dosing and thus improving efficacy as therapy. The present invention encompasses Compound 1 (and pharmaceutically acceptable salts, hydrates, and solvates thereof) which is an agonist of the $S1P_1$ receptor and has exhibited no or substantially no bradycardia in male Sprague-Dawley® rats (see WO2010/011316, Example 9).

A phase 1 study with Compound 1 was conducted with single dosing at 0.1 mg, 0.35 mg, 1 mg, 3 mg, and 5 mg. Compound 1 was administered as the L-arginine salt. Lower doses of 0.1 mg through 3 mg were well tolerated by subjects with only minor adverse events reported, the most common of which were headache and contact dermatitis. A dose-dependent reduction in heart rate was seen in all doses >0.35 mg, however, no adverse events related to bradycardia were reported at doses lower than the 5 mg dose. Dose limiting adverse events were observed at the dose of 5 mg, with 3 (50%) subjects experiencing 4 AEs of bradycardia with first or second degree atrioventricular (AV) block, which resulted in discontinuation of dose escalation. The maximum tolerated dose in the study was 3 mg. There were no deaths or serious adverse events in the study.

There were no other clinically significant safety issues with respect to vital signs, ECGs, pulmonary function tests, ophthalmoscopy, or clinical laboratory tests with the exception of expected pharmacological effects on peripheral blood lymphocyte counts. Dosing at the 3 and 5 mg induced a dose responsive decline in the absolute number of peripheral blood B cells, T cells, NK cells, and all T cell subsets except TEM cells. Total peripheral blood lymphocyte (PBL) counts were reduced by 2-4 hours after dosing, reaching a nadir by hour 8 which persisted for 24 hours with recovery to baseline over the next 4 days. PBL counts were reduced by ~40% and ~55% at the 3 mg and 5 mg dose levels. TEM cells do not express CCR7 and are able to recirculate independently of S1P receptor expression. These findings are therefore consistent with the anticipated pharmacodynamic effects of S1P receptor agonists in preclinical studies and in humans (Gergely et al., *Br J Pharmacol* 167(5):1035-1047, 2012; Brossard et al., *Br J Clin Pharmacol* 2013 Apr. 18. doi:10.1111/bcp.12129. [Epub ahead of print] PubMed PMID: 23594176, and Kovarik et al., *J Clin Pharmacol* 44(5):532-537, 2004.)

$S1P_1$ receptor agonists are useful to treat or prevent conditions where suppression of the immune system or agonism of the $S1P_1$ receptor is in order, such as diseases and disorders mediated by lymphocytes, transplant rejection, autoimmune diseases and disorders, inflammatory diseases and disorders, and conditions that have an underlying defect in vascular integrity or that relate to angiogenesis such as may be pathologic.

In one embodiment, the present invention encompasses compounds which are agonists of the $S1P_1$ receptor having good overall physical properties and biological activities and having an effectiveness that is substantially at least that of prior compounds with activity at the $S1P_1$ receptor.

$S1P_1$ receptor agonists are useful for treating or preventing conditions where suppression of the immune system or agonism of the $S1P_1$ receptor is in order, such as diseases and disorders mediated by lymphocytes, transplant rejection, autoimmune diseases and disorders, inflammatory diseases and disorders (e.g., acute and chronic inflammatory conditions), cancer, and conditions that have an underlying defect in vascular integrity or that are associated with angiogenesis such as may be pathologic (e.g., as may occur in inflammation, tumor development and atherosclerosis). Such conditions where suppression of the immune system or agonism of the $S1P_1$ receptor is in order include diseases and disorders mediated by lymphocytes; conditions that have an underlying defect in vascular integrity; autoimmune diseases and disorders; inflammatory diseases and disorders (e.g., acute and chronic inflammatory conditions); acute or chronic rejection of cells; tissue or solid organ grafts; arthritis, including psoriatic arthritis, and rheumatoid arthritis; diabetes, including type I diabetes; demyelinating disease, including multiple sclerosis; ischemia-reperfusion injury, including renal and cardiac ischemia-reperfusion injury; inflammatory skin disease, including psoriasis, atopic dermatitis, and acne; hyperproliferative skin disease, including acne; inflammatory bowel disease, including Crohn's disease, and ulcerative colitis; systemic lupus erythematosus; asthma; uveitis; myocarditis; allergy; atherosclerosis; brain inflammation, including Alzheimer's disease, and brain inflammatory reaction following traumatic brain injury; ankylosing spondylitis; central nervous system disease, including spinal cord injury, or cerebral infarction; pathologic angiogenesis, including as may occur in primary and metastatic tumor growth; rheumatoid arthritis; diabetic retinopathy, atherosclerosis; cancer; chronic pulmonary disease; acute lung injury; acute respiratory disease syndrome; sepsis; and the like. In addition, $S1P_1$ receptor agonists are useful for treating microbial infections, and viral infections or diseases.

In some embodiments, the sphingosine 1-phosphate subtype 1 ($S1P_1$) receptor-associated disorder is selected from: a disease or disorder mediated by lymphocytes, an autoimmune disease or disorder, an inflammatory disease or disorder, ankylosing spondylitis, biliary cirrhosis, cancer, psoriasis, psoriatic arthritis, rheumatoid arthritis, Crohn's disease, transplant rejection, multiple sclerosis, systemic lupus erythematosus, inflammatory bowel disease, ulcerative colitis, type I diabetes, hypertensive nephropathy, glomerulosclerosis, myocardial ischemia-reperfusion injury and acne.

In some embodiments, the $S1P_1$ receptor-associated disorder is a disease or disorder mediated by lymphocytes.

In some embodiments, the $S1P_1$ receptor-associated disorder is selected from a microbial infection or disease and a viral infection or disease.

In some embodiments, the $S1P_1$ receptor-associated disorder is an autoimmune disease or disorder.

In some embodiments, the $S1P_1$ receptor-associated disorder is an inflammatory disease or disorder.

In some embodiments, the $S1P_1$ receptor-associated disorder is ankylosing spondylitis.

In some embodiments, the $S1P_1$ receptor-associated disorder is biliary cirrhosis.

In some embodiments, the $S1P_1$ receptor-associated disorder is cancer.

In some embodiments, the $S1P_1$ receptor-associated disorder is psoriasis.

In some embodiments, the $S1P_1$ receptor-associated disorder is psoriatic arthritis.

In some embodiments, the $S1P_1$ receptor-associated disorder is rheumatoid arthritis.

In some embodiments, the $S1P_1$ receptor-associated disorder is Crohn's disease.

In some embodiments, the $S1P_1$ receptor-associated disorder is transplant rejection.

In some embodiments, the $S1P_1$ receptor-associated disorder is multiple sclerosis.

In some embodiments, the $S1P_1$ receptor-associated disorder is systemic lupus erythematosus.

In some embodiments, the $S1P_1$ receptor-associated disorder is inflammatory bowel disease (IBD).

In some embodiments, the $S1P_1$ receptor-associated disorder is ulcerative colitis. In some embodiments, the $S1P_1$ receptor-associated disorder is moderately to severely active ulcerative colitis.

In some embodiments, the $S1P_1$ receptor-associated disorder is moderately active ulcerative colitis. In some embodiments, the $S1P_1$ receptor-associated disorder is severely active ulcerative colitis. In some embodiments, the $S1P_1$ receptor-associated disorder is mildly to moderately active ulcerative colitis. In some embodiments, the S1P$_1$ receptor-associated disorder is mildly active ulcerative colitis.

In some embodiments, the S1P$_1$ receptor-associated disorder is type I diabetes.

In some embodiments, the S1P$_1$ receptor-associated disorder is hypertensive nephropathy.

In some embodiments, the S1P$_1$ receptor-associated disorder is glomerulosclerosis.

In some embodiments, the S1P1 receptor-associated disorder is myocardial ischemia-reperfusion injury.

In some embodiments, the S1P$_1$ receptor-associated disorder is acne.

Also provided is the use of (R)-2-(7-(4-cyclopentyl-3-(trifluoromethyl)benzyloxy)-1,2,3,4-tetrahydrocyclopenta[b]indol-3-yl)acetic acid (Compound 1), or a pharmaceutically acceptable salt, hydrate, or solvate thereof, as described herein, in the manufacture of a medicament for the treatment of a sphingosine 1-phosphate subtype 1 (S1P$_1$) receptor-associated disorder, the treatment comprising prescribing and/or administering to an individual in need thereof a standard dose of Compound 1, or a pharmaceutically acceptable salt, hydrate, or solvate thereof, in an amount equivalent to about 1.5 to about 2.5 mg of Compound 1.

Also provided is the use of Compound 1, or a pharmaceutically acceptable salt, hydrate, or solvate thereof, as described herein, in the manufacture of a medicament for the treatment of a sphingosine 1-phosphate subtype 1 (S1P$_1$) receptor-associated disorder, the treatment comprising prescribing and/or administering to the individual Compound 1, or a pharmaceutically acceptable salt, hydrate, or solvate thereof, one or more doses, each of which is less than the standard dose, for a first period of time and then prescribing and/or administering to an individual in need thereof a standard dose of Compound 1, or a pharmaceutically acceptable salt, hydrate, or solvate thereof, in an amount equivalent to about 1.5 to about 2.5 mg of Compound 1.

Also provided is the use of Compound 1, or a pharmaceutically acceptable salt, hydrate, or solvate thereof, in the manufacture of a medicament for the treatment of a sphingosine 1-phosphate subtype 1 (S1P$_1$) receptor-associated disorder, the treatment comprising prescribing and/or administering to an individual in need thereof a standard dose of Compound 1, or a pharmaceutically acceptable salt, hydrate, or solvate thereof, in an amount equivalent to about 0.5 to about 2.5 mg of Compound 1, wherein the individual had demonstrated an inadequate response to, loss of response to, or intolerance of at least one of agent selected from oral 5-aminosalicylates, corticosteroids, immunosuppressives, TNFα antagonists, and integrin antagonists.

Also provided is the use of Compound 1, or a pharmaceutically acceptable salt, hydrate, or solvate thereof, in the manufacture of a medicament for the treatment of a sphingosine 1-phosphate subtype 1 (S1P$_1$) receptor-associated disorder, the treatment comprising prescribing and/or administering to an individual in need thereof one or more doses, each of which is less than the standard dose, for a first period of time and then prescribing and/or administering to an individual in need thereof a standard dose of Compound 1, or a pharmaceutically acceptable salt, hydrate, or solvate thereof, in an amount equivalent to about 0.5 to about 2.5 mg of Compound 1, wherein the individual had demonstrated an inadequate response to, loss of response to, or intolerance of at least one of agent selected from oral 5-aminosalicylates, corticosteroids, immunosuppressives, TNFα antagonists, and integrin antagonists.

Also provided is the use of Compound 1, or a pharmaceutically acceptable salt, hydrate, or solvate thereof, in the manufacture of a medicament for the treatment of a sphingosine 1-phosphate subtype 1 (S1P$_1$) receptor-associated disorder, the treatment comprising prescribing and/or administering to a fasted individual in need thereof a standard dose of Compound 1, or a pharmaceutically acceptable salt, hydrate, or solvate thereof, in an amount equivalent to about 0.5 to about 2.5 mg of Compound 1.

Also provided is the use of Compound 1, or a pharmaceutically acceptable salt, hydrate, or solvate thereof, in the manufacture of a medicament for the treatment of a sphingosine 1-phosphate subtype 1 (S1P$_1$) receptor-associated disorder, the treatment comprising prescribing and/or administering to a fasted individual in need thereof one or more doses, each of which is less than the standard dose, for a first period of time and then prescribing and/or administering to a fasted individual in need thereof a standard dose of Compound 1, or a pharmaceutically acceptable salt, hydrate, or solvate thereof, in an amount equivalent to about 0.5 to about 2.5 mg of Compound 1.

Also provided is the use of Compound 1, or a pharmaceutically acceptable salt, hydrate, or solvate thereof, as described herein, in the manufacture of a medicament for the treatment of a sphingosine 1-phosphate subtype 1 (S1P$_1$) receptor-associated disorder selected from: a disease or disorder mediated by lymphocytes, an autoimmune disease or disorder, an inflammatory disease or disorder, ankylosing spondylitis, biliary cirrhosis, cancer, psoriasis, psoriatic arthritis, rheumatoid arthritis, Crohn's disease, transplant rejection, multiple sclerosis, systemic lupus erythematosus, inflammatory bowel disease, ulcerative colitis, type I diabetes, hypertensive nephropathy, glomerulosclerosis, myocardial ischemia-reperfusion injury, and acne, the treatment comprising prescribing and/or administering to an individual in need thereof a standard dose of Compound 1, or a pharmaceutically acceptable salt, hydrate, or solvate thereof, in an amount equivalent to about 1.5 to about 2.5 mg of Compound 1, as described herein.

Also provided is the use of Compound 1, or a pharmaceutically acceptable salt, hydrate, or solvate thereof, as described herein, in the manufacture of a medicament for the treatment of a sphingosine 1-phosphate subtype 1 (S1P$_1$) receptor-associated disorder selected from: a disease or disorder mediated by lymphocytes, an autoimmune disease or disorder, an inflammatory disease or disorder, ankylosing spondylitis, biliary cirrhosis, cancer, psoriasis, psoriatic arthritis, rheumatoid arthritis, Crohn's disease, transplant rejection, multiple sclerosis, systemic lupus erythematosus, inflammatory bowel disease, ulcerative colitis, type I diabetes, hypertensive nephropathy, glomerulosclerosis, myocardial ischemia-reperfusion injury, and acne, the treatment comprising prescribing and/or administering to the individual Compound 1, or a pharmaceutically acceptable salt, hydrate, or solvate thereof, one or more doses, each of which is less than the standard dose, for a first period of time and then prescribing and/or administering to an individual in need thereof a standard dose of Compound 1, or a pharmaceutically acceptable salt, hydrate, or solvate thereof, in an amount equivalent to about 1.5 to about 2.5 mg of Compound 1.

Also provided is the use of Compound 1, or a pharmaceutically acceptable salt, hydrate, or solvate thereof, as described herein, in the manufacture of a medicament for the treatment of a disease or disorder mediated by lymphocytes, the treatment comprising prescribing and/or administering to an individual in need thereof a standard dose of Compound 1, or a pharmaceutically acceptable salt, hydrate, or solvate thereof, in an amount equivalent to about 1.5 to about 2.5 mg of Compound 1, as described herein.

Also provided is the use of Compound 1, or a pharmaceutically acceptable salt, hydrate, or solvate thereof, as described herein, in the manufacture of a medicament for the treatment of a disease or disorder mediated by lymphocytes, the treatment comprising prescribing and/or administering to the individual Compound 1, or a pharmaceutically acceptable salt, hydrate, or solvate thereof, one or more doses, each of which is less than the standard dose, for a first period of time and then prescribing and/or administering to an individual in need thereof a standard dose of Compound 1, or a pharmaceutically acceptable salt, hydrate, or solvate thereof, in an amount equivalent to about 1.5 to about 2.5 mg of Compound 1.

Also provided is the use of Compound 1, or a pharmaceutically acceptable salt, hydrate, or solvate thereof, as described herein, in the manufacture of a medicament for the treatment of a microbial infection or disease and a viral infection or disease, the treatment comprising prescribing and/or administering to an individual in need thereof a standard dose of Compound 1, or a pharmaceutically acceptable salt, hydrate, or solvate thereof, in an amount equivalent to about 1.5 to about 2.5 mg of Compound 1, as described herein.

Also provided is the use of Compound 1, or a pharmaceutically acceptable salt, hydrate, or solvate thereof, as described herein, in the manufacture of a medicament for the treatment of a microbial infection or disease and a viral infection or disease, the treatment comprising prescribing and/or administering to the individual Compound 1, or a pharmaceutically acceptable salt, hydrate, or solvate thereof, one or more doses, each of which is less than the standard dose, for a first period of time and then prescribing and/or administering to an individual in need thereof a standard dose of Compound 1, or a pharmaceutically acceptable salt, hydrate, or solvate thereof, in an amount equivalent to about 1.5 to about 2.5 mg of Compound 1.

Also provided is the use of Compound 1, or a pharmaceutically acceptable salt, hydrate, or solvate thereof, as described herein, in the manufacture of a medicament for the treatment of an autoimmune disease or disorder, the treatment comprising prescribing and/or administering to an individual in need thereof a standard dose of Compound 1, or a pharmaceutically acceptable salt, hydrate, or solvate thereof, in an amount equivalent to about 1.5 to about 2.5 mg of Compound 1, as described herein.

Also provided is the use of Compound 1, or a pharmaceutically acceptable salt, hydrate, or solvate thereof, as described herein, in the manufacture of a medicament for the treatment of an autoimmune disease or disorder, the treatment comprising prescribing and/or administering to the individual Compound 1, or a pharmaceutically acceptable salt, hydrate, or solvate thereof, one or more doses, each of which is less than the standard dose, for a first period of time and then prescribing and/or administering to an individual in need thereof a standard dose of Compound 1, or a pharmaceutically acceptable salt, hydrate, or solvate thereof, in an amount equivalent to about 1.5 to about 2.5 mg of Compound 1.

Also provided is the use of Compound 1, or a pharmaceutically acceptable salt, hydrate, or solvate thereof, as described herein, in the manufacture of a medicament for the treatment of an inflammatory disease or disorder, the treatment comprising prescribing and/or administering to an individual in need thereof a standard dose of Compound 1, or a pharmaceutically acceptable salt, hydrate, or solvate thereof, in an amount equivalent to about 1.5 to about 2.5 mg of Compound 1, as described herein.

Also provided is the use of Compound 1, or a pharmaceutically acceptable salt, hydrate, or solvate thereof, as described herein, in the manufacture of a medicament for the treatment of an inflammatory disease or disorder, the treatment comprising prescribing and/or administering to the individual Compound 1, or a pharmaceutically acceptable salt, hydrate, or solvate thereof, one or more doses, each of which is less than the standard dose, for a first period of time and then prescribing and/or administering to an individual in need thereof a standard dose of Compound 1, or a pharmaceutically acceptable salt, hydrate, or solvate thereof, in an amount equivalent to about 1.5 to about 2.5 mg of Compound 1.

Also provided is the use of Compound 1, or a pharmaceutically acceptable salt, hydrate, or solvate thereof, as described herein, in the manufacture of a medicament for the treatment of ankylosing spondylitis, the treatment comprising prescribing and/or administering to an individual in need thereof a standard dose of Compound 1, or a pharmaceutically acceptable salt, hydrate, or solvate thereof, in an amount equivalent to about 1.5 to about 2.5 mg of Compound 1, as described herein.

Also provided is the use of Compound 1, or a pharmaceutically acceptable salt, hydrate, or solvate thereof, as described herein, in the manufacture of a medicament for the treatment of ankylosing spondylitis, the treatment comprising prescribing and/or administering to the individual Compound 1, or a pharmaceutically acceptable salt, hydrate, or solvate thereof, one or more doses, each of which is less than the standard dose, for a first period of time and then prescribing and/or administering to an individual in need thereof a standard dose of Compound 1, or a pharmaceutically acceptable salt, hydrate, or solvate thereof, in an amount equivalent to about 1.5 to about 2.5 mg of Compound 1.

Also provided is the use of Compound 1, or a pharmaceutically acceptable salt, hydrate, or solvate thereof, as described herein, in the manufacture of a medicament for the treatment of biliary cirrhosis, the treatment comprising prescribing and/or administering to an individual in need thereof a standard dose of Compound 1, or a pharmaceutically acceptable salt, hydrate, or solvate thereof, in an amount equivalent to about 1.5 to about 2.5 mg of Compound 1, as described herein.

Also provided is the use of Compound 1, or a pharmaceutically acceptable salt, hydrate, or solvate thereof, as described herein, in the manufacture of a medicament for the treatment of biliary cirrhosis, the treatment comprising prescribing and/or administering to the individual Compound 1, or a pharmaceutically acceptable salt, hydrate, or solvate thereof, one or more doses, each of which is less than the standard dose, for a first period of time and then prescribing and/or administering to an individual in need thereof a standard dose of Compound 1, or a pharmaceutically acceptable salt, hydrate, or solvate thereof, in an amount equivalent to about 1.5 to about 2.5 mg of Compound 1.

Also provided is the use of Compound 1, or a pharmaceutically acceptable salt, hydrate, or solvate thereof, as described herein, in the manufacture of a medicament for the treatment of cancer, the treatment comprising prescribing and/or administering to an individual in need thereof a standard dose of Compound 1, or a pharmaceutically acceptable salt, hydrate, or solvate thereof, in an amount equivalent to about 1.5 to about 2.5 mg of Compound 1, as described herein.

Also provided is the use of Compound 1, or a pharmaceutically acceptable salt, hydrate, or solvate thereof, as described herein, in the manufacture of a medicament for the treatment of cancer, the treatment comprising prescribing and/or administering to the individual Compound 1, or a pharmaceutically acceptable salt, hydrate, or solvate thereof, one or more doses, each of which is less than the standard dose, for a first period of time and then prescribing and/or administering to an individual in need thereof a standard dose of Compound 1, or a pharmaceutically acceptable salt, hydrate, or solvate thereof, in an amount equivalent to about 1.5 to about 2.5 mg of Compound 1. Also provided is the use of Compound 1, or a pharmaceutically acceptable salt, hydrate, or solvate thereof, as described herein, in the manufacture of a medicament for the treatment of psoriasis, the treatment comprising prescribing and/or administering to an individual in need thereof a standard dose of Compound 1, or a pharmaceutically acceptable salt, hydrate, or solvate thereof, in an amount equivalent to about 1.5 to about 2.5 mg of Compound 1, as described herein.

Also provided is the use of Compound 1, or a pharmaceutically acceptable salt, hydrate, or solvate thereof, as described herein, in the manufacture of a medicament for the treatment of psoriasis, the treatment comprising prescribing and/or administering to the individual Compound 1, or a pharmaceutically acceptable salt, hydrate, or solvate thereof, one or more doses, each of which is less than the standard dose, for a first period of time and then prescribing and/or administering to an individual in need thereof a standard dose of Compound 1, or a pharmaceutically acceptable salt, hydrate, or solvate thereof, in an amount equivalent to about 1.5 to about 2.5 mg of Compound 1.

Also provided is the use of Compound 1, or a pharmaceutically acceptable salt, hydrate, or solvate thereof, as described herein, in the manufacture of a medicament for the treatment of psoriatic arthritis, the treatment comprising prescribing and/or administering to an individual in need thereof a standard dose of Compound 1, or a pharmaceutically acceptable salt, hydrate, or solvate thereof, in an amount equivalent to about 1.5 to about 2.5 mg of Compound 1, as described herein.

Also provided is the use of Compound 1, or a pharmaceutically acceptable salt, hydrate, or solvate thereof, as described herein, in the manufacture of a medicament for the treatment of psoriatic arthritis, the treatment comprising prescribing and/or administering to the individual Compound 1, or a pharmaceutically acceptable salt, hydrate, or solvate thereof, one or more doses, each of which is less than the standard dose, for a first period of time and then prescribing and/or administering to an individual in need thereof a standard dose of Compound 1, or a pharmaceutically acceptable salt, hydrate, or solvate thereof, in an amount equivalent to about 1.5 to about 2.5 mg of Compound 1.

Also provided is the use of Compound 1, or a pharmaceutically acceptable salt, hydrate, or solvate thereof, as described herein, in the manufacture of a medicament for the treatment of rheumatoid arthritis, the treatment comprising prescribing and/or administering to an individual in need thereof a standard dose of Compound 1, or a pharmaceutically acceptable salt, hydrate, or solvate thereof, in an amount equivalent to about 1.5 to about 2.5 mg of Compound 1, as described herein.

Also provided is the use of Compound 1, or a pharmaceutically acceptable salt, hydrate, or solvate thereof, as described herein, in the manufacture of a medicament for the treatment of rheumatoid arthritis, the treatment comprising prescribing and/or administering to the individual Compound 1, or a pharmaceutically acceptable salt, hydrate, or solvate thereof, one or more doses, each of which is less than the standard dose, for a first period of time and then prescribing and/or administering to an individual in need thereof a standard dose of Compound 1, or a pharmaceutically acceptable salt, hydrate, or solvate thereof, in an amount equivalent to about 1.5 to about 2.5 mg of Compound 1.

Also provided is the use of Compound 1, or a pharmaceutically acceptable salt, hydrate, or solvate thereof, as described herein, in the manufacture of a medicament for the treatment of Crohn's disease, the treatment comprising prescribing and/or administering to an individual in need thereof a standard dose of Compound 1, or a pharmaceutically acceptable salt, hydrate, or solvate thereof, in an amount equivalent to about 1.5 to about 2.5 mg of Compound 1, as described herein.

Also provided is the use of Compound 1, or a pharmaceutically acceptable salt, hydrate, or solvate thereof, as described herein, in the manufacture of a medicament for the treatment of Crohn's disease, the treatment comprising prescribing and/or administering to the individual Compound 1, or a pharmaceutically acceptable salt, hydrate, or solvate thereof, one or more doses, each of which is less than the standard dose, for a first period of time and then prescribing and/or administering to an individual in need thereof a standard dose of Compound 1, or a pharmaceutically acceptable salt, hydrate, or solvate thereof, in an amount equivalent to about 1.5 to about 2.5 mg of Compound 1.

Also provided is the use of Compound 1, or a pharmaceutically acceptable salt, hydrate, or solvate thereof, as described herein, in the manufacture of a medicament for the treatment of transplant rejection, the treatment comprising prescribing and/or administering to an individual in need thereof a standard dose of Compound 1, or a pharmaceutically acceptable salt, hydrate, or solvate thereof, in an amount equivalent to about 1.5 to about 2.5 mg of Compound 1, as described herein.

Also provided is the use of Compound 1, or a pharmaceutically acceptable salt, hydrate, or solvate thereof, as described herein, in the manufacture of a medicament for the treatment of transplant rejection, the treatment comprising prescribing and/or administering to the individual Compound 1, or a pharmaceutically acceptable salt, hydrate, or solvate thereof, one or more doses, each of which is less than the standard dose, for a first period of time and then prescribing and/or administering to an individual in need thereof a standard dose of Compound 1, or a pharmaceutically acceptable salt, hydrate, or solvate thereof, in an amount equivalent to about 1.5 to about 2.5 mg of Compound 1.

Also provided is the use of Compound 1, or a pharmaceutically acceptable salt, hydrate, or solvate thereof, as described herein, in the manufacture of a medicament for the treatment of multiple sclerosis, the treatment comprising prescribing and/or administering to an individual in need thereof a standard dose of Compound 1, or a pharmaceutically acceptable salt, hydrate, or solvate thereof, in an amount equivalent to about 1.5 to about 2.5 mg of Compound 1, as described herein.

Also provided is the use of Compound 1, or a pharmaceutically acceptable salt, hydrate, or solvate thereof, as described herein, in the manufacture of a medicament for the treatment of multiple sclerosis, the treatment comprising prescribing and/or administering to the individual Compound 1, or a pharmaceutically acceptable salt, hydrate, or solvate thereof, one or more doses, each of which is less than the standard dose, for a first period of time and then prescribing and/or administering to an individual in need thereof a standard dose of Compound 1, or a pharmaceutically acceptable salt, hydrate, or solvate thereof, in an amount equivalent to about 1.5 to about 2.5 mg of Compound 1.

Also provided is the use of Compound 1, or a pharmaceutically acceptable salt, hydrate, or solvate thereof, as described herein, in the manufacture of a medicament for the treatment of systemic lupus erythematosus, the treatment comprising prescribing and/or administering to an individual in need thereof a standard dose of Compound 1, or a pharmaceutically acceptable salt, hydrate, or solvate thereof, in an amount equivalent to about 1.5 to about 2.5 mg of Compound 1, as described herein.

Also provided is the use of Compound 1, or a pharmaceutically acceptable salt, hydrate, or solvate thereof, as described herein, in the manufacture of a medicament for the treatment of systemic lupus erythematosus, the treatment comprising prescribing and/or administering to the individual Compound 1, or a pharmaceutically acceptable salt, hydrate, or solvate thereof, one or more doses, each of which is less than the standard dose, for a first period of time and then prescribing and/or administering to an individual in need thereof a standard dose of Compound 1, or a pharmaceutically acceptable salt, hydrate, or solvate thereof, in an amount equivalent to about 1.5 to about 2.5 mg of Compound 1.

Also provided is the use of Compound 1, or a pharmaceutically acceptable salt, hydrate, or solvate thereof, as described herein, in the manufacture of a medicament for the treatment of inflammatory bowel disease, the treatment comprising prescribing and/or administering to an individual in need thereof a standard dose of Compound 1, or a pharmaceutically acceptable salt, hydrate, or solvate thereof, in an amount equivalent to about 1.5 to about 2.5 mg of Compound 1, as described herein.

Also provided is the use of Compound 1, or a pharmaceutically acceptable salt, hydrate, or solvate thereof, as described herein, in the manufacture of a medicament for the treatment of inflammatory bowel disease, the treatment comprising prescribing and/or administering to the individual Compound 1, or a pharmaceutically acceptable salt, hydrate, or solvate thereof, one or more doses, each of which is less than the standard dose, for a first period of time and then prescribing and/or administering to an individual in need thereof a standard dose of Compound 1, or a pharmaceutically acceptable salt, hydrate, or solvate thereof, in an amount equivalent to about 1.5 to about 2.5 mg of Compound 1.

Also provided is the use of Compound 1, or a pharmaceutically acceptable salt, hydrate, or solvate thereof, as described herein, in the manufacture of a medicament for the treatment of ulcerative colitis, the treatment comprising prescribing and/or administering to an individual in need thereof a standard dose of Compound 1, or a pharmaceutically acceptable salt, hydrate, or solvate thereof, in an amount equivalent to about 1.5 to about 2.5 mg of Compound 1, as described herein.

Also provided is the use of Compound 1, or a pharmaceutically acceptable salt, hydrate, or solvate thereof, as described herein, in the manufacture of a medicament for the treatment of ulcerative colitis, the treatment comprising prescribing and/or administering to the individual Compound 1, or a pharmaceutically acceptable salt, hydrate, or solvate thereof, one or more doses, each of which is less than the standard dose, for a first period of time and then prescribing and/or administering to an individual in need thereof a standard dose of Compound 1, or a pharmaceutically acceptable salt, hydrate, or solvate thereof, in an amount equivalent to about 1.5 to about 2.5 mg of Compound 1.

Also provided is the use of Compound 1, or a pharmaceutically acceptable salt, hydrate, or solvate thereof, in the manufacture of a medicament for the treatment of inflammatory bowel disease, the treatment comprising prescribing and/or administering to an individual in need thereof a standard dose of Compound 1, or a pharmaceutically acceptable salt, hydrate, or solvate thereof, in an amount equivalent to about 0.5 to about 2.5 mg of Compound 1.

Also provided is the use of Compound 1, or a pharmaceutically acceptable salt, hydrate, or solvate thereof, in the manufacture of a medicament for the treatment of inflammatory bowel disease, the treatment comprising prescribing and/or administering to an individual in need thereof one or more doses, each of which is less than the standard dose, for a first period of time and then prescribing and/or administering to an individual in need thereof a standard dose of Compound 1, or a pharmaceutically acceptable salt, hydrate, or solvate thereof, in an amount equivalent to about 0.5 to about 2.5 mg of Compound 1.

Also provided is the use of Compound 1, or a pharmaceutically acceptable salt, hydrate, or solvate thereof, in the manufacture of a medicament for the treatment of moderately to severely active ulcerative colitis, the treatment comprising prescribing and/or administering to an individual in need thereof a standard dose of Compound 1, or a pharmaceutically acceptable salt, hydrate, or solvate thereof, in an amount equivalent to about 0.5 to about 2.5 mg of Compound 1.

Also provided is the use of Compound 1, or a pharmaceutically acceptable salt, hydrate, or solvate thereof, in the manufacture of a medicament for the treatment of moderately to severely active ulcerative colitis, the treatment comprising prescribing and/or administering to an individual in need thereof one or more doses, each of which is less than the standard dose, for a first period of time and then prescribing and/or administering to an individual in need thereof a standard dose of Compound 1, or a pharmaceutically acceptable salt, hydrate, or solvate thereof, in an amount equivalent to about 0.5 to about 2.5 mg of Compound 1.

Also provided is the use of Compound 1, or a pharmaceutically acceptable salt, hydrate, or solvate thereof, as described herein, in the manufacture of a medicament for the treatment of type I diabetes, the treatment comprising prescribing and/or administering to an individual in need thereof a standard dose of Compound 1, or a pharmaceutically acceptable salt, hydrate, or solvate thereof, in an amount equivalent to about 1.5 to about 2.5 mg of Compound 1, as described herein.

Also provided is the use of Compound 1, or a pharmaceutically acceptable salt, hydrate, or solvate thereof, as described herein, in the manufacture of a medicament for the treatment of type I diabetes, the treatment comprising prescribing and/or administering to the individual Compound 1, or a pharmaceutically acceptable salt, hydrate, or solvate thereof, one or more doses, each of which is less than the standard dose, for a first period of time and then prescribing and/or administering to an individual in need thereof a standard dose of Compound 1, or a pharmaceutically acceptable salt, hydrate, or solvate thereof, in an amount equivalent to about 1.5 to about 2.5 mg of Compound 1.

Also provided is the use of Compound 1, or a pharmaceutically acceptable salt, hydrate, or solvate thereof, as described herein, in the manufacture of a medicament for the treatment of hypertensive nephropathy, the treatment comprising prescribing and/or administering to an individual in need thereof a standard dose of Compound 1, or a pharmaceutically acceptable salt, hydrate, or solvate thereof, in an amount equivalent to about 1.5 to about 2.5 mg of Compound 1, as described herein.

Also provided is the use of Compound 1, or a pharmaceutically acceptable salt, hydrate, or solvate thereof, as described herein, in the manufacture of a medicament for the treatment of hypertensive nephropathy, the treatment comprising prescribing and/or administering to the individual Compound 1, or a pharmaceutically acceptable salt, hydrate, or solvate thereof, one or more doses, each of which is less than the standard dose, for a first period of time and then prescribing and/or administering to an individual in need thereof a standard dose of Compound 1, or a pharmaceutically acceptable salt, hydrate, or solvate thereof, in an amount equivalent to about 1.5 to about 2.5 mg of Compound 1.

Also provided is the use of Compound 1, or a pharmaceutically acceptable salt, hydrate, or solvate thereof, as described herein, in the manufacture of a medicament for the treatment of glomerulosclerosis, the treatment comprising prescribing and/or administering to an individual in need thereof a standard dose of Compound 1, or a pharmaceutically acceptable salt, hydrate, or solvate thereof, in an amount equivalent to about 1.5 to about 2.5 mg of Compound 1, as described herein.

Also provided is the use of Compound 1, or a pharmaceutically acceptable salt, hydrate, or solvate thereof, as described herein, in the manufacture of a medicament for the treatment of glomerulosclerosis, the treatment comprising prescribing and/or administering to the individual Compound 1, or a pharmaceutically acceptable salt, hydrate, or solvate thereof, one or more doses, each of which is less than the standard dose, for a first period of time and then prescribing and/or administering to an individual in need thereof a standard dose of Compound 1, or a pharmaceutically acceptable salt, hydrate, or solvate thereof, in an amount equivalent to about 1.5 to about 2.5 mg of Compound 1.

Also provided is the use of Compound 1, or a pharmaceutically acceptable salt, hydrate, or solvate thereof, as described herein, in the manufacture of a medicament for the treatment of myocardial ischemia-reperfusion injury, the treatment comprising prescribing and/or administering to an individual in need thereof a standard dose of Compound 1, or a pharmaceutically acceptable salt, hydrate, or solvate thereof, in an amount equivalent to about 1.5 to about 2.5 mg of Compound 1, as described herein.

Also provided is the use of Compound 1, or a pharmaceutically acceptable salt, hydrate, or solvate thereof, as described herein, in the manufacture of a medicament for the treatment of myocardial ischemia-reperfusion injury, the treatment comprising prescribing and/or administering to the individual Compound 1, or a pharmaceutically acceptable salt, hydrate, or solvate thereof, one or more doses, each of which is less than the standard dose, for a first period of time and then prescribing and/or administering to an individual in need thereof a standard dose of Compound 1, or a pharmaceutically acceptable salt, hydrate, or solvate thereof, in an amount equivalent to about 1.5 to about 2.5 mg of Compound 1.

Also provided is the use of Compound 1, or a pharmaceutically acceptable salt, hydrate, or solvate thereof, as described herein, in the manufacture of a medicament for the treatment of acne, the treatment comprising prescribing and/or administering to an individual in need thereof a standard dose of Compound 1, or a pharmaceutically acceptable salt, hydrate, or solvate thereof, in an amount equivalent to about 1.5 to about 2.5 mg of Compound 1, as described herein.

Also provided is the use of Compound 1, or a pharmaceutically acceptable salt, hydrate, or solvate thereof, as described herein, in the manufacture of a medicament for the treatment of acne, the treatment comprising prescribing and/or administering to the individual Compound 1, or a pharmaceutically acceptable salt, hydrate, or solvate thereof, one or more doses, each of which is less than the standard dose, for a first period of time and then prescribing and/or administering to an individual in need thereof a standard dose of Compound 1, or a pharmaceutically acceptable salt, hydrate, or solvate thereof, in an amount equivalent to about 1.5 to about 2.5 mg of Compound 1.

Also provided is a compound that is Compound 1, or a pharmaceutically acceptable salt, hydrate, or solvate thereof, as described herein, for use in a method of treatment of a sphingosine 1-phosphate subtype 1 ($S1P_1$) receptor-associated disorder, the treatment comprising prescribing and/or administering to an individual in need thereof a standard dose of Compound 1, or a pharmaceutically acceptable salt, hydrate, or solvate thereof, in an amount equivalent to about 1.5 to about 2.5 mg of Compound 1.

Also provided is a compound that is Compound 1, or a pharmaceutically acceptable salt, hydrate, or solvate thereof, as described herein, for use in a method of treatment of a sphingosine 1-phosphate subtype 1 ($S1P_1$) receptor-associated disorder, the treatment comprising prescribing and/or administering to the individual Compound 1, or a pharmaceutically acceptable salt, hydrate, or solvate thereof, one or more doses, each of which is less than the standard dose, for a first period of time and then prescribing and/or administering to an individual in need thereof a standard dose of Compound 1, or a pharmaceutically acceptable salt, hydrate, or solvate thereof, in an amount equivalent to about 1.5 to about 2.5 mg of Compound 1.

Also provided is a compound that is (R)-2-(7-(4-cyclopentyl-3-(trifluoromethyl)benzyloxy)-1,2,3,4-tetrahydrocyclopenta[b]indol-3-yl)acetic acid (Compound 1), or a pharmaceutically acceptable salt, hydrate, or solvate thereof, for use in a method of treatment of a sphingosine 1-phosphate subtype 1 ($S1P_1$) receptor-associated disorder, the treatment comprising prescribing and/or administering to an individual in need thereof a standard dose of Compound 1, or a pharmaceutically acceptable salt, hydrate, or solvate thereof, in an amount equivalent to about 0.5 to about 2.5 mg of Compound 1, wherein the individual had demonstrated an inadequate response to, loss of response to, or intolerance of at least one of agent selected from oral 5-aminosalicylates, corticosteroids, immunosuppressives, TNFα antagonists, and integrin antagonists.

Also provided is a compound that is (R)-2-(7-(4-cyclopentyl-3-(trifluoromethyl)benzyloxy)-1,2,3,4-tetrahydrocyclopenta[b]indol-3-yl)acetic acid (Compound 1), or a pharmaceutically acceptable salt, hydrate, or solvate thereof, for use in a method of treatment of a sphingosine 1-phosphate subtype 1 (S1P$_1$) receptor-associated disorder, the treatment comprising prescribing and/or administering to an individual in need thereof one or more doses, each of which is less than the standard dose, for a first period of time and then prescribing and/or administering to an individual in need thereof a standard dose of Compound 1, or a pharmaceutically acceptable salt, hydrate, or solvate thereof, in an amount equivalent to about 0.5 to about 2.5 mg of Compound 1, wherein the individual had demonstrated an inadequate response to, loss of response to, or intolerance of at least one of agent selected from oral 5-aminosalicylates, corticosteroids, immunosuppressives, TNFα antagonists, and integrin antagonists.

Also provided is a compound that is (R)-2-(7-(4-cyclopentyl-3-(trifluoromethyl)benzyloxy)-1,2,3,4-tetrahydrocyclopenta[b]indol-3-yl)acetic acid (Compound 1), or a pharmaceutically acceptable salt, hydrate, or solvate thereof, for use in a method of treatment of a sphingosine 1-phosphate subtype 1 (S1P$_1$) receptor-associated disorder, the treatment comprising prescribing and/or administering to a fasted individual in need thereof a standard dose of Compound 1, or a pharmaceutically acceptable salt, hydrate, or solvate thereof, in an amount equivalent to about 0.5 to about 2.5 mg of Compound 1.

Also provided is a compound that is (R)-2-(7-(4-cyclopentyl-3-(trifluoromethyl)benzyloxy)-1,2,3,4-tetrahydrocyclopenta[b]indol-3-yl)acetic acid (Compound 1), or a pharmaceutically acceptable salt, hydrate, or solvate thereof, for use in a method of treatment of a sphingosine 1-phosphate subtype 1 (S1P$_1$) receptor-associated disorder, the treatment comprising prescribing and/or administering to a fasted individual in need thereof one or more doses, each of which is less than the standard dose, for a first period of time and then prescribing and/or administering to a fasted individual in need thereof a standard dose of Compound 1, or a pharmaceutically acceptable salt, hydrate, or solvate thereof, in an amount equivalent to about 0.5 to about 2.5 mg of Compound 1.

Also provided is a compound that is (R)-2-(7-(4-cyclopentyl-3-(trifluoromethyl)benzyloxy)-1,2,3,4-tetrahydrocyclopenta[b]indol-3-yl)acetic acid (Compound 1), or a pharmaceutically acceptable salt, hydrate, and solvate thereof, as described herein, for use in a method of treatment of a sphingosine 1-phosphate subtype 1 (S1P$_1$) receptor-associated disorder selected from: a disease or disorder mediated by lymphocytes, an autoimmune disease or disorder, an inflammatory disease or disorder, ankylosing spondylitis, biliary cirrhosis, cancer, psoriasis, psoriatic arthritis, rheumatoid arthritis, Crohn's disease, transplant rejection, multiple sclerosis, systemic lupus erythematosus, inflammatory bowel disease, ulcerative colitis, type I diabetes, hypertensive nephropathy, glomerulosclerosis, myocardial ischemia-reperfusion injury, and acne, the treatment comprising prescribing and/or administering to an individual in need thereof a standard dose of Compound 1, or a pharmaceutically acceptable salt, hydrate, or solvate thereof, in an amount equivalent to about 1.5 to about 2.5 mg of Compound 1, as described herein.

Also provided is a compound that is Compound 1, or a pharmaceutically acceptable salt, hydrate, or solvate thereof, as described herein, for use in a method of treatment of a sphingosine 1-phosphate subtype 1 (S1P$_1$) receptor-associated disorder selected from: a disease or disorder mediated by lymphocytes, an autoimmune disease or disorder, an inflammatory disease or disorder, ankylosing spondylitis, biliary cirrhosis, cancer, psoriasis, psoriatic arthritis, rheumatoid arthritis, Crohn's disease, transplant rejection, multiple sclerosis, systemic lupus erythematosus, inflammatory bowel disease, ulcerative colitis, type I diabetes, hypertensive nephropathy, glomerulosclerosis, myocardial ischemia-reperfusion injury, and acne, the treatment comprising prescribing and/or administering to the individual Compound 1, or a pharmaceutically acceptable salt, hydrate, or solvate thereof, one or more doses, each of which is less than the standard dose, for a first period of time and then prescribing and/or administering to an individual in need thereof a standard dose of Compound 1, or a pharmaceutically acceptable salt, hydrate, or solvate thereof, in an amount equivalent to about 1.5 to about 2.5 mg of Compound 1.

Also provided is a compound that is Compound 1, or a pharmaceutically acceptable salt, hydrate, or solvate thereof, as described herein, for use in a method of treatment of a disease or disorder mediated by lymphocytes, the treatment comprising prescribing and/or administering to an individual in need thereof a standard dose of Compound 1, or a pharmaceutically acceptable salt, hydrate, or solvate thereof, in an amount equivalent to about 1.5 to about 2.5 mg of Compound 1, as described herein.

Also provided is a compound that is Compound 1, or a pharmaceutically acceptable salt, hydrate, or solvate thereof, as described herein, for use in a method of treatment of a disease or disorder mediated by lymphocytes, the treatment comprising prescribing and/or administering to the individual Compound 1, or a pharmaceutically acceptable salt, hydrate, or solvate thereof, one or more doses, each of which is less than the standard dose, for a first period of time and then prescribing and/or administering to an individual in need thereof a standard dose of Compound 1, or a pharmaceutically acceptable salt, hydrate, or solvate thereof, in an amount equivalent to about 1.5 to about 2.5 mg of Compound 1.

Also provided is a compound that is Compound 1, or a pharmaceutically acceptable salt, hydrate, or solvate thereof, as described herein, for use in a method of treatment of a microbial infection or disease and a viral infection or disease, the treatment comprising prescribing and/or administering to an individual in need thereof a standard dose of Compound 1, or a pharmaceutically acceptable salt, hydrate, or solvate thereof, in an amount equivalent to about 1.5 to about 2.5 mg of Compound 1, as described herein.

Also provided is a compound that is Compound 1, or a pharmaceutically acceptable salt, hydrate, or solvate thereof, as described herein, for use in a method of treatment of a microbial infection or disease and a viral infection or disease, the treatment comprising prescribing and/or administering to the individual Compound 1, or a pharmaceutically acceptable salt, hydrate, or solvate thereof, one or more doses, each of which is less than the standard dose, for a first period of time and then prescribing and/or administering to an individual in need thereof a standard dose of Compound 1, or a pharmaceutically acceptable salt, hydrate, or solvate thereof, in an amount equivalent to about 1.5 to about 2.5 mg of Compound 1.

Also provided is a compound that is Compound 1, or a pharmaceutically acceptable salt, hydrate, or solvate thereof, as described herein, for use in a method of treatment of an autoimmune disease or disorder, the treatment comprising prescribing and/or administering to an individual in need thereof a standard dose of Compound 1, or a pharmaceutically acceptable salt, hydrate, or solvate thereof, in an amount equivalent to about 1.5 to about 2.5 mg of Compound 1, as described herein.

Also provided is a compound that is Compound 1, or a pharmaceutically acceptable salt, hydrate, or solvate thereof, as described herein, for use in a method of treatment of an autoimmune disease or disorder, the treatment comprising prescribing and/or administering to the individual Compound 1, or a pharmaceutically acceptable salt, hydrate, or solvate thereof, one or more doses, each of which is less than the standard dose, for a first period of time and then prescribing and/or administering to an individual in need thereof a standard dose of Compound 1, or a pharmaceutically acceptable salt, hydrate, or solvate thereof, in an amount equivalent to about 1.5 to about 2.5 mg of Compound 1.

Also provided is a compound that is Compound 1, or a pharmaceutically acceptable salt, hydrate, or solvate thereof, as described herein, for use in a method of treatment of an inflammatory disease or disorder, the treatment comprising prescribing and/or administering to an individual in need thereof a standard dose of Compound 1, or a pharmaceutically acceptable salt, hydrate, or solvate thereof, in an amount equivalent to about 1.5 to about 2.5 mg of Compound 1, as described herein.

Also provided is a compound that is Compound 1, or a pharmaceutically acceptable salt, hydrate, or solvate thereof, as described herein, for use in a method of treatment of an inflammatory disease or disorder, the treatment comprising prescribing and/or administering to the individual Compound 1, or a pharmaceutically acceptable salt, hydrate, or solvate thereof, one or more doses, each of which is less than the standard dose, for a first period of time and then prescribing and/or administering to an individual in need thereof a standard dose of Compound 1, or a pharmaceutically acceptable salt, hydrate, or solvate thereof, in an amount equivalent to about 1.5 to about 2.5 mg of Compound 1.

Also provided is a compound that is Compound 1, or a pharmaceutically acceptable salt, hydrate, or solvate thereof, as described herein, for use in a method of treatment of ankylosing spondylitis, the treatment comprising prescribing and/or administering to an individual in need thereof a standard dose of Compound 1, or a pharmaceutically acceptable salt, hydrate, or solvate thereof, in an amount equivalent to about 1.5 to about 2.5 mg of Compound 1, as described herein.

Also provided is a compound that is Compound 1, or a pharmaceutically acceptable salt, hydrate, or solvate thereof, as described herein, for use in a method of treatment of ankylosing spondylitis, the treatment comprising prescribing and/or administering to the individual Compound 1, or a pharmaceutically acceptable salt, hydrate, or solvate thereof, one or more doses, each of which is less than the standard dose, for a first period of time and then prescribing and/or administering to an individual in need thereof a standard dose of Compound 1, or a pharmaceutically acceptable salt, hydrate, or solvate thereof, in an amount equivalent to about 1.5 to about 2.5 mg of Compound 1.

Also provided is a compound that is Compound 1, or a pharmaceutically acceptable salt, hydrate, or solvate thereof, as described herein, for use in a method of treatment of biliary cirrhosis, the treatment comprising prescribing and/or administering to an individual in need thereof a standard dose of Compound 1, or a pharmaceutically acceptable salt, hydrate, or solvate thereof, in an amount equivalent to about 1.5 to about 2.5 mg of Compound 1, as described herein.

Also provided is a compound that is Compound 1, or a pharmaceutically acceptable salt, hydrate, or solvate thereof, as described herein, for use in a method of treatment of biliary cirrhosis, the treatment comprising prescribing and/or administering to the individual Compound 1, or a pharmaceutically acceptable salt, hydrate, or solvate thereof, one or more doses, each of which is less than the standard dose, for a first period of time and then prescribing and/or administering to an individual in need thereof a standard dose of Compound 1, or a pharmaceutically acceptable salt, hydrate, or solvate thereof, in an amount equivalent to about 1.5 to about 2.5 mg of Compound 1.

Also provided is a compound that is Compound 1, or a pharmaceutically acceptable salt, hydrate, or solvate thereof, as described herein, for use in a method of treatment of cancer, the treatment comprising prescribing and/or administering to an individual in need thereof a standard dose of Compound 1, or a pharmaceutically acceptable salt, hydrate, or solvate thereof, in an amount equivalent to about 1.5 to about 2.5 mg of Compound 1, as described herein.

Also provided is a compound that is Compound 1, or a pharmaceutically acceptable salt, hydrate, and solvate thereof, as described herein, for use in a method of treatment of cancer, the treatment comprising prescribing and/or administering to the individual Compound 1, or a pharmaceutically acceptable salt, hydrate, or solvate thereof, one or more doses, each of which is less than the standard dose, for a first period of time and then prescribing and/or administering to an individual in need thereof a standard dose of Compound 1, or a pharmaceutically acceptable salt, hydrate, or solvate thereof, in an amount equivalent to about 1.5 to about 2.5 mg of Compound 1.

Also provided is a compound that is Compound 1, or a pharmaceutically acceptable salt, hydrate, or solvate thereof, as described herein, for use in a method of treatment of psoriasis, the treatment comprising prescribing and/or administering to an individual in need thereof a standard dose of Compound 1, or a pharmaceutically acceptable salt, hydrate, or solvate thereof, in an amount equivalent to about 1.5 to about 2.5 mg of Compound 1, as described herein.

Also provided is a compound that is Compound 1, or a pharmaceutically acceptable salt, hydrate, or solvate thereof, as described herein, for use in a method of treatment of psoriasis, the treatment comprising prescribing and/or administering to the individual Compound 1, or a pharmaceutically acceptable salt, hydrate, or solvate thereof, one or more doses, each of which is less than the standard dose, for a first period of time and then prescribing and/or administering to an individual in need thereof a standard dose of Compound 1, or a pharmaceutically acceptable salt, hydrate, or solvate thereof, in an amount equivalent to about 1.5 to about 2.5 mg of Compound 1.

Also provided is a compound that is Compound 1, or a pharmaceutically acceptable salt, hydrate, or solvate thereof, as described herein, for use in a method of treatment of psoriatic arthritis, the treatment comprising prescribing and/or administering to an individual in need thereof a standard dose of Compound 1, or a pharmaceutically acceptable salt, hydrate, or solvate thereof, in an amount equivalent to about 1.5 to about 2.5 mg of Compound 1, as described herein.

Also provided is a compound that is Compound 1, or a pharmaceutically acceptable salt, hydrate, or solvate thereof, as described herein, for use in a method of treatment of psoriatic arthritis, the treatment comprising prescribing and/or administering to the individual Compound 1, or a pharmaceutically acceptable salt, hydrate, or solvate thereof, one or more doses, each of which is less than the standard dose, for a first period of time and then prescribing and/or administering to an individual in need thereof a standard dose of Compound 1, or a pharmaceutically acceptable salt, hydrate, or solvate thereof, in an amount equivalent to about 1.5 to about 2.5 mg of Compound 1.

Also provided is a compound that is Compound 1, or a pharmaceutically acceptable salt, hydrate, or solvate thereof, as described herein, for use in a method of treatment of rheumatoid arthritis, the treatment comprising prescribing and/or administering to an individual in need thereof a standard dose of Compound 1, or a pharmaceutically acceptable salt, hydrate, or solvate thereof, in an amount equivalent to about 1.5 to about 2.5 mg of Compound 1, as described herein.

Also provided is a compound that is Compound 1, or a pharmaceutically acceptable salt, hydrate, or solvate thereof, as described herein, for use in a method of treatment of rheumatoid arthritis, the treatment comprising prescribing and/or administering to the individual Compound 1, or a pharmaceutically acceptable salt, hydrate, or solvate thereof, one or more doses, each of which is less than the standard dose, for a first period of time and then prescribing and/or administering to an individual in need thereof a standard dose of Compound 1, or a pharmaceutically acceptable salt, hydrate, or solvate thereof, in an amount equivalent to about 1.5 to about 2.5 mg of Compound 1.

Also provided is a compound that is Compound 1, or a pharmaceutically acceptable salt, hydrate, or solvate thereof, as described herein, for use in a method of treatment of Crohn's disease, the treatment comprising prescribing and/or administering to an individual in need thereof a standard dose of Compound 1, or a pharmaceutically acceptable salt, hydrate, or solvate thereof, in an amount equivalent to about 1.5 to about 2.5 mg of Compound 1, as described herein.

Also provided is a compound that is Compound 1, or a pharmaceutically acceptable salt, hydrate, or solvate thereof, as described herein, for use in a method of treatment of Crohn's disease, the treatment comprising prescribing and/or administering to the individual Compound 1, or a pharmaceutically acceptable salt, hydrate, or solvate thereof, one or more doses, each of which is less than the standard dose, for a first period of time and then prescribing and/or administering to an individual in need thereof a standard dose of Compound 1, or a pharmaceutically acceptable salt, hydrate, or solvate thereof, in an amount equivalent to about 1.5 to about 2.5 mg of Compound 1.

Also provided is a compound that is Compound 1, or a pharmaceutically acceptable salt, hydrate, or solvate thereof, as described herein, for use in a method of treatment of transplant rejection, the treatment comprising prescribing and/or administering to an individual in need thereof a standard dose of Compound 1, or a pharmaceutically acceptable salt, hydrate, or solvate thereof, in an amount equivalent to about 1.5 to about 2.5 mg of Compound 1, as described herein.

Also provided is a compound that is Compound 1, or a pharmaceutically acceptable salt, hydrate, or solvate thereof, as described herein, for use in a method of treatment of transplant rejection, the treatment comprising prescribing and/or administering to the individual Compound 1, or a pharmaceutically acceptable salt, hydrate, or solvate thereof, one or more doses, each of which is less than the standard dose, for a first period of time and then prescribing and/or administering to an individual in need thereof a standard dose of Compound 1, or a pharmaceutically acceptable salt, hydrate, or solvate thereof, in an amount equivalent to about 1.5 to about 2.5 mg of Compound 1.

Also provided is a compound that is Compound 1, or a pharmaceutically acceptable salt, hydrate, or solvate thereof, as described herein, for use in a method of treatment of multiple sclerosis, the treatment comprising prescribing and/or administering to an individual in need thereof a standard dose of Compound 1, or a pharmaceutically acceptable salt, hydrate, or solvate thereof, in an amount equivalent to about 1.5 to about 2.5 mg of Compound 1, as described herein.

Also provided is a compound that is Compound 1, or a pharmaceutically acceptable salt, hydrate, or solvate thereof, as described herein, for use in a method of treatment of multiple sclerosis, the treatment comprising prescribing and/or administering to the individual Compound 1, or a pharmaceutically acceptable salt, hydrate, or solvate thereof, one or more doses, each of which is less than the standard dose, for a first period of time and then prescribing and/or administering to an individual in need thereof a standard dose of Compound 1, or a pharmaceutically acceptable salt, hydrate, or solvate thereof, in an amount equivalent to about 1.5 to about 2.5 mg of Compound 1.

Also provided is a compound that is Compound 1, or a pharmaceutically acceptable salt, hydrate, or solvate thereof, as described herein, for use in a method of treatment of systemic lupus erythematosus, the treatment comprising prescribing and/or administering to an individual in need thereof a standard dose of Compound 1, or a pharmaceutically acceptable salt, hydrate, or solvate thereof, in an amount equivalent to about 1.5 to about 2.5 mg of Compound 1, as described herein.

Also provided is a compound that is Compound 1, or a pharmaceutically acceptable salt, hydrate, or solvate thereof, as described herein, for use in a method of treatment of systemic lupus erythematosus, the treatment comprising prescribing and/or administering to the individual Compound 1, or a pharmaceutically acceptable salt, hydrate, or solvate thereof, one or more doses, each of which is less than the standard dose, for a first period of time and then prescribing and/or administering to an individual in need thereof a standard dose of Compound 1, or a pharmaceutically acceptable salt, hydrate, or solvate thereof, in an amount equivalent to about 1.5 to about 2.5 mg of Compound 1.

Also provided is a compound that is Compound 1, or a pharmaceutically acceptable salt, hydrate, or solvate thereof, as described herein, for use in a method of treatment of inflammatory bowel disease, the treatment comprising prescribing and/or administering to an individual in need thereof a standard dose of Compound 1, or a pharmaceutically acceptable salt, hydrate, or solvate thereof, in an amount equivalent to about 1.5 to about 2.5 mg of Compound 1, as described herein.

Also provided is a compound that is Compound 1, or a pharmaceutically acceptable salt, hydrate, or solvate thereof, as described herein, for use in a method of treatment of inflammatory bowel disease, the treatment comprising prescribing and/or administering to the individual Compound 1, or a pharmaceutically acceptable salt, hydrate, or solvate thereof, one or more doses, each of which is less than the standard dose, for a first period of time and then prescribing and/or administering to an individual in need thereof a standard dose of Compound 1, or a pharmaceutically acceptable salt, hydrate, or solvate thereof, in an amount equivalent to about 1.5 to about 2.5 mg of Compound 1.

Also provided is a compound that is Compound 1, or a pharmaceutically acceptable salt, hydrate, or solvate thereof, as described herein, for use in a method of treatment of ulcerative colitis, the treatment comprising prescribing and/or administering to an individual in need thereof a standard dose of Compound 1, or a pharmaceutically acceptable salt, hydrate, or solvate thereof, in an amount equivalent to about 1.5 to about 2.5 mg of Compound 1, as described herein.

Also provided is a compound that is Compound 1, or a pharmaceutically acceptable salt, hydrate, or solvate thereof, as described herein, for use in a method of treatment of ulcerative colitis, the treatment comprising prescribing and/or administering to the individual Compound 1, or a pharmaceutically acceptable salt, hydrate, or solvate thereof, one or more doses, each of which is less than the standard dose, for a first period of time and then prescribing and/or administering to an individual in need thereof a standard dose of Compound 1, or a pharmaceutically acceptable salt, hydrate, or solvate thereof, in an amount equivalent to about 1.5 to about 2.5 mg of Compound 1.

Also provided is a compound that is Compound 1, or a pharmaceutically acceptable salt, hydrate, or solvate thereof, for use in a method of treatment of inflammatory bowel disease, the treatment comprising prescribing and/or administering to an individual in need thereof a standard dose of Compound 1, or a pharmaceutically acceptable salt, hydrate, or solvate thereof, in an amount equivalent to about 0.5 to about 2.5 mg of Compound 1.

Also provided is a compound that is Compound 1, or a pharmaceutically acceptable salt, hydrate, or solvate thereof, for use in a method of treatment of inflammatory bowel disease, the treatment comprising prescribing and/or administering to an individual in need thereof one or more doses, each of which is less than the standard dose, for a first period of time and then prescribing and/or administering to an individual in need thereof a standard dose of Compound 1, or a pharmaceutically acceptable salt, hydrate, or solvate thereof, in an amount equivalent to about 0.5 to about 2.5 mg of Compound.

Also provided is a compound that is Compound 1, or a pharmaceutically acceptable salt, hydrate, or solvate thereof, for use in a method of treatment of moderately to severely active ulcerative colitis, the treatment comprising prescribing and/or administering to an individual in need thereof a standard dose of Compound 1, or a pharmaceutically acceptable salt, hydrate, or solvate thereof, in an amount equivalent to about 0.5 to about 2.5 mg of Compound 1.

Also provided is a compound that is Compound 1, or a pharmaceutically acceptable salt, hydrate, or solvate thereof, for use in a method of treatment of moderately to severely active ulcerative colitis, the treatment comprising prescribing and/or administering to an individual in need thereof one or more doses, each of which is less than the standard dose, for a first period of time and then prescribing and/or administering to an individual in need thereof a standard dose of Compound 1, or a pharmaceutically acceptable salt, hydrate, or solvate thereof, in an amount equivalent to about 0.5 to about 2.5 mg of Compound.

Also provided is a compound that is Compound 1, or a pharmaceutically acceptable salt, hydrate, or solvate thereof, as described herein, for use in a method of treatment of type I diabetes, the treatment comprising prescribing and/or administering to an individual in need thereof a standard dose of Compound 1, or a pharmaceutically acceptable salt, hydrate, or solvate thereof, in an amount equivalent to about 1.5 to about 2.5 mg of Compound 1, as described herein.

Also provided is a compound that is Compound 1, or a pharmaceutically acceptable salt, hydrate, or solvate thereof, as described herein, for use in a method of treatment of type I diabetes, the treatment comprising prescribing and/or administering to the individual Compound 1, or a pharmaceutically acceptable salt, hydrate, or solvate thereof, one or more doses, each of which is less than the standard dose, for a first period of time and then prescribing and/or administering to an individual in need thereof a standard dose of Compound 1, or a pharmaceutically acceptable salt, hydrate, or solvate thereof, in an amount equivalent to about 1.5 to about 2.5 mg of Compound 1.

Also provided is a compound that is Compound 1, or a pharmaceutically acceptable salt, hydrate, or solvate thereof, as described herein, for use in a method of treatment of hypertensive nephropathy, the treatment comprising prescribing and/or administering to an individual in need thereof a standard dose of Compound 1, or a pharmaceutically acceptable salt, hydrate, or solvate thereof, in an amount equivalent to about 1.5 to about 2.5 mg of Compound 1, as described herein.

Also provided is a compound that is Compound 1, or a and pharmaceutically acceptable salt, hydrate, or solvate thereof, as described herein, for use in a method of treatment of hypertensive nephropathy, the treatment comprising prescribing and/or administering to the individual Compound 1, or a pharmaceutically acceptable salt, hydrate, or solvate thereof, one or more doses, each of which is less than the standard dose, for a first period of time and then prescribing and/or administering to an individual in need thereof a standard dose of Compound 1, or a pharmaceutically acceptable salt, hydrate, or solvate thereof, in an amount equivalent to about 1.5 to about 2.5 mg of Compound 1.

Also provided is a compound that is Compound 1, or a pharmaceutically acceptable salt, hydrate, or solvate thereof, as described herein, for use in a method of treatment of glomerulosclerosis, the treatment comprising prescribing and/or administering to an individual in need thereof a standard dose of Compound 1, or a pharmaceutically acceptable salt, hydrate, or solvate thereof, in an amount equivalent to about 1.5 to about 2.5 mg of Compound 1, as described herein.

Also provided is a compound that is Compound 1, or a pharmaceutically acceptable salt, hydrate, or solvate thereof, as described herein, for use in a method of treatment of glomerulosclerosis, the treatment comprising prescribing and/or administering to the individual Compound 1, or a pharmaceutically acceptable salt, hydrate, or solvate thereof, one or more doses, each of which is less than the standard dose, for a first period of time and then prescribing and/or administering to an individual in need thereof a standard dose of Compound 1, or a pharmaceutically acceptable salt, hydrate, or solvate thereof, in an amount equivalent to about 1.5 to about 2.5 mg of Compound 1.

Also provided is a compound that is Compound 1, or a pharmaceutically acceptable salt, hydrate, or solvate thereof, as described herein, for use in a method of treatment of myocardial ischemia-reperfusion injury, the treatment comprising prescribing and/or administering to an individual in need thereof a standard dose of Compound 1, or a pharmaceutically acceptable salt, hydrate, or solvate thereof, in an amount equivalent to about 1.5 to about 2.5 mg of Compound 1, as described herein.

Also provided is a compound that is Compound 1, or a pharmaceutically acceptable salt, hydrate, or solvate thereof, as described herein, for use in a method of treatment of myocardial ischemia-reperfusion injury, the treatment comprising prescribing and/or administering to the individual Compound 1, or a pharmaceutically acceptable salt, hydrate, or solvate thereof, one or more doses, each of which is less than the standard dose, for a first period of time and then prescribing and/or administering to an individual in need thereof a standard dose of Compound 1, or a pharmaceutically acceptable salt, hydrate, or solvate thereof, in an amount equivalent to about 1.5 to about 2.5 mg of Compound 1.

Also provided is a compound that is Compound 1, or a pharmaceutically acceptable salt, hydrate, or solvate thereof, as described herein, for use in a method of treatment of acne, the treatment comprising prescribing and/or administering to an individual in need thereof a standard dose of Compound 1, or a pharmaceutically acceptable salt, hydrate, or solvate thereof, in an amount equivalent to about 1.5 to about 2.5 mg of Compound 1, as described herein.

Also provided is a compound that is Compound 1, or a pharmaceutically acceptable salt, hydrate, or solvate thereof, as described herein, for use in a method of treatment of acne, the treatment comprising prescribing and/or administering to the individual Compound 1, or a pharmaceutically acceptable salt, hydrate, or solvate thereof, one or more doses, each of which is less than the standard dose, for a first period of time and then prescribing and/or administering to an individual in need thereof a standard dose of Compound 1, or a pharmaceutically acceptable salt, hydrate, or solvate thereof, in an amount equivalent to about 1.5 to about 2.5 mg of Compound 1.

Also provided are pharmaceutical compositions comprising a standard dose of Compound 1, or, a pharmaceutically acceptable salt, a hydrate or solvate thereof and, optionally, one or more pharmaceutically acceptable carriers. Also provided are pharmaceutical compositions comprising an initial dose of Compound 1, or, a pharmaceutically acceptable salt, a hydrate or solvate thereof, optionally, one or more pharmaceutically acceptable carriers. The carrier(s) must be "acceptable" in the sense of being compatible with the other ingredients of the formulation and not overly deleterious to the recipient thereof.

In some embodiments, Compound 1, or, a pharmaceutically acceptable salt, a hydrate or solvate thereof, is administered as a raw or pure chemical, for example as a powder in capsule formulation.

In some embodiments, Compound 1, or, a pharmaceutically acceptable salt, a hydrate or solvate thereof, is formulated as a pharmaceutical composition further comprising one or more pharmaceutically acceptable carriers.

Pharmaceutical compositions may be prepared by any suitable method, typically by uniformly mixing the active compound(s) with liquids or finely divided solid carriers, or both, in the required proportions and then, if necessary, forming the resulting mixture into a desired shape.

Conventional excipients, such as binding agents, fillers, acceptable wetting agents, tabletting lubricants and disintegrants may be used in tablets and capsules for oral administration. Liquid preparations for oral administration may be in the form of solutions, emulsions, aqueous or oily suspensions and syrups. Alternatively, the oral preparations may be in the form of dry powder that can be reconstituted with water or another suitable liquid vehicle before use. Additional additives such as suspending or emulsifying agents, non-aqueous vehicles (including edible oils), preservatives and flavorings and colorants may be added to the liquid preparations. Parenteral dosage forms may be prepared by dissolving the compound of the invention in a suitable liquid vehicle and filter sterilizing the solution before filling and sealing an appropriate vial or ampule. These are just a few examples of the many appropriate methods well known in the art for preparing dosage forms.

The compounds described herein can be formulated into pharmaceutical compositions using techniques well known to those in the art. Suitable pharmaceutically acceptable carriers, outside those mentioned herein, are known in the art; for example, see Remington, *The Science and Practice of Pharmacy*, 20$^{th}$ Edition, 2000, Lippincott Williams & Wilkins, (Editors: Gennaro et al.)

Pharmaceutical formulations include those suitable for oral, rectal, nasal, topical (including buccal and sub-lingual), vaginal or parenteral (including intramuscular, sub-cutaneous, and intravenous) administration or in a form suitable for administration by inhalation, insufflation or by a transdermal patch. Transdermal patches dispense a drug at a controlled rate by presenting the drug for absorption in an efficient manner with a minimum of degradation of the drug. Typically, transdermal patches comprise an impermeable backing layer, a single pressure sensitive adhesive, and a removable protective layer with a release liner. One of ordinary skill in the art will understand and appreciate the techniques appropriate for manufacturing a desired efficacious transdermal patch based upon the needs of the artisan.

The compounds of the invention, together with a conventional adjuvant, carrier, or diluent, may thus be placed into the form of pharmaceutical formulations and unit dosages thereof and in such form may be employed as solids, such as tablets or filled capsules, or liquids such as solutions, suspensions, emulsions, elixirs, gels, or capsules filled with the same, all for oral use; in the form of suppositories for rectal administration; or in the form of sterile injectable solutions for parenteral (including subcutaneous) use. Such pharmaceutical compositions and unit dosage forms thereof may comprise conventional ingredients in conventional proportions, with or without additional active compounds or principles and such unit dosage forms may contain any suitable effective amount of the active ingredient commensurate with the intended daily dosage range to be employed.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are capsules, tablets, powders, granules or suspensions, with conventional additives such as lactose, mannitol, corn starch or potato starch; with binders such as crystalline cellulose, cellulose derivatives, acacia, corn starch or gelatins; with disintegrators such as corn starch, potato starch or sodium carboxymethyl-cellulose; and with lubricants such as talc or magnesium stearate. The active ingredient may also be administered by injection as a composition wherein, for example, saline, dextrose or water may be used as a suitable pharmaceutically acceptable carrier.

For preparing pharmaceutical compositions from the compounds of the present invention, the suitable pharmaceutically acceptable carrier can be either solid, liquid or a mixture of both. Solid form preparations include powders, tablets, pills, capsules, cachets, suppositories, and dispersible granules. A solid carrier can be one or more substances which may also act as diluents, flavoring agents, solubilizers, lubricants, suspending agents, binders, preservatives, tablet disintegrating agents, or encapsulating materials.

In powders, the carrier is a finely divided solid which is in a mixture with the finely divided active component.

In tablets, the active component is mixed with the carrier having the necessary binding capacity in suitable proportions and compacted to the desired shape and size.

The powders and tablets may contain varying percentage amounts of the active compound. A representative amount in a powder or tablet may be from 0.5 to about 90 percent of the active compound. However, an artisan would know when amounts outside of this range are necessary. Suitable carriers for powders and tablets include magnesium carbonate, magnesium stearate, talc, sugar, lactose, pectin, dextrin, starch, gelatin, tragacanth, methylcellulose, sodium carboxymethyl cellulose, a low melting wax, cocoa butter, and the like. The term "preparation" is includes the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

For preparing suppositories, a low melting wax, such as an admixture of fatty acid glycerides or cocoa butter, is first melted and the active component is dispersed homogeneously therein (e.g., by stirring). The molten homogenous mixture is then poured into convenient sized molds, allowed to cool and thereby to solidify.

Formulations suitable for vaginal administration may be presented as pessaries, tampons, creams, gels, pastes, foams or sprays containing in addition to the active ingredient such carriers as are known in the art to be appropriate.

Liquid form preparations include solutions, suspensions, and emulsions, for example, water or water-propylene glycol solutions. For example, parenteral injection liquid preparations can be formulated as solutions in aqueous polyethylene glycol solution. Injectable preparations, for example, sterile injectable aqueous or oleaginous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds according to the present invention may thus be formulated for parenteral administration (e.g. by injection, for example bolus injection or continuous infusion) and may be presented in unit dose form in ampoules, pre-filled syringes, small volume infusion or in multi-dose containers with an added preservative. The pharmaceutical compositions may take such forms as suspensions, solutions, or emulsions in oily or aqueous vehicles and may contain formulatory agents such as suspending, stabilizing and/or dispersing agents. Alternatively, the active ingredient may be in powder form, obtained by aseptic isolation of sterile solid or by lyophilization from solution, for constitution with a suitable vehicle, e.g. sterile, pyrogen-free water, before use.

Aqueous formulations suitable for oral use can be prepared by dissolving or suspending the active component in water and adding suitable colorants, flavors, stabilizing and thickening agents, as desired.

Aqueous suspensions suitable for oral use can be made by dispersing the finely divided active component in water with viscous material, such as natural or synthetic gums, resins, methylcellulose, sodium carboxymethyl cellulose, or other well-known suspending agents.

Also included are solid form preparations which are intended to be converted, shortly before use, to liquid form preparations for oral administration. Such liquid forms include solutions, suspensions and emulsions. These preparations may contain, in addition to the active component, colorants, flavors, stabilizers, buffers, artificial and natural sweeteners, dispersants, thickeners, solubilizing agents, and the like.

For topical administration to the epidermis the compounds according to the invention may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents.

Formulations suitable for topical administration in the mouth include lozenges comprising the active agent in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

Solutions or suspensions are applied directly to the nasal cavity by conventional means, for example with a dropper, pipette or spray. The formulations may be provided in single or multi-dose form. In the latter case of a dropper or pipette, this may be achieved by the individual administering an appropriate, predetermined volume of the solution or suspension. In the case of a spray, this may be achieved for example by means of a metering atomizing spray pump.

Administration to the respiratory tract may also be achieved by means of an aerosol formulation in which the active ingredient is provided in a pressurized pack with a suitable propellant. If the compounds of the present invention or pharmaceutical compositions comprising them are administered as aerosols (e.g., nasal aerosols, by inhalation), this can be carried out, for example, using a spray, a nebulizer, a pump nebulizer, an inhalation apparatus, a metered inhaler or a dry powder inhaler. Pharmaceutical forms for administration of the compounds of the present invention as an aerosol can be prepared by processes well known to the person skilled in the art. Solutions or dispersions of the compounds of the present invention or a pharmaceutically acceptable salt, solvate, hydrate or derivative thereof in water, water/alcohol mixtures or suitable saline solutions, for example, can be employed using customary additives (e.g., benzyl alcohol or other suitable preservatives), absorption enhancers for increasing the bioavailability, solubilizers, dispersants and others and, if appropriate, customary propellants (e.g., carbon dioxide, CFCs, such as, dichlorodifluoromethane, trichlorofluoromethane, dichlorotetrafluoroethane, and the like). The aerosol may conveniently also contain a surfactant such as lecithin. The dose of drug may be controlled by provision of a metered valve.

In formulations intended for administration to the respiratory tract, including intranasal formulations, the compound will generally have a small particle size for example of the order of 10 microns or less. Such a particle size may be obtained by means known in the art, for example by micronization. When desired, formulations adapted to give sustained release of the active ingredient may be employed.

Alternatively the active ingredients may be provided in the form of a dry powder (e.g., a powder mix of the compound in a suitable powder base such as lactose, starch, starch derivatives such as hydroxypropylmethyl cellulose and polyvinylpyrrolidone (PVP)). Conveniently the powder carrier will form a gel in the nasal cavity. The powder composition may be presented in unit dose form (e.g., capsules, cartridges) as for gelatin or blister packs from which the powder may be administered by means of an inhaler.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules and powders in vials or ampoules. Also, the unit dosage form can be a capsule, tablet, cachet, or lozenge itself, or it can be the appropriate number of any of these in packaged form.

In some embodiments, the compositions are tablets or capsules for oral administration.

In some embodiments, the compositions are liquids for intravenous administration.

Some embodiments of the present invention include a method of producing a pharmaceutical composition for "combination-therapy" comprising admixing at least one compound according to any of the compound embodiments disclosed herein, together with at least one known pharmaceutical agent as described herein and a pharmaceutically acceptable carrier.

It is noted that when $S1P_1$ receptor agonists are utilized as active ingredients in a pharmaceutical composition, these are not intended for use only in humans, but in other non-human mammals as well. Indeed, recent advances in the area of animal health-care mandate that consideration be given for the use of active agents, such as $S1P_1$ receptor agonists, for the treatment of an $S1P_1$ receptor-associated disease or disorder in companionship animals (e.g., cats, dogs, etc.) and in livestock animals (e.g., cows, chickens, fish, etc.). Those of ordinary skill in the art are readily credited with understanding the utility of such compounds in such settings.

Also provided is a titration package for enabling compliance with a regimen of changing dosage of medication over a period of time for the treatment of a sphingosine 1-phosphate subtype 1 ($S1P_1$) receptor-associated disorder, wherein the medication is (R)-2-(7-(4-cyclopentyl-3-(trifluoromethyl)benzyloxy)-1,2,3,4-tetrahydrocyclopenta[b]indol-3-yl)acetic acid (Compound 1), or a pharmaceutically acceptable salt, hydrate, or solvate thereof, the package comprising:

a first number of daily units of a pharmaceutical composition comprising an initial dose of Compound 1, or a pharmaceutically acceptable salt, hydrate, or solvate thereof, is in an amount equivalent to about 1 mg or less of Compound 1, and a second number of daily units of a pharmaceutical composition comprising a standard dose of Compound 1, or a pharmaceutically acceptable salt, hydrate, or solvate thereof, is in an amount equivalent to about 1.5 to about 2.5 mg of Compound 1.

Also provided is a titration package for enabling compliance with a regimen of changing dosage of medication over a period of time for the treatment of inflammatory bowel disease, wherein the medication is (R)-2-(7-(4-cyclopentyl-3-(trifluoromethyl)benzyloxy)-1,2,3,4-tetrahydrocyclopenta[b]indol-3-yl)acetic acid (Compound 1), or a pharmaceutically acceptable salt, hydrate, or solvate thereof, the package comprising:

a first number of daily units of a pharmaceutical composition comprising an initial dose of Compound 1, or a pharmaceutically acceptable salt, hydrate, or solvate thereof, is in an amount equivalent to about 0.5 mg or less of Compound 1, and a second number of daily units of a pharmaceutical composition comprising a standard dose of Compound 1, or a pharmaceutically acceptable salt, hydrate, or solvate thereof, is in an amount equivalent to about 1.0 to about 2.0 mg of Compound 1.

Also provided is a kit comprising a titration package as described herein, and instructions indicating that the medication is to be administered to an individual in need of treatment of a sphingosine 1-phosphate subtype 1 ($S1P_1$) receptor-associated disorder.

Also provided is a method of treating a sphingosine 1-phosphate subtype 1 ($S1P_1$) receptor-associated disorder comprising providing a kit as described herein to an individual in need thereof.

Further embodiments include the embodiments disclosed in the following Examples, which is not to be construed as limiting in any way.

EXAMPLES

Example 1

Formulations composed of immediate-release, hard gelatin capsules containing an L-arginine salt of Compound 1 were prepared as shown in Table 1.

TABLE 1

|  | Formulation | | | | |
| --- | --- | --- | --- | --- | --- |
|  | 0.1 mg | 0.35 mg | 0.5 mg | 1 mg | 2 mg |
| L-arginine salt of Compound 1 (mg/capsule) | 0.14 | 0.48 | 0.69 | 1.38 | 2.76 |
| Empty capsule weight (mg)* | 38.0 | 61.0 | 61.0 | 61.0 | 61.0 |
| Total capsule target weight (mg)** | 38.14 | 61.48 | 61.69 | 62.38 | 63.76 |

*Approximate weight. Based on capsule specification
**Theoretical total weight calculated by combining fill and empty capsule weights together Placebo formulations composed of hard gelatin capsules containing microcrystalline cellulose was also prepared as shown in Table 2.

TABLE 2

|  | Placebo for 0.1 mg | Placebo for 0.35 mg and 1 mg | Placebo for 0.5 mg, 1 mg, and 2 mg |
| --- | --- | --- | --- |
| Microcrystalline cellulose - Avicel PH102 (mg/capsule)* | 0.0 | 0.0 | 1.0* |
| Empty capsule weight (mg) ** | 38.0 | 61.0 | 61.0 |
| Total capsule target weight (mg)*** | 38.0 | 61.0 | 62.0 |

*Approximate weight ±15%
** Approximate weight. Based on capsule specification
***Theoretical total weight calculated by combining fill and empty capsule weights together

Example 2

A randomized, double-blind, placebo-controlled, sequential, ascending, multiple dose study to assess the safety, tolerability, and pharmacokinetics of the L-arginine salt of Compound 1 administered to healthy adult subjects was conducted. This study was designed to evaluate the safety, tolerability, pharmacokinetics, and pharmacodynamics of the L-arginine salt of Compound 1.

Tables 3 and 4 below provide a summary of demographic data by treatment group and a more detailed analysis of the safety population.

TABLE 3

|  | Placebo | 0.7 mg | 1.35 mg | 2.0 mg | 0.35 mg, 2.0 mg | 0.5 mg, 3.0 mg |
|---|---|---|---|---|---|---|
| No. of Subjects Randomized | 10 | 10 | 10 | 10 | 10 | 10 |
| No. (%) of Subjects in Safety Population[a] | 10 (100.0%) | 10 (100.0%) | 10 (100.0%) | 10 (100.0%) | 10 (100.0%) | 10 (100.0%) |
| No. (%) of Subjects Who Completed Study[a] | 10 (100.0%) | 10 (100.0%) | 9 (90.0%) | 10 (100.0%) | 10 (100.0%) | 10 (100.0%) |
| No. (%) of Subjects Withdrawn Early from Study[a] | 0 (0.0%) | 0 (0.0%) | 1 (10.0%) | 0 (0.0%) | 0 (0.0%) | 0 (0.0%) |
| Withdrawal of Informed Consent | 0 | 0 | 1 (100.0%) | 0 | 0 | 0 |

[a]Number of group subjects in each column is used as the denominator for percentage calculations.

TABLE 4

| Demographics | Placebo (N = 10) | 0.7 mg (N = 10) | 1.35 mg (N = 10) | 2.0 mg (N = 10) | 0.35 mg, 2.0 mg (N = 10) | 0.5 mg, 3.0 mg (N = 10) |
|---|---|---|---|---|---|---|
| Age (years) | | | | | | |
| N | 10 | 10 | 10 | 10 | 10 | 10 |
| Mean (SD) | 35.6 (7.4) | 34.2 (8.8) | 31.4 (9.0) | 30.1 (7.0) | 32.8 (6.0) | 29.0 (7.2) |
| Median | 36.0 | 35.0 | 29.5 | 26.5 | 33.5 | 27.0 |
| Min-Max | 21-45 | 18-44 | 19-45 | 21-44 | 22-41 | 20-41 |
| CV | 20.8% | 25.6% | 28.7% | 23.2% | 18.2% | 24.7% |
| Age Group | | | | | | |
| 18-24 | 1 (10.0%) | 2 (20.0%) | 2 (20.0%) | 1 (10.0%) | 1 (10.0%) | 3 (30.0%) |
| 25-34 | 3 (30.0%) | 2 (20.0%) | 5 (50.0%) | 6 (60.0%) | 5 (50.0%) | 4 (40.0%) |
| 35-45 | 6 (60.0%) | 6 (60.0%) | 3 (30.0%) | 3 (30.0%) | 4 (40.0%) | 3 (30.0%) |
| Race | | | | | | |
| White | 8 (80.0%) | 7 (70.0%) | 8 (80.0%) | 7 (70.0%) | 6 (60.0%) | 3 (30.0%) |
| Black or African American | 2 (20.0%) | 3 (30.0%) | 1 (10.0%) | 3 (30.0%) | 4 (40.0%) | 5 (50.0%) |
| Asian | 0 (0.0%) | 0 (0.0%) | 1 (10.0%) | 0 (0.0%) | 0 (0.0%) | 0 (0.0%) |
| American Indian or Alaska Native | 0 (0.0%) | 0 (0.0%) | 0 (0.0%) | 0 (0.0%) | 0 (0.0%) | 2 (20.0%) |
| Ethnicity | | | | | | |
| Hispanic Or Latino | 6 (60.0%) | 3 (30.0%) | 5 (50.0%) | 5 (50.0%) | 3 (30.0%) | 5 (50.0%) |
| Not Hispanic Or Latino | 4 (40.0%) | 7 (70.0%) | 5 (50.0%) | 5 (50.0%) | 7 (70.0%) | 5 (50.0%) |
| Sex | | | | | | |
| Male | 2 (20.0%) | 5 (50.0%) | 3 (30.0%) | 4 (40.0%) | 5 (50.0%) | 4 (40.0%) |
| Female | 8 (80.0%) | 5 (50.0%) | 7 (70.0%) | 6 (60.0%) | 5 (50.0%) | 6 (60.0%) |
| Weight (kg) | | | | | | |
| N | 10 | 10 | 10 | 10 | 10 | 10 |
| Mean (SD) | 75.7 (8.7) | 79.6 (14.2) | 73.9 (12.9) | 74.4 (17.3) | 78.2 (12.1) | 79.1 (9.4) |
| Median | 76.3 | 82.7 | 73.2 | 73.1 | 76.2 | 79.8 |
| Min-Max | 64.3-88.7 | 54.5-97.8 | 54.7-95.3 | 51.6-98.1 | 62.4-96.9 | 67.0-98.4 |
| CV | 11.5% | 17.9% | 17.5% | 23.2% | 15.5% | 11.9% |
| Height (cm) | | | | | | |
| N | 10 | 10 | 10 | 10 | 10 | 10 |
| Mean (SD) | 160.6 (10.6) | 166.0 (8.4) | 165.4 (9.0) | 166.0 (12.2) | 169.2 (9.0) | 169.0 (6.4) |

TABLE 4-continued

| Demographics | Placebo (N = 10) | 0.7 mg (N = 10) | 1.35 mg (N = 10) | 2.0 mg (N = 10) | 0.35 mg, 2.0 mg (N = 10) | 0.5 mg, 3.0 mg (N = 10) |
|---|---|---|---|---|---|---|
| Median | 161.0 | 165.3 | 162.0 | 165.8 | 168.3 | 168.5 |
| Min-Max | 145.0-180.5 | 156.0-179.0 | 157.0-183.0 | 150.0-186.5 | 156.0-185.0 | 154.5-176.5 |
| CV | 6.6% | 5.0% | 5.5% | 7.3% | 5.3% | 3.8% |
| BMI (kg/m$^2$) | | | | | | |
| N | 10 | 10 | 10 | 10 | 10 | 10 |
| Mean (SD) | 29.5 (3.8) | 28.9 (4.5) | 26.9 (3.1) | 27.0 (5.8) | 27.2 (2.1) | 27.7 (2.2) |
| Median | 29.9 | 29.8 | 27.3 | 26.0 | 27.4 | 27.9 |
| Min-Max | 23.8-34.1 | 21.5-33.8 | 21.8-30.8 | 19.1-40.1 | 24.1-30.5 | 23.5-31.6 |
| CV | 12.7% | 15.6% | 11.4% | 21.6% | 7.7% | 8.0% |

Cohort 1 was dosed with 0.7 mg (by administering two 0.35 mg formulations) for 21 days. Cohort 2 was dosed with 1.35 mg (by administering both a 0.35 mg formulation and a 1 mg formulation) for 21 days. Cohort 3 was dosed with 2.0 mg for 21 days. Cohort 4 was dosed with 0.35 mg for 7 days and then with 2.0 mg for 14 days. Cohort 5 was dosed with 0.5 for 7 days and then with 3.0 mg (by administering both a 1 mg formulation and a 2 mg formulation) for 14 days.

The following safety assessments were conducted: physical examinations with ophthalmoscopy, clinical laboratory tests (serum chemistry, coagulation, and urinalysis), vital signs, continuous telemetry (12 lead ECG), safety ECGs, pulmonary function testing (PFT), serum protein electrophoresis (SPEP) and serum immunoelectrophoresis (IEP), and adverse event reporting.

The L-arginine salt of Compound 1 was tolerated at all dose levels. The most common adverse events included contact dermatitis and leukopenia, followed by constipation, diarrhea, nausea, and abdominal pain. The contact dermatitis observed is consistent with what is generally seen with the adhesive tape from the ECG leads used in the study and did not occur more frequently in the treated group. The majority of adverse events were mild. There were no other clinically significant safety issues with respect to vital signs, ECGs, PFTs, ophthalmoscopy, or clinical laboratory tests. No subjects were discontinued due to an adverse event. No SAEs or deaths occurred during the study.

No second degree heart block was found. Three subjects developed new (not present before dosing) $1^{st}$ degree atrioventricular block: 1 subject in placebo group, 1 subject in 2 mg group, and 1 subject in 0.5, 3 mg group. One subject (1.35 mg dose) had mildly abnormal reproducible (NCS) pulmonary function test findings (FEV1 below 80%, FVC) post-dose.

Two subjects had mildly abnormal non-clinically significant post-treatment liver function tests (elevated alanine aminotransferase (ALT) & aspartate aminotransferase (AST)≤2× upper limit of normal (ULN)): 1 subject in 2 mg group and 1 subject in 0.5 escalating to 3 mg group.

Figure 1B:
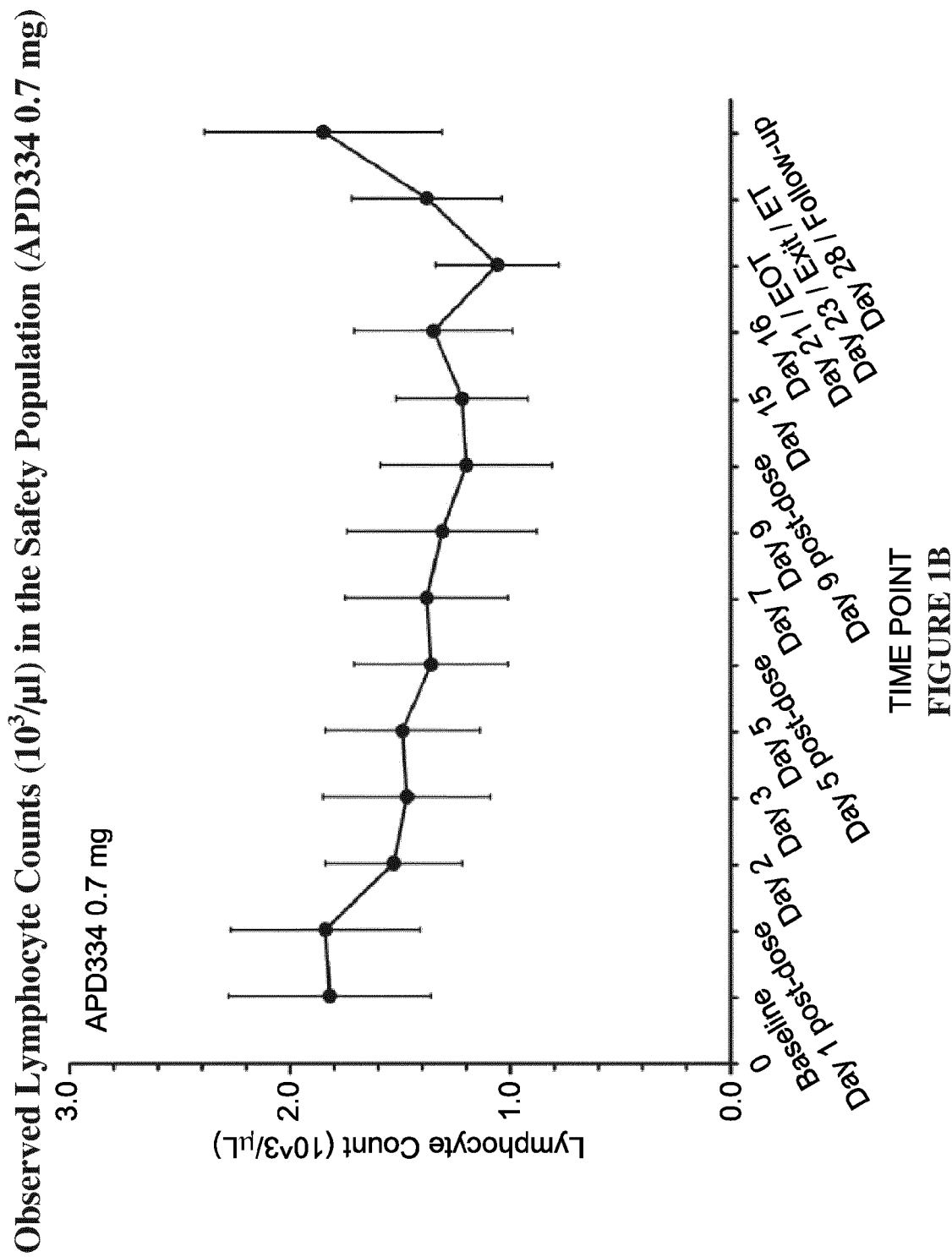
Figure 1C:
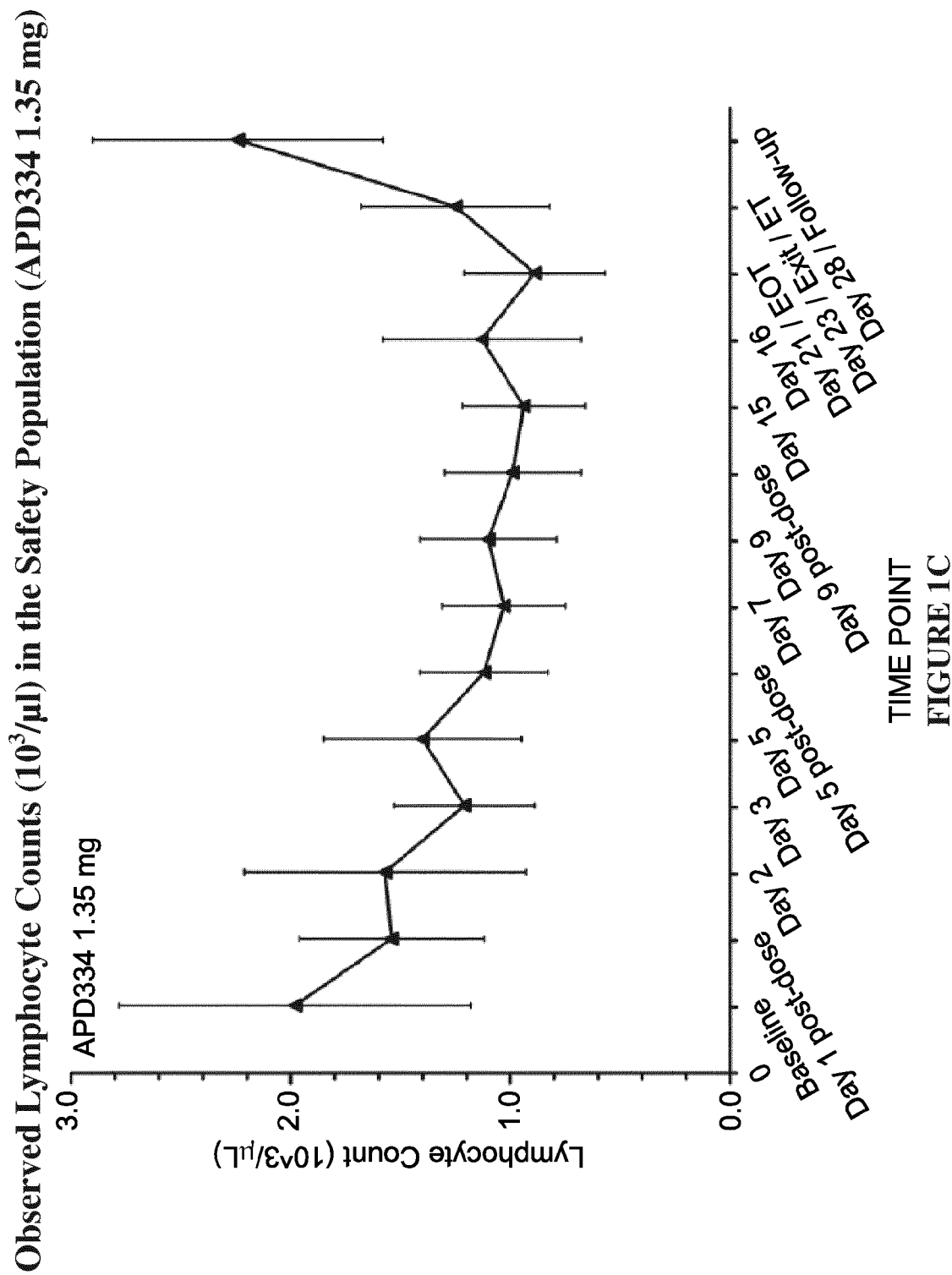
Figure 1D:
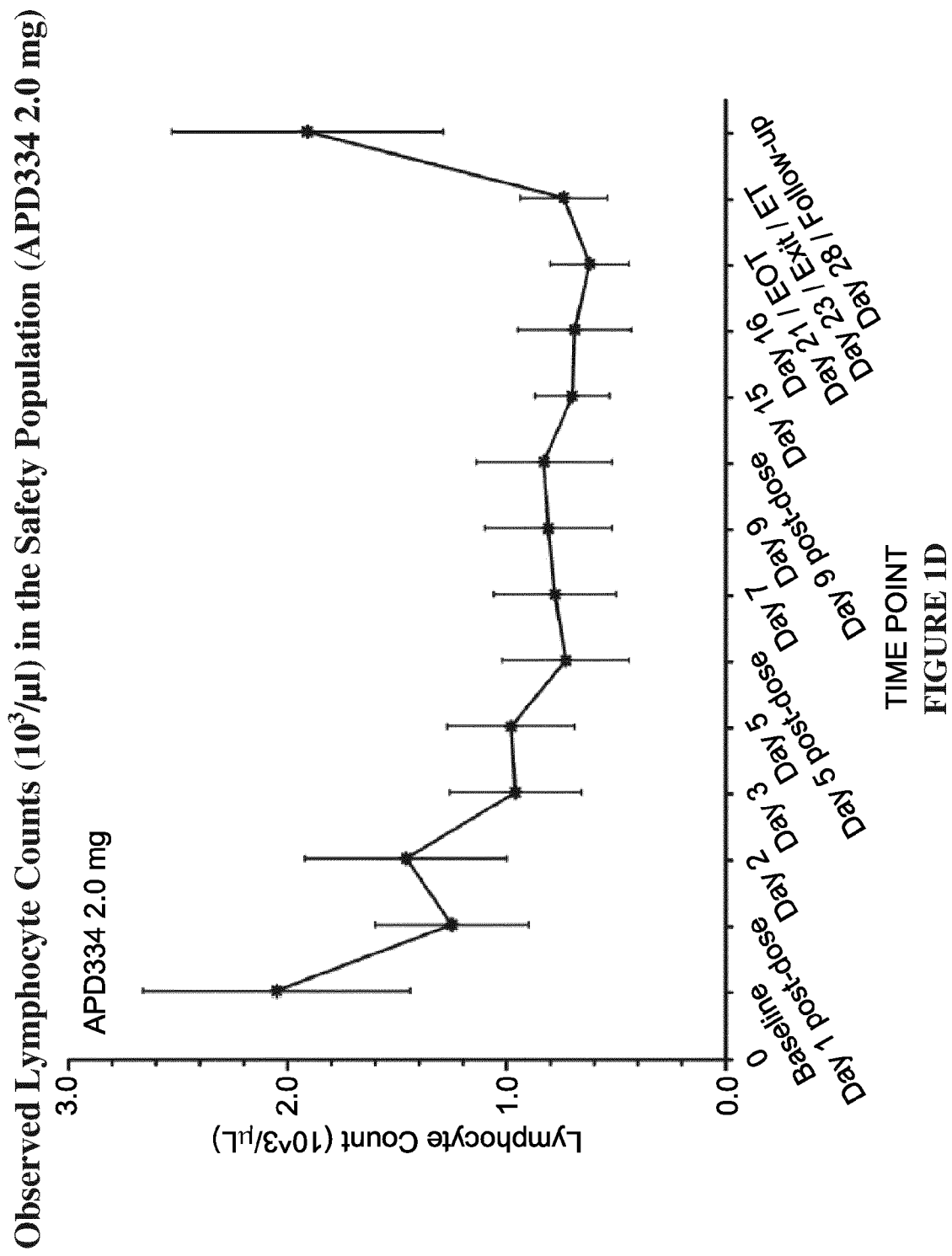
Figure 1E:
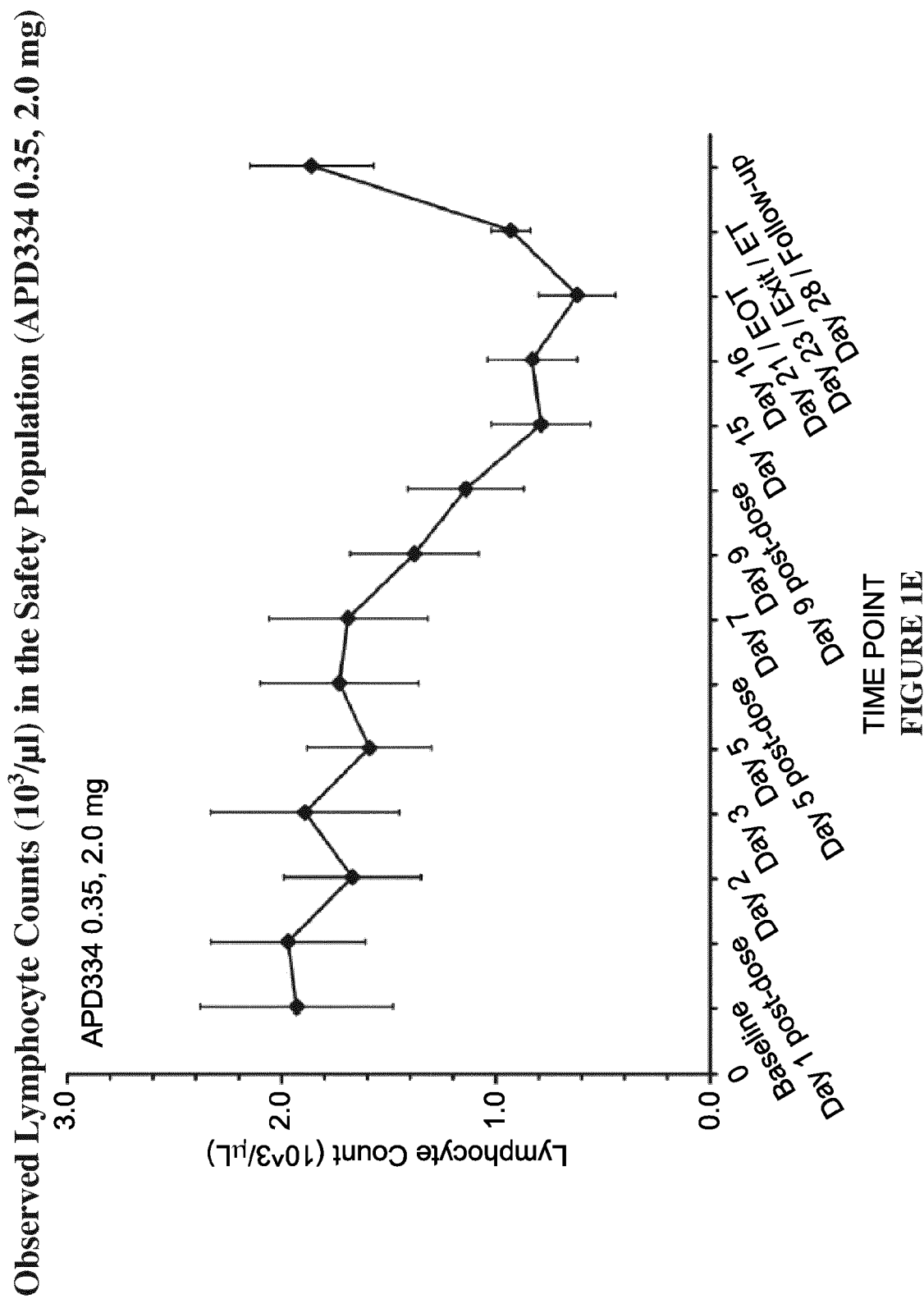
Figure 1F:
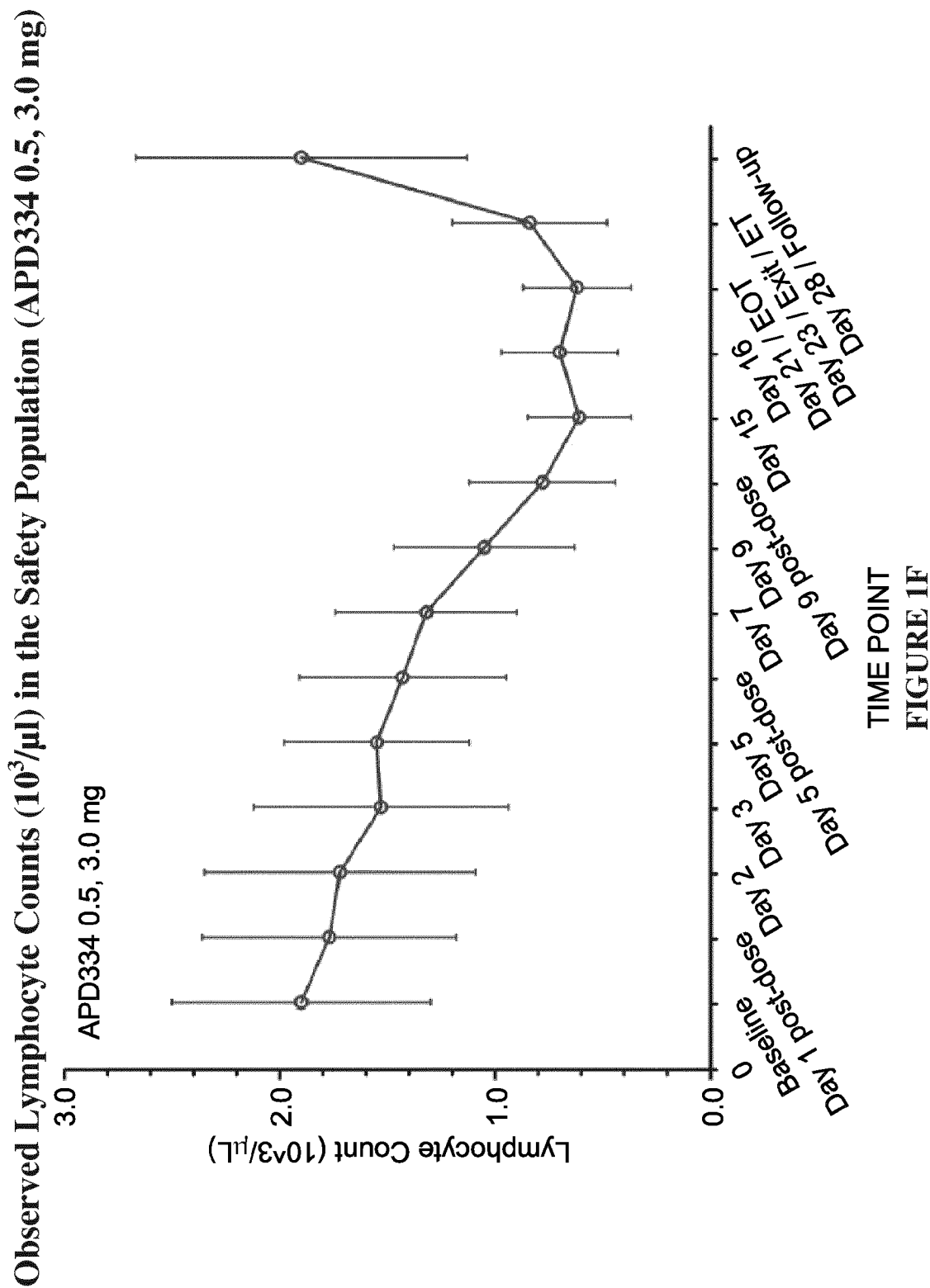
Figure 2A:
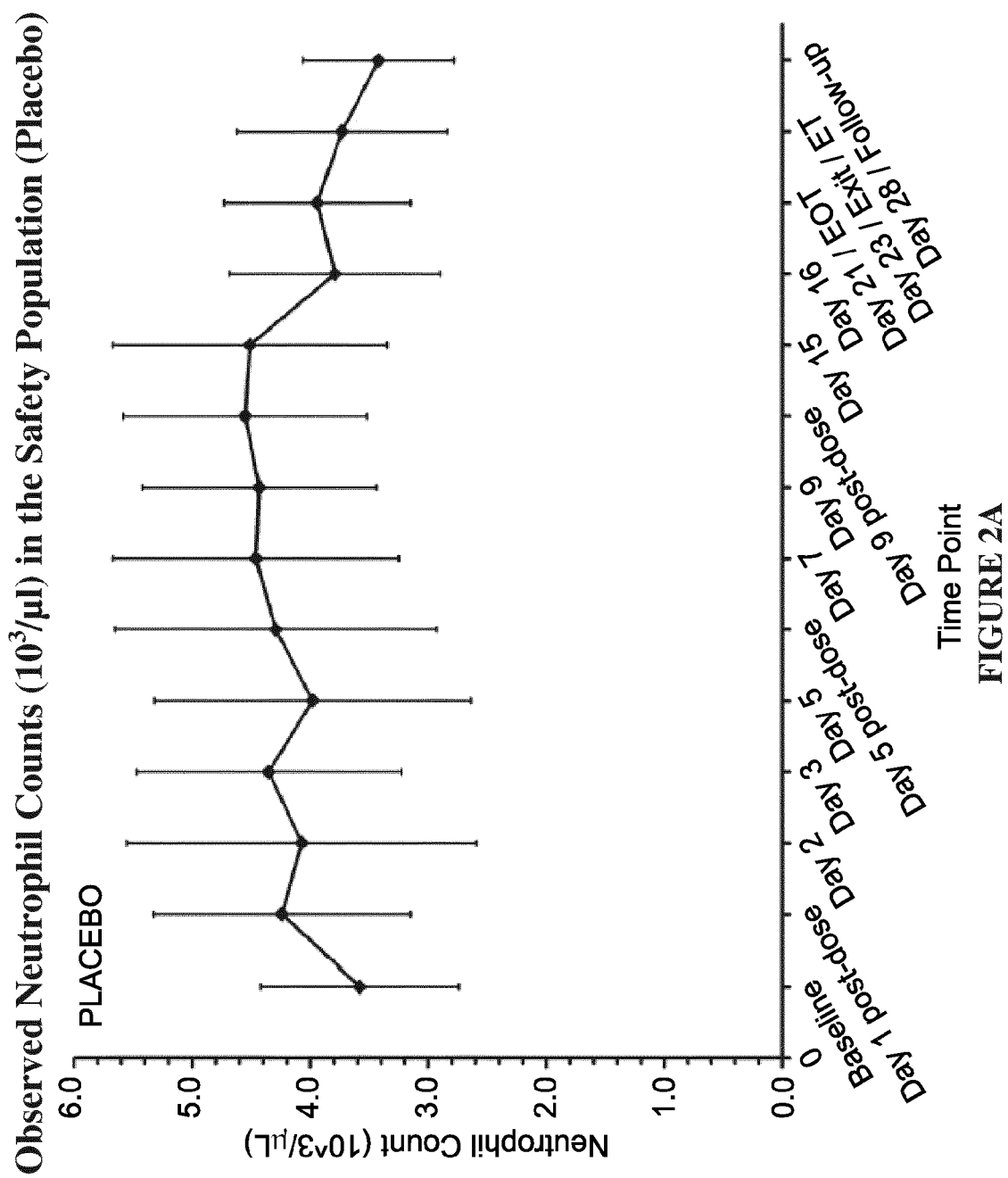
FIG. 2 shows observed neutrophil counts ($10^3/\mu L$) in the safety population.
Figure 2B:
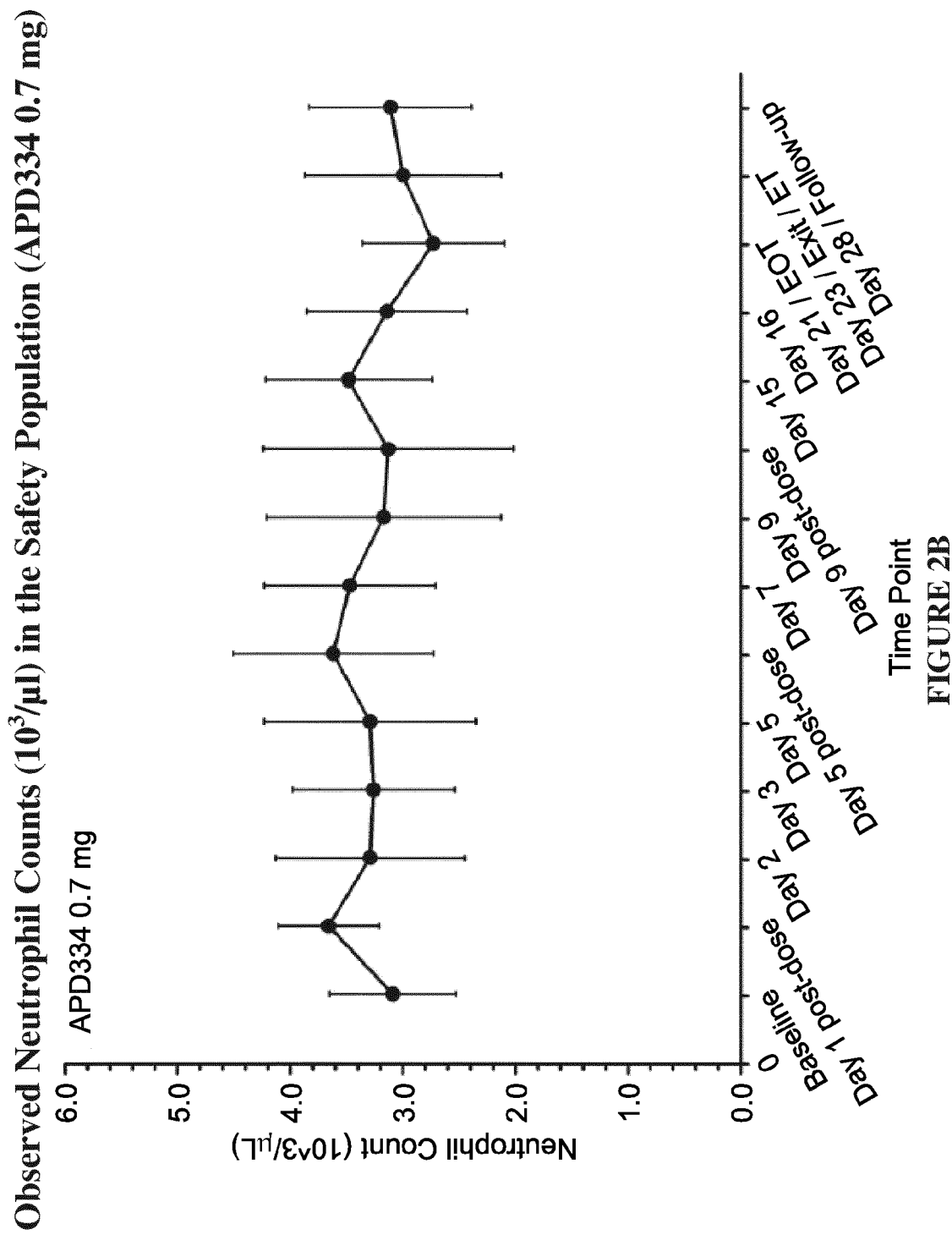
Figure 2C:
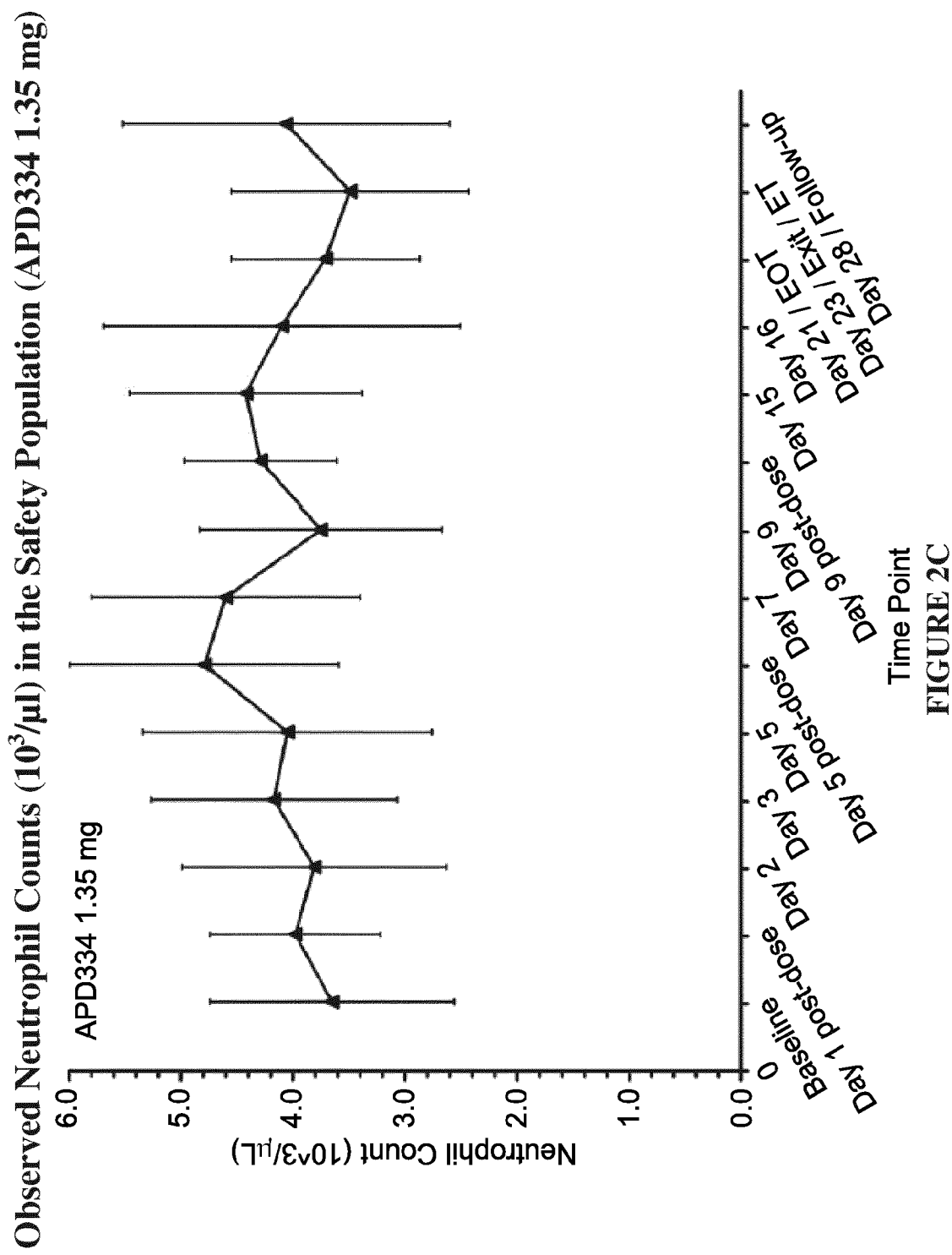
Figure 2D:
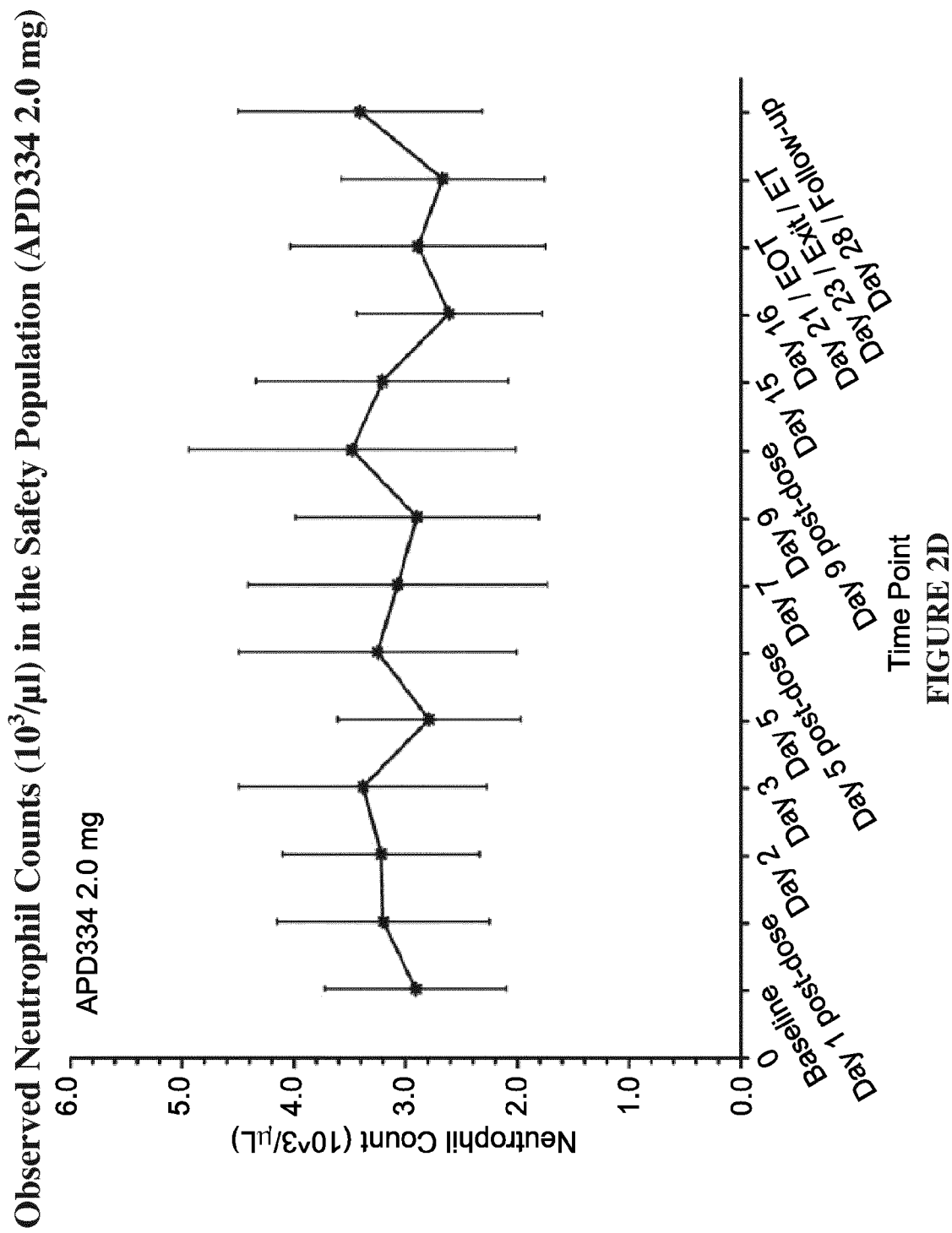
Figure 2E:
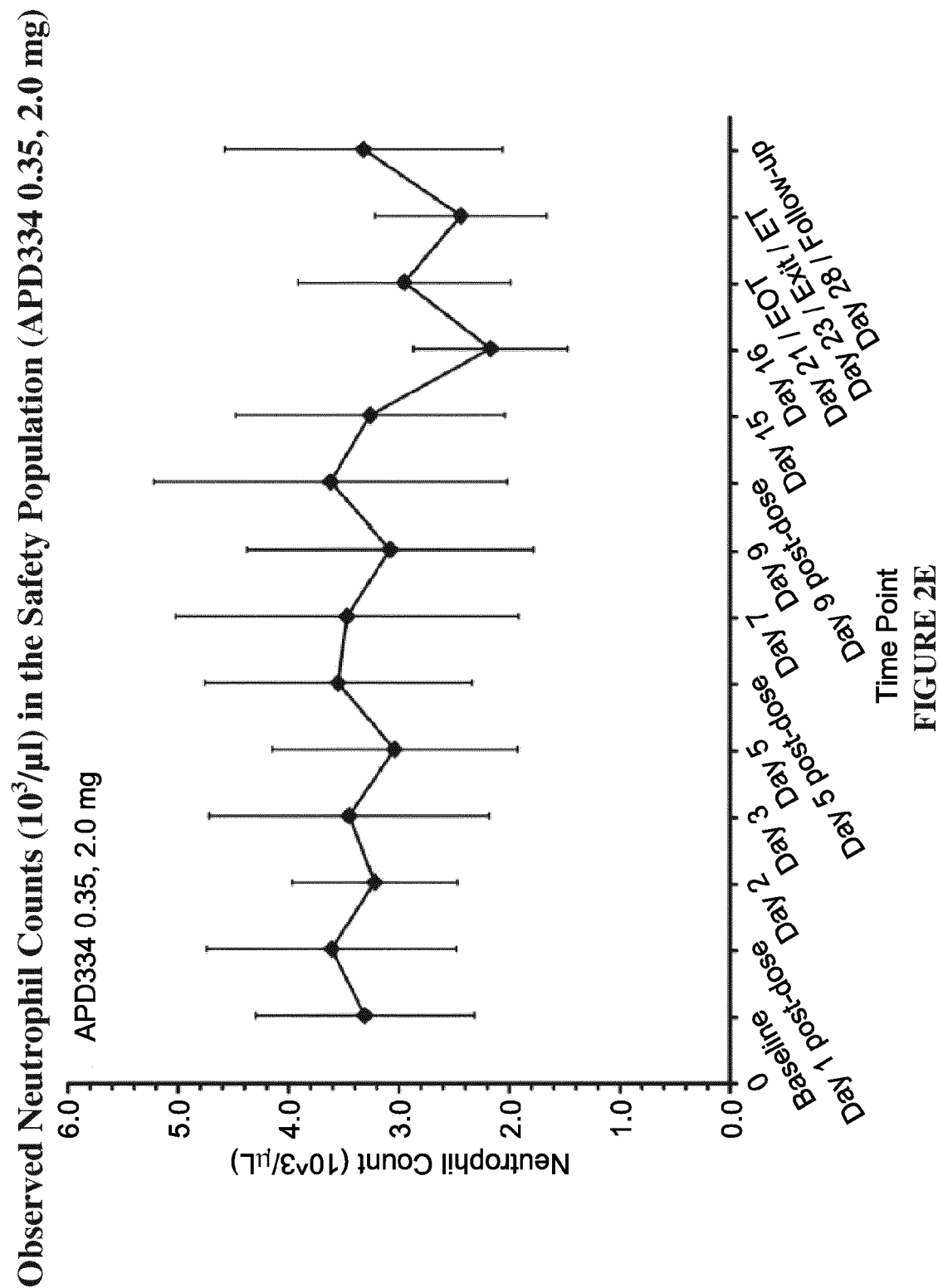
Figure 2F:
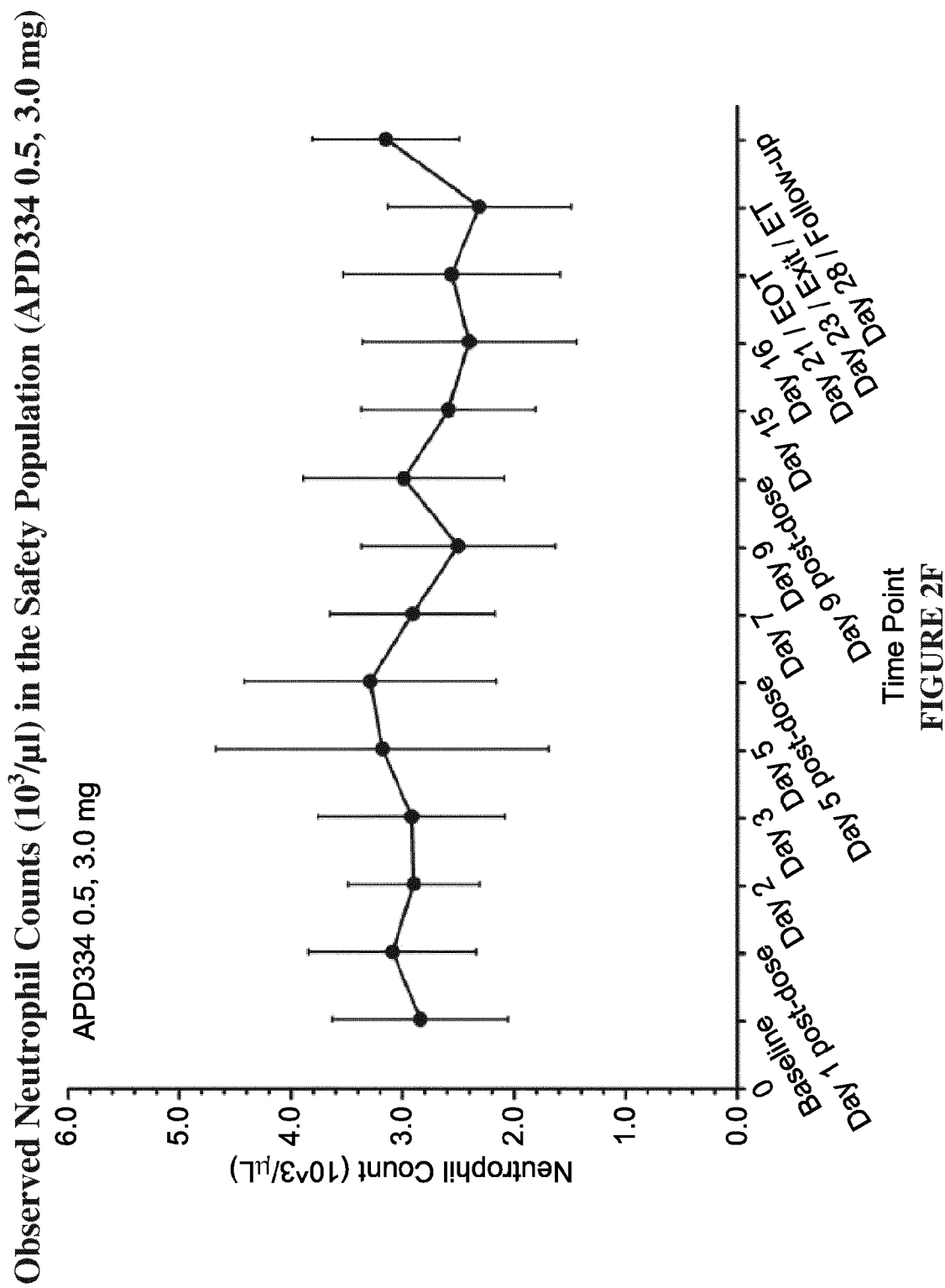

No clinically significant change from baseline in ophthalmoscopy findings were found on exam. FIG. 1 shows observed lymphocyte counts ($10^3/\mu l$) in the safety population. FIG. 2 shows observed neutrophil counts ($10^3/\mu l$) in the safety population. Table 5 shows a summary of percent change from baseline at day 21 in lymphocytes ($10^3/\mu l$): safety population.

TABLE 5

| Parameter Treatment | N | Baseline Mean (SD) | On Treatment Mean (SD) | Mean (SE) | Percent Change from Baseline Median | Min, Max |
|---|---|---|---|---|---|---|
| Placebo | 10 | 1.81 (0.44) | 1.86 (0.31) | 5.08 (4.24) | 7.67 | −17.39 to 23.08 |
| 0.7 mg | 10 | 1.82 (0.46) | 1.06 (0.28) | −41.03 (3.19) | −40.37 | −55.56 to −23.08 |
| 1.35 mg | 9 | 2.03 (0.83) | 0.89 (0.32) | −53.43 (4.74) | −51.85 | −68.75 to −30.77 |
| 2.0 mg | 10 | 2.05 (0.61) | 0.62 (0.18) | −68.81 (2.60) | −69.44 | −80.00 to −55.56 |
| 0.35, 2.0 mg | 10 | 1.93 (0.45) | 0.62 (0.18) | −67.34 (2.13) | −67.54 | −77.27 to −57.14 |
| 0.5, 3.0 mg | 10 | 1.90 (0.60) | 0.62 (0.25) | −66.16 (3.40) | −65.02 | −85.19 to −53.85 |

Note:
Baseline was the last measure prior to first dose.

Figure 3A:
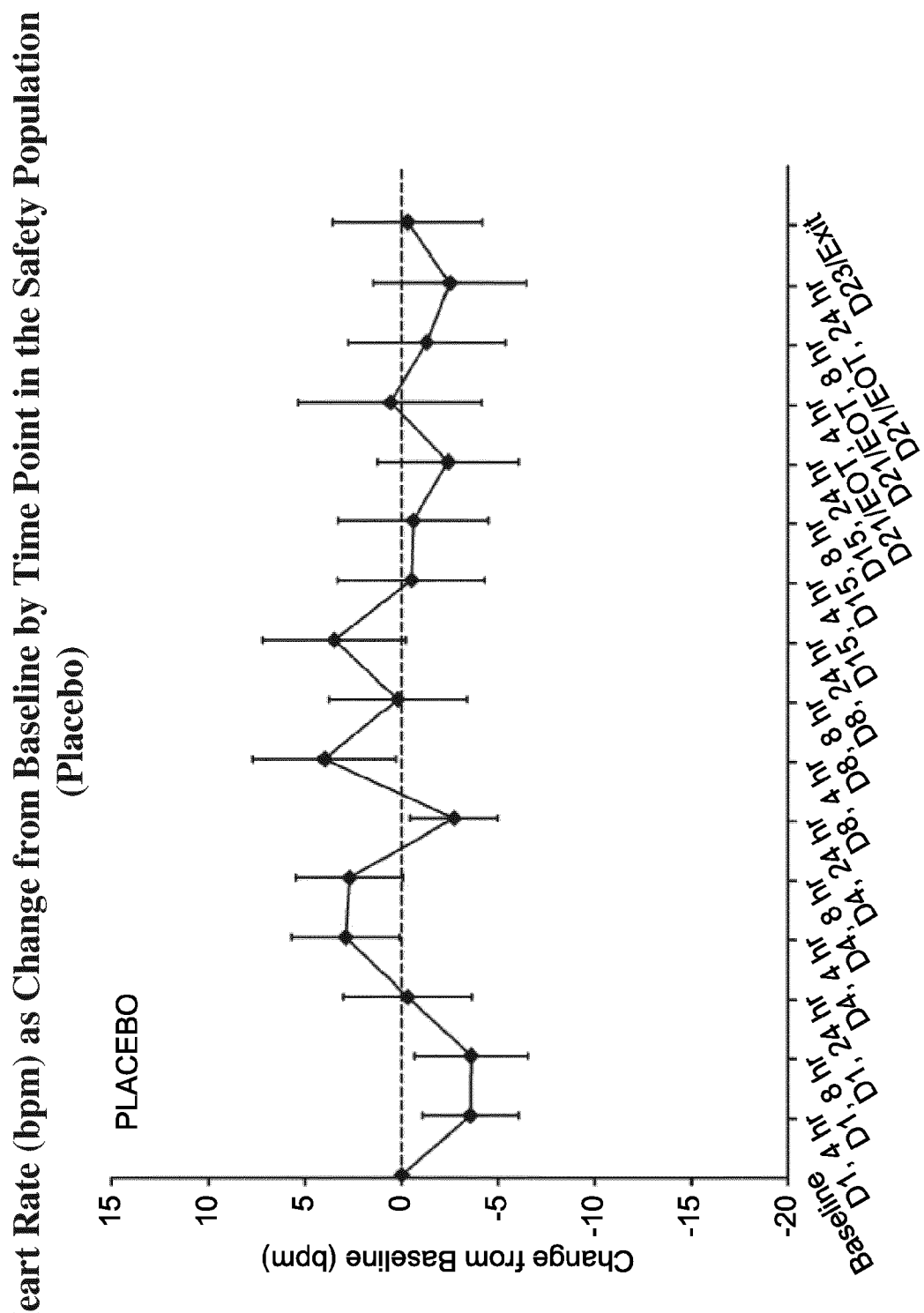
FIG. 3 shows ECG heart rate (bpm) as change from baseline by time point in the safety population.
Figure 3B:
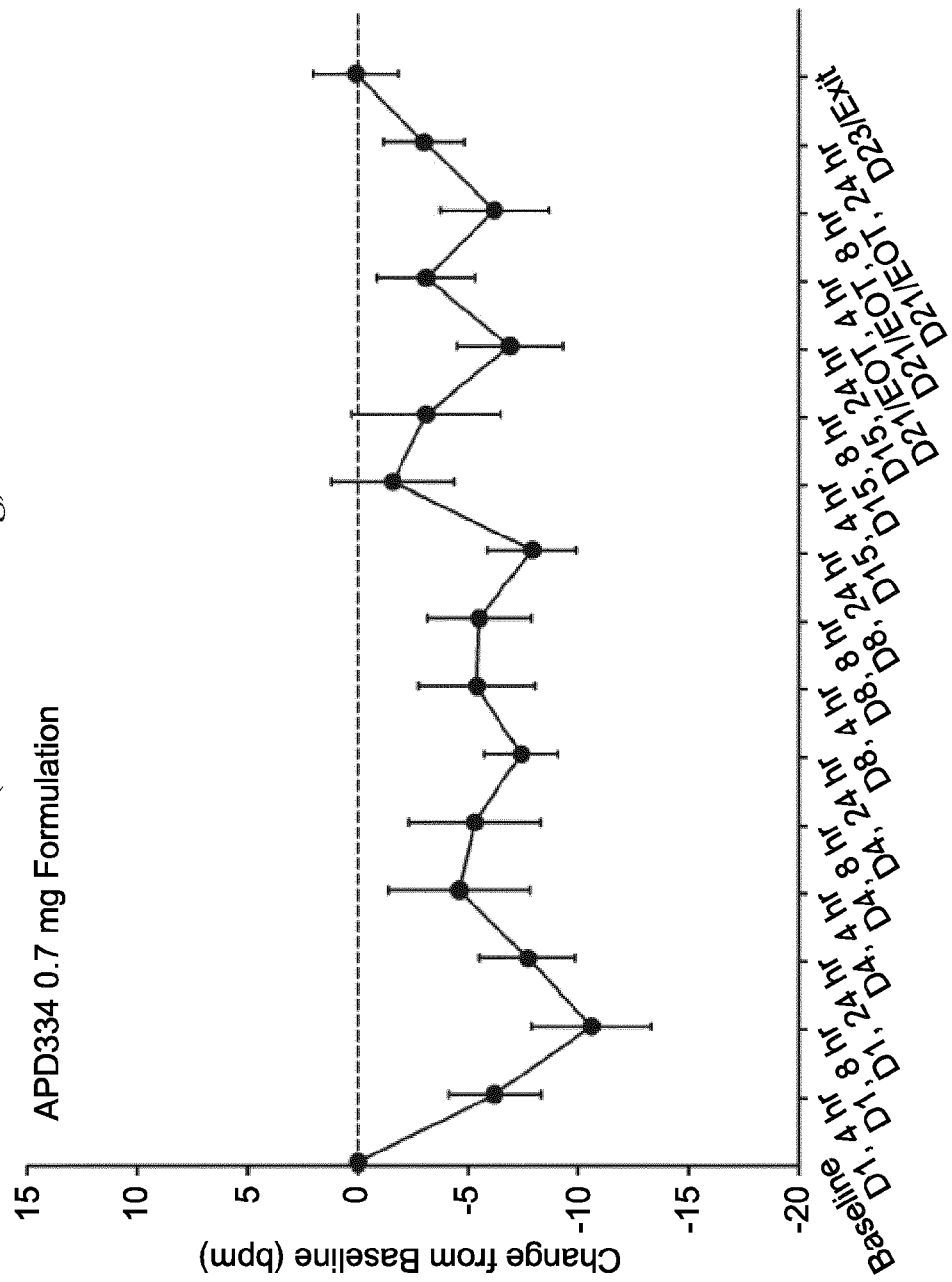
Figure 3C:
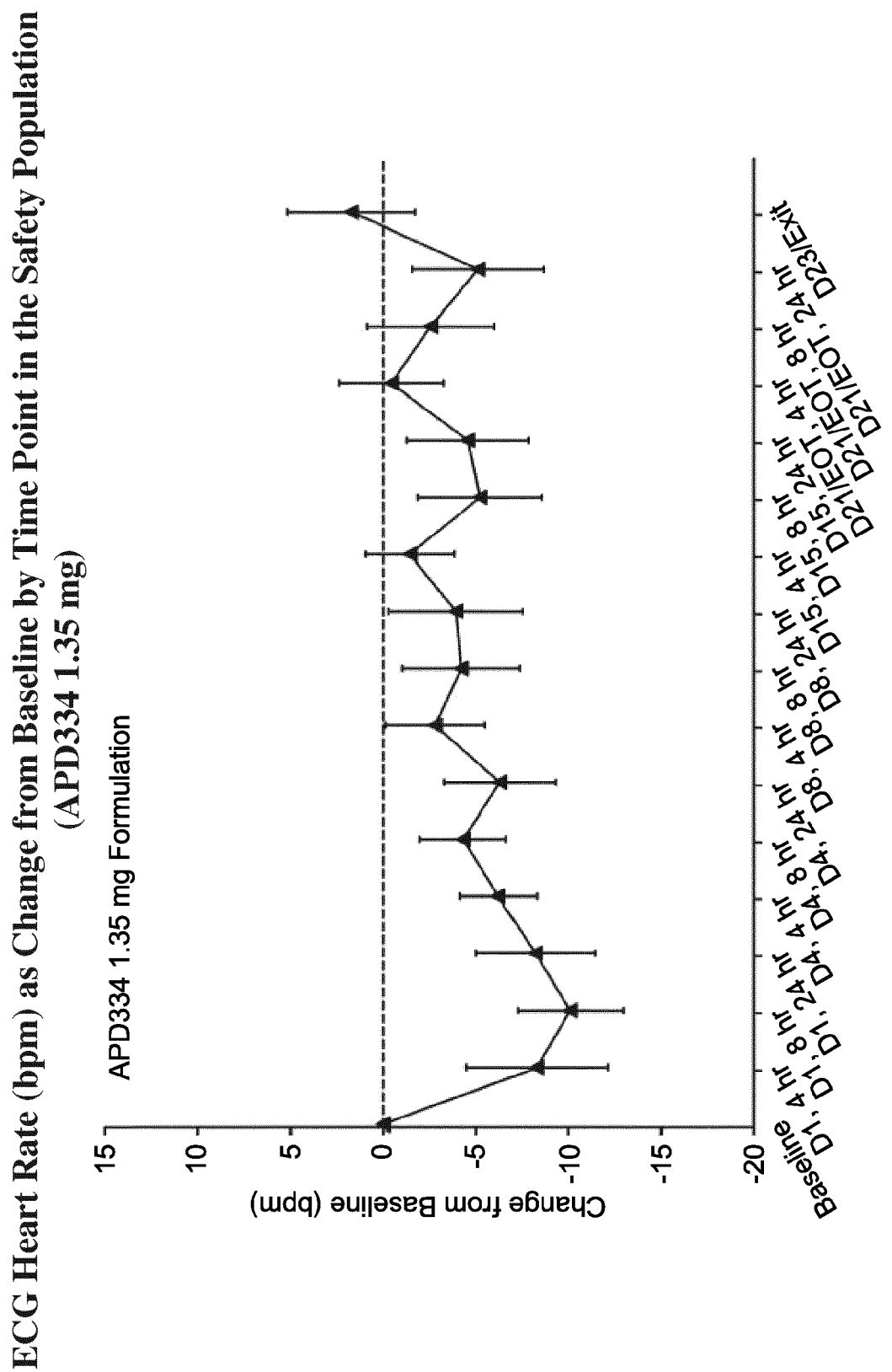
Figure 3D:
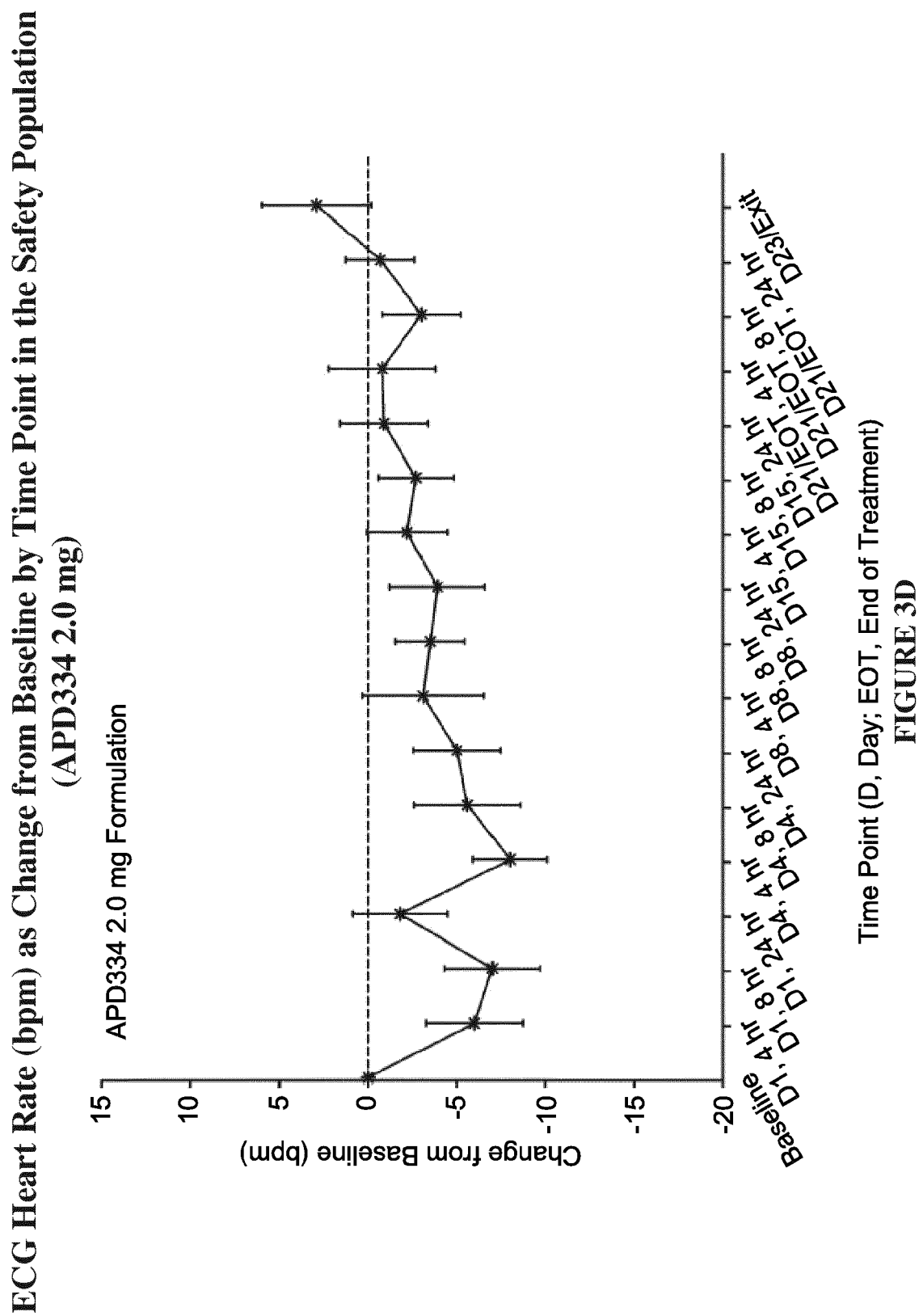
Figure 3E:
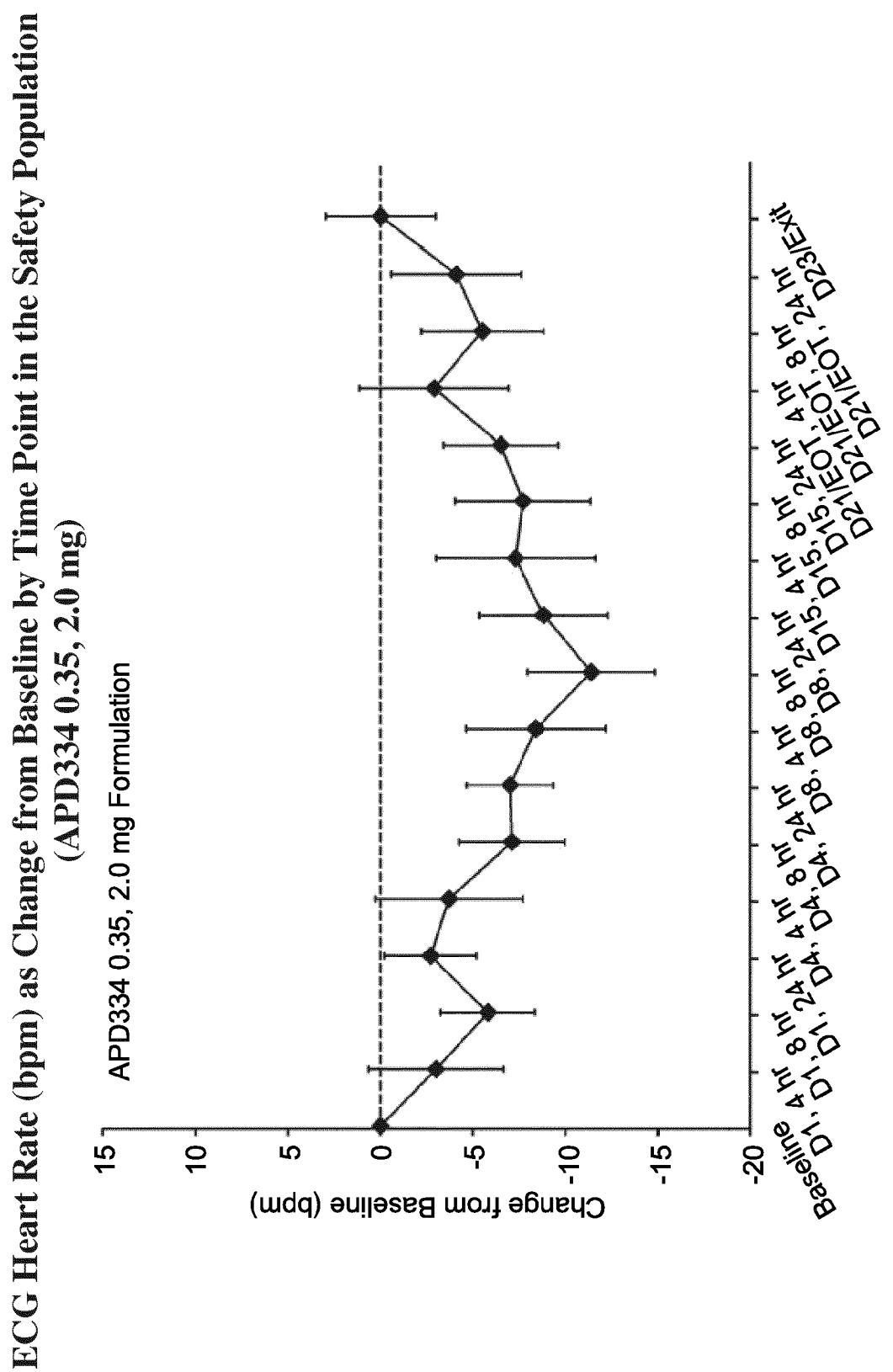

Table 6 shows a summary of change from baseline in minimum value for post-dose (day 1 to day 28) in heart rate (BPM): safety population. See, also FIG. 3.

TABLE 6

| Parameter Treatment | N | Baseline Mean (SD) | On Treatment Mean (SD) | Change from Baseline Mean (SE) | Median | Min, Max |
|---|---|---|---|---|---|---|
| Minimum Value for Post-dose (Day 1 to Day 28) in Heart Rate (BPM) | | | | | | |
| Placebo | 10 | 61.20 (9.73) | 56.50 (5.99) | −4.70 (2.17) | −2.00 | −17.00 to 4.00 |
| 0.7 mg | 10 | 59.70 (3.89) | 54.20 (4.05) | −5.50 (0.95) | −5.00 | −12.00 to −1.00 |
| 1.35 mg | 10 | 60.60 (6.62) | 54.40 (4.09) | −6.20 (1.91) | −5.00 | −18.00 to 3.00 |
| 2.0 mg | 10 | 59.30 (4.72) | 51.00 (4.78) | −8.30 (1.40) | −7.50 | −16.00 to −3.00 |
| 0.35, 2.0 mg | 10 | 62.60 (12.14) | 52.00 (4.74) | −10.60 (3.51) | −7.00 | −35.00 to 3.00 |
| 0.5, 3.0 mg | 10 | 61.10 (3.93) | 53.80 (4.73) | −7.30 (1.33) | −6.50 | −14.00 to −2.00 |

Note:
Baseline was defined as minimum of pre-dose values.

Table 7 shows a summary of change from baseline in minimum value for post-dose (day 1 to day 28) in systolic BP (mmHg): safety population.

TABLE 7

| Parameter Treatment | N | Baseline Mean (SD) | On Treatment Mean (SD) | Change from Baseline Mean (SE) | Median | Min, Max |
|---|---|---|---|---|---|---|
| Minimum Value for Post-dose (Day 1 to Day 28) in Systolic BP (mmHg) | | | | | | |
| Placebo | 10 | 104.90 (4.84) | 95.40 (6.19) | −9.50 (1.75) | −8.00 | −23.00 to −3.00 |
| 0.7 mg | 10 | 105.80 (8.24) | 96.10 (7.72) | −9.70 (1.57) | −9.50 | −16.00 to −1.00 |
| 1.35 mg | 10 | 109.00 (10.62) | 100.10 (8.99) | −8.90 (2.79) | −8.00 | −22.00 to 3.00 |
| 2.0 mg | 10 | 100.60 (8.18) | 90.80 (8.73) | −9.80 (1.50) | −9.00 | −18.00 to −4.00 |
| 0.35, 2.0 mg | 10 | 107.30 (8.60) | 94.30 (12.50) | −13.00 (3.03) | −13.00 | −28.00 to 0.00 |
| 0.5, 3.0 mg | 10 | 101.00 (12.00) | 93.20 (8.66) | −7.80 (2.36) | −5.00 | −18.00 to 5.00 |

Note:
Baseline was defined as minimum of pre-dose values.

Table 8 shows a summary of change from baseline in minimum value for post-dose (day 1 to day 28) in diastolic BP (mmHg): safety population.

TABLE 8

| Parameter Treatment | N | Baseline Mean (SD) | On Treatment Mean (SD) | Change from Baseline Mean (SE) | Median | Min, Max |
|---|---|---|---|---|---|---|
| Minimum Value for Post-dose (Day 1 to Day 28) in Diastolic BP (mmHg) | | | | | | |
| Placebo | 10 | 58.50 (4.97) | 52.20 (4.71) | −6.30 (1.44) | −5.50 | −13.00 to 1.00 |
| 0.7 mg | 10 | 62.10 (8.84) | 56.00 (8.31) | −6.10 (1.92) | −6.00 | −16.00 to 2.00 |
| 1.35 mg | 10 | 58.90 (7.96) | 53.70 (4.03) | −5.20 (1.93) | −7.50 | −11.00 to 6.00 |
| 2.0 mg | 10 | 56.50 (5.62) | 45.30 (7.42) | −11.20 (1.88) | −9.00 | −21.00 to −4.00 |

TABLE 8-continued

| Parameter Treatment | N | Baseline Mean (SD) | On Treatment Mean (SD) | Change from Baseline Mean (SE) | Median | Min, Max |
|---|---|---|---|---|---|---|
| 0.35, 2.0 mg | 10 | 58.70 (6.48) | 50.80 (5.65) | −7.90 (2.00) | −6.00 | −19.00 to −1.00 |
| 0.5, 3.0 mg | 10 | 56.50 (6.77) | 50.20 (4.21) | −6.30 (1.89) | −7.00 | −13.00 to 3.00 |

Note:
Baseline was defined as minimum of pre-dose values.

Table 9 shows a summary of change from baseline in maximum value for post-dose (day 1 to day 23) in QTc (MS): safety population.

TABLE 9

| Parameter Treatment | N | Baseline Mean (SD) | On Treatment Mean (SD) | Change from Baseline Mean (SE) | Median | Min, Max |
|---|---|---|---|---|---|---|
| Maximum Value for Post-dose (Day 1 to Day 23) in QTc (MS) | | | | | | |
| Placebo | 10 | 416.70 (10.40) | 416.10 (14.79) | −0.60 (3.39) | −2.50 | −11.00 to 24.00 |
| 0.7 mg | 10 | 414.80 (15.90) | 418.40 (16.56) | 3.60 (2.20) | 3.50 | −8.00 to 16.00 |
| 1.35 mg | 10 | 415.40 (14.65) | 423.60 (16.14) | 8.20 (3.10) | 6.00 | −5.00 to 25.00 |
| 2.0 mg | 10 | 417.20 (6.51) | 421.20 (10.61) | 4.00 (2.53) | 4.50 | −8.00 to 13.00 |
| 0.35, 2.0 mg | 10 | 411.20 (19.10) | 411.10 (19.88) | −0.10 (3.24) | 0.50 | −19.00 to 17.00 |
| 0.5, 3.0 mg | 10 | 419.50 (15.34) | 425.10 (13.90) | 5.60 (2.18) | 5.00 | −5.00 to 15.00 |

Note:
Baseline was defined as maximum of pre-dose values.

In conclusion, the clinical trial showed a dose-dependent effect on lymphocyte lowering with maximal effect at 2 mg dose. The L-arginine salt of Compound 1 was well tolerated at all doses tested.

Other uses of the disclosed methods will become apparent to those in the art based upon, inter alia, a review of this patent document.

What is claimed is:

1. A method of treatment of ulcerative colitis comprising:
   administering to an individual in need thereof (R)-2-(7-(4-cyclopentyl-3-(trifluoromethyl)benzyloxy)-1,2,3,4-tetrahydrocyclopenta[b]indol-3-yl)acetic acid (Compound 1), or a pharmaceutically acceptable salt, hydrate, or solvate thereof, in an amount equivalent to about 2.0 mg of Compound 1.

2. The method of claim 1, wherein the Compound 1, or a pharmaceutically acceptable salt, hydrate, or solvate thereof, is administered in an amount equivalent to 2.0 mg of Compound 1.

3. The method of claim 1, wherein the Compound 1, or a pharmaceutically acceptable salt, hydrate, or solvate thereof is administered once daily to the individual.

4. The method of claim 1, wherein the Compound 1, or a pharmaceutically acceptable salt, hydrate, or solvate thereof, is administered orally.

5. The method of claim 1, wherein the Compound 1, or a pharmaceutically acceptable salt, hydrate, or solvate thereof, is formulated as a capsule or tablet suitable for oral administration.

6. The method of claim 1, wherein the Compound 1, or a pharmaceutically acceptable salt, hydrate, or solvate thereof, is selected from:
   Compound 1;
   a calcium salt of Compound 1; and
   an L-arginine salt of Compound 1.

7. The method of claim 1, wherein the Compound 1, or a pharmaceutically acceptable salt, hydrate, or solvate thereof, is an L-arginine salt of Compound 1.

8. The method of claim 1, wherein the Compound 1, or a pharmaceutically acceptable salt, hydrate, or solvate thereof, is an anhydrous, non-solvated crystalline form of an L-arginine salt of Compound 1.

9. The method of claim 1, wherein the Compound 1, or a pharmaceutically acceptable salt, hydrate, or solvate thereof, is an anhydrous, non-solvated crystalline form of Compound 1.

10. A method of treatment of Crohn's disease, comprising:
    administering to an individual in need thereof (R)-2-(7-(4-cyclopentyl-3-(trifluoromethyl)benzyloxy)-1,2,3,4-tetrahydrocyclopenta[b]indol-3-yl)acetic acid (Compound 1), or a pharmaceutically acceptable salt, hydrate, or solvate thereof, in an amount equivalent to about 2.0 mg of Compound 1.

11. A method of treatment of inflammatory bowel disease, comprising:
    administering to an individual in need thereof (R)-2-(7-(4-cyclopentyl-3-(trifluoromethyl)benzyloxy)-1,2,3,4-tetrahydrocyclopenta[b]indol-3-yl)acetic acid (Compound 1), or a pharmaceutically acceptable salt, hydrate, or solvate thereof, in an amount equivalent to about 2.0 mg of Compound 1.

12. The method of claim 1, wherein the ulcerative colitis is moderately to severely active ulcerative colitis.

13. A method of treatment of ulcerative colitis comprising:

administering orally to an individual in need thereof (R)-2-(7-(4-cyclopentyl-3-(trifluoromethyl)benzyloxy)-1,2,3,4-tetrahydrocyclopenta[b]indol-3-yl)acetic acid (Compound 1), or a pharmaceutically acceptable salt thereof, once daily, in an amount equivalent to about 2.0 mg of Compound 1.

14. A method of treatment of ulcerative colitis comprising:

administering to an individual in need thereof (R)-2-(7-(4-cyclopentyl-3-(trifluoromethyl)benzyloxy)-1,2,3,4-tetrahydrocyclopenta[b]indol-3-yl)acetic acid (Compound 1), or a pharmaceutically acceptable salt thereof, in an amount equivalent to 2.0 mg of Compound 1.

15. The method of claim 14, wherein the Compound 1, or a pharmaceutically acceptable salt thereof is administered once daily to the individual.

16. The method of claim 14, wherein the Compound 1, or a pharmaceutically acceptable salt thereof, is administered orally.

17. The method of claim 14, wherein the Compound 1, or a pharmaceutically acceptable salt thereof, is formulated as a capsule or tablet suitable for oral administration.

18. The method of claim 14, wherein the Compound 1, or a pharmaceutically acceptable salt thereof, is selected from:
Compound 1;
a calcium salt of Compound 1; and
an L-arginine salt of Compound 1.

19. The method of claim 14, wherein the Compound 1, or a pharmaceutically acceptable salt thereof, is an L-arginine salt of Compound 1.

20. The method of claim 14, wherein the Compound 1, or a pharmaceutically acceptable salt thereof, is an anhydrous, non-solvated crystalline form of an L-arginine salt of Compound 1.

21. The method of claim 14, wherein the Compound 1, or a pharmaceutically acceptable salt thereof, is an anhydrous, non-solvated crystalline form of Compound 1.

* * * * *